(12) United States Patent
Jiang et al.

(10) Patent No.: US 7,666,599 B2
(45) Date of Patent: Feb. 23, 2010

(54) CALPASTATIN MARKERS FOR FERTILITY AND LONGEVITY

(75) Inventors: Zhihua Jiang, Pullman, WA (US); Jennifer J. Michal, Albion, WA (US); Matthew D. Garcia, Colfax, WA (US)

(73) Assignee: Washington State University Research Foundation, Pullman, WA (US)

( * ) Notice: Subject to any disclaimer, the term of this patent is extended or adjusted under 35 U.S.C. 154(b) by 101 days.

(21) Appl. No.: 11/650,345

(22) Filed: Jan. 5, 2007

(65) Prior Publication Data

US 2007/0298421 A1   Dec. 27, 2007

Related U.S. Application Data

(60) Provisional application No. 60/756,383, filed on Jan. 5, 2006.

(51) Int. Cl.
C12Q 1/68 (2006.01)
C12P 19/34 (2006.01)
C07H 21/02 (2006.01)

(52) U.S. Cl. ............... 435/6; 435/91.2; 536/23.1

(58) Field of Classification Search ............... None
See application file for complete search history.

(56) References Cited

U.S. PATENT DOCUMENTS

| | | |
|---|---|---|
| 2004/0115678 A1 | 6/2004 | Barendse |
| 2005/0059021 A1 | 3/2005 | Farid et al. |
| 2005/0065736 A1 | 3/2005 | Bauck et al. |
| 2005/0096458 A1 | 5/2005 | Dumas Milne Edwards et al. |
| 2005/0137805 A1 | 6/2005 | Lewin et al. |

FOREIGN PATENT DOCUMENTS

WO   WO2006097787 A1   9/2006

OTHER PUBLICATIONS

Juppner H. Bone (1995) vol. 17, No. 2, pp. 39S-42S.*
Hacker U.T. et al. Gut (1997) vol. 40, No. 5, pp. 623-627.*
Parmely J.L. et al. BioEssays (2007) vol. 29, pp. 515-519.*
Garcia M.D. 'Mapping of Quantitative Trait Loci Associated with Fertility in Dairy Cattle', (Dec. 2005) Doctor of Philosophy Dissertation, Washington State University, Department of Animal Sciences, 117 printed pages.*
Tsuruta S. et al. J. Dairy Sci. (2005) vol. 88, pp. 1156-1165.*
Ben-Aharon I, Ben-Yosef D, Amit A, Shaigi R. Expression and immunolocalization of the calpain-calpastatin system in the human oocyte. Fertil Steril 2005; 83:1807-1813.
Butler WR. Review: effect of protein nutrition on ovarian and uterine physiology in dairy cattle. J Dairy Sci. 1998; 81:2533-2539.
Cong M, Thompson VF, Goll DE, Antin PB. The bovine calpastatin gene promoter and a new N-terminal region of the protein are targets for cAMP-dependent protein kinase activity. J Biol Chem 1998; 273:660-666.
Kitahara A, Takano E, Ontsuki H, Kirihata Y, Yamagata Y, Knaagi R, Murachi T. Reversed distribution of calpains and calpastatin in human pituitary gland and selective localization of calpastatin in adrenocorticotropin-producing cells as demonstrated by immunohistochemistry. J Clin Endocrinol Metab 1986; 63:343-348.
Koide SS, Wang L, Kamada M. Antisperm antibodies associated with infertility: properties and encoding genes of target antigens. Proc Soc Exp Biol Med 2000; 224:123-132.
Li S, Goldberg E. A novel N-terminal domain directs membrane localization of mouse testis-specific calpastatin. Biol Reprod 2000; 63:1594-1600.
Li S, Liang ZG, Wang GY, Yavetz B, Kim ED, Goldberg E. Molecular cloning and characterization of functional domains of a human testis-specific isoform of calpastatin. Biol Reprod 2000; 63:172-178.
Liang ZG, O'Hern PA, Yavetz B, Yavetz H, Goldberg E. Human testis cDNAs identified by sera from infertile patients: a molecular biological approach to immunocontraceptive development. Reprod Fertil Dev 1994; 6:297-305.
Lucy MC. Reproductive loss in high-producing dairy cattle: where will it end? J Dairy Sci. 2001; 84:1277-1293.
Macmillan KL, Lean IJ, Westwood CT. The effects of lactation on the fertility of dairy cows. Aust Vet J 1996; 73:141-147.
Murachi T. Calpain and calpastatin. Rinsho Byori 1990; 38:337-346 (abstract only).
Orwig KE, Bertrand JE, Ou BR, Forsberg NE, Stormshak F. Involvement of protein kinase-C, calpains, and calpastatin in prostaglandin F2 alpha-induced oxytocin secretion from the bovine corpus luteum. Endocrinology 1994; 134:78-83.
Roche JF, Mackey D, Diskin MD. Reproductive management of postpartum cows. Anim Reprod Sci 2000; 61:703-712.
Royal MD, Darwash AO, Flint AP, Webb R, Woolliams JA, Lamming GE. Declining fertility in dairy cattle: changes in traditional and endocrine parameters of fertility. Anim Sci 2000; 70:487-502.
Sheldon IM, Dobson H. Reproductive challenges facing the cattle industry at the beginning of the 21st century. Reprod Suppl. 2003; 61:1-13.
Thompson VF, Saldana S, Cong J, Luedke DM, Goll DE. The calpain system in human placenta. Life Sci 2002; 70:2493-508.

(Continued)

*Primary Examiner*—Stephen Kapushoc
(74) *Attorney, Agent, or Firm*—Judy Jarecki-Black; Merial Limited; Thomas Kowalski, Esq.

(57) ABSTRACT

Aspects of the present invention provide novel compositions and methods based on novel calpastatin (CAST) genetic markers, such as missense mutations in exon 3 that result in G48D or P52L substitutions (NM_174003.2:c.271G>A and 283C>T), a G/T substitution in intron 3 (AAFC02060381.1: g.2110G>T) and a GAAA repeat in intron 8 (AAFC02060381.1:g.6700[(GAAA)4]+[(GAAA)5]. Particular aspects provide novel markers for fertility (e.g., daughter pregnancy rate, DPR) and longevity (e.g., productive life, PL) in, for example, dairy cattle. Additional aspects provide for novel methods comprising marker-assisted selection to improve fertility and/or longevity in dairy cattle. Therefore, in particular embodiments, a combination of genetic selection based on one or more of the novel CAST markers, and high PTA potentials of milk production traits, provides for improved reproductive traits in association with continued high milk production traits. Further aspects disclose a previously unrecognized XL domain in the human CAST gene, and thus provide for the use of human CAST XL domain mutants/variants as markers for human fertility and longevity.

1 Claim, 43 Drawing Sheets

OTHER PUBLICATIONS

VanRaden PM, Sanders AH, Tooker ME, Miller RH, Norman HD, Kuhn MT, Wiggins GR. Development of a national genetic evaluation for cow fertility. Dairy Sci 2004; 87:2285-2292.

Wang LF, Miao SY, Yan YC, Li YH, Zong C, Koide SS. Expression of a sperm protein gene during spermatogenesis in mammalian testis: an in situ hybridization study. Mol Reprod Dev 1990; 26:1-5

Washburn SP, Silvia WJ, Brown CH, McDaniel BT, McAllister AJ. Trends in reproductive performance in Southeastern Holstein and Jersey DHI herds. J Dairy Sci. 2002; 85:244-251.

Wei SG, Wang LF, Miao SY, Zong SD, Koide SS. Expression of the calpastatin gene segment during spermiogenesis in human testis: an in situ hybridization study. Arch Androl 1995; 34:9-12.

* cited by examiner

```
AACTGTCTGAAACACAGCACCGCAGAGAGCAGTGACCCCGAGGCTCACATTGTCAATGCCATGGCAGGGT
TAACAGGTTTTCTTCTGTCAGATCTTCACAAACTGGCAGCAACCACAGGCAGACAATCACTGCAGAGGAG
GAGCCTTTTCTAGTCTGGCTTATAACATTTCACTTCAAGCTTGTTATAATTCACAGCCCCAAACCAGGAA
GTGCTCTTTAAGATGAACAAAGACAAAAGCAATCTGGCCTCCTCGCAAACGAAATTCAACAGCCTCCTG
AAAGGCAATGGGGTTTAAATTTAGGACTGTTCTTCGGTTTTGATTGGAACCCAAGACTTGTTCCACATGA
ACATCATTGCACTTTCAAAACAAGTAAAGCCGCACAAAACACACCCAGGCCCGTGTGTGTACACACACA
CACACACACACACACACACACACACACACACACACACAATCACAACACACGGAGTCACACACAGACCA
ATTTGTTTCTGCAATCCGCTTCCTCATCCAGAGGGTCCAGGCCCCGGGCCATCTGAGTTGGTAAATTCTC
CTCCTAGTTAACTCAGAGCAGATTGCAGAAATGCTGTCTAATTCTTGAGATTCTTAGGGAGTGGGCTTG
AGATGTAGACGGGGCCACGCCCCGGTTCCGCTCTCCTTGCACAACTGCAAGCCAAGTCTAGGCAAGTCGG
GGGGAAAACCCCGCCATCTCCAGCCCCTCCTCTCTGCGACCCACTGGGGCACCAAGGCGACCTCGGGTGG
GGTGGGGTGTCCCTGGGAGAAGATACGGGACCCAGGGTGTGAGTTGCAAACAGGCAGCCCCGGGCTGCTG
CCGCCCGGGCGCTGCCAACTGCAGGCAGGAAGGGGAGGGCCCTGCCCGGCGAAGGGGAGCTCTCGCGGGT
CGGGGCTGGGTCGGAAAAGCTGCCTCACAGGCGCGCCCGCCAGCCCCTCCGCGCCCTCGCTCCCTCCCAG
CGCTCCCCGGCTCCAGCCTCCCTTCCAGGCTCCGCCGCGCCCGCCCGGAGGCAGCGCTCGCACCGGCCTC
GCCATGTCCCAGCCGGGCCCGAAGCCCGCCGCCTCCCCGCGGCCCCGGCGCGCTGCCCGCCACACCCAGG
AGGTGAGTGGCGCTCCTACCGCCGGGGTTGAGCGCGGGGAGGATCTCGGGGCCCCCCGAAGCCTCGGGTC
CACCTTCAGAGGAGGGTTAGCCTTCCTGGCCTTCTGTCCCTGGGCGCCACCCCTCCCAGGCCCGGAGAAA
CATCTGGAGAGAGACGGGTGTGGACTCAGAACCTGCCTCTGGGCAGGTGACCGGAGGGGCCCGCGGATGG
CCCTGGGTCCCGGCCAAGTTCACTGGGCGCGGCGCAAGCCACATTGGAGTGGGCTTCCCTGGCGGCTCAG
CTGGTGAAGAATCCGCCTACAATGCGGGAGACCTGGGCTCGTTGGGTTGGGAAGATCCCTGGAGAAGGG
AACTGGCTCCCAGTATCCTGGCCTGGAGAATTCCCTGCACTGGATAGTCCATGGGTGGCAGAGTCAGGAC
ACGACTGAGCGACTTTTGCTCACTTGTCACTCATGCGTTGGGAAAAGTTGGTGGATGAGACAGGGGTGGG
TGAGAAGCGGATAAGGGTAAAAGGAGAATGAAATTCATTTGGGACCCCCGGGATTCCGGAGTCTGTAAG
ATCAGCAGAAAAGTCTGGTCTTCCGCCCAGTCAGGGCTGCAGGGCGTGGCTGCCTGGAGCAATAACACTT
CTTCCCTAAGCAGCTTTGAGCCAAACCGGCAGGGCGGGGCGGGGCGGGGCGGGGCGGGGGCGGGGAGGGG
CGGGGAGAGGGCGGGGTCAGCCCGAGGGGCGGGTCTGGGTAGGCCCCGCCCAGCTGTCTTGCCCACCCC
CTGACAGCCTAGGTGCTTACA**GAGTTAGTCCCAGTCAGGTCTGCGGCAGGTGGAGTGCGAACCCGTGGCC
CTTTGCTGCGCTGCACCCGTGTCCTCGCCGGGTCCCTCGGGTCTCTCGCTGCGTCTCTCGGAACACATCC
ATCGTCGCC***ATGGCATTTGCAAGCTGGTGGTACAAGACG*GT*AAATAGGAGTGATCGTCCCTGGGCAGGAC
TGGGAAGGGAATGTGCTCTGTCTTCCTGGGCTGTAGGCGAGGTCACTGTTCAGATTTTCGGGCGAGGGTT
GGGGAGCAGGTTGTGACCTCCTCTCAGACCTTCAGGGGAGGCTCCGGGAGAGGCTGAGACCCACCCTGCT
GTGGAATGTGGGAGCCAGCTCGGACGTACACGTGCTAGTCGGCGTGAGTTCAGGCTCACAAGTTGAATGG
CATAGGGATTGTTGCTGGACGAATTCTGCCCTCGGACGCGGATTCCTGGATGAACGCGGACTCAGAAAGC
GCTCAGCTCTAGAGTTTGTTTTTAACTCATAAGTAAAGCACAAAACTTTCAGAGGCGTGTTGTTGGGCGT
GTATTTTCCAGCGCCAAGTAGACAGGTAACTAAGATAGTGGGGTGGGGCAAGGAAAAAAATCCCAAAACT
CCAAGGAACATAAACAACTGAGATCAAGACCCTTGTTGAGAATGAGAGAGAGAGAGGGAGACTCTATACT
TTATTGCTTGGATCGGGGCAAAGATGTTCCATTTATTTAATGCACTGAATGCTTGTCCAACTATGTAAG
TGTGATATCCAGTCAAGCTGGTACTTGTAATGTTTTGAACCAGGAAGCATGCTTTAATATTAGGATGCTT
TCCAAAATAATAACAATACACATAAGTCTTGTTGACAGAAAGGATAGAAATATTTATATCCCATTGATTT
ATGATGAGAGTTGGAAAAAGAAGTATACCCTTCTCTTTCATCATGTGGTACTGGGAACAACAAGAGTGT
TGTAATCAGACACTCTTTAGAAGGAAACCTTGTACTGGAACCAGTAAAATGTCCCTTTTCATCCCGTGGC
CATTCACTGAGCATCTACTATGTGTCAGACTCAGTGTTAGCCTCAAAGTGGAAAATGGACAGAATTCTTG
TTCTCTTTTTTCAACCGGTTTCCACATCTATAAAACGTGGGTGATAATAGGTACCACATAAGGGTTGCTG
AAGACTTAATTCCTGAATAAAAGTACCATACCCATACATCGCTGCTGCTGCTGCTGCTTCTGCTGCT
GCTAAGTCGCTTCAGTCGTGTCCGACTCTGTGCGACCCCATAGAGGGAAGCCCACCAGGCTCCCCCATCC
CTGGGATTCTCCAGGCAAAGAACACTGGAGAAAATTTCCATTTTCCTTGAGATGTTTCTTCATGAATGCT
TCCTTGTACATTTTCTGGGTTTTTTTGAATGTAGCATCTTATTGATGTGCTAAGAGCAAAAGTTTACTTT
GAGTCATTATCGTCTTAAGCTCTGAACTACTGTTATTGATATTTGCAGATAATTCATATGGTGCATTTTG
ATAAGAACATGAATTATCTGCAAATATCAATAACAGTGGTTCAGAGCTAACATCACTTTTCTTCCAAATT
CATGATTCTTCAAAGGAAATTATGCCTGGATTATTGGGATGAAAATAGTTTAAAGGTATGTTTTTAACCC
TATTATGTTTAGGCACAGTCTGACATCTTTGCTGAAACCTCTCTTATAATTCAGTGTCAGAACTATTCTA
AATTTTCTTTTTCTGCTAGTAGGAACCTCCTAGAATCAGTAACCTGCCAGTGATGAAGCGCTAACTTTTC
CCCAACCAGAGCTGGTCAAATATAGTGTGAGCCACATATGTGATTTTAAATTTTCTAGTAATTACATTAG
```

FIG. 2A

```
CTGACAGAGGAAATTAAAACGACATATTTTAATTAGCCCACTATATTCCAAATGGTACTATTTCAACATG
GAATCAATGTGCAAATCATTGGGATATTGTAAATTTTCTTTTTCATTTTCTTCAAAATCTGGTGTGTATT
TTACACTTAGAGCACATCTCAGTTAACACGACATATTTCAAGTGCTTAATAGGCATGAGTGGCTAATGAC
TACTGTATTGGACAGTATAGCTCTAGACATTGGTTTCTAACCACTTTCCTTTGGTGGCTGTGAGGGGATG
ACCACAGCCATTTTGAGAATTAAATGAAAGTCGTGGACCACTTTCCCACAACAAAATGTACACACATACA
GAAGACCATCTATAATCCCTTAAAGACCCGTGGAGCCAATTTATATATGTGTATACACACATATATATGA
TTTATATTATATGCTATTAAATATAACATTTATGCAGTTTATTAATACAAAAATTTTATACAAAAACACG
ATATAATACATATCTGCATATATGTATATCATGCTTCAGTAAGTCCTATAATTAAAATGTCTTTACTGAG
ATCCTTTAATTACTGAAAAAGATTGTGAATGAGCTAACTTTAAAAATTTAGGCAGAATAAGGTAAAATAA
TTGAAGGGTGTATCTTTTGTTTTATTTTGTTTAAGGGATTGCCACCTATAAAGCCAATCAAAGAAACGCT
TCAGTATATATTTTCCCAGTGAATACCATCAGTATTATGAATCTGATCTTTTGAAGAACTATGTGGTTTT
AGTAAAAAAAAAAAAAAAAAAATTTACAAAGCTAGATTTGAAGGACATCTGATGACCTTCATAATGATG
AAGCATGACGGAGAGTAAATTTTGTTGGCTGACACCAGTAATCATATTCCTGAGTCATAAGTTGACTCTA
TTAGACCGTGTTAATTAAAGATGTTTCTTGGCCTAATTAGACCCATTGGTCCAACGGCAGAGTCATCTAG
GAGCAGTCATTTGGGAGGCCCCGCCATTGTGACCAGCCTGGGAAGAGTGTCACAAACCTTCCTGGCAGG
ACAGACCACTTGGCTGCAGCGACTTTTAAGAATAAGGAATGTAAATTATAGATTCTGCAAAAAGGGCACA
GCACCACCACCTTCTGCCTCGCCCCCAACCCGCCCCTCAACCCATCCCCCGCCTCTGTCTCTGAATTGGT
TTGCTTCCCATTGCAGATAAGACTTAAGAGTACACCTGATGATATTATTCTTTAATCCATTTTGATACTT
CCCAGAAATTTAATTGTATAAATACTTTTTAAAGAATGACGTAGCTTGCCGCTGGTGGTATAAATGGTGG
GTGGCCACTGGAGGTTCCAGGTGAACTAGTGGGTAATTAGTTCTGAGTAGACTGTCTCAATGGAGTATA
AAACCTCTAAGCAAACCATCTTTGTTTTGTTTTTTCCTTGAGGTTTTAAAAAAAATTTTATTGTGGTAAC
ATACAGCAAATGTGCCGTCTTTACCATTTATAGCTGTAAAGTTCAGTGGAAGTAAATATTCATAATTCTT
GTGCGACTATCACTACCATCTAGCTTCAGAACAATTTTTATCTTGCAGAACTGGGACTCTATACTCATTA
AACAATAAATTCTCATTCAATTTTCATATCTACATTTAAACGCATGGTACTATATTCCAGTATCTGTGTT
CCTTATCATTTTTATTGTATTATGAAAGCATTTAACCTGAAATGTACCCTTTTAACAAATTTTTAAGTAT
ACAGTGCATTATTGTTCACTGTAGGTACAATATTGTACAGCAGATCTCTGGAGCTTATTCATTTTCCTTG
ACCAAACTTTATGCCTGTTGATCAGTAACTCTGAATTCTCCTCTCCCTCAGTCCCTGCCAGCCATCAT
TCTACTTTCTGTCTCTATGATTTTGACTATCCTAGGCACCTCACATCAGTGGAGTTTTATAGTATATGCC
TTTTTGTGACTGGCTTATTTCACTGGACTTCCCCGGTGGCTCAGATGGTAAAGCGTCTGCCTACAATGTG
GGAGACCTGAGTTTGATCCCTGGGTTGGGAAGATCCCCTGGAGAAGGAAATGGCAACCCACTCCAGTATT
CTTGCCTGGAAAATCCCATGGACGAAGGACCCTCATAGGCTACAGTCCATGGGGTCACAAACAGTCGGAC
AGGACTGAGCGACTTCACTAATCCCCTCAAGATTCATCCATGTTAAAGCATATATCAAAATTTTCTTCCT
TTTAAGGCTGAAATACACACACACACACACACAGAGTATTGTGCTCATCCATACAACTACTGTGGAAA
ACAGTAAGGTGGTTCCTCAAAAAACGGCCATCCACGGAAGCAACCCAAGTATACTTGACGACGTCTCTCA
GGTCCTATAGGCTCTGTTTGTCGTTGCTGTACTAGTCACTCAGTCGTGTCTGACTCTTTGCAACCTCATG
GACTGTAGCCCGCCAGGCTCCTCTGTCCACTGGATTCTCCAGGCAAGAATCCTGGAGTGGGTTGCCATGT
CCTCCTCCAGGGGATCTTCAACCCAGGGATCAAACCTAGATCTCCTGCATTGCAGGCAGATTCTTTACCA
TCTGAGCCACTTGGGACACCCTGCGGGCTCTATTTACTTTAATCATTTTCCTTTCTGTTCCTCAGACTGT
ATAATTTCAGTTGTCCTATTTTTGATTGCAATGATTCTTTCTTCAGCCTCCTCAAGTCTGCCTTTGAATC
CCTCTAGTGATTTTTTTCATTTCAGTTATTATATGTCTCCACTCTATAATTTTTTTTGGTTTCTTTTTA
GATGATATATTTTTTATTGGTATTTCCATTTTGTTTATGCATTGGTTTCTTGACTGTCTCCACACTTGCT
TTAGTTCTTTGAGCATCTTTAAGGCAGTTGTTTTAAAGTTTTTATCTAGTGTATCTACTATCAGCTCTTA
GGGACAGTTTCTGTTTTTTATTTGTTTTTTGTTTTTCTCCTTGATTGGGCAATACATCTCTGTTTCTTTG
CATGCTTTGTGATTTCTTTTTTTTTTTTTTGGTTGAAAACTGGACATTTGAATCATTGAAAGTTTTGGA
AATCAAATTCTCTTCTTTCCCTAGGGTTTGCTGTTTTGTTTTTGGTAATGATGGGATCTTTTTGTGCCAA
GGTTCAGCCAAAAGTGTACACTGAAGAGCTTCTCAGGTCTTTTCTGATTCTGCACCTTTCCCTGGGCGTG
AGCAATCTGTGATCAGAATACAGATCTGCAGTATTTGGAGGGCAGAGTCCTTTGCATGCTCCAGGGCAC
ACTTGCATGAGCTGTGTGCGCACACTTGCTGTGAGTTGTGTGTGCTCAGTCACTCAGTCCTGTCTGACTC
TGTGACCCCATGGACTACAGCCTGCTCAGCTCCTCTGACAACTGGATTTTCCAGGCAAGAATACTGGAGT
GGGTTGTCATTTCCTCCTCCAGGAGATCTTCCCAACCCAGAGATCAAACCCACGTCTCCTGAGTCTTCTT
TACCCCTGAGCCACCTGAGCTGTGAATTGGGGACGAGGAATGGGCAGCTGCTGCTGAGCAGAGCTAAAAT
GGATGCAAATTAACCAAAACTTACCATTTAAATGTTCCCCTGGAAGTTGCAAGTCTTTGATAGACTCCAG
AACTTACAGTAGTTACATCAGACAGATTCTGCCAGGGAGAATTTGTTCCAGATCAGGGGATGGATTCCTG
```

FIG. 2B

```
GTACCTCTTACTTCATCTTCCCAGAATCTTCCCTTTAAACTGTTTTAAGGATTGAAATCCTGTTAATGTG
ATTCTAAACCTCTATTCTTCAAGTTGTCTCATTTTCTTTTCATAAAAAATGACCCAGAAAGCTTTGCAGC
TACCATAAAGAAAAAATATCCAGTGTCTTTCACTTAAGAGAAGTGTGAAATTACTTGATCCAATGAGTAC
CATCTATGTAAGTTGCTTCCTCAGATGGGAGCGTCATTTAACTCCAGAAAATAAAGGGTCTATGGTTAGT
TTTCCTAAAATTTATGGAATTCCTTCTGACTCTGGAGAACTTACAGAATATAAAAGTGCTTTGGTAAAGG
CCAAAGATGTTCACAGTTGCTTATAGCCCACCTACTATGTGTCATGTGTTGAACAGGGTGCCCTGGACAC
AAAAATTGTGCTGATGGTCCATTCCTGGTCTTCTCTTGCCTTTCTCATAGATAAAAATCACAAGCACAGC
CTAAAGACTAGTACAAAAGTAGCAGAGTAGCTATTGAATTCTCATGGCGTCGTCTTTGACTCAGAGGAA
ATTAAAAAAGCCTTACTACAGTGGAACCCCTAAGCTAAACAAGGCAGAAAGGCAATCAATGTTACTTCTG
AAAACTGGGCAAAAGAAGGTGCACCCTTACACTGCCACCTGGGCATATCCACCAGAATGTTAAAATGTT
AGAGAAAAGCAAAGGGAGTTCAGGGAAACATGAGGATTTCAGAATTATACATATGTTGCTGCTGCTGCTG
CTAAGTCGCTTCAGTCGTGTCCGACTCTGTGTGACCCCATAGATGGCAATCCACCAGGCTCCCCATCCC
TGGGATTCTCCAGGCAAGAACACTGGAGTGGGTTGCCATTTCCTTCTCCAATGCATGAAAGTGAAAAGTG
AAAGGGAAGTCGTTCAGTTGTGTCCGACTCTTTGCGACCCCATGGACTGCAGCCTACCAGGCTCCTCCAT
CCATAGGATTTTCCATGCAAGAGTACTGGAGTGGGGTGCCATTGCCTTCTCCATATACATATGCATTTAA
ACCTTAATTTGCGTCTTCTTTTTTATGAGAACCCCAAAGAAGCTTATCCTGTATTTCTATAGTTTAATAA
CAAATGTTTTCAGAGAAGCAGAAAGATACCATGCATCACACCTTTCATTTCCTTTCTTTAAATAATTATT
CCCCCTATAAAACCTAGCACACAGCAGCTGCTCACTGATTATTTTTTTAGTAAATGAATTCTTCCTCTCA
TACTAGCCTTCTCCATTATTTTGGGGTTTTCAGTATTAAAAGCAAGTAAAAATGGCTAGGATATTCCCTT
TGTGTGACTCTGTTGTTGTTCAACTGCTAAGTTGTATCCAACTCTTTTGCAGCCCCATGGATTGCAGCCT
GCCAGGCTCCTCTCTCCCTGGGATTTCCCAGGCAAGAATCCTGGAGTGGGTTGGCATTTCCTTCCCCAGG
GGAATCATCCCTTCCCAGGGATTGAACCCATGACTCCTGCATTGGCAGGTGGATTCTTTACTACTGAGTC
TCCAGGGAAACCCTTTGTGTAACTTTAGGGAGATACAAGCTCTCAAGAAGATTCAAAAAATTTTTAAACT
TTTTTTTTTAGCACAGAGGCAGAGAGAATAATATAACACCCTCCTCTTGTACCCATCACCTTCTATAATT
ATCAGCGTAACACTGTGCCTATCCTGCCTTATCTATCTTACTAGAAGCCCCACCAACACACACACACCCC
ACACCGTTGAAGTATTTTATAGCATGGGAATTGCACAATAAGTGCTATCCCTGTGACCAGCTTGGTGTTT
GTTGTGTGAAAAACTGAGTTCTCTGTTCCCTGTGTACTTTGTTTCCTCATCTGTACTATGGAAATGTGAG
ACTAACGTGACACAGTGTCGTGAGGTAGGCAAAGTACTAAACATAAACTTAGCAGATGACTCTCGCTCCT
TTGTACTTACGGCCAGTTAAAATCTAAATTCCCTGCTATATTATTTATAGCCTTAGAAAATGAAAGCTTA
AACCTCTGTTTCTTCTCATATTCATTTATTGTCTCATAATTCAGCATGCCAGTGAAAAAGAAGGGAGTG
AAGTGACCTTTATTGTGTTCTTAAAATGAACGAGCCAATGGACCAGACTCCTCATTAACAGTGGACTGGG
CTCCTCCTCACTTGTTTTGTACGTAAGCCAGCCCCTGGGGTAGGCATCATGACCTGCATTTTACAAGGAG
AAAACAGAAAGTTTAAATCATTGGCTCAAAGTCTCATAGCATTGCAGACCCACATTCTTCCTGTCTTATC
CGAGTTTGGGGAATGGAATGGAATGCAGGGAGCTGGTTGCCAGGTAACAGAAAAGGCCGGAAAGCCAACT
GGGGTGGATGAGGCAACACAGGGGTTAGAAATCTAGGAAGCTGCTACCATTCCTAGACTGGAGGGGAAGC
AGGATCACCTTGCAGAAGCTGAAACCACTGCTGGCCTGTCCTGCAGGAGGCTCCCATGGAGGCAGCCATC
ACACATTCCTACTACACCAACTGACCGGGGTCAGGGCAGGGAGTCCACCCTAGGGCAAGCAGGTCCACTT
CGGCCTGCACCAGGGAGCCTGTTTTAAAGCAAAACCAGCTTTCCATCTTGAGCCTTATGTTTGTTGGCTG
AACAGTCTTATTTTAGAAAGCAGAATACATGGAAAAATAAATTTTTAAGGGACTTTGCAGGAAATCCAGT
TTGCATATTGTCTGTTAATTTTTCAAGCTATTCTGTTTTTCAGCTTTAAAAAAGTCTTTTACCTAGTCT
ACTAACCTGAAAAGAGCAAAAGTACTTCCCAAGGAATGTTAGAGGTTTGTGGAAATGCAGTCATCAGTCA
AGAATTGTTTGTCGGACCGCTGCCACGGTACTAGGAAAAAAATTTAATCTACCATCTGGCTGAGCAGGC
AAAATACACATTTATGAAGTAATCAGTGAGCAGGAGCGTATATAATAAAGTGCTGATTGGTTTGCTTTAC
TAAGAAAATAGAGACTTACATGCAACATGAAGATCTGATGTGCCATTAGCAGGACAAGGCTCAGAACTAG
TCAGGAAATGCTGGGTTGAACACAGGGCACTGGGTTCCTGCCTTGAGCAGTTGGTTTACCCAGGAGGCCC
TGAGCTGCCCTGGCCTGTCTGACTTGGGGAAGCTCCCATGGGTGCTGACTCAGTGGGGTGATTGGAGGAG
TAGAAACCTCCACTTCCTGACATGGTGCCCACAGAGCTCCTCTCCAAGCAGTGGTTTCAGTCCTAGCCGG
GTGTTAGTTTCAGCTGGGGAAGTTCAGGGATGTACATCTGTCCCCAGCATCACCCTGGATAAACTAAATC
TGAATCCCCAGACTCTAGCTTAAGTGTTTCCAAAAGTGCTTGGGCACTTGTGACCTGCACTGAAAGACGA
GTTGTTGTTCGGTCACTAAGTCTTGTCTGACTCTTTTTGACACCATGGACTGCCACACACTAGGCTTCCC
ATCCTTTACCATCTCCCTGAGTTTGTTCAAGCTCATGTCCGTTGAGTCAGTGATGCCATCCAATCATCTC
ATCCTCTGTCGCCCACTTCTTCTCCTGCCCTAAGTCCTTCACAACATCAGGGTCTTTTCCAATGAGTTGG
CCAAAGTACTGGAGCTTCAGCTTTAGTATCAACCCTTCCAATGAATATTCAGGGTTGGTTTCCTCTAGGA
```

FIG. 2C

```
TTTACTGGTTGGAATCTCCTTGCAGTCCAAGGGACTCTCAAGAGTCTTCAACACCACAGTTCAAAGGCAT
CTATTCTGTGGTGCACAGCCTTCTTTCTGGTCCAACTCTTACATCTGTGCATGACTACTGGAAAACCGT
TGCATTGACTATACAGTCCTTTGTCAGAAAAGTAATGTCTTTGCTTTTTAATATGCTGTCTAATTTGGTC
ATAGCTTTTCTTTCAAGGAGCAAGTGTCTTTTAATTTCATGGCTGCAGTCACCATCTGCAGTGATTTTGG
AGCCCCCTAAAATAAAATCTGTCACTGTTACCATTTTTCCCCGTCTATTTGCCATGAAGTGATGGAACCG
GATGCCAAATTTTAGTTTTTTCGGATGTTGAATTTTAAGCCAACTTTCTCACTCTCCACATTCACCTTCA
TCAAAAGACTCTTTAGTTTCTCTTTGCTTTCTGCCATTAGTGGTGTCATCCGCATATCTGAGGTTATTGG
TATTTCTCCCGACAATCTTGATTTCAGCTTGTGATTCATCCAGCCTGGTATTTCACATGATGTACTCTGC
ATATAAGTTAAATAAGCAGGGTGACAATACATAGCCTTGACATACTCCTTTCCCAATTTTGAACCAGTCC
ATTGTTCCATGTCCAGTTTTAACCATTGCTTCTTGACCTGCATACATGTTTCTCGGAGGTCAGGTAAGAT
GGTCTGGTATTCCCATCTCTTTGATATGCTGTCTAGGTTTGTCATAGCTTTTCTTCCATGGAGCAACCTA
CAGCTAAATGAAGGCTTTTTGATCCTTAGGGAGCACCCCTACCCCACCCTCCCCAGCAAGCCTTTGTCTC
TGTGTGCAGCAGTGGTGCAGGGAGGGAGCTAAGCGGTGTGCACCAGGCTCCAGAGGGCCCTGGGATTACG
TATCATTACTTCTTGATTTTGCCATAGCTGTCTCTGGACATGCAAACATTGATCTCCGTCAGCATTCCCC
AAATTGCAGAAGGAAGATCTTCCAGCTGTTTTCACATAATCTTTATTATTTTCTTAAACAGCTTTATTTG
GATATAATTCATAATTTACCTTTAAAATACACAATTCAGTATTTTAATATTTTAATATTTTATTATTGA
AAGTGAAAGTGAAAGTTGCTCAGTCATGTCCGACTCTTTTCAACCCCATGGGCTATACAGTCCATGGAAT
TCTCCAGGCCAAAATACTGGAGTGCGTAGCCTTTCTCTTCTCCAGGGGATCTTCCCCACCCAGGGATTGA
ACCTAGGTCTCCTGCATGTTGGCGGATTCTTTACCAGCTGAGCCACAAGGGAAGCCCCATTTTATTATTA
ACTCAGTATTATTATTTTATTAGTACTGAGTACAGAGTTGTCCAAGCATCACTTTAAGATCATTTTACAA
TGTTTTTGTCACCCTTAAATGAAACTCAGTACCTTTTTGGGGGGGGTTTAAATCTAACAGAGGCATTTCA
GAAGCACACTAGTTTTTGATGCTCTTTCACAGCTGAGCTTAGGCTTGCAGAAGCTCAATTTTTGTCTGTC
TTCCTTCTCTTCTTATATGTGTAGAAGTTCGAGCTTCAGCTCATCCTGTGACACATACCCTTGTCTCTGA
GTGTGTCAGGGTGTATCTGGGTTGCCCTGGGGAGGCGACCCCAAATGCTGCAGAGCCAAAGCCTGGCGCT
GGCATACGTCCTTAGCTGGGTGGGAGCACAGTGCCAAGCTTCATGGCTCCTTGCTCCTGTTGATTTCCTG
AGACGTTTGTGAGATTGCTAGGGCAGAAAATTGTATGCATATTAATGCTGTCTTCTAGAATGAGGACAAA
GGACAGCTATGCTTACCAAATATATAGCAATGCCAGGAGGTGGAAACAGGTTGGAAAATTCTTTTTGAAG
CAAGACCAAAAAACCCTTTATCTGATATTTTCTCTGCCTCTAAACTCCTGTCACTCTTGTTCTTTCACGT
GTTTTCATCTTAGCTCCTGGCTTCCGGGGCCGTATCCTCTGAGTGAAATGTCTCCTACTTTAGGACCAGC
ATCCTGCACTTCCTGTCTTTGCTCCCGTCCAGCTCCTAAAACATCCTAAAACAGGATGACACTTTGGTAT
TGTGTGTCTGATTAATTTCACACACACAAAAAAGAACAGTTTTAGAATAGGAAGGTTTTATCTGGGTT
TTGTTGATTTTTTTTTTTGAGTTGTTTTCCTTTTAGAGCATTGGATTGAGACTTTCTTGACGGGCATC
AAAAGTTTTCAGCTAGCTTAACCAGCCCAGTCTCTGGCTTCCAGACTATAACCCACACATGTAGCTGACA
TGTAGTGTGACTGAGGAGGATCTTACGTTTCACATTCTATTTCTTTATCAATAAAATGAGCTGCCAGTTG
TGTCTCTTTTTTTACTGCTATGGCAGTCAAGGAGACCACAGAGAGGAAATGCCCAGTGCTGGGCTCACAAA
GGAGATGCTTAGAACATGTTAGTTTCTTTCCACTCTTACAGAAAAGTCCTTCCTGGATATTTCAGGTTTG
TGGTTCAGTCCCTTTTCCATGTTTCTCTCAGCTCATCCTGACCCACCAACTACATGTAGTGATAGTAGAC
GAAGGTTTCTTTCTTCACTCTTTGAGATACTTGCTGCAGCTTCCTAAGCTGGATCAAATCTGAAATGTAT
AATTTTCAAACATTTATTTCATCAGCAGAATGGAAAGTATGTGGAAAGTACACAGTTATTCCATGAATGT
AGAAATCAGGCACTTTGAATCTCTCTCAATGAAAAGATATAACTGATTTTGTATCATTAATAAGCTACTG
AATGGGGTTCCCTGGTGACTCAGATCGTAAAGAATCCGCCTGCAGTGTGGGAGACCTGGGTTCGATCCCT
GGGTTGGCAAGATCCCCTGAAGGAGGGCATGGCAACCCACTCCAGTATTCTTGCCTGGAGAATTCCATGG
ACAGAGGAGCCTGGCGGGTTACAGTCCATCGGATTGCAAAGAGCTGGACACGACTTAGCGACTAAGCACA
GCACAGCACCAGCTACTGAATATGAATAAGCGCCATTTCTTGGTCAGGGCAATGATTCACTTATAAAGTT
TCCATTTACTGGAAATTGAATGGCATTAGGTAATTCTTATTAATTCTATTAGAGTTTTGTTAGAGTGAGG
ATGTATTGTAATTATAGAGGGAAAAGTCCTCAGTTTAAGGACATGCTTGATAAAATGTTTAGGGGTAAAG
TCTCAGGATATCTTCAATTTACTTTCAAATGCTGGTACATATGCAAATATATGTAGATCATGTGTCTGTC
CATAATATATGATGAGATGTCAGTATATGGCAACAATAGTTAATAGTTGTTGACTCTCAGTGATGGGACT
ATGGATATTTTCTTTCAACTTTTCTGTATGTTAGAAAATTTTTATAATAAAAGCCAGGTTAAAAAAAC
TAGAAAAAATATAATCCTGATAGTTACTAAAAAATGTCATTTCACTATGTGATTTTTATTTATATTATTA
TACTTACTCTATTGAGAGCAAATCTTTCTTTGAAGTTAAAAAATGACAATTCTTATAGTACATAATTTTT
ATAATTTGTCATTACAATTCAACATTTTAAAAGCATTTTCTTTTTTAAAACCTCATTTCGTAAAACATA
TATTTATAATAGACATTTTAAGCAAAAAAGCATTTGTTATATATTTATATATATCCCTCTCAAACTATT
```

FIG. 2D

```
ATTTGGAAACTATGTAATTGTGAGAGATTTTGAGCATTTCAGTGGAAGCAAGTAACTGATGATGTTGGTT
AATCTGGAGGACTGCAATTTTGAAATACCAGGGAATCAACTTTATAAACGTTTTATAGTAAGATATCTAT
CTACCTTTATTTTAAAGAGAAAAGGCTGTCTGCATGTTTCCTGTAGGGTAGATCGTAATGTATGTTTCCC
ACCTGAGCAAGAACCGAAATGGGACCTTGCGGAGAGCATGGAGCCTTGCCCAAGACAAGAGCGAGTTGTG
TGTCTGTATTCTCATTTCTAAAATGGAACTTCACACGTGGTGCTAGTGCAAAGCATCCGCCTGCCAATGC
AGAAGACTCAGGAGATGCGGGTTCAGTCCCTGGGTTGGGAAGATCCCCTGGAGGAGGAAATGGCAACCCA
CTCCAGTATTCTTGCCTGAAGAATCCCATGGAGAGAGGAGCCTGGTGGGCTACAGACCTCGGGGTCACAA
AGAGTCGGACGCGACTGAGCGAGTAAGCACATTTCTAAAATGGAGTAATCATACTTCCTAAAAGTAAATG
AGGCTGTATGTTCAGTGTGTATGCTCAAACAGTGGGTATTGTTGTGACTAGATATTACCTATATCTAACC
TGAAAAATATATAGAATTGGTGATAAAAATGAATTTGATATCATGGTTCTAAATTTACCAGTTCTGAAAG
GAGACAAATTGAATAAATTTGTGTCATGTAGACCCATCCCTCTCAAATTCTCTCTCCAAACACTGAATAA
TTCTTCTCTTTTGCTCACCTATTATTCTTAAAGCTTATCAATGGCCATCTAGCTCTGACATATATATGTG
GGCTTTTAAATGGCTCTTGTTTTTTCAAGATTCATTAATTACTCAATAGCTATTGCTCTCAACTGTGGAC
AAACTCTTTTTTTTTTAAACACACACCACATCTTCTTTATTCATCATCTGTTGATGGATACAGGTTGCTT
CCATGTCTTGACAATTGTAAATAATGTTGTAAATGTAAACATGAACATTTTTGTCGTTGCTAGGTTGTGT
CCACCTCTTTTGTGACCCTATGGAATATAGCCCGCTATACTCCTCTGTCTGTGCTTCCCTTGTAGCTCAG
TTGGTAAAGAATCTTCCTGCAATGCAGGAGATCTGAGTTCAAGTCCTGGGTCGGGAAGATCCCCTGGAGA
AGGAAATGGCAACCTGCTCCAGTATTGCCTGGAAAATCCCATG (SEQ ID NO: 1)
```

FIG. 2E

GTCTACTATCACTACATGTAGTTGGTGGGTCAGGATGAGCTGAGAGAAACATGGAAAAGGGACTGAACCACAAAC
CTGAAATATCCAGGAAGGACTTTTCTGTAAGAGTGGAAAGAAACTAACATGTTCTAAGCATCTCCTTTGTGAGCC
CAGCACTGGGCATTTCCTCTCTGTGGTCTCCTCGACTGCCATAGCAGTAAAAAAGTGTCCCACCCAGCAGTTCAT
GATAGGGATAACGTTTCCTTCTCCAGGGGGTGGGCAAACTCTTGACTAGGTCATCTGGGTGAAACAAGCCCTGTA
GAGAGCTTCATTAACCAAGCTACTGCAATCTGCCTGCTTTTCTGTGGGCAGAAATTCATGAGAGGTTTCTGTTTG
GGGGAAAGTTTTCCATTTGTGAAAGTGATTTATTTCTAGTTTTTATACAAAGAACTACTGCACATGTCTAATATT
GCTTAGCCTTTTTATTTTACAAAAATATCTGTTGATATGATTTAAAGAAATATTATCTTGTTTTATTTATCATAG
TATGTGTGATATAGTTGGTAAGTCATGTCCAACTCTTTTGATCCCACAGAGTATAGCCTGTCAGGCTCCTCTGTC
CACTGGATTTCCCAAGCAAGGATACTGGAGTGGGTTGCAATTTCTTTCTCCAGGGAATCTTTCCAACCCAGGGAT
CAAACCCAGGTCTCCTACATTGCAGGCAGATTCTTTACCGACTGAGCCATCAGGGAAGCTCTTATCATAGTATAG
AGACAATAGATTTGCTGTCAGAAAACCAGCTTTGCAAGCTTTTCTCATTTACTGGGTGTATCTTTTTGTGAAAAG
CGCATCACATGACTTTTATTCTTAATTTTTTTTAATCCATGAACTCAGGTGAGCATCTTTTTTTGTATCAGATAA
AAATATATATGAAAGTTCCTGTAAGTAATAAAAAATGATAAACATTATTATTACTATTATTACTGTTATTGCCAT
TCTTTTTAATTTGAATAACTTGAGTGACATGCATATCCAGGTTTTGATTCCACTTTAGGGAACATGATGGGGTTT
TATGTTTCAATGTAACTAAAGATGATTGGGCTAAGACCCAATAGTGAGCTTTTCATTTTCTTATATTTAGGTTCC
TTTTCCCACTTTCTTGCATATCCCACTTGTATAAGAAATAATTCTTTATCCCTAATTTTCAGGAACATAAAATAT
TTTCATTTCTCAAAAAAATTCAAGAATGAGAACTTCCCTGATGGTCCAGTGGTTGGGAGTCTGCCTTTCAGTGCA
GGGGGTGAGGGTTTGATCCCTGATGGGGGAAATAAGATCCCACATACTGTGGGCGACTAAGCACCACCCCAGCA
ACTAGAGAGGCCACACACCTCACCTGAGACCCAATGCCACCAAAAATAAATAAAATAAATATTTTTAAAAGTACA
ATAATGTTCATGGCTTCTTTTATCTTATCAAACCAAATAGCGTGTAAACTACTTGACGCTTTTATATACCACATA
AAAATACTTCCTTGCCAACGCAGGAGATGTCAGAGAAGCATGCGAATTGGCTCCCTGGGTTGGGAAGATCCCCTG
GAGGAGGGCATGGCAATCCCCTCCAGTGTTCTTGCCTGGAGAATCCCATGGACAGAGGAGCCTTCCTGGCTGCAG
TCCATAGGGTCGCAAAGAGTCAGACATGACTGAAGCAGCCCACCATGCATGCAAAAATACTCCCATTCATCACCA
GTGTTCTTGTGAGAAAAATAATTCTGATTTAGGACATAATGAAATCCTAAAGCCATAAATAATGAACGTTGGAGG
TATGGGGTTCCCAATGCACGCTTTATCTTTCTGTTTTGGTAAGTAGACAGAACTCCAGAGAATTTCCTCCCTTGA
GTTTATGCTGAACTGAGGCTTAAGTAATGGCTTCAGCTCAACATGGTCCTCAGACATCTCATCTCCATGAGGAAC
CAAATGTCGCCTATGCTGGCAATTTGGGCTTTGAAATTCCAGGAGGCATTTTGTAGGAGACGAGATGCCGCCTTG
GCACCACCATCAGATCTATGTCTGGTTAATTACAGACTTACTTTCTGCATCCCAAATAAATGTCTATAGCTTCCC
TTTATTTTTGAAGGCCACCTATGTCAATGGAGAATTATTAACAGTTCTCAGGAGGAAGATTAAAGGTGTCCTTGT
TTTTACAGTCTGTGTATTTAGCCCTTTGGGATTAAAGTCACTATTATATAATCTTGTATCACCTCCCTCTATTAA
ATGTTATCTCTTTTAATATTTTTAC|AG|CATGTCAGTAGAAAAACCAGTGGATCGCCTTCCAAGTCAGGAGAAAG
AAAGGATCAGATGAC|GT|AATTTCTACAATACTGAATTTTCATTTTCTCCTGTTTTTAAATTGTGAATTCTATCAT
GAAATAAATAATGAGGTAGCAAATATCTCCTACTAAAATGTTGGCAAATTTAGTTTTAACTAAGAGCTGCTTCAA
TGCTGTAAGTGGAAATCATTAAAATAAATAAAGTGTTCCTCAGAGAGGAACTATTTCCTCCAGAAATAGTTTTCA
TTTAGGAGAACTCAGTTATTTAGGGTGTTGTCTCTATAGGAATTGGTGAATCTTAACTGTTTTTTCTGTTTTTTT
TTTTTTTTTTTAACAAAAACATACAGAAGGGAAACCAAATGCTACTGTTGAAAAGGAAATCTTTTTTTATGAGAG
TCATTGTGAAAGGAGAACAGTGATAACCTAGACTAAACCAGTCATTCAGGTTCACAAACAAAAGGGAGAGAAAAA
GACTATTTTTATTTGGTTCCATCCTGTGGAAATACTAGTGGAAGCAAGCCTCACTTTCAGATGGGTTGTCTTTGA
GTCCGTGAATTTCTCCTTTCACTGAACGATACCCCATTATGTTCACTATCAGCATCGTCTGGTCTCCATGAATGG
GTCGTGTGAAAGTGCTAGCCTCTGAGAGGGTCCTAGGCTTGCTTCCTTTTGCTGCTTTTTACATTTTAAATCTCA
ATGGAATATTCATCTTCATTCAGTAGAAATAATTATCATCATTCATCCCAGTTTGTAAAAGAGCCAGGTCCTGAA
AGGTACCTGGAAATTTAAAAAGCATAGAGTAACCATTTTGGTTTTTCTCTCTTATTAACATGCTTCCAGAAATCT
AGCTTCTCTTTCTGCTTATTTTCTGCAGTTTTGAAATAGTCCATATATTTCTGTATATTCAGTATGAACGGAGCC
ATTATGACTAGATCTTGCTATGAATTCTGCACGAAGGTTTAGTCCTCAGCTGTCTACTATTGTTTCCATTACCAA
CACCCAAGTCAATATAATTTAGATTATTTCTTACCATGCAAATCTGCAGTGAATATTTTGTTTCCATGGAAGAA
AATTTTCTTTACAAAGTAAAAATAAACTTTTATTAAGGTTTTATCCTGGCTCTTAGTTAAATTATTTAAACTTTT
TTTCCATGAGAACAAGCCAACTTTTACTAGCATGAAGATCTATGTACCTAATATCACTCAGTTCCCCTATCAATC
CTTCTCTTTAAATATCTTCCCAGATAAGTTATCTACCAAATAGGTTTCCTGTTGAATAAAGAGACAACTATAGTG
TCTCTTTATTGTCCAGATCAGGAAATAATGTTTTAGATGTTATTCTTTATGTTAATATTAATCAAGTTGAAAAC
ATTTGCACAAGAAAGGAAATCTTCCAGTTCAATCAAGTGGATAGTGACCTAATTCTAAGAATCCTAGATCTTAGA
GGATTATTCTCAACAATTACGTTTTTATGTGGAAGCTTAAATGTTATGTCTTGAATGTACAGATATCATTGGTTA
AGGCAGCAGCTGCTCCCCCAGTGTTAGATCTCTTTTAATATCTGGACTATAAAATGCCTCATTTTCATTTTTATA
AAGGGCTTGGGAAAATTGATAAGGAGTCCTGTTATCAGTACAATCAGAGGAGAATTCAAGACTTCTGTGTCTGTG
TGATGACTGTGCTTGCAGTTCTTTGAAAGTGAAAGGCTGAGCTTCCATCTCAGGAGAAGAAAGAAAGAATTTTTC
TTTTCTTTATCAGCAGTTGAAGCAAGTCTGACTTTGTTTCATAACACGTCTGGGAAATTCAGATTCACAGCTCTT
GCGTTTGTGCCAGAACCTGGTCATCTGGGTCTG

FIG. 3A

```
TTCTGCTCCACCCCAGCTGGCTGACAGAGAGGAGAGCCAGGCTTCGCCCTGCTCCCGTGACATAAATCACTGCAG
AGGTTCAGATAGCCTGAGACTGAAGACTGCTTATTATCTCGCCAAATTCTGCCCGTATCTATTTGATAGGGTGGA
CGGATGTGTAAGTTGAATCATCTAGTGGTCTAGTTATATTTCTAATGTAGTCTGTCTCCAAGGAGTCTCTCATTC
CGTATGTCATGGATGACATATTATGGCCCTGGAGACAÀTTCAAGGAAATCATCCGTTTGGCATTATTTTTACTCT
ATGTTCGTGATTATAAAACCACGTGCAGTCTGGACTTGTCATCTGCCCTGCCTACCATCTACAACCAGTTACTAT
CGTCTTCAGATTACTAGGGAAAGATTTCCTAAAACTGATTCTTTCGCACAAATGCTTTCTTATCTGCTGTTCTGT
TGAACAAGAAGTAAGATTAAGAAGCTTATTGGGGGGGTTTGGTTATCCATTTTCAAACTAGCATCTACCTCCAAA
GAGTAAACAGCTTGTTGTCCCCAAGCATATGCAAACATACTGGTTAAGCTTCCAAGGACTAAGCCAGGCCTTTGA
AATAAAGTCAGTTTGAAAATGTGCTTTCTCTGCTCAGGGATACTTCTCCAGTGCCTTTCATTTGGAGGTGCAAGA
AAAAGGGTACAGAGAAGGGCTTCGGGAAGATTTAACCAGGATTGAAAATGATTAGGATCAGACAAGAACCATTAT
GATATTGTCATAGGCAAAACTACCTGGGGATGAATGCAGCTGTGTGAATTTCAGAGTTCTTTCTCTTCTGCTGCC
ATAAATGGTTTTTATTTATCTTGAATATTACTCCTATACACCCACTAAGTGATCCTAGGATGTCTGCAGTTATTT
TAATAGACTATTGCAACTAAAATATCATTTGTCATGTTGCATTTGCAGTATAAATGCTTGAGGATGGAGTTGAGT
AAGTTTCTTTGAAAATGTATGTTTTGTTTTTTGTGACAATTGTTAAGAACTTAAGTTCTTCTCAGGTGTAGAGGA
ACTGTAAGACCAAAAGTTGAATGGACTAAAAAAACCAAAGATAAAATGACTACAGAGTAGGAAAGAGAAAAATGA
AAACATTTAGCAGCACCTTTAAATACAGTGGAACAAAGTTGTCTTTCCAAACCTGCAATCACATCTATTTAAAGT
GTTTGACTGACACATCTGACCACCCTGGGGGAGTGTGAGCATCTTAGCAGCATATTTCCGTGACGTCCTGAGAAA
TAGAATTTAAGACATGGGATGCACACGATCTCACAGAGCCTGTTTTAAGGACTTCAGATTTAATGATGGATATAT
TTTTATAGGTAAAGAAAGGGAGATGTATAGAGTCTAAACTGCTCCTTGAAGGTATTTGATAAATTCTCTGTACCA
TAACAGCTTTCGTGGTATTCTTCCCTCAGTGTGTTTACCTCTCCTGCTTCTAAAGTCCATGAATTACTCCAACAT
TTTAAAATTTCTTTCTAACATATTTTTTCTCTTGATGAGATTAGTCTTTTTTAATTGCAAAAGTAATATGTACTT
GTGAAAAGCAAAAGTATTTACCCTGTCTTACCACTTAAGTTATCACTGCTGCTACAAAATTTTGTGTGTACTCTC
AAATCATTGTGATGATATTATATGTTCATAGTTATTATATATACTGATTTTTGTAGCTTTTAAATAATGATGCAG
CTCTTACATATCATTATAGAAACGTATTTCAATATGTTTCTTCTAAAGAAAATTTAGAAGGTATCAACAATTTTA
AAGAAATAAACACTGTCATCTAGAATTCCAGCCCTACAGAAATGGCCACTATTTCTATCTTTGAGTATTTTCCTT
CATCTTTTTTTCTATGTGTGTTCATGTTAGTCACTTAGTCTTGTCCTACTCTTTGCGATCCCATGGACCACAGTCC
ACCAGGCTCCTCTGTCTATGGAATTCTCCAGGCAGGAATACCGGGATGGGTAACCATTCCCTTCTCCAGAGGATC
TTCCCGACCCAGGGATCTAACCTGGGTGTCTTGCATTGCAGGCAGATTTTTTACCATCTGAGGCACCAGGGAAGC
CATATTTTATGTTTAAGCTGAGATAACAAAGGAACATTACTAGACTAAAAGGGCCTAGACTAAAGATGATAAACA
ATGTGCTTTGTGATAGATAAATATTTTCCAATTGAGAGAAGTCATCATTGTGTGTGGCTTTTAAATACATGGGGT
TTTCCAGGTGGCGCTAGTGGTAAGAATCTACCTGCCAAAGCAGGAGATGTAAAAGATGCTGGTCCCACCGAGTTG
GGAAGATCCCCTGGAGAAGGGAATGGCAACCCACTTCAGTGTTCTTGCCTGGAGAATTCCACAGACATGGAGCCC
ACCAGAGGAGCCTGGTGGGCTACAACCCATGAGGTCGCAAAGAGTCGGACATGACCGAGCGACTAACACTTCCAC
TTTTAAATACATAGAAATCGTATTTAAGTACCTTGGCATTTCACATAATATTTAATCTGGTTATTATTTTGTGC
TGTGTGTTTGAGAGAGGAAAACAAGTTTCTTGTTAACAAGTTTTCTGGGACAGTGTTCCGGCCAACAAGTGATAA
AGCCGTCCTTAGCAAATTCTGGAAAAGTGCCACAGCAAATGTTATTTTAAGGGGTGTTAAGTCATTACAATCTCT
TGTCCACTTTAATTGTGGGGACTTGATTGTGCTGGACAAGTTCATGTCCCAGTGCCAAGAAGGAGGCAACTCTGA
AAACGTGCCCCAAGGGCAGTCCCGTCTGTCTTACCTGGAGATCCAGAACTCTGCTGGGTGTCCGATTTGAAAGG
CTAAACTCACTAAAGGAAGTTCCAAAATCCTTTTCAATTGCAGTTTCCAATTTTTTTTTTAATTCTAAATTTTT
ATTATTTTCCAATTAACTAAAATATTTTAAGATAATTTATTTTTCAATGAAGGCATATGGATGGTGATTTTCTG
CATCTGTGTGGATCTAAGCATGCTTTTCTGCTGGCCTCACACAAGGTGCTACTACAAAATTGTACGTTTTGGGGT
AACAGTTCTGTTCCCTTAAAATATTCTACCTGTTTCTCCATAGTTTTCTGACTTTTTGTGCTATAGAAAAGATGT
CTGAGGGAGCCTAATTGTTATTTATTTTTAGAGAACTTGTTTTTCCTGCTTTGGTGTATTTGTGATTTCTTTTTC
TTTTATTCTTACAATTTTAAAAATTGCCAGGATGTGCCTACATGTGTGTTTTTCTATTAATTTTTTCCTAGAGTG
TCTATTATGTAGTTATCGGTCTTATTTCAGTTTCTTTTTAAACATACATATAGTTCTGAGATCAGACATTCATTA
GGCACCTGCCTCAGTTTTCTCTTTGACCTTCACCTTTGTATTCTGCTAGAGTTTCTGAACTTTATCCCCCATATT
TTTATTTCTGTCATTTAAATTCTGCTCCTTGAAACTTCCAATACAGGTTTAAATTTTGCCTTTTCCCCTGTTGCA
TTGTACCCCTCTCTAATCCAGTCTTCCTGCCCTCTCTCTGTTTCACTCTGTTATTTTCCCATCTCCATCTTCT
CTGTGTCTGTGGCTCTCTACCTGGCTTTCACGGGGGCAATGCCATCTCGTTTCCTATTAAGGATGCAGACAGTCT
TCTGAAATTTTCTTCTTGTAGTGTATCATTTTATGAGATTTACTGTCTCAGTCTTCAGGAAAACGGCATCTTTCT
TGACTGTTTTCCTTCTTCTCACTTATCTGATTAAATGTCTTTTTTGGAACTCAGGCAAGGCCTAGGAGGCCAAA
GTTTTTCTGCAAACCAGAGGCAGTGGAGGATGTGGTGAGTGGGTGGGAGGTGGCCTTTCCCGGGAAGCCTCCACA
GGGTCCTGCTCAGTTACTGTCAGGGTGGAGATTTACCTCAGTTTTGGCAATTCCCTGACTTCCTTTGTTGTTGA
GTCAAATTCCAGCCTCTTCTGTGAGAAGATGATTAGAAAACTGCTGTCGAGATTATTTTGTAGTAGCCATTCCCG
GAGTGGTCTCCTAATGACTCTCTTTCACGTCTTGAATCCAGTCTCCCCTTTTCTAGCCTCCTTCGGGTATAACCT
GTGAAGTAGGCCTTCACTGCGGACTCTGTTCTG
```

FIG. 3B

```
TTTATTAACTGTGTGTAGCTCCTCATGAGTTTCACCAGAAGGGCTTGAGGTGTAGGGCTTCGGGAGCATTCCATG
TCGCCTCTTTTCTGGAATTTCTCTGACTGGTTTCCGGTGCGTGGGCCTCGTTCTGTGCGTGTGTCGTCATGACGT
GCTTTAGGTACTGCTTGCGTCTCAGCGCCTGATACTTGTGTACGCACGTAATAGAGTTTGTATTTTCTTATGTGG
AGCCTGCCATATGGGTCTTCGCCAGCCATCTATGGATTTAAGGTCAAAACCTATGGTTAGAATACCAGCCATTAT
GTAGCCATTCAAACAGCCTGTTTATCGGAAGACATGTTTTCAGGTTGAATTCTGAGAAAAACACAGGGAGTTTCT
CAAATTCAGGACAAAAATTCTTTGCCGTCTTGAGACCACTGTAAGAGCATCTTCTTTCTCATGTGCCGTGGGAGC
GCTGAAAAGCTCCCCAGTTAGCCCGCCCCCAGTCCACAGTGCCTAAAGAGGCAGCACGCTGTAGTTGCTGAGAGC
AGGCCCTGGAGTCCCAGTGTGTGGACTTGTCCCCAGCTCTGCAACCTCCTAGCTGGGTGTTCTTAGGCAGATTCC
TTTGCCTCCCTAAGGGTACCTTTCTCATGTGTCCATGGAGACAGCGATAGGTTCTACATGAGTTAATGTGAAGAT
CAATGAGACCAAGCAAATGAAGTGTCTAGAACAGTGCCTGGGACATGCGACGGTGTTAGCTGCTATCATGGTTAT
TATTATTACTACTGTTATTACTTTTACTAGCCAATGAGGAGAACTTGTTTGGCAATAAAGGTAAGCCCCTTATAG
CTTTAGAGCCAGGACTCAAATTCTTTTGTTGACTATATATTGCCAAGCCTTTCCCATTAAAAAAGGAAGGAAGTT
TGGTAGTTCATTAAGCTTAGTAGTCTTTCTTTGTTTCAAAACAACTCTGTTAACACCCAAAAATATATGCCAGTT
GCTAGAAAATACAGTCCCTCTGTAACCAAGAACATGAAAATAATTTGCTGTTAAATTAAGAATCTGTGATATACA
AAATGTTATCTAAGTAGTAGTGAGTGACTAATAAAAATAGTTATTATTGCACTTCAGAGTAATGAGCCTAACTGC
GTAAGATCTTAGGTCCTACCAAAATTGTCTCTGAAGACTATACCTTATAGCATAGGGAATTAGAATAAAAGTTAA
AAAAAAATCAAAGGAATTGAATAGAAGTTACATTTCTTGGCTTTAGAATAGATCTTAAGTCCTGGAAACCCGAG
GGACAAATCAATTAAATATTAATCCTGAAATACACTGTTTTAACATTTATATTTTTTTCAGTCTTCTCTCTAGAC
TTTATTAGCTTCTAAAAGATAATGGAATGACTGATTCAGAAGGGAGGATGACCTAAAATTGTGCCCACAGCAAGA
AACCTTTATCATTTAAGGACTGAATATGTATGATTCTTGTCATAAAGTCAGTAATATTTTATCATATACCAATGT
ACATAATAACTTGTTAAGACCTTCCAAAAACAGTTCACTTGTGAAGTCAAAATCTCTTAGCAAGTTGACATCATA
AATTAGTCTTTTATATTTCAATCCACATTATTACAGAACCCTTAGTAAATGTATAGAGCGCTGTTCATTTCAGTT
CAGTTCAGTTGCTCAGTCGTGTCCAACTCTTTGTGACCCCATGGACTGCAGCACGCCAGGCCTCCCTGTCCATCA
CCAACTCCCAGAGTTTACCCAAACTCATGTCCATTGAGTCAGTGATGCCATCCAACCAGCTCATCCTCTGTCATC
CCCTTCTCCTCCCACCTTCAATCTTTCCCAGCATCAGGGCCTTTTCAAATGAGTCAGCTCTTCACATCAGGTGGC
CAAAGTATTGGAGTTTCAGCTTCAGCATCAGTCGTTCCAATGAACACTCAGGACTGATTTCCTTTAGGATGGACT
GGTTGGATCTCCTTGCAGCCTAAGGGACCCTCAAGAGTCTTCTCCAACACCGCAGTTCAAAAGCATCAATTTGTT
AGTATCATAAAAATTTATTTTAAACTTTGTTCCTCATCTCCTAGGACATTACATGAGATTATGCAATATTTCTCA
AGTTTAAGCATGCCTATGAATCACCTGGACATAGTATGAAAAATTCAGACTCCTGGGCCCAGATCAGGGTGAGAT
CAGGCTTTCGGTATTTTTCCCAGTCACTCAGGTGACTCTTCTGACGGTGGTCTTCTGAGCACTTTTCGAGTAACA
CAGATAATTCTTACAGATCTCATAATGCAGTTCCTGGAAAATATGAGCTTTTCTTCCTTTTTTCCTTTCTCATT
TCCTTTTCTTTTTGAAATGCCTGCCCACCCCACCCCATCCCTCAGCCGTCTCCTGTCTCCATGTCCTGGGGACAG
CGTGGCTCTGAAGCACATTGAGGGCACTGTGGTTTCAAGGAGTCATTGGACCAGATGGGGAGGCTTTGGTTGCAA
GGGAGAAATGCAGAAATGCAAACCCTATTTCTTCCTACTTCTCCTAGGACCTCGTTCCTTAACTCTTCCCTCATT
CCTTTTGTTATTGTTGTTTTTGAGTCACTAAGTCGCATCCCATTCTTTTTTTTTTCTTTTTACTCCTTATTTAAT
GACTCCTCTTTAGACGACATTTTAGTTTAGTCTTCCTCATCATGAACTATTTTAAAATATTTCGTTTGAAGCTGC
TCAAGCTTCCATTCCATCTTCCTTTTTAACCCTCACTGCCAAAATTCTTGGTTGAAATTATTGAAGAAGCGAGTA
GGGAGAAAGAAGAGAGAAACCAAAAGCAAATGTTAATAAATGGCTGCCTGAAGTAGGTAGGAAGGAGACACCAGT
GAACGAGTCAAAGAAGCAGAAACAAAAGGGGTGGGGGAGCCTGGATGTTGCCGGGTCATGGGTCGGAAGGCTGGA
AGGAGCACCTAGGCTGAGGATAGACCCGGGACTGGGAGCTGAGGGAGCTTTCTTGTTTGGAGACTGGGATATCGT
CGGTTCACTTGAGAGCTGTTTCTGTTACGAGCCAGAGGCTGCTGAGTCAGTGGAGATTCGGCACCGATGACTCTT
TTCCTCCAGTGTACGTGCATTTATAGTGAGCATCAGATAAAACAAAAGAAAAGAAAAGTTTAAATCAGTGTTTA
TTTACACAGAAAGAGATAAGTGTTGCCATGTGTCACATGGTACAGATTTCTTGGATTGCTTGCCAGGTGTTTATA
GGTAAATGGATTCATTTATCAATTGACCAATATCAAATAAGAAAGACATTATTTGGGAAGAGCTCAGGAATGAAT
TCTACACATATGTTTATCTTAATCATTAGGACTGTGGGCTTCGTGGTTGGTTTTTCACGTTAAGGTGGGCACCCC
TGTTCTCTTTCTTTTTCAAATCAAGTCTCTGATTCCTAAGCGATCTAATTTGAGCTCAAAGTACGTAATGTTTGG
ACTTCAGCACCTTCCAGAAATATATCACTCTGAAGTCTGCAAAGTACAGTTTCAAAGAAAACACTTTTTTTACAG
GAAACAGAGAGCTAAAGTGATCTCATGTTCACATTCCAATTTTGGTTTCACTTAGTGCTTGGGATAAAAATTACT
TCTCTGAATGCAATATTGTTACTTTTTTTTTTCCTGCTTACCTTCTTAAAACACTGAGTTTACTCAGTCAAGTCT
GAAACCATGCATCTCTTTCCCAGAAAAATGAAAGCTGACAAGAAAGTTGAATGACTAATTTTTAAAATATTGCAT
TTAAAAAATAATGAGGGTTCCTTGTACCAGCTATATGATGAGAGATTGCTGAACTATTTGTTAGATAGGATCTGG
TGATACCTGCCTAACTTTAAAAATAGGATTCAGGGGACACCCAGTGGTTAAAAGGAGGAAATTCCTCCTGAGGTG
CAGTGTTCAGTTAGAATAAGTATTTCTTGTCTCAGCAGTCAAAATGTTGATACATTGCTGATTTTGTCTTTCTGA
ATAAGCATATGTTAGCTGTATGTGTGTGCTTTAAGAAGAAAGGGACTTGGTTTTGACATTTATATGAATTTTCTT
CAAGTATTTGAAAACTTACAAATTATAAGGTTAGAAATGTTAGAAATGTGATTAAACTTTTCTTTTAATGAAGAC
ACAATAATATTAATAAATGAGAAATAAGCAACC
```

FIG. 3C

```
CAGAGTCATAAATAAGAAAAACAATTAAAATTTTTTGACCCAGAAATTCCAGTTCTAGAAATTTTTTTCAAATAC
ATAATCAGAGGTGTACTTGATGCCTGTGTACAAAGTATTCACCATAGCTTTATTTACAGTGATAACAAACTAGAG
AAACAAACATACAGCTTTAATGAACTGGTGACGTTAACAGCACAAAAATAGTGAGTAAGGTATCTTTAACACCAT
GCTTTCAAGAACATTTAACAATGGAGGAAAATGTTTATGATAGGTAAAAAACGATGATAAAAGACCAGTAATTCC
ATGTATTTAACAAATTGTGTATATTTTGATTTGCATAAAAATAGAAAAATAACTGAATGTGGTTGTCTTGATTGG
CAAGATTTCGAGTAATTTGTATTCTCTTCTTTATACTTTTCTCTTTATTCTAAACTTTTTTTTTTCATTAGAGGG
AGAAGAATAATAAACAGCATAGATAATAAAAGGATAATGGAAGAAAATGTTGTAACAATGATCAAAGCTAAATCT
GTGAATCTATCTGCTTAGACCTTAAAGGGAGAAATGTTTTATGTGCCTTTTTCCTTTGGAACCTTCAAGAGATGT
TTCCAGAGTAAAGCTGCTGCTGCCACCCTTTGTGTGTGTGTGTGTGAGTGTGTGTGTGTGTGTGTG (SEQ
ID NO: 2)
```

FIG. 3D

```
ACTCCCAACTTCATCTCCTCAGCCCAGACAGACAGACAGCCACCGCATAATCCAACAGCTGGAAGCTCCGCGGGC
AGTAGACGGTGGCAATCACAGGGCATCCCTGGTTTGTTTTCCCTCTCTGGGGGACCCCGTCCTTGCTGACTGGTG
TCCAGCATCTGGAAACCGCTGTAGCATATAGTGGTCTAGGGTTTTCTTTAGTTATTTAAGGCAGAAACACTCCTT
CCTTTTTAATCTCAATTTACTTACATAAGACTGTCATCAGTGTAAAAGGGAAACAAACCTGTGTTTGCCAGGAGG
CTGTGGCCCAGCTTACAAACCGAAGTTCCTTCTTTTACTGTGAAGGGATTTGAGTTGTGACAGTTTTCTCATTTA
TACGCCTGGTCACTGACTTGCTTCTTTGTTCATTTAGCAATGCGCTTGAGTGTTCTGCAGGTATTTTACTAATAT
TGAAATGTGCCACAAAGGCTGTTGAAATCGCCTATCCCATATCCTGTCCTGACACCCTGTAGTACCTCAGAAGGA
GGCTTGCCACTCCCAGAAACACTGAGGTCATGTTTATTCCTGCGGATCTTGATGACGCTGGATCACCCTCCCACA
CACACACTCACACACCGTGTGAGGCCTAGGGGAGCGAGGTCCAGAGGGGCCGGCATCTGTCACAGCTGACGCACG
AGCACCAGGACCTGCTGCTCTGGCTCTGGAAGGCCACACTCATCACGGAAGCCTTTCAGCATTGACCCCGGAAGT
GATCCCAGGTTCCCCTCAGCTAGCAGTTATCGGGCTCCCAGGCGGCGCTAGTGGTAAAGAACCAGCCTACAATG
CAGGAGACTTAAGAGACATGAGTTCAGTCCCTGGGTCGGGAAGATGCCCTGGAGGAGGGCATGGCAACCCGCTTC
AGTATTCTTGGCCTGGAGAATCCCATGGCCAGAGGGGCCTGGTGGGCTAGTCCATGGGGTCACAAAGAGTCAGAC
ATGACTGAAGTGACTTACCGTGCACAGCAGTTATTGAGTAATCACAGTATCTCTGAGTGTGGGCTTAGATGCACT
GTATATATAATTTCATATCATCTCCAGAGTTCCTGTAAGACCAGTCACAGGACATGTTCTCACCAGTCAGAATCA
CTGGGTACAGTACTCACTGTATTGAAAAAAATTAGTTCTGCTCTGAAGGCTGCTCTTGTTCAACCTAACAAAGCT
TAAAAGCAAACCTCAAAAGGATCAAATTTTTTCCAGGTAATAGAATCATGACCAGTCCTTAAAAAAAAAAAAAAT
CACTTTCTTTTCAATGAAAAACTATTCTTCTATTATATAAATGGGCTTCCCTGGTGGCTCAGGTGATAGAAAAT
CCGCCTATGATGTGGGAGACCTGAGTTCAATCCCTGGGTTTGGAAGATCCCTTGAAGGAGAGCATGGTAACCCAC
TCCAGTATTCTTGCCTGGAGAATCTCCATGGACAGAGGAGCCTGGAGGGCTGCAGTCTATGGGGTTGCAAAGAGT
CGGACATGACTGAGTGACTAAGCACATGTATTATATAGATAACAAAGCTCCAAAAAAATTCTCAGCAGCCACTAA
GACCCATTATGAGTTAAAATTAGATGCACAGGGGTTGCCCTGGGTTGATGAGTCTGTCCCAGTGCCACTGGTTCA
AGGCCTTGGGCCTCTCTCTCCCCCAGAGCAGCAATTTCTAACCTGTGAGCCACAGACTTCAGGCCACACTTCATT
TCATACAGTCCTCTCAGTCTCTCTCTGAGATACAAATAGGATTATTTTCATTGCTCAGGTGAGAAAGTGAGTGTT
TAATAGTGCTCATAAACTTGACCGAGGTCTCATAGTTGGCATTTGGTTGCAGCCAGGATTTTCCTGCCACATGTA
TCAAAGAGCAGGACCATTATTCTAGAGGATTTGGCACTTTTCTGTGTAGAGCCATCAGGTCTCAGGCTGGCATGA
GGCCTCACTTAAGGGGCCTTTCCTGAGATTTTAGAAGATAGTGACACAGCAGCTTTGCCTGGCTCTCGGAATTTC
ATTGTTACTTTGAAAACTTGAATTCTTATTTTGAGACTTGAGTTCTGATTCATTCAATAAAAACTTTTGTTATGA
ACCACAACAGACATCCAAGAAATGCATGCCGTTAATTCCTTTCATGTCCTCCTGCAACAGCGGACAGGATGGATG
TAATCTGTGCGTTCTTTATCCATCTTGTCTGCTCAAGACGAGGTGCCGTTTTATGGATCTCCTGGCCGGCAGACT
CTGAACTTCTTTCGAGATGGGAGAGGCAGCTTCTAGCAGAAGGTGTGGATTCATGGTCCATGGAAACAGGGTCTA
TGTCTTCTCAGGAGTCTGCACCTGAGCAGGAAAAAATCACACAAATTCCCTATAAATGGACCGGACCTGATGACC
TGGAGTCAGAGTCCAGTAGAGGCAGATCTGGCATGGATGGTGACACTTCTGTCAACTGTTTTTAAGACTGAGGCC
CTATGACAGGCTGGCCTGCCAGGAAGGGTGACTCAGCCTTAGACGAGGGGCAGACTGTTCCTGACCATTTCCTTT
CTATAAAACTTAAGTAAAACAGAGACGTGCTCGTAAATGTTAGAAGGAATGCGGTTGAATGGCAAGGGAGAATCT
GTTCAGTGGCCTCGAAGAAAATTAGTTGAACTCAAACTTTGAATTGTCCTGGTACCGGTGTTCTCACGTAACAG
CTTAATCGTGTAGAGACCAGAGCGTGTCTGTGTGTGAAGACAAAGACAGAATCCTACAGGAGTGAGCTTGTTGCG
AGTTTTCCCTTACTGTGAGTAAATGAATTCCATTCTATCCAGGGGTAGACCCAGCCCTGTCAGAGCTGTGAATGT
GCAGACCTAGCTGGGTGAGAAATGTGTCCAGGCCAGACTGCGATTTCTAAGGACTGATGCTCATGGTTGGGGGGA
GAGAGGGGGTGAGGATGAGGAAGACTGCACAAGTTAAGTTCACGCTGACGTGAAGCCAAGGGACTTTGAGAACTT
TTCCCGTGGAGACAAGAAAGACTCCCAAGGACTAGATGGTAGGTACCCAGAGAAGGCAGGAAGCCAGCCAAGGCC
TGCAAGAAACTGGTGGTCCCAGCCCACCTGACTGTGGGTCTGTCATGAACCCACCGCTTCGGACTCAGCATCTTG
GTTCAGCATCCTGTATCACCTTGTTCCATGCTTGCTGGTGCCCACGTTGCTTCAGCGGCAGCAACTTCCCTCTGT
TCCTCCAGCTAGCTAAACCCAGCCCAGGACCCTTATCCGTGCCGCCCTATCCACCTCGAGTGCCTCCCTTCCCCC
GTGCCGCACTTTATGCTTGATTTATTTATACCAGATCTCAGTCAAATGTCACTTCTTTGTCTATCCTGTCTAAGG
AACCCTTAGCCAGTTACTCTCTGTTACATGACCCTGTTTTATTATCTTTACAACACTCTTCACTCTCTGAAACCA
TCTTGATTTTTATTGACTTATTTAGAGTCCAAGTCCTCTTACTGGAATGTAAGCAGTACAGGAGTAAGACCTGTT
TTGTTCAATTGGTCATTATATCACCACTGCCTAGAGGAGGACCAGGCTTCTAGCCAGGGTTCAGTAAATGTCCAG
TGAGTAAAGGGATGGTGGTGATGGGTGGTTTAGTCGCTAAGTTGTATCCAACACTTGCGACCCCATGGACTGTAG
CCCGCCAGGCTCCTCTGTCCGTGGGCTTCTCCAGGCAAGAATACTGGAGTGGGTTGCTGTTTCCTTCTCCAGAGG
GGTCTTCCTGACCCAGGAATCGAACCTGGGTCTCCTGCATTGCAGACAGATTCTTTACCAAATGAGCTACAAGGG
AAGCCCGGAGTAAAGGGATGCATGAAGTCAAATACAGCTGAAGAGAGAACCACGTCATGTATGTGTGGTTCACAG
TGAAAACAATGTGTAACAATACAAATCTGAGAATAAGGGGTTTGTGCTGTGGTATATGTGTGCATATCTAAGCTT
TTGTGCTGTGTTTCAAGTGCCTGACATTGTTAAGAGCTCTATAAATATTACATAATGGAAGATCATTTTTTACAA
ATTCTACTCCTGTTTCAGCTAAACTAAATTGGTCCTTTGTAAACTAGATAATTCAGTTGTCTCAAAGAACAAAGC
AAGGTCATACCCACAGGAAAGCTGAGATACCCA
```

FIG. 4A

```
TCCTCAGTTGAGTTAAAAGATACTGAATTTAATAATAATTTTAAAATTACCTTTTAAAGTAAACGTTAAGTTTAT
ACACAGGTAAAATAAAAATCATTATGTATGTTAAATTTATATTAAAAAAAAAGGCATGTGTATCAAGTTATTTTT
AACTTAATGGTTTTGTAACTCAGCCAAAAGTTTTTAATTTTTGTGGGCAAATCTTAGCTAACGGGTGAAGTAGAA
TTCATTTACAGATAAGTCTGGGTCTGGTATGTGCATTCTGATGTGAGAATTGAAGCTGCAGTTAGTGCAGGATTG
CAACGTGACCTTCCCTGATTACAGCTGGGACCACAAGTTAATAGCTGGAGCAGTGGACAGTGATTGGACTTTGCC
AGGCTTCAGTCTCCTCACTGGAAATGAGGAGGTTGAAATGGAAAATGCAAGTATAATGAATAACCCCAATGCTAT
ATGCTTGTCTTCCTTTCTTATATCCAACCCCTTACACGGAATCCATGTTATGCACTATGATTATCAGAAGCTGCT
TGGCTCCTCTGTCCATGGTATTCTCCAGGCAAAAATATTGGAATTTGGTAGCCATTCTCTTCTCCAGGGGATCGT
CTCCACCCAGGGATCAAACCCAGGTCTCCTGCATTGCAGGCAGATTCTTTACCATCTGAGCCACCAGGGAAGCCC
TCTTTAATTCTATCACATTTATCTAGGATTTTTTTCTTCCTCTGGTTGATGGTAGTGCATGAATGCTTGGGAGAG
ACTACTTAGTTTACAGTTGATACTTTGGAGTCTGGGGCCCTGCAGAGGCCTCTGAAGACCCTCAGACACCCATT
AAAACGTGTCCACCCTGTTGATTCAGTGGGCACCCTGCAGGGCTCTGAGAATGGCCAACCAGTGGACACATGACC
ATTGGACTTTGAGGACAGCAAGCTGAGTTTCATCTTTTCTACTTGCTAAGACAGTATTTGCCCTGAAGGGAAACA
AGGCTTCAGCTCAAACTTCAGCTCAAATTGTGGCAGACAGTTTCACAAAATTAAGCAATATAAATTTTGCTGAAT
ATCTTCTAAATGTTAAAGAATTCAACCAAATTCTTCTCAATTATATATTTTTCAAAAAGTGTCCAAAGTTGTGTG
TAAGTGGAAATGTAACTCTTTACAGTGTTATATATCACCTAATCGGCATGATAACCCCTCCTATGTATTCAATGC
TTATAGTACATGCTTCATGTTTTATAGATACTGGATCATAATCTCGCCATGTTGCATTATAAACTTTATATGCTT
GCTTCTCTGAAATACATAAGTAAAATTCATAAGTAAAAGATACAAGATATCAAGTCCTTGTGGAGAAAGCAACTG
TATATTTTATCTTCCCCCCTTGTTTATTATCCATTTGTCACTTAAGTAGTTATATGCCACTGCCGCTGCTAAGTC
GCTTCAGTCGTGTCCAACTCTGTGCGACCCCATAGACGGCAGCCCACCAGGCTCCCCTGTCACTGGGATTCTCCA
GGCAAGAACACTGGAGTGGGTTGCCATTTCCTTCTCCAATGCATGAAAGTAAAAAGTGAAAGTGAAGTCACTCAG
TCATGTCTGACTCTTAGCAACCCCATGGACTGCAGCCCACCAGGCTCCTCTGTCCATGGAGTTTTCCCGTCAAGA
GAACTGGAGTGGGGTGCCATTGCCTTCTCCAAGTAGTTATATAAGAAAATAAAAAAAAAAAAGAACTCTTAACCC
CACGATCAGAAAATAACCCCACATAAACTTCAGAGATCATACTATGCATGTTACTTTATAATGTGGCTTTTCTTT
ATGTAAAATATAAGTTAAGTATTTTCATTTAATGCAGTGTTCTTCTAAACATGATCTTTAAACAACCACATGACA
TTTCATCCTGTAGCTGTTCATAGCATGACCTCTTATGTGGGAGGCAGTGTAGGTAGGTGAGAGAATAAGGTCTGA
AATAGACATTTTGCTTTTTACAAGCTGTGACCACGGCCAAGTTATATACTCACCCCATTCCTCCATCTCCTTACC
CATAAAATGGGGATAACAATAGTAACAGCCTTATATTGTGTAATTTTAAGATTAACTAACTTGTTATACATGATA
CATGTTACATATTTATCATGTTATATGATGTTATACACGTTACACATGATGATGCTTAGAGCACTTACAATAGTA
CTGTAATATATTGTATTATTAGAGCATTATTTTATTATTATCTATAATTTAGTTATTCTGATGGAACAATTACCT
GATACACATTGAGTAAGAACTCAATGTGCAGTGAAAATGAAGTGAAAGTCGCTCAGTTGTGTCTGACTCTTTGAG
ACCCCATGGACTATACAGTCCATGGGATCTCCAGGCCAGAATACTGGAGTGGGTAGCCTTTCCCTTCTCCAGGGA
TCTTCCCAGCCCAGGAATCAAACTGGGTTCTCCTGCATTGCAGGCAGATTCTTTACCAACTGAGCTATCAGGGAA
GCCCTTATGGAGTGGGTAGCCTTTCCCTTCTCCAGGGGATCTTCCAGCCCAGGAATCGAACCTAGGTCTCCCACA
TTGCATTCGGATTCTTTACTGGCTGAGCCACAAGGGAAGCCCAAGAATACTGAAGTGGGTAGCCTATCCCTTCTC
CAGCGGATCTTCCTGACCCAGGCATCGAACTGGGGTCTCCTGCATTGTAGGCAGATTCTTTACCAACTGAGCTAT
CAGGGAAGCCCAAGAACTCAAATAATTTATTATTATGCATCATTGTATTCTAACTTCAAAAAGCAAAAAACAGTA
TAGGTAATAAAGGACTCAATAAACATTCATTATTACCTATATTGTGTTTTGCTTTTTGAAGTCAGAATACCGTGA
TGAATATCTGTGAAAAAAAAAAGGCTTTTGCTCTTGTACTATTATTTCCCTAAGATAAGTTTCTTAGACATAGGA
TTGCATCCTTGCTGCTGAGTCACCCTCTGCAGCCTGTGCTAACGCCTGCTCTGCAGCGCTCAGGGTAAGAGAGAA
AGAACGCACCCTGTCCCAGTGAGTGATGCTGTTCTGGGAATGCATGGCAGTGGAAAATGGCACCTGGCCATGTGA
GGAGTTCGGCAGTTTTCCAAAACCATTGACTATTGAACAATTGCAATTTACTCAATGCACTCTTTCTTTTTAATA
TTTATATAGTCTTCAGGCTAAGATATAACAAATTAAAAACTTGTTTCACTTTTTGTGTGCTTAGCATTGAGTATA
TTAGTCTGAATTTTGCTTGAAAAGATACTTGTATTGACAGAAAAATTTGCGGTTGACCACACTGTTAAGGTATCT
TCCCCCATCGAAGCTAATATTTTCTTTTTTTTTTTTCAG AAAAAAGCAACAAGCCTTGGGAGCAGTCAGCTCT
CCAGAACTCAGGCTGATGAAAAAGCCCTGGTCCCAAGGTCAGTCATTTCCTGGACATGAAAAGACACCTACTTT
ACAGATGTATCACTAGTGGGGGGTGGGACTTGTAGGGAAAACAGACATGTCAAATATGTCACTGAAAATGGAACA
AAGTATCATTTCTGGGCAGGTGGGGAGGTACAAAGCAACAGGCATAACATTTCTTAATAAGGATTGATGATTTA
AGACCTAATAAAGACATTTGTGTTATTATTCTTACTGGCATCTAATAGTAAGAGTCCAAAAATATTAATCATTAT
TCTAAATGTTTATAAATAATATTTGATTTTTGCACATATTATGAGTAGAAATATAGTTTTTTCATTTCTTCAGAA
AATAATTCAAATTATCTTTATGAGTATTAAGCATAGCAGGTTCTTGCTAAATGTGCTGTGTAATTATCTTATGTT
ATCTGTCACAACCTTATAATTATTATTCCTTTATACTTGAGGAAACCTGGGGTCAGAGAGGTTAAGTAACCTTGA
CAAGATCACAAAGCCAGTAAGATGGAGGTAGGGTTCAAACCCAGGCTTCCAGTTCACAAAAGATCCTGGACCTTT
TAAAGTCTGACCAAGCCTTCTTCGGCAATATAACACTACCAAGTTTTGCAGCTTATAAAAACCACTGAAATTTCA
TCTTTCAAGATAAGCTGTAACTCCAATTTAAGCTAATAGTTTTTAATATATAAAGTAAAAGCTATCTATGCTCCT
TCCACTTCAGCTGGTGATCTTCCAGTATGTCCA
```

FIG. 4B

```
GGATTATCCAAACCTTAACCTGTTTCGGGATTGCCTATATGACTACTGAAAATAAGCCTTTTTTTCCCATTGAAA
CTGGTAGCTCTCCTGTGGAGGGCTGTGGACTTCCTCATTCATGTATGTTACTTGCTTGGTGAAGAGTGCATATTT
TAGAGCCTCCTGGAGCCTCAGCTGCTGTCCAAACCCCTTATAAGTATCCAAACTAAAACCCAGCTGAGACATGAG
AAGAGGCTGGGCCAGGGTATCTCTGCTGCCATTGCCCTTGTTAGTCCTCATACTCTCTTGTTTGGAGGTCTCCAA
CTAAAATATATTTTCTAGACATGTCCTATCTTTTGTAATATTATGACTTTTATTTAACTTGCACTTAAGTTATGC
CTCTAAAAATTTGAAGCTTCATTAGTTCAGTCTCTCAGTCGTGTCCGTCTTTGTGACCCCATGGACTGCAGCAT
GCCAGGCCTCCCTGTCCATCACCAACTACCGGAGTTTACTCAAACTCATGTCCATCGAGTTGGTGATGCCATCCA
AACATCTAATCCTCTGCTGTCCCCTTCTTCTCCGGCTTTCAATCTTTCCCAGCATCAGGGTCTTTTTCAGTGAAA
AGACTGGTTCTTTGCATCAGGTGGCCAAAGCTTCATTAGCCAGACCTCAATCTCAAGAGATTTTTAGTGAATCAT
TTGTAAATGGTTTCTAGAGTTGTCATTACCTAAACTCTTGGAGTTTCAGTACATTGTCCAGATCTCCTGCCTGGG
AAGGGCCTTTATTCATTTCATTCATTCAAACTCTTGGAGGGTCAGTCCATTGTGGAAAATCACACTTAGGTATTT
TTGTTTCCTTTATTTCCTGCCCACCCGCTCCTTGAATTTAGTGGTAAGAAGCAGTCCCTTTTACATTTTTTTCT
ACCCAGGAGTATCATACACTCATTTCTAGGTAGAATTCTTGTGAAGAATTTGGCAATTCTCCTCAAACCTTGCCC
CTGCCTCAGGAAGCTGTGGGAGGGAGTGTAGCTAGGAGGCAGAGACATTTAGCCACACAGTGACTGATTTAGTAT
TTACTGGCAGACTTGTAATTCTCTCCTTGGCTTCTCCCATCCCATTCTTCTATTGTTCTTTATCACTGTGGTTTC
CTGACTGGAGTTCCTTCACCAATTTCCTGAATATTGTTTTTTCCAGGATTTAATTCTTCATTCCTTCCTTTTTAT
ATCTTTAACCCTTACAGAGTATTAGAAATACATATATATATACACTTATATATGTGCATAATATATATACTTATA
TATGTGCATACATATATATTATATATATATATAATATATATATACTTTCTTAGTTTTTTAACTTTGTCTTTTGAT
ACTAGATTGAAAGTCCTCAGTATCATCATCACTTAAAAATGACCATTCCCATGCATCATTTAATAGCATTTGTGA
CCCCTTGAAGCCTTTTATTACACAATAAATTATCACAACACACAGGCAAATGATATTCTCCCGACACATAACATG
ACAATAGTAGATATAATTGGTAGTGAGAATTAGTTCTGGTTTTCTTGATTCTGGACACATTCAACTCAAAGTAAG
TGACAATTTTACTTATTAAGAAAAACTTCAGTTCAGTTCAGTTCAGTCGCTCAGTCGTGTCCAACTCTTTGTGAC
CCCATGAATTGCAGCACGCCAGGCCTCCCTGTCCATCACCAACTCCCGGAGTTCATCGAGTCAGTGATGCCATCC
ATCCATCTCATCCTCTGTCGTCCCCTTCTCCTCCTGCCCCAATCCCTCCCAGCATCAGAGTCTTTTCCAATGAG
TCAACTCTTCGCATGAGGTGGCCAAAGTACTGGAGTTTCAGCTTTAGCATCATTCCTTCCAAAGAAAAACTTAGT
CTGTATTAAAATTTCAGTATGGCAATAGCACCCCACTCCAGTACTCTTACCTGGAAAATCCCATGGACAGAGGAG
CCGCAAAGAGTTGGACAGGAATGAGCCACTTCACTTCACTTTCACTTTTCACTTTCATGCATTGGAGAAGGAAAT
GGCAACCCACTCCAGTGTTCTTGCCTGGAGAATCCCAGCGACGGCGGAGCCTGGTGGACTGCTGTCTATGGGGTC
GCACAGAGTCAGACACGACTGAAGCGGCCTAGCAGCAGCAGCAGCAGCAGCGAGCTGTATATAGCTGTATATTAG
AGACTGGTTACCATGTATTGCAGAAATGTTTTATGAGAATTCTTACAAAATCAGTAGTTATGTGTACAAATAATA
TCACTTCTGCCATACAGTCCTGGGTTTGGAGGTCCAAAATACTTAAGTGGCATAGATATTTCTAATTCAAAATCA
TTATTTTAAGGTGTTTAGTGCTTAAAATTGGAGAAGGCGATGGCACCCCACTCCAGTACTCTTGCTTGGAAAATC
CCATGGATGGAGGAGCCTGGTAGGCTGCAGTCCATGGGTCACTAAGAGTCAGACAGGACTGAGCTACCTCACTT
TCACTTTTCACTGTCATAGATTGGAGAAGGAAATGGCAACCCACTCCAGTGTTCTTGCCTGGAGAATCCCAGGAA
CGGAGGAGCCTGATGGGCTAACCTCTATGGGGTCGCACAGAGTCAGACACGACTGAAGCGACTTAGCAGCAGCAG
CAGCAGCAGTGCTTAAAATTGAATTTTTATAAATTAATAATGAGGTCTAATGAGGCTATAGAAATTAGACTCTTA
CTAAATAAATAGCTGGGGTCCATAATCAGTCATGCAGTTGT (SEQ ID NO: 3)
```

FIG. 4C

CTTGAATATTTCGGTTACTGTTTATCGCCTTTTGCCCTCCAGGGAGGAGTCTGTTTTGCCCTCCAGTTCTGATCT
GCTAAGTTGCTTCAGTTGTGTCCGACTCTGTGCGACCCCATAGACAGCAGCCCACCAGGCTCCCCCATCCCTGGG
ATTCTCCAGGCAAGAACACTGGAGTAGGTTGCCATTTCCTTCTCCAATGCATGGAAGTGAAAAGTGAAAGTGATG
TCACTCAGTCATGTCCGACTCTTAGAGACCCCATGGACTGCAGCCTTCCAGGCTCCTTCGCCCATGGGATTTTCC
AGGCAAGAGTACTGGAGTGGGATGCCATTGCCTTCTCCGAGTTCTGATCTACTTGAGTCTATTTCCCAGAGCTGT
GCCTACTCTTCTGTCTGGTATAATACCTTAGAAATAATGCCCTGGCAATTTTATGAGCGCCTAGAATGTGCAGGC
GTTTTACCCACATTATCTCAAATACATGCAGCCCTGCAAAATAGGTATTATAGGCTCCATTTTATATATTTGGAA
AAGTTAAGACCCAAAGTCACAGAGCTAGTAATGGGGAAAGCTGACATTTGAACAAAATTCTCTAAGTTTCCAAGT
CGATGTTCCTTCTGAAAATAATACAAACAAAAATTAGAATGATATTTTGTTGTTGTTGTTCAGTCGCTCAGTTTA
TCTGACTCTTTGCGACCCCATGGACGGCAGCATGCCAGGCCTCCCTGTCCATCACCAACTCCTGGAGCTTACTTA
AACTCATGTCCATTGAGTCAATAATGCCATGCAACCATCTCATCCTCTGTCGTCCCCTTCTCCCGCATCTTTCCC
AGCATCAGGGTCTTTTCCAATGAGTTGGCTCTTCGAGTCAGGTGGCCAAAGTATTGGAGCTTCATTTTCAGCATC
AGTCCTTCCAATGAATATTCAGGACTGATTTCCTTTAGGATGGACTGGTTGGATCTCCTTGCAGTCCAAGGGACT
CTCAAGAGTCTTCTCCAACACCACAGTTCAAAAGCATCAATTCTTTGGTGCTCAGCTTTCTTTATAGTACAACTC
TCATATCCATACATGACCACTGGAAAAACCATAGCTTTGACTAGATGGACCTTTGTTGGCAAAGTAGTGTCTCTG
CTCTTTAATACGCTGTCTAGGTTTGTCAGCTTTTCTTTCAAGGAGCAAGTGTCTTTTAATTTCATGCCTGCAGTC
ACCATCCATAGTGATTTTGGAGACCAAGAAAATTGTCACTGTTTCCATTGTTTCCCCATCTGTATGCCATGAAGT
GATGGAACTGGATGCCTTGCTCTTAGTTTTTTGAATGTTGAGTTCTAAGCCATTCTCCACTTTCACTTTCATCAA
GAGGCTCTTTGGTTCCTCTTTGCTTTCTGCCATAAGGGTGGTGTCATCTGCATATCTGAGGTTATTGAGCACTTA
ATTACCAGGCAGCAATAGACTTAGAAGGTCTTTATTTCCTATGGAAGAAAATCAAGCAGAAACTAAAGATCAGA
GTGTTTAAGTAGCTTGCCCAAGATTATTTACTATGTAGCACACCCAAAATTTGAACCCATTTGGAGTGATTACAA
AGGTTTTACCCACTGGACAACACCATGTACTGAACTTTCATGGGAGTGTTACTCTCAGTTCAGTTCAGTTGCTCA
GTCGTGTCCAACTCTTTGCGACCCCATGAATCACAGCACGCCAGGCCTCCCTGTCCATCACCAACTCCCAGAGTT
CACTCAAACTCATGTCCATCGAGTCAGGGATGCCATCCAGCCATCTCATCCTCTGTAGTCCCCTTCTCCTCTTGC
CCCCAATCCCTCCCAGCATCAGAGTCTTTTCCAATGAGTCAACTTTTCGCATGAGGTGGCCAAAGTACTGGAGTT
TCAGCTTTAGCATCATTCCTTCCAAAGAAATCCCAGGGCTGATCTCCTTCAGAATGGACTGGTTGGATCTCCTTG
CAGTCCAAGGGACTCTCAAGAGTCTTCTCCAACACCACAGTTCAAAAGCATCAATTCTTCGGTGCTCAGCTTTCT
TCACAGTCCAACTCTCACATCCATACATGACCACAGGAAAAACCATAGCCTTGACTAGACAGACATTGTTGGCAA
AGTAATGTCTCTGCTTTTCAATATGCTATCTAGGTTGGTCATAACTTTCCTTCCAAGGAGTAAGCATCTTTTAAT
TTCATGGCTGCAATCACCATCTGCAGTGATTTTGGAACCCAAAAAATAAAATCTGATACTGTTTCCACTGTTTCC
CCATCTATTTCACATGAAGTGGTAGGACCAGATGCCATGATCTTCATTTTCTGAATGTTGAGTTTTAAGCCAACT
TTTTCACTCTCCTCTTTCACTTTCATCATGAGGCTTTTTGGTTCCTCTTCACTTTCTGCCATAAGGGTGGTGTCA
TCTGCATATCTGAAGTTATTGATATTTCTCCCGGCAATCTTGATTCCAGCTTGTGCTTCTTCCAGCCCAGTGTTT
CTCATGATGTACTCTGTATATAAGTTAAAAAAACAGGGTGACAATATACAGCCTTGATGTACTCCTTTTCTATTT
GGAGCTTGTCTATTGCTCCATGTCCAGTTCTAACTGTTGCTTCCTAACCTGCATATAGGTTTCTCAAGAAGCAGG
TCAGGTGGTCTGGTATTCCCATCTCTTTCAGAATTTAACACAGTTTATTGTGATCCACACAGTCAAAGGCTTTGA
CATAGTCAATAAAGTAGAAATAGGTGTTTTTCTGGAACTCTTGCTTTTTCAGTGATCCAGCAGATGTTGGCAATT
TGGTCTCTGGTTCCTCTGCCTTTTCTAAAACCAGCTTGAACATCTGGAAGTTCACAATTCACGTATTGCTGAAAC
CTGGCTTGGAGAATTTTGAGCATTACTTTACTAGTGTGTAAGATGAGTGCAATTGTGCGGTAGTTTGAGCATTCT
TTGGCATTGCCTTTCTTTGGGATTGGAATGAAAACTGACCTTTTCCAGTCCTGTGGCCACTGCTGAGTTTTCCAG
ATTTGCTGGCATATTGAGTGCAGCACTTTCGCAGCATCATCTTTCAGGATTTGGAATAGCTAAACTGGAATTCCA
TCACCTCCACTAGCTTTGTTCGTAGTGATGCTTTCTAAGGCCCACTTGACTTCACATTCCAGGATGTCTGGCTCT
AGGTGAGTGATCACACCATCGTGATTATCTTGGTCGTGAAGATCTCTAGGTGAGATAAAACCAAGGTAAAGAGTT
AAAAGTAAGTATGGTTAAAAGGGACTTCCACCATGACTCATATGGTAAAGAATCTGCCTGCAATGCAAAAGACCC
AGCTTCCATCCCTGGGTCGGGAAGATCCCCTAGAGAAGGGAATGGCAACTTACTCCAGTATTCTTGCCTGGAGAA
TTCCATTGACAGAGAAACCCGGCAGGCTACAGTTCATGAGGTTGCAAAGAGTCAGCCACGATTGAGTGACTAACA
CTACTACACTGCTGTGGTTAAAAGGAGGTGGAGGACAAAGCAGGGTGTAGGTTAACTAGGCTCAAACTTCCTGTT
TCTTTTCTTTCTAGGTAACTACTTCCTCTGCGTCAGCCAGCAAGTCTTCCAGTATGAATCCCACAGAAGCCAAG
GTATGGAGAGTCTTCAAGGGTCAACTTGGGTGAAAGCCTTCATTTTGTAAAGCAAAATGAATAGAGACTTTGACA
GATAGCTTGTGTGTCCTAGGAGACTTACACTATGGAAGTAAATATTTTCTTCTTAATTAATGAGGGTCTTTGAAA
ACTCAGCTTTCCTTTCAGTATTTGCCTCAAACACCATCTATATACTTATACAGGATTTTAGAATATCTAGAAAAG
TGTAGTCCGTGAGAGTTCTTTTGGTTCTAGCCTTGAGTTTTTTAAATTGTAAAAAGTATCTCTAAGTACATTTA
TCAAGATCTAGATAGAAATATAAATTCTTAATTTCTTACTAAAACGGTTTTATTATCCTAACCATTTAAAACGAA
ATCCAAGAATGAGAAAGTTTACACTAAATGAACATAGAAAGAAGTGACACAGACTCTGGTTATTTCAGATGCTTT
CTGAAGTTTTTTTCTGACATTTGAGTCATGTGGGTCACCATCTTATTGATAAACTGTGGTTGAGCTCTTGGGGTG
TATTCTGATAATTTCTTGGAATTTCAGAATTAGA

FIG. 5A

```
AATAAAAGAATGGCCTGCAGTGGGATTGCCACATAGAATAATAAGCCTACTTCTAAAGAGTTGACTGAGCGACCT
AAACCCTCTCACCGACTTACCATGACTCGAACTGAGTTTCTCGGGAATGTTCTAGGTTGGAAGATTAAAGAGGAA
GCATTTTTCAAGATGCTCTCAACTAATTCTTATGAGCTAATATTCTTCAGTGCCTGTAGGAGCTACCCCAGCTCC
ATTATTATCAAATTGCCCTTGTTTAAAATTACCAACACACTTTTGCTTTGTGTTTTCCTTGTTACTTTACTGTCC
CAAGTAGAATCCTATGCCATAATTTAATACTGGCACCATAATGTAGTACTGTTTAGTAATCCTGTGGCATCATCT
TGAACTGTATTTAAAGGAGATTGAAACTATCTTGAAACACGCTGTCAAACTCTAAGCCCTTATCCAATGTCATTT
AGCACTCATTTTTATTTTTAAATGTAAAATTATGTTTTTATTTAGTAATTAATTTCTTAATTTTTTCAAAATACA
TGTTATCTGATTCGTGATTAACCACCTATTAGGTGTCACTACTTATTTATACCAAAGTGAAGTGAAGTCGCTCAG
TCGTGTCTGACTCTTTGTGACCCCATAGACTGTAGCCTACCAGGCTCCTCTGTCCATGGGATTTTCCAGGCAATA
GTACTGGAGTGGATTGCCATTTCCTTCTCCAGGCTGATCTTTAAAATGATCTTAAGACTATAGAAAAAAACATTT
AGCCCCTGCCCCCGAAAAATTCTCATTGAACTTAGAGTCCGTGAAAATTAAAGTAAGGAGATAAAAAGGAGAGCC
AGAAATATGAGATTTCCTTTTTCTTATTATTTTGGTTCACATTTGACATGATGCCTCATTATAATTCATCCCTGC
TGACACTCAGCTTAAGGGCCGATGCTTATTTCAAGTGTGTCCTGTTTTCCAGAGTAAATGTCAGCAAATGCTTCA
GCCATTGCGAGCGTGAATCATGAGAATTCTTGGCACTCCTATAGACGTGGACTGAGGGGAGAGAGAGAGGAAAGT
AGGAGAGGGAAGAAAGGGAGGAACAAAACTAAGATGCGCCAGTCGATGACTCAGAACCACTCTTGGCCTTAATTC
TCTGTCCTTGGTGGATTTCAGTCATACTGTTCTCATTAATCATCTTATCTTCGTGTGCTTCTTTAATTTTTTTTA
ATTTTAATTAATTTTATTTAATTTAATTTGTATTTTATATTGTAGTAGGCTTCCCAGGTGACTCAGTGGTAAAGA
ATCTGCCTCCCAATGCAGGAGCTGTAGGCTTGATCCTTAGGTCAGGAAGATGCCCTGGAGAAGGAGATGGCAACC
CACTCCAGTATTCTTGCCTGGATAATCCCATAAAGAGGGATAATCCCACAGAGGAGCCTGGCGGGCTGCAGTCCG
TGGGGTCACAAAGAGTCAGACACAACTGAGCGACCGAGCAGCCACACCCACAGTTGATTTACAGTGTTATGTTAG
TTTATGGTGTGCATACTTTTTCCATTTATTGCAGAATATTGAGTAGAGTTCCCTGTACTATACAGAAGATCCTTG
TTGGTTATCTATTTTAAATACTAGTGTGTATATGTCAATCCCAAACTCCCAGTTTATCCCCCCTCCTTTCCCCTT
TAATAACCATAAGCTTCTTTTCTGTTTCTGTTTTGTAAATAAGTTCTTTTGTATCATTTTTTTAAGATTCCCCAT
GTAAGAGATACCATGCTATTTGTCTTTCTGTGTCTGAATTAGTTCACTTAGCCCAGTAATCTCCAGGGCTATCCA
TGCTGCCACAAATGGCATCATTTCATTCTTTTTAATGGCTGAGTAATATTCATATATATATATATTTTAATCC
ATTCATCTGTTGATAGACTTATAGGTTGCTTCCATGTGTTGGCTATTGTAAACAGTGCTTCAATGAACATTGGAA
TACACGTATCCTTCTGAGCAATGGTTTTCTCTGGACCTGTTGCCAGGAGTGGGATGACTTGATCTTATGGTGGTT
CTTTGCTTAGTTTTCTAAGGAACCTCCATACTGTTCTCCATCGTGGCTGTACCAATTTAACATTCCCACCAACAG
TATGGGAGGGCTCCCTATCTCACACCCTCTCTGGCATTTAGTGTTTGTAGACTTTTTGATGATGGCCATTCTGAC
TGGAGTTAGGTGATATCTCATTTTAGTTTTCATTTGCATTTCTCTAATAATTAGTGATGTTGCACATCTTTTGAT
GTTCCTCTTGGCCCATTTGTGTGTCTTCTTTAGAGAAATGGCTATTTAGGTCTTCCCATTTTATAACTTTTTTTT
TTTTAATATTGAGTTGTGTGAGCTGTTTGTAAATTTTGGATATTAATCCCTTGTCAGTCACATCATTAGCAAACA
TTTTCTCCTATTCTGTAGGTTGTCTTTTCACTTTGTTTGTGGTTTTTTTTAATGTGAGAAAGCTTTTAATTAGGC
CCCATTTGTTTATTTTCATTTTTACTCCCATTATTCTGGGAGATGGATCCAAAAATATATTGCTGTGATTTATGT
TGAAATGTGTTCTGCCTATGTTTTCCTCTGAGAGTTTTATACAAGTATCTGGTCTTGTATTTGGGTCTTCAGCCC
ATTTTGAGTTAATTTTTTGTATGAAATTACAGAATTTTCTAGCTTAATTCTTTCACACGTAGCTGTCCAATTGTC
CTGGTACCACTTTTTGAGGAGACTATCTTTTCTCCATGGTATAGTCTTGCCTCCTTTGTTGAGATTAATTGACCA
TAGGTACATGAGTTTCTTTCCAGAATTTCTATCCTATTCTGTTGATTTGTATTTCTCTTTTTATATATTTCTGTT
TTTATAGTTATTTGGTGATTGTAGCTTTGTAGTATAGACTGAAGTCTGGGGCCTGATTCCTCCAGCTCCATTTT
TCTTTTTCTAGATTGCTGTGGCTATTTGGGTTCTTTTGTTTCTCCATACAGGTTTTAAAATTTTTTGTTCTAGGT
CTGTGAAAAATGCCGTTATTTTGTAGAGATTGCATTGAGTCTGTAGATGGCCTTGGGTAGTTGAGTCATTTTGAC
AATATTGATTCTTCCAATGCAAGAACGTGGTGTATCTTCCCATTTGTTTATGTCATCCTCAGTTTCTTTCATGAG
TGTCTTACAGTTTTTGAAGTACAGATCTTCTGCCTCGTGAAGTAGGTTTATTCCTAGGTATTTTATTCTTTTCGA
TGTGATGGTAAATGGGATTGTTTGCTTAATTTCTCCTGATCTTTTATTGTTGATGTCTTGAAATGCAACAGTTTT
CTCTGTGCTGATTTTGTATCCTGCAACTTTACTAGATTCATTGCTGAGCTCTAGTAGTTTTCTGGAAGCATCTTT
TGGATTTTCTACATACAGTATTGTGTCACTATGCCAAAGCCTTTGACTGTGTGGATCACAATAAACTATGGAAAA
TTCTGAAAGACATGGGAATACCAGACCACCTGACCTTCCTCTTGAGAAACCTATATGTAGGTCAGGAAGCAACAG
TTAGAACTGGACATGAACAACAGACTGGTTGTTCCATGTCCAAATAGAAAAGGAGTACGTCAAGGCTGTATAT
TGTCACCCTGCTTATTTAACTTATACGCAGAGTACATCATGAGAAATGCTGGGCTGGAAGAAGCACAAGCTGGAA
TCAAGATTGCCAGGAGAAATATCAATAACCTCAGATATCCAGATGACACCACCCTTATGGCAGAAAGTGAAGAGC
AACTAAAAAGCCTCTTGATGAAAGTGAAAGAGTAGAGTGAAAAAGTTGGCTTAAAGCTCAACATTCAGAAAATGA
AGATCATGGCATCCAGTCCCATCACTTCATGGGAAATAGATGGGGAAACAATGGAAACAGTGTCAGACTTTATTT
TGGGGGGCTCTAAAATCACTGCAGATGGTGATTGCAGCCATGAAGTTAAAAGACACTCACTCCTTGGAAGGAAAG
TTATGATCAGCCTAGATAGCATATTCAAAAGCAGAGACATTACTTTGCCAACAAAGGTCCGTCTAGTCAAGGCTA
TGGTTTTTCCTGTGGTCATGTATGGATGTGAGAGTTGGACTGTGAAGAAGGCTGAGCACCGAAGAATTGATGCTT
TTGAGCTGTGGTGTTGGAGAAGACTCTTGAGAG
```

FIG. 5B

```
TCCCTTGGACTGCAAGGAGATCCAACCAGTCCGTTCTGAAGGAGATCAGCCCTGGGATTTCTTTGGAAGGAATGA
TGCTAAAGCTGAAACTCCAGTACTTTGGCCACCTCATGCGAAGAGTGGACTCATTGGAAAAGACTCTGATGCTAG
GAGGGATTGGGGGCAAGAGGAGAAGGGGATGACAGAGGATGAGATGGCTGCACGGCATCACTGACTCGATGGACG
TGGGTCTCAGTGAGCTCCGGGAGTTGGTAATGGACAGGGTGGCCTGGCGTGCTGTGATTCATGGGGTCGCAAAGA
GTCGGACATGACTGAGTGACTGATCTGATCTGATCTGATTGAAACAAAATGTCTAGATGTGAGACAGCTACTAAG
GTCAGGAACACACACTAACAGAAATACAATAATGGACTCTCCTCATCAGAATCCAGGGGTGCAGTGGGAATCACA
GCTCATGGATATGGCAGGAATGTTTTTTTTTAATTAATTTTTTTATTGAAGGATAATTGCTTTACAGAATTTTGC
TGTTTTCTGTCAAACCTCAACATGAATCAGCCATAGGTATACATATATCCCAAATCAAGCAGCTGAACTTTCTTT
CAGCTTAAATCCTTTTCACAATTGAACAACCAGTCCATGCTAAAGGAAATCAATCCTGAATGCTCATTGGAAGGA
CTGATTTGAAGCTGAAACTCCAATACATTGGCCACCCAATGGGAAGAACTGACTCATTTGAAAAGACCCTGATGC
TGGGAAGATTGAGGGCAGGAGGAGAAGGGGACGACAGAGGATGAGATGGTTGGATGGCATCACCAACTGAACGG
GCATGAGTTTGAATAAACTTCGGGAGTTGGTGAGGGACAGGGAGGTCTCGTGTGCTGTAGTCCATGGGGTCGCAA
AGAGTCAGACACAACTGAGCGACTGAACTGAACTGAACTGAAATTGTATGAAATGCTCATCTCAAGCATTTTGAA
TGTAAGCAATTTTGCAGCCTCGTAATTGGGGTAGAGCAGTTTCTTCCCCTGTGATACCTCTTTTGTGCAGCATAG
TCGTACCCACACAAAGCCACAAACACCTCCTGTAACAAAAATGTGACTAGTGCACCTCCCTCGTGCTAACACTCT
TCTGGGCCCTGAGGAAAGATCAGTGAGCAAAAGAGACAAAGTCACCACTGCTCTATTAGTCAGACTTGGCTTAAC
AGGTCAGCTTTACTGTGTGTGATTCCCAGAGTCAGGGCTTCAGAGTTGATCTAACCTGTCGTGATTCCTGGCTCT
GTGTGACCATAAACAAGTGTTTATATATCTCTCTTTATAGACACTATATATGTGTATATACATATATATTATACA
CTATATATGATATATATCATATATATGGTATATATATATTATATATATACCATATATTATATATGCTATATATAA
TATATATACCATACATTGTATATACTACATATATAATTTATTATATATGTGCTATATATAATACTATATATTATA
CTACTATATATAATATATAATACTATATATTATATACACTATATATGTATATAAATATATATATTTATCACATCC
AATCTATGGTGATTCCTGGCTCTGCATGATCATGAAGACGTGTGTATATAGAAGTTCATAGTAGACATGTACTGA
ATAAAACACTGCATAAATCGTAACCATTATATTTATGAGCATTTGTTGAAAAAACCCCTTCTTCAAACATGTTGC
CATTTAAAGGAGAGCTGCTAAGTCGCTTCAGTCATGTCCGACTCTATGTGACCCCACAGACAGCAGCCCACCAGG
CTCCCCGTCCCTGGGATTCTCCAGGCAAGAACACTGGAGTGGGTTGCCATTTCCTTCTCCAATGCATGAAAGTGA
AAAGTGAAAGTGAAGTCGCTCAGTCGTGTCCGACTCTGTGGGACCCCATAGACAGCAGCCCACCAGGCTCCCCGT
CCCTGGGATTCTCCAGGCAAGAACACTGGAGTGGGTTGCCATTTCCTTCTCCAATGCATGAAAGTGAAAAGTGAA
AGTGAAGTCGCTCAGTCGTGTCCGACTCTGTGGGACCCCATAGACAGCAGCCCACCAGGCTCCTCGTCCCTGGGA
TTCTCCAGGCAAGAACACTGGAGTGGATTGCCATTTTCTTCTCCAATGCATGAAAGTGAAAAATGAAAGTGAAGT
CACTCAGTCATGTCTGACTCTTAGCGACCCCATGGACTGCAGCCTACCAGGCTCCTCCGTCCATGGGATTTTCCA
GGCAAGTGTACTGGAGTGGGGTGCCATTGCCTTCTCCGTTAAAGGAGAGCAATATCCCCCAAATACTAATTTAAG
AGCTGAAATTTCACCCCAGAGAGAGAGAGAGAGAAACGGACGGGTTTGTGAGGGCGGGAATGCGGAGGTGCCACCAC
AGAGCACGGGTGTTGCTGGGTGGCCCTGTTCTGAGAGGGCAAGACTGCCAAGACCTGTGAGGAAGTGCGCTTCA
GACAGGTTGTGAAAGGGAGTGTTGAAAGAGTGGAAGAGAAAAACTTGAGCAAGGAGATCCAAAGCCTCATAAAGA
CAGCCTAAAATGTGAACTCAATCACACAGAGAGAAGGAAGCCCTTCTTCCTAAGAATGTTGTGGAGACACAACCT
GAGTAAAGGTGGTTAACTCTTTCTAGCCTAGATGCTCAAATCAGAGTTCAGATTTGCAAGAGGCATTTCCTGGTA
CAGGAAGAAACTGCGAAAGGTCTGAATCATTTCTGAGCTGGGTCTTTATGCCTGTGTCCAGCATTCTGCCTCCTG
GGTGTATTTGTTGGCTAAGTCTGCCATAACAACAGCTAGGGCTGGCTTAGAACAACTGAAATGTATTCTGTCTTA
GTTCTGGAGGCTGAAGCCCAAAAGCGGCGTGTTGGCAGGGTCTCAGTCCTTTTGCAGATGCCTGTCTCAGGTCTC
TCTCCAGCTTCTGGTAGTTTCTCAGCTTTCAGCAGCATAACTCCAGTCTGCACACAATGTCTACACTGTGTGTGC
ATCGGTACCCCAATTTTTTCTTTTTATGACATCCATCATCCTGGATTAGGGCCCATCTAATGACCTTATTTTACC
TTTTCTATTTCTATAAAACCCTATCTCCAAATAAGGTCAAATTCTGTTGTATGGGGTTAAGATTCCAATGTACCT
TTTTTGGAGGGACACAGTTAAACTCATAACACAGAAAAAGGAAACAGACCTCATCATTAAAGTACTATTGGTTT
GAATAGTACAAAGTGAAGTGAAGTGAAGTCGCTCAGTCGTGTCTGACTCTTTGCGACCCCATGGACTGTAGTCTA
CCAAGCTCCTCCATCCATGGAATTTTCCAGACAAGCATTCTAGAGTGGCCTGCCATTTCCTTCTCCAGGGGATCT
TTCCAACCCGGAGATCGAACCCAGGTCTCCTGCACTGCAGACAGACGCTTTACCATCTGAGCCACCAGGAAAGCC
CCAATAGTACAAAGCAATAACGTATTTGCGAATTCATATCAAGTAAAAATCCTATAGAAGCAAACGAGTTTTACA
ATGCAATGAAGCTTCTTTGCAAGAAGGCTGTTTTACCACAGAACTACGCTGTGTTGATTTGAATAACAAGTCAT
GCTTAAAGCAAGATCTCCTGTTATCCATACTTTTAGAGTCTGAACTGGGTCTAATTAACAAACAGTGTTATGAAA
CCAAAAGGGTACTTTTGACCCTGCGGATACAGAGAACTGGGCTGTTAGCAGAGTAGAGTTTCCTTTACAGTTCTC
TGTGTGTAACTGGGCAGCAACAAACCACCCTCCACTAATCGCATTGCAGACATGACGGCTGCACCAGCAGAAAAG
TCAGGCCACTTTACAGAAACAAAAATCATCCAAGTCTCAAAAGTATTCCAGAAAGAGGTGGCAGGACACGGGACA
AACATATAGCCCCTGTCCTGCCGTCTTTTTCTGGAATAGTTTTTCAGTATTCAAAAAACTTTTTACCTGCTTGTT
AGTTCATAGCAGAGAGGCTTCAACTTCACCCTCCCAATTGTAATCACCTTTGTAAGTTTTATAAAATAGTTCAAA
AAATAAGAATAATGTTTTTATATTTTAAAATAATTTGAGTGTAAGCTGGACTTAATGACTTGCTTCCGAAGAATA
GCGTATAAGAAGGGAGAGACTAGAACTCCTCAG
```

FIG. 5C

```
TGGAGGAACCCAGCAAACACCACCTTACTTAAGTGATGGAGATCACCATCGCTAGTGACAGAGCATGTGGATATC
ATTGTACCTTCAAGAGGACGTGATGAGAAGCCACTCACTACTGTAGTATTCTTCCCCCAGACCCACAGCCCCAGC
CTACTCACCAGAAAAACATCAGATAACGTCAAATTGAGGGACGTTCTACAGAACACCTGACCAATACTCCTCAAA
ACTGTCAAAGTCATGAATGCCTGTCAAGAAAAGACTGAAGAGCTGTCACAGTGCACAGAGGAGTCTGAGAAGATG
TGACGATAGTGTGAGATCCTGGATTACAGCCTCAAACAGAAAGAGGACATTAATGAGATAACTGGTGAAATAAAG
TCTGGGGTTTGGTGAACAGTAATATACTAACTAATGTTGGTTTCTTAGCTTTGATGAATGTGTCACATAAGATGG
TGACATTAGGACAACTGAAACTGGGAACTTTATACTACCTTTGCAGCTTTTTTCTAACTCTAAAATTATTACAAA
ATAAAATTTTACTAGAAAAATGATTTCCTATTTTAACAAGAATTTTCTGAGAATAAACACCCCTAAAAATTTGAA
ATAAACTTTTATTTGTAATCACCATGTTTAAAGGTTTAAAGATAATCTTCCAGTCGCACATTTACTGCTTGAAGG
AGGTAACCAACATACTACCTGAATCTGCCAGGTAACAAAAGCACTCCTGTGGTGAGTATCTCTTCCAAAATCCTT
GAAGGAGCAGCAAATATAAGTGGGTAAACAGAAGTTTAAGTGGAAGACCTGTACTCCAGAAGGATCCTAAAGTGT
TCTTTTGAAATTCATAGATACCCATCGTGATGAAATAGATTTGTTTTAAAGGAAGTATTTTTTAAAAAACAGCT
TAATCGAAATATCTTTCACATACTACACAATTCACTCAATTTAACTATGCAATTCAGTGGTTTTAGTATATTCA
CGAACATGGAAAGCACTAGTCAATTCTAGGATTTTTTTTTATCACCTCGAAAAGAAACCCCAAACCCTTTAGCTA
TCACCCTTCTGTCATAGGGCTTCCCTGGTAGCTCAGCTGGTAAAGAATCCACCTGCAATGCAGGAGACCCCAGTT
CTATTCCTGGGTCAGGAAGATCCTCTGGAGAAAGGATAGACCCACTCCAGTATTCTTGAGCTTTCCTGGTGGCTC
AGCTGGTAAAAAATCCACCTGCAGTGTGGGAGTGGAAGACCTGGGTTCAATCCCTGGGTTGGGAAGATCCCCTGG
AGAACGGAACGGCTACCCACTCCAGTATGCTGGCGTGGAGAATTCCATTGACTGTATAGTCCACGGAGTCACAAA
GAGTCAGACACAACTGAGCGACTTTCACTTTCTCCTGTCCTTACAACCTTCTCTCCCCACCAGCCAACCCAGAAC
AGTTGCTAATCAACTTTTTGTCTCTATAGATTTGCATATTCTGAGCATTTTGTGTAAAAGGAATCATATATGACC
TTTGATGACTGGCTAGCCATATTATTTTTATAATCTCCAGATGTACTCTGAAGAACAGATAGTTAAGGTACCTTG
GAAAATTCACTGTTATCATTACAGATATTGAATCACCCATTTTGAAATATAATCTCAATTCCCAACCCACAAGAT
ATATGTAGCCATCCACATTCCACTCCCCAGGCCATTATCAGTGTCTGTATGTAGCAAAGAATAACCTTAGCATAG
TGGTTAGGCACCCACATCAGGAAGCGAGACCTCCAGATTCAAATGCTAGGGCTGTCACTTAGCAGCTCTGCAACC
CAGGGCAAATTATTCAGTTTCTCTGGGCCTTAGTCTCCTCATCTGTAGCATGGGGGAAGTAACGGTCCCTACGTC
ATAAGGGTGAAACGAGCAAATATGACCTAGTGTGGAGAGCCATTCGGCGCAAATAGTACCACTGAGTGTTTAGAC
AGTACTGCTGACTTCCTGATCTTATGTGATCAGAGACGGTTTCAGTCATAAGCGTCTTTTTAAATTACCCAGTCC
ACTCCTTTCATCTTTTGAAGACGGAAGTTTAGCTTGGAAAGACTCAACAGTGCATTCTTACTCATTCCATAAATA
TTTTTTGAGGACATAGTCTGTGCCAGGGAGAGTCTCAAGTGTTGTGCATAAGATTGAAATGGTCTGTTTCATCAT
GGAGTCTAGTGGAGGATATGGATAAGCAGGCAAAAGGTGAATCAGAGAACATTAATATACACCTTTAGGAGGAAT
TGCATCATGGCAGAAGGAAACAAGGGGGATTAGAACAAAAGAACATCTGGTTGATTTCTGAAGTGTTTATAGAAG
AACTTTCTGAGCAGGGGGTTGGGGAACGTAGTTAAAGTAAGATACAGAGAGAAAGGATTTTAAAGATGTTTTGC
TGAGTGTTCAGATTCTGTGCCCACTCAGGCACCTTCAACTGCAGTGAAGATTGAAATGCTTTTAGTTCCTTTTGG
AGCACTGAGCCACTATTTCTTTAAATATAAGCCAAATTTAGGATTGAGCCGTGTCCTGGGCTGCAGTGCTGGGGA
AGGTTAGAGCCTTGGGGATGGGAAGGCAGGAGTATTTCAGAAGGAAAGTGAGTGAAGGGAGCAACTGGGAAGAGC
GGGCGTCCCCCAGGACCTGAAGGCAGGAAGGCAAGGCTGGAGAATGGTGGCCTGAATGTACAAGGTTGCAGATAG
GGCTGCCTGGGACAGGACCATCCTGCAGGTCCTGGGAGGCCATGTTAAGGGATCACCCCCATTGGCACCGAGGAA
CCAGCAGGGACCGTAAACAAGAAAAGGAATGACTCACACATGGATCGTTAGCTGTTGGCCCACAAGCATAGTGCA
CTAACTGTGCAAACTGAGCCCTTTTTAGGAACCCGTACTCTCAGGATGGAAGGTTGCAAACTTACTTTTTGGGGA
AACTAGCCAGGAAACTTCGGGAAATTAGCAAGGAAGGCAGAAGAAGCTGAAGGCTTAGAGCTTCGGGGCAAACAA
AGGATGTCTTCTACCCACCTCCTCACCTGCTGCTGGACCTAAAGAGCAATCTTTTTGTTTGTTTGCTTGTTTTAA
TACTACGAGACAAACCTAGAAAAAAAAGGTTATTTTCTCTTTATTTCTACCCGTTCTTAGCAATAACAGTGGTA
AAATTGTTGTTTCCATGTATCTAGATACTAGTATTGACAGCATGGCTGCTCTGTGAAACAAGGTGTTCCTCTCTT
TTGCCTTCTTGAAGACAAACTCAACTGTAAAAGGAGGAAAATTTTAATTAAATGGGTTATGCTTTCAAACCTAAT
GTTCTGTTATATAGCAGTTTGACAGCACATATTTGCAACATTTATTCTCTCCTCCATTCTTTTTGCAAAGTTCTA
TGGTGCTACATAGCCTTGAGGGGTGTAGCAGATGTGATAAACTACCTGAATTCCGCCCAGGGATGAAAGAGCCCT
ACCCAGGTTCCTACCCCAGCTCCTTGGAGTGCTGCCAGCTGGTAACCCTCATCAGCCCCCTTAGGGGTTCCCACC
ACTTAAAGGAGACACCCCCCCCCCTTCCTTAAAGTCACACTCCCTCCCCCTTCAACTGCATCTAAGGACTGGTTG
ATGCAGGCTTATTAAGGCTCAGCTCTCTCTTGCCAACCCTGGACATCTCTAAAGGGTACCACATCTTCGTCATTC
CCTGCAGGATTATGTGAGACTTCTGCCAGGTCTGCACTCCAGCTCAACTTCTTCCTTTGCCCATCTTTCCTTACC
TTAACCAGGTATTGAGCCCAAGAGGAGTCCCTAATATCTCCCTGGAAACTCAGCCCTCTGTGTTCCACCGAGACA
AGAAGCAGAACATTGTGTCCAGCTGAAGAACAAGGCCTGAGGGTATATGCGGGTGTCTTACTCCCTTCAATTCAG
TTCAGTTGCTCAGTCATGTCCAACTCTTTGCAACCCCATGAACCACAGCACCCCAGGCCTCCCTGTCCATCACTA
ACTCCTGGAGCTTACTCAGACTCATGTCCACTGAGTCAGTGATGCCATCCAACCATCTCATCCTCTGTTGTCCCC
TTCTCCTCCTGCCCTCAATCTTTCTCAGCATCAGGGTTTTTTCAAATGAGTAAGCTCTTCACATCAGGTGGCCAA
AGTATTGGAGTTTCAGCTTCAACATCAGTCCTT
```

FIG. 5D

```
CCAATGAACACCGAGGACTGATCTCCTTTAGGATGGACTGGTTGGATCTCCTTGCAGTCCAAGGGACTTTCAAGA
GTCTTCTCCAACACCACAGTTCAAAAGCATCAATTCTTTGGTGCTCAGCTTTCTTTATAGTCCAGCTCTCACATC
CATACATGACCACTGGAAAAACCATAGCCTTGACTAGACAGACCTTTGTTGGCAAAGTGATGTCTGACTCCCTGG
AGGGACGTAAAGGCTGGGAAGTAAAACCTGAGATCCCCTGTACAGGTGTGTGTATGATTCAAGTTCTTGTTTGGT
AGTAGTGAAAACTAAAAGCTATCTCATCTGCTCTTGATTCTCTTTCCTGTCTTCCTCCTCTGACCCTCCAATCTT
CCATTCTTTCTCCCTCCCCCTCCTCATCTGCCATTCACGCACAAGCCCGGGGTGAGCTGAGAAGCAAGGTGTCTT
AGTCCATTCAGGCAACTATAACAAAACACCACAGACTGCAGGGCTTAGGAACAACAGAAATGTTTTTTCTCAAAG
TTCTGGAGGCCAGAAGTCTGAAATCAGAGTGCCAGCCTGGTTGGGTGAGGGCCTCTTCCAAGTGGCAGACTTCTT
GTTGCATTTTCATAAGATGGAAAGGACAAGGGGGCTCTCACAGGGATATTGCATAAGGGCATTAATTTCATTCAT
GAGGGCTGTGTCCTCAGGACCTAACACTTTGGAAGGTCTCACCTACTAACGCCACCAGCTTGGACACTGGCATCC
CAATTTAGGAATTTGAGGGGACACAGACATTAAGGCAACGGCAAGCCTCCTGTGGTCTAAACATCGACTCCTCCA
GGTCAGCACTCCCATTTCCTTTATGCACAGAACTTCAGGGCTTCCTGGTGGCTCAGCTGGTAAAGAATTCGCCT
GCAATGCAGGAGACCTGGGTTTGATCCCTGGGTTAGGAAGATTCCCCTGGAGAAGAGAATGGCTACCCACTCCAG
TATTCTGGCCTGGAGAATTCCATGGATTGTATAGTCCATGAGGTCACAGAGAGTCAGACACGACTGAGTGACTTC
CACTTTTCACTTTTTCACCCCTGACGGCATTCTTCAAGATAATTCAAGACAGAAGCAGGAAGCTCCTACTCAGAT
ACATGTTTGTTAAAAGGGAAAGGAGACTCTGAGAGCCTTTGAATATTTTACTACTCAGTCTTTGCTGGTGTGCGC
GCATGTTTATTTTCTGGTTTACTTAGGCAAACATTACTATGGAGTGGAGCAAACTTGGCTGTGAATGTTGAAATG
GCCAACAGGACAGGCACGTTTCAGTAGCATCAGAGGGCACTTGAATGCCAGCCAGAAGATCCAGGTTTTCAGGGG
TAAATTCCCCTCCGGGGGTGTAGAAAGAAATACCATCCAAAGTGAAGGGCACTGTGCATCCCTTCGAAAATGCT
CTGCCTCCTTTTAAGTTTTTACCCACCAGCTGCGTTACCAAAAACCTCTCAGCTGTCAGAGCCAATGGACACTCC
CTGCTTTGTCTGACCCAACTTTTGAGTGAGGTTTTATACTATGGGGTGGAGAAGGCACTGGCAACCCACTCCAGT
ACTCTTGCCTGGAAACTCCCATGGACGGAGGAGCCTGGTAGGCTGCAGTCCATGGGGTCGCTAAGAGTTGGACAT
GACTGAGTGACTTCCCTTTCATTTTCCACTTTCATGCATTGGAGAAGGAAATGGCAACCCACTCCAGTGTTCTTG
CCTGGAGAATCCCAGGGACGGAGGAGCCTGGTGGGCTGCCATCTATGGGGTCGCACAGAGTTGGACATGACTGAA
GCGACTTAGCAGCAGCAGCAGCAGTTATACTATGGAGTGGGGCTTCCCTGTTAGCTCAGCTGGTAAAGAATCCAC
CTGCAATGCAGGAGACCCCAGTTTGATTCCTGGGTCGGGAAGATCTGCTGGAGAAGGAGTAGGCTACCCACTCCA
GTATTCTTGGGCTTCCTTTGTGGCTCAACTGGTAAAGAACCCACCTGCAGTATGGGAGACCTGGGTTCCATCCCT
GGGTTGGGAAGATCCCCTGGAGAAGGGAAAGGCTACCCACTCCAGTGTTCTGGCCTGGAGAATTCCATGGACTGT
ATAGTCCATGGGATTGCAAAGAGTCAGACACGACCGAGCGACTTTCACTTCCCTTCCCTTCATTTACACCGGGGG
TCAGCCTTTCCTTTCAGAAGGCCCTCCTCCCTGAATCTTAGGGCTCACTTTTCCACCATCTTCCTTCTGCTCCTT
GCCTGCACCTTCTCAGGCTGCCCTGGTTTCTTCTCTGGACATCATCCTGCCTTTATTTTTCTTCTTCATGCATTT
CCTGATGAAAAGTGATGGAGGAGGGGAGTGGTGAGGCTGGGGAGGAGATACAATGTGGAGATTGTTCAGAGCAGG
TTTCAACTCAAGTCAGAGATGAGGGAAGGATGCAGCCCTGAGCTCTCTCCTGTCCCCAGACCACCTGTCCCTCAG
TCAGAAAGAGAAGCCCCTCCAGGGAACCAACAAGGCTCTTAGGCTGTCTCTGCTGGCAGCTGCCCTCATCGCATG
GTCATTGTGGATTCATTCGTCTGTCTTCCCTACTAGATTCTGAGATCCTTGAGCTCCTGTTGCCTCCCCAGAGCC
TGACATAGAGCAGGCATCCTGTTACAGACTAAATAAAGGAATAAAACAGAGCCATGTGTCCAGGCTCTATTGCAA
CCTCACTTTACTGTGCATTAAGGGCTTCCCTCATTAGCTTTCCCAGTCTTTCAATCTGGGAAAGACTGAGGGCAG
GAGGAGAAAGGGATGACAGAGCATGAGATGGTTGGATGGCATCACTGACATGATGGACATGAGTTTGAACAAACT
CCAGGAGTTGGTGATGGACAGGGGAGACTGTTGTGCTGTAGTCCATGGGGTTGCAAAGAGTTGGACAAGACTAAG
TGATTGAACTGAACAGAACTGGTTAGCTTAGACAGTAAAGAATCTGCCTGCAATGCAGAAGACCCAGGTTCAATC
CCTGGGTTGAGAAGATCCCCTGGAGAAGGGAATGGCAACCCACTCCAGTATTCTTGCCTAGAGAACTTTGTGAAA
AGAGGCTACAGACCATGGAATCACAAACAGTTGGACATGACTGAGCAATGAATACACTTTACTGTGCATTACAAA
GACCTTGTTTTTTACAAATTGAACATTTGCAGCAACCTTCCTTGGATCAAGTCTATCAATGCTATTTTTCTAGCA
GCATTTGCTCATATCATGTCTCATATTTTTGCAAATTCACCAATTTACAGACTTTTTCATTATTATTATAGTTAT
GGTGATCTATGATCATTGATCTTTGATGTTAACATGATAATTGATTTTGGTTTATATTTTTAAATTAATACATAT
ACATTACTTTTTTAGAAATGTTGTTTATTGCACACCTAATGGATACAGTGTAAACATAACTTTTATCTTTAGTTC
AGTCAGTTCAGTCAGTCATGTCCAACTCTTTGTGACCCCATGGACTGTAGACGCAAGGCTTCCCTGTCCATCACC
AACTTCCAGAGCTTACTCAAACTCATGTCCATTGAGTCAGTGACACCATCCAGCCACCTCATCCTCTGTCATCCC
CTTCTCCTCCCACCTTCAATCTTCCCCACCATCGGGGTCTTTTCCAATGAGTCAGTTCTTCACATCGGGTGGCCA
AAGTACTGGAGTTTCAGCTTCAATATCAGTCCTTCCAATGAATATTTAGGACTGATTTCCTTTAGGATGGAGTGG
TTGATCTTGCAGTTCAAGGGATTCTCAAGAGTCTTCTCCAACACCACAGTTCAAAAGCATCATTCTTCAAAATCA
TCAATCAGTTGTGGATGTGACTTGTGATGGAAGTAAAGTGTGATGCTGTAAAGAGCAATATTGCATAGGAACCTG
GAATGTTAGGTCCATGAATGTTAGTTCCAGCTTTCTTTATAGTCCAACTCTAACATCCATACATGACTACTGGAA
AAACCATAGCTTTGACTAGATGGACCTTTGTTGGCAAAGTAATGTCTCTGCTTTTTAATATGCTATCTAGGTTGG
TCGTAGCTTTTCCTCCAAGAAGCAAGCATCTTTTAATTTCATGGCTGCAATCACCATCTGCAGTGATTTTGGAGC
CCCCCCAATAAAGTCTGTCACTGTTTCCATTGT
```

FIG. 5E

```
TTCCCCATCTCTTTGCCATGAAGTGATGGGACCGAATGCCATGATCTTAGTTTTCTGAATGTTGAGTTTTAAGCC
AACTATTTCACTCTCCTTTTTCACTTTCATCAAGAGGCTCTTTAGTTCCTCTTCACTTTCTGCCATAAGGGTGGT
GTCATCTGCATATCTGAGGTTATTGATATTTCTCTCAGCAATCTTGATTCCAGCTTGTGCTTCATCCAGCCCAGC
GTTTCTCATGATGTACTCTGCATAGAAGCTGAATAAGCAGGGTGACAATACACATCCTTGACGTACTCCTTTTCC
TATTTGGAACCAGTCTGTAGTTCCATGTCCAGTTCTGACTATTGCTTCCTGACCTGCATACAGATTTCTCAGGAG
GCAGATCAGGTGGTCTGGTATTCCCATCTCTTTCAGAATTTTCCACAGTTTGTTTTGATCCACATAGTCAAAGGC
TTTAGCATAGTCAATAAAACAGAAGTAGATGTTTTCTGGGAGTTTCTTGCTTTTTCAATGATCCAATGGATGTTG
GCAATTTAATCTCTGGTTCCTCTGCCTTTTCTAAATCCAGCTTGAACATCAGGAAGTTCATGGTTCATGTACTGT
TGAAGCCTGGCTTCGAGGATTTTGAGCATCACTTTACTAGTGTGTGAGATGAGTGCAATTGTGCGGTAGTTTGAG
CATTCTTTGGCATAGTCTTTCTTTGGGATTGGAATGAAAACTGACCTTTTCCAGTCCTGTGGCCACTTCTGAGTT
TTCCAAATTTGCTGGCATATTGAGTGCAGCACTTTAACAGCAATCATCTTTTAGGATTTGAAATAGCTCAGCTGG
AATTCCATCACCTCCACTAGCTTTGTTCATAGTGATGCTTCCTAAGGCCCACTTGACTTCACATTCCAGGATGTC
TAGCTCTAGATGAGTGATCACACCATCATGGTTACCTGGGTCATGAAGATCTTTTTTGTATAGTTTTCTGTGTA
TTCTTGCCACCTCTTAATGTCTTCTGCTTCTGTTAGGTCCATACCATTTCTGTCCTTTATTGTACCCATCTTTGC
ATGAAATGTTCCCTTGGTATCTCTAATTTTCTTGAAGAGATCTCTAGTCTTTCCCATTCTATTGTTTTCCTCTAT
TTCTTTGCATTGATCACTGAGGAAGGCTTTCTTATCTCTCCTTGCTATTCTTTGGAACTCTGCATCCAAATGGGT
ATATCTTTCCTTTTCTCCTTTGCCTTTTGCTTCTCTTCTTTTCTAAGCAATTTTTAAGGCCTCCTCAGACACCAT
TTTGCCTTGCTGCATTTCTTTGTCTTGGGGATGGTCTTGATCCCTGTGTCCTGTACAATTTCAGGAGCCTCCGTC
CATAGTTCTTCAGGCAGTCTGTCTATCTGATCTAATCCCTTGAATCTATTTCTCACTTCCACTCCGGGAGTTTGT
GACGGACAGGGAAGCCTGACATGCTGTAGTCCATAGGGTTGCAAAGAGTCGGATATGACTGACTGAACTGAACTG
AACTGATCCCCACTTTCTTCTAACCACATCCCACCAGCCAGTCAGCCAGCTCAAGCCTGCTTTCCCTTCCTATAG
TCCCCCAAACCCACAGAACCCCAAATTCCCAAAGTGCGTTTGTATTTATTCACCCACTGTGTGTCTTTCAATGCC
ACCCAAATGATCATGGGTTACAAATGCTATATGACTTCAGCTAAACTGTGAAGTCCCTGGAGGGCAGGAAATACG
TATTTTAACCTTTATATCGCTCCGTCTACAGTCCTTTTCATCGTGCTTTACATGGAAGCCTTTCAAATATGACAC
TAGCCAGTTTAAGCTCAGTTTTATTTTTATTTTTGGTTGTGCTGGGTCTTCACTGCTGCGCACAGGCTTTCTCTA
GTTGGACGAGGGGCACTACTCTGTTGTGGTGCGTGGGCTTCTCATCTCTGCGGCTTCTCTTGCTGTGAAGCACAG
GCTCTAGGTGCGTGGCTTCAGTAGCTGCAGCCTGTGGACTCAGTAGTCATGGCACAAGGGCTTACTTGCCCCGTG
TAGCATGTGAAATCTTCCTGGACCAGGGACCAAACCTGTGTCCCCTGCATTGACAGGCAGATCATTATCCACTGT
ACCACCAGGGAAGTCCCAAGTCCAATTTCAATACTCCATTAAAAAATGACTCAGACTTTAATGGGAACTGTTCTT
TCAGAGTCAGAATAATGTACTCGGGGATACTGAATCTAGGCCCTTTAGGATCCTGGGAGAGGTGGTTCCAATTCC
TGGGCCTGGAGGTAGGGCCATTATATCACTCCTTTCATTTTATGTTTGCTTAAATTACTGTAGGTGTTTGGTCAC
AATCATAAAAGCATTTTTCAGGTTTATGACATATTTTCTTTCATTGTGAATGTAACTGATGCCATCAATCAGTTT
TTCTTGAATGGGCAATCATAGGCCCCATATTCAAGTTGATTCAAATTATGTATAAGTTGT (SEQ ID NO: 4)
```

FIG. 5F

ACACTCACTCCTTGGAAGGAAAGTTATGATCAGCCTAGATAGCATATTCAAAAGCAGAGACATTACTTTGCCAAC
AAAGGTCCGTCTAGTCAAGGCTATGGTTTTTCCTGTGGTCATGTATGGATGTGAGAGTTGGACTGTGAAGAAAGC
TGAGCACTGAAGAATTGATGCTTTTGAACTGTGGTGTTGGAGAAGACTCTTGAGAATCCCTTGGACTGCAAGGAG
ATCCAACCAGTCCATTCTAAAGGAGATCAGCCCTGAGTGTTCTTTGGAAGGAATGATGCTAAAGCTGAAACTCCA
GTACTTTGGCCACCTCATGCGAAGAGTTGACTCATTGGAAAGAGTCTGATGCTGGGAGGGATTGGGGGCAGGAG
GAGAAGGGGACGACAGAGGATGAGATGGCTGGATGGCATCACCAACTCGATGGACATGAGTCGGAGTGAACTCCG
GGAGTTGGTGATGGACAGGGAGGCCTGGTGTGCGGAGATTCATGGGATCGCAAAGAGTCGGAAACAACTGAGTGA
CCGAACTGAACTAAGTGTGGGAAGATGCAAGAACCTGGGCTCACCTGCAAACAAGGGCATTTGTAGGTCTTCTTT
TCCAATTTGTATTCTTTTTATTTCTTTTTCTTCTCTGATTGCCATGTCCTAGACTTCCAAAACTATGTTAATAA
AAGTGGTAAAAGTAGACATCTTTGTAGTGTTCCTCATATTAGAGGAATTGCTTTCAGCTTTTCACTGTTGAGTGT
GTTGTTAGCTGTAGGTTTGTCATATATGGCCTTTATTATTTTGGGGTATGTTCCCTCCATGCCCACTTTGCTGTT
TTTCCCTTGATGCTTTCAATATTTTCTCCTTGTCTTTAATTTTTGCCAATTTGATTGTGATATTTGTTTAGTTTT
TTGTGGCTGCTGGTGTTTGATTTTTGTTGATGGCTGTTCAGCGGTTACTTGTGATTTTAGTGTGTCCGTGAGAGC
TCATGTCCTCCCACTCCACCATCTGTCTCCACCTCCCTTCATATACTTCTGGTATTTGGCTTATAACATTTATAC
TAGCCTCCTCCTGGGGATTTTTGGAAATTGTATGAGCATATTTCTATAAATATTTTGAGCTTTTAGAGAAAAGGT
GTTAATGCAAGGTGAAGCCTGTATCAAATCTTTGTCAGGTTCGGCACCTTTAAAATGAGAGTCAGTCTGGCTGTG
GCAGTATGTCTGGGTCTCAGGTCTCTCTCTTGTCCCTCATACTTGTTAGGCACACTGCTGTGTGTAGGGTGAAAG
GTCAGATCATTGTTCATAAGGGGAGATCCCTTAGAGATTATGTATAGTGGACACTGGAGCCCAGTGGCTTGGCTT
TTATTCCTGGTTCCATGCTGGCTATGATATTGGAAAACTCCTCCTAACTTAATTTTAAACTTAACTGAACTTAAT
TTTTACTTTATGTTAGCGTACAGTTGATTGACAATGTTGTGTTAGTTTCAGGTGTACAGCAAAGAGATTCTTTGT
GTCATGAAATGGGGATGATGGTGGTGATGATAATAATGATACTCACCATACCTTTCTTACAGGAATATTGTGAGG
ACTCCGAGAGTTTAGAACAGTCCCTTGTACTGAGGGGCTATCAATAAGCGTTAGTTATTATTGTCATCATTACTA
TGTTCATCAGCCTCACTGCCACCAAAAATAAACTAAAGAGATGTGTTAGTGATTACTGATTAAAATGTATATTTC
ATTAGAACCTGCTTGATTCTGTGATTATACATTCTTTCTTGTGATTATACATTCTTAATTGTATTGTAGAGTTCT
TCCATGCTAAATATTGCCATAACGCCAGATTACAAATTAGAAGCTATTGATAGACTCAAACCACTACAGTACCAG
CTGGCTTATTTTCCTTGTTAATCATTTAATAGATTACATTTGCATAAACTAAAAAAAAGCAGTGTTGCAAGTATA
GAAACTCATTAACAAGGATCCAGTTTGAAACGAACCAAAATTTTAAATTTTAAAACATTTCTTTGTTCATGAAC
TTTGTTTCCTTCCCAAAGCAATGTGTGCTGGCATAAAAGTGTTGTTATGTGAAGAGCACATGTACCTTCATTACT
GAAGCATAAGACCTGATAAATTAAGAGGAGTTTTAATCAGTGTCTTCAGATAATATAGTAAAATATAGAAGTTTG
TGCTGATACCACCAAGCACATAAAAAGGAAAGAAATAGCAGGAAGCATCAGGCTTCATTTTTAATCTCTTCTTTT
GAGAAGTTCATAAACTGTTTCATCAAGTTTTATTCTTGTTTTTATTTCCTCCCTATATGGAGAAGGGATGTATGC
ACTTAAGGAATTGTCTTTTTGATACAGGTAACTTTGGATTGGGTGAAACTGTCAAATACTCCACTAAAGAACCTG
AATCACAGCCAGCTCTTCAGAAGCATTCCTCAAACTTTAGATTTGATCACAGATTTTTATTGTGCAACAAAGAAT
CTATGCACTGTTTGATCAAACTGTCATAATATTGTGCAGACAGCATTTCAGAAAACTTTTGATAAAACCTTTAGC
TTTGTTAATTCGTGTTGCTTACTTGACTGTCAGATAAAATAAAGTCACACTTGGGGCTGTGCTCTTATATT*AG*GC
*TATTCCAGGCAGCAAACAGCTGGAAGGACCGCATTCTCCTAACAAGAAAAGACACAAAAAACAG*GTGATGTGGTT
CATTGTACCAGGGAACACGTATGTTTACTAATGGTCACTGCAGCTGCCTAGCACGAGCTAATAATTTCAGTTCAC
CATCTTCTGTAACGCTTTGGCCCATCACAGAATTCTAGTAGGCTTAGTTACCCATCACTCACATTCTGGCACTAA
AAATAAACTTCACTGCTTCCTATGTTCTCAACACTGTCAGCATCCCATTCTTTTACCTCATCAGCTGAAACCTGT
GCTGAATATTCCACTCATAAAGAGGTCAAACATGTTAATGGCTTTGAGGGATGAGGGTTTTATTTTCATTTATG
TGTTAGCTACAATGTTCATGGTAATAAATCTCTACATATCTGTAATACTCGCAGAAGTAAAATGCAGATTGCCAT
CTCAGTCGTAAGAGCTGACTGTTAATTGATGTGCTTCTATCTAAAGAGTTGCAATTCCGGGAATTCCCTGGCAGT
CCAGTGGTTAGGACTCTCTGCTTCCCCTGGAGGGGACACAGATTTGACCCCTGGTTGGGGAACCAGGATCCCAGA
AGCCATGTGGCATGGCCACATAAATAGCAGTTCCAATTCCAAGAAAAGCATAATAATCTTAACTCACAACACTTA
CATTGATCAATACATAAAACTTATCTTTTAGCTCCCTTAGTTGAAGAAAATATATGATAAACTTTATAAACTCTG
TTTATTTTTCCTTCCCTTCTTTTTCTTTCTTTTGCATTT*AGGCTGTAAAAACAGAACCTGAGAAGAAGCCACAAT*
*CATCTAAG*GTAAATGATTTAAGTCGACTAATGAATTATTGGGATTCTTTGAAATAATAATGAATAGCTAATTTTC
TACATTGATTACTGAATGGTAAAAAAAAAAAAAAATGGTCAGCTAACTAATTTTGGATTCCCCTTTTGATCATG
ATTATATAGAGTGTATATAAAATAATTATAATGTTATCTATATATATATATTGTTAAGATGAATAATATTTTATA
AATGAAAACAGTTTACTTCAGAAAGCATTTTGTTCAAATCTAGGTCTTCGTTATAGCTGAAGTAATTAAAAAGAA
AAAAAAAAACAGAAACAAAGGACAAGAGACAAAGGGTAATGAGTATCTGATTAATGATGAGACATGGAGGACAAA
GGTGTCTATTGAACCCGGCACCTAGATAACTAAAGATGACAGCCTCTCCTCAGAGGCCCTGGGTTTACCGTGGTG
GTCTCACCTCCGTCGGTGGACTACTTGTCAGTTGCTCAGGATACAGCTCTCACTTGCCCTTGGGAACGGCTTCCC
TTTCTTTCCTGATGCGTGGCTGTCTAGACTGAAAGCCGATTCCCGTCTGTGTGGAGACGGACCCCGGAATGTCTG
CAGGTGGGGCAAGTGTCTCTCTTCTGAAAGGTGCTGTGCGTTCCTTCTCTCAAGCACACTTGAGCAGTTGCTCAG
ATACGATTGCAAGGTTTCCTGTCGGAAAGCACA

FIG. 6A

```
AACGTGGTTTGGGCTGGAGTACTTTAAGTGCAGGCAGGGGTCGGGGCGCCAGGGTCATCTGGGTAAAAGATGACG
CTTATGTGATTCTGTGTAAGACCTCTTGGTGGCCCCTATAGACGTATAATTCAGCAGCTGGTGGAAGTTGTCTTC
TATTCCAAATTTAAATGTTTTTGGTTACCCAGCCTCAAGAGAATTGGGTTTCTGGTGATACCTGTCTTCTCTACT
TGTAACGCAGAAAAGATCATATAAATCATTTAACTGAAAAAAATATAGTGTTCATCTCCTATGAAAGGAGTTTTT
TTTTTAATTAATTTTAATTTCTAGAGTAGGATCCCCTATAAACAAACTCAGTGTTCAGAGTGATCTTTTTGATG
TTTCTGTGGATGGACTTGCAGTTACCAAATGATCTACATGAATTGTGAGAAACAGCCTATAATGTAGATACATAC
CTGTGTGAAAAATCATTCCAGATGAAATACTACATTTTCCATTATTTTTTAATAATTATTGTTTTCAGACTGTT
GCTAGGATTATTATCAACCAGACACCAACAGCCATTTCTCTCCCTAGGCCTTTCTCAAGAGAGGCAGAATGGTCT
AATTGGGATCTTTGTTTCTGAGCTTATTTGCAAAACAAAAACAATGGCCTAGAATGTAATTGCAATTTTATCTTT
TGAAATTGAC AG CCATCTGTGGTTCATGAGAAAAAAACCCAAGAAGTAAAGCCAAAGGAACACACAGA G GT AAG
TAATCATTATTAGGACTTGATATCATAAGATGAAGCCTTTTTTTTTTTCCCTTATTTTTGTGAAGGATAAAATT
TTGAACTCTCATCTTTCAACACTTAAGTCCTACCTAGAATGGCAGTTATTTGTTTTTCTGTTAAAACGGCACCTC
TGTGTGGCATCAGCAGGTATTGCAATTTGCTTGTGTGATTCTTGCTGAATTTGGAGGGAAGGAATTGCATTGTTT
CAAATTTTCTACCCAAAGTGAAATTTGTCACATGTAAATCATACTAATTTAAATTCTCACAATTGACTACATAAA
ACACAAGTGTTATGAATTGCTTTCTACTCCTCAGAGAAAAGTAGCAATATGTGTCATATTATTAACCCCATGGGG
TGTATGCGTGTTTTC AG CCAAAAAGCCTACCCAAGCACTCATCAGATACAGGAAGCAAGCATGCTCCTAAGGAAA
AAGCCGTTTCCAAATCAAGTGAGCAGCCACCATCAGAGAAATCAACAAAACCAAA GT AAATAAAGCAGACAGAT
GAAAGAAAGAAAGAAAGAAAGTGAAGTCTCTCAATCGTATCCAACTCTTTGAGACCCCATGGTTCCCCCAGGAAC
CTACCAGGTTCCTCTGTCCATGGAATTTTCCAGGCAGGAGTGCAGGATTGGATTGCCATTTCCTTCTCCAGGGGA
TCTTCCCGACCCAGGGAGTGAACCCAGGTCTCCTGCATTGCAGGCAGATGTTTTACCAGACGGATAGATGGGAAA
ACGCTAATGTCAGCTAGGGAATAAGACACAGATCCTCTACCTACACTGATGTGTGTAGGTGACTCTTCGGAGCTA
TGCCAAATGTATCTAGTATAGTCAAGATTTGGTGCTGTCACTTCCCTGGTGTTGCAAATAGGCTTGAGGGGACCT
GGGACTATGTAAGGCCTGAGGAGGGCATCAGACGGGTCTGGGGATGTTCCGCCACGCCCTGTCACTGCCCAGCA
GTACTCAGTTGTGACCTTGAGGGAGCAGGCTCCGGTGTCTTACAGAGAGGAAGCTGGGAGTTGAGGCTGCCTCCT
GCACCCCTCTTCTTGTGGCAGTTTAGTTGCCAAGTCATGTCTGACGCTTGCTGTAGCCCACCAGGCTCCTCTGTC
CATGGGATTCTCCAGGCCAGGCCACTGGAGTGGGTCACCATTTCCTTCTCTAGGGGATCTTCCCAACCCAGGGAT
TGAATCCGGGTCTCCTACATTTCAGGTAGATGATTTACCAACTGAGCTATGAGGGAAGCCCTCTCCTTATGGGCT
GTGGGAATTCAGATGCCCTGCGTGATCTGCTCCTTACCTGGAGGTCTTAGAGTTTTATGGCTCTTACTGGAGACA
TCAACTTACAGAGCCAAAAAAATCAGAAATATAGTGTATTTCCAGAACTAACAGGAGTCATATATAAGAAGAATA
AAATCTATGAGAAGGACTTCTTCGTTATGAGCTCCTGGAAGACCGTGTATCTTGTATACAACATGCCTTGTATCA
GGATTGCCGTGTGGCCCACTGACTGCAGCCACTTGTGTATGTTATTTGGCTTACTGGAATTAAAATGAATTTTAA
TTAGCTGCTAACAATTACAGTCAGAATAGTTCATATAAATGCCAATTTCTAGCTTCTCTTGAAAAACTGGAATC
GCTGGCAGCAGTGGGCCCCCATGGCAACACCTGACTGGCGTCCTTACAGCCTGGTGTGAGCCTCCCCGGCCCACC
TCACCTGCGTGGCCTCTGTAGGCTCTGGCGTCCAGCTCTGTGTGCCCCGCCTTGCATCATGTCCAGCAGAAGCTA
GTGACCATTTCCCTACAAGATGCTCACTAGGGGAAACGGGCTCCCTGGTAACATTTGAAATGTTTGATCTTGAAA
ATGGTCATTCAAAGTTAACTTAGTTCTGTCGATCTTTT AG ACCAAGTCACAGGACAAGATCTCCGGTGGTGGAAA
GAGCACTGTTCCTGCTGCTGCTGCTGCAGCATCTGCCGAACCAGCTGACAAG GT GAGCACACGTGAAAGATACGG
CGTGTGCGTGGGCCCTGACGCTTGTCAGGTCTGTTTATGAGAAACATGCTCAGCGAAGACCCCTTCTCCCTGGGT
TGGCCTCTGTTTAACCATTCAGTGTTCCAGCGCCGTCATACCCAAATAACCTGTCATTCGGTAAAACTGAACACG
TCGTGTGTGACATTTGATGAAGAGGAGCGTGCGTCTAAAGGATAGAGAAGAGAGCAAGGCACCAAAAATGAATTT
AAAATTCCTGTATTCAGTACAGTTACCGGGCACCTGCCATGTGTAAGGCCTCGTGTCAATACCAAGAAAATTAAA
ATGCAGGTGGACTCAGACCCTGCCAGCAGGATTTATAGGTTTGAAATGAAGCAGATAAAACTGCCGTGAGCATTT
GAATTAGCATTACTCTCAGCGTTTCATATGAACACTACCGTCCTGAAGCAAGTAAACCATGTGCGGTCACAGCAC
CTACATGAATTGATAGGGGAGGTTTTCGACGGGGTCTCACAAGCCCTCTCAGGAGTATATGTGCCCTGCTGGCAA
ATTATGGGCAGCTTCGCGAGATCCTTTGAAGGGACTAGCCCGAGAGTGTAAGACAAGAAATGGTCTGCTGGTTCT
ACTCAGAGCAATACAGAGTTAGCAGTTGGTTAGTAATCAGTTTGGAAGTCATCTTGTCCCAGAATTGCTAGTACT
TATTTCTCTTAAAGCCACAGGTAACTAATTGCAGTAACAATAAGATGGAAATGAAAGCAAAAAAAAAAAAAAGTA
ACATGTTTATTTTCCTGCTTCTCAAAATGGGAACTGTTATCCCCTGCAGGCTAGATGGTAAGGAAAGTCATAGG
ATAAAGTATGGCCCAGTCTCCCTGAAACATCTGTTTTTCTTAGATTTTGAAAAGGATAAAGCATGCTTATTTTT
CTCCAAACTAATGCAGATACCAGGTGGCATGATGGCAAAATTTACATGAACTTTAAATGGAAATACTCAAATTTT
AAACTGTTTTGTTTTTCCCAGCAGACCCCCCTGTATGTCCCTTGAGACTCCCCCTCCCTACCCCAGGGTACACCT
CACTCTCTTGTGTTGATGAGAGATACTTAGATGCTACAGATGGAAAAGTGGATAGCTTAAAGGTGGAGGATTGGA
TCTCTTGGAATAGATTTAAAATGCACTCAAAATTTGAAAATGTATGCCACACTTTATTTAGCCAGGGTTATCTAT
AAAATCAAACAGTAAAGTCAGGCAAGGTTTATATGGGATTCTGCTGTGCATTGGCTTGTGCTGGGCTTGGGGCA
AATTATTTCACTTTTCTTTGCCTCTAATTTGT
```

FIG. 6B

```
CTCCTAGAAAATGAGGTTGATAAGATCTGCTTTTTCTTTTTCAGTCCACACTGTGTGTAAAGCACTGTGGACTGT
GGTCTGGCTCTGCAGGACATTGAGCTGCAGGCTGGCCTCTCTTTTTTTGGATGTGCTGTGCTCAGTCATGTCCAG
CTGTTTGTGACCCCATGGACTATAGCCCACCAGGCTCCTCTGTCTCCTCTTGCCTGGAGAATCCAGGCAAGAATA
CTGGAGTGGGTTGCCATTTCCTCCTCCAGGGCTTCTTCTGGACCCAGGAATCAAGCCCAAGTCTCTTATAGCTCC
TGCATTGGCAGGCGGGTCTTTACCACTGAGCCACCTGGGTATCCCTGGCCCCTCTAATGTGCCTGGGGCTGCAT
TCAGGCAGATTGAAACAGGCCCCCACAGGGAGCTGTTTGTGGAGACAGGGATTCTGTCTGATTTGGAGAACCCGG
GAGGACTTTGAGTGCATATAGTCTGAGTAAGTCATTAAAGGAAAGCTGGGATTGCAGGCTTGCAAACAAAACAAG
AGAGAAAATAGAAGTGTGATCTGAGTGCAAAGGGCATTCCAGTGTGCGTGAAGCACAGGAGACATGAGTGGGAG
TGTAAGACCAGAAAGACAGGTCGAGGCGCTGCTGAGGAGCACACTGAGATGCATTAATCCCATGGTAATGATAAT
AGCTGGCCCACGTAAACACTGGGGATCAGAGGACAGATGGAGCGATGTGATGGGATTAAAACCAGGCTGCAGGAG
GATTAAGTGACTTCAACGGCTACGATGAGACAGCATAGAGATTGGAAAGAGGGAGGCTGGTCAGGGGCTGTTCTG
GGGAGCCGAAGTCAGCCTGAATTAGAGCTAGGATAGAATCAGTGAGTAGGGAGCAAGGCAGGAGGTGTTGCAGAG
GTGCAAGCTAAGAGTTGGACACGACTGAGCGACTTCACTTTCACTTTCCACTTTCATGCATTGGAGAAGGAAATG
GCAACCCACTCCAGTGTTCTTGTCTGGAGAATCCCATGGACGGAGAAGCCTGGTAGGCTGCAGTCCATGGGGTCA
CACAGAGTCGGACACGACTGAAGCCACTTAGTAGTAGTAGTAGTAAGATCTCAGATGACCCAGGGCCTCAGTGTC
TGAATGGACTAGGTTGGCAACCCTAAGGTGAGACAAGAGAGCCGGGTATCACTGCTAGGTTTGTGCCAGTGCAGA
GTCAGCACCCATGAGGCGAGCATCTTCTTAAGCGGGGAGCCCGGCCCTGGTTACCACTGACGGGTGGACAGAGGT
CAGAAGGAGGGGAATTGGTGGAGGTGGAAAACGGATGCCTGCCTTTGGACAGGCTGAAGTTTCTGAGGTGTCCCG
AGAGAGGTGATTCGAACATCGCTTTGGAGCCCAGGTGACGATGGAGAAGGAGAAGCGGGCTGGGGGAGAGAGTG
ACACTGAGTGAACACCTGCGCAAGGCTGTGGATGAATCGAGGAACTGAATTCAGTTGCCAGGACTTGGGTTCACC
CTGGTGCCTCCACAGTATCTTTAATACAACAATCACAGCAACTGCTTATGTAGTACTTCGGAAGAGCTTAGCATG
TGCCCAACCACCAGCTTTCTCACTGTGATCGATTAATTAGTTGAACCCTCACAACCCTCTGCAGTAGGTGCATTG
ACTGCCCTGGTTCTCACACACGAGGATACAGAGGTTCAGAAGGAGACGTGACCTGCTGGCAGCCTCCTGGAGCCA
GTGTGTGTTGGGGGCTGATGTGCAAACCCAGAGCATCTGAGCCTGTACGCTCCGCCTCCAAGCTCTGCTGCGTGG
ATTTCAGAGACCTTCAAATAAGACAGTTTTCTATTGTCTTCAACCCAATGACCTCACCATTTAGTTCCTGCCTGG
CCCCGAAAGCATCTGGCCCCTGATCCTAGAGAATGATTGCCTGGGCCCAGCAGCACAGTAGAAACACACAGAGTG
TGCGGGCGAGGAGCAAAGCAGAAGATTTGCCAGACGGGGCAGAGAACAGAGGCCACAGGTGCCAGTGTGGAACC
AGGGTGGTGCTGTGAGAGATAAGAGTCAGGAGACGGGTGCTGGGCAGAGGAATGGAGGGAAGATTATGATGTCTG
GGTAAAGGCATGGAAATCGCAGGTTAGAAAGTTGTCAGCAGTTACTGACAGAGCAACTGACGCAGTGGTGGGAAG
GGCATTCATTTCACGGAAATGAAAGAAACAGTGTGTGATGATTTGACAAAACAAGGGGTGTGGAGGTCTTGATGT
GTGGGTACAAAGACTGAGAGAACAGCGCCTAGAAGCAGTGGCTGCCTTGTGATAAGAAAGAATTCATGAGCATTG
CAAAGACTAGCTGTGGGTCCTGGGAGAGGCAGCCAAGAGCAATGAAGAGATGGGTAGACCTGGATTCATATCCTA
GTGCTATCCTTTACTGAGTGACCTGAGAAGTGACTCAGCCTCTCTGAGCCTTGTTTGTTGCATCGCTAAATGAGA
TTAATATCATTGTTATTATTACTTCTGCTGTTCTGAAAAGTATATAACACGTATAGTGTCTGGCACAGAGCAGAT
GTCCAGTGTATGAGCGATATTATTTATGTTACAGCGTATTCATTTTCAAGTATGTAATATTATTAAGCTTGATCA
AAGTATATGAGGAGTTTTTATCTCTTTCTCAACCCCACC AG AATAAAGAAAATAAATTGTTAACATCGGCCGTAC
CAGCTGAATCTAAACCAAGTAAACCATCTGGAAAG GT ATGAAGACAGCAGGGCATTTTGCATAGGTATTTCTTC
ACAGTCTCTGTGTTTGTCATGATCCGATTTCTCGAGGGCAAACAATATGAGGTGAGGTTAGCTTAAAGGACCTTT
TTAATGAATTGTTGTTTGAAGCTAATGAAACTGGGTTGGAAGTGTGACTTTCTTCATGTATGTCTATAACATTTT
ATATTGTAACCCTCTGTTCTGAAAACTCCAATTATATCGAGGAGTTTACATTCCAGTTTCCCTCCTGCAAATG
TACTTTCTTTAAACAGAGGTTTAAAGGAATCTAAAGAATGCCAGGCACTTCTTTATTCTGAAATTTCCATTTGAA
TCACCCCAGAGCTAACAGACCCCAGATTCTATTACACAGTCTGGTGAGTTCCTGAAGTTGTAGTAGATATATGGT
AGTTGCAAAAAAAAAGTAAGCGATCATTTTAAGCTGAATTAAATAGTAAAGGGTCTTTCTTCAACTTGTTATT
TTTCCCTTTGAAAGCAGCTTAGTCTTCACAATGAATCATTAAAAAATAATAATAATAACAAGTTGTTTTATTTAT
TTGGCCATACTGTGAGACATGTGGAACTTCTCTCACCAGGAATGGAACCCTTGCCTTGCAATGCCCCCTGCCGT
GGAAGGGTGGAGTCTTAACCACTGGACTATAGGGAAGTCTCACAATGTATGATTCTTAACCTCAAAAATAGGGT
GGAGTCACTGTTTCTTTTACCATTTTAAGCCCATATCGACAGAATAAACTGTCGCTTCTTATAAATTTAACATCC
CTTTCAGGAAATTTCTATTTGTAAACATCCTCAGACAAGCAAGTGAACAGAAAACCACAAATGAATAAAAGAGCA
CAGGGCAATCCGTTCATGAGATGCATTTTATTTGGAAGAGGTGGAAACAACTGATAAAAAAAACCAAGCATCTTT
CCTCTTTCATATAGCAACATGGTCATCATTCTTTGCATTTTGTTTCTTCTTTCTTTTGACTATCGGTACAGTGG
TCTGGCAGCCATAATGAACCATATGCTTGTTCCCCTAGTTAATAATGCTGCTTATTTTGCTGCTGCTGCTAAGTC
GCTTCAGTCGTGTCCGACTCTGTGCGACCCCATAGACGGTAGCCCACCAGGCTCCCCCGTCCCTGGGATTCTCCA
GGCAAGAACACTGGAGTGGGTTGCCATTTCCTTCTCCAATGCGTGAAAGTGAAAAGTGAAAGTGAAGTCGCTCAG
TCGTGTCCGACTCCTAGCAACCCCATGGACTGCAGCCGACCAGGCTCCTCTGTCCATGGGATTTTCCAGGCAAGA
GTACTGGAGTGGGGTGCCATTGCCTTCTCCA
```

FIG. 6C

AATAATGCCTTTAGACTTACTGAAATTGTGATTCTTACTTGAATGTGGCTTTCTATCTTGCCAACCTAGAGTCTG
TACTCTGGGACTTTAATAAGTTCTATTACAGGCCAGATTTTAACCATTTTGATAGCTGAAGAACTTTTGGTGTTT
GCTATTTTTCTACATAGAATTTCTTTTGATGATTAAAATGTCAAAGTGAAGGATGTGCAGCAAGTAGCATTTACA
TATCTGCTCTGTTTTCC[AG]*TCAGACATGGACACTGCTCTGGATGACTTAATAGACACTTTAGGAGAACCTGAAGA*
*GATGAAAGAAGATAACACAACATATACCGGACCGGAAGTGTCG*[GT]ACGTGACCTTGATGTCTCTAAAGATTCGTA
CCTAGTGAGTAAGAGGGCTGGTAGGTCATGGCCCTGATGCACGCAAGGATGCACCGTGTTCTGTCACTTGAAGAG
AAAGAGGATGCTGTTAGCGTCCGTGGTAGCAAATGAACATGAGTGTTGTGGTTGGAAACTGTCCCAGGGAGCTAT
GCAAGCTGTGCTGATCAGCAAACCCCGATTGCTTGTTTCTTCTGAGACTACAGCTGGGATGTACTCTGTTGAGTC
ACAAAGACTTACTTTCTGTCTTCGAGGTTTACATCCTCATGGTTTCCAGATATTTCCATCCTGTGACTTGAGCTT
ATTCTGACGTCTAGATATTTTCTGCCCGCAGTTCATTTCTACTCCTGATTCATAAAAAGCAATTGTATATTCTTT
GGTATTAAGAAAGATGTTCCATAGATTGGAAGAAAATATTGCAACAGACACAACAAAGGACTTGTTTCTAGAGTT
TATGAAGAATTTTTGAAAGTGAGAAAAAACAATCCAGTATAAAATTAGGAGAAAATTTGACCAGTAGACACATGA
AAGTCTCCCTAGTAATTGGGAAAATGATACTAAAACGCAGAGGGATAGCACTTCACACTTACCTGATTGGCAGAA
GTGTAGACGTCTGACACGTGACAGAGGCTGTGGTTGTCACCTGAATATAAGCATTCCCTCTAACCAGCACTTCCA
TGTCTAGACAGATTCCCGGGAGGGGGGCCTTGCACAGTGTGTAAGGAGTTATAAGAACAGGTGAAACATTTGGAA
ATAATTGCATTCAACAGGAAACAAGATGATGACAAGTGGAATGCTTTATAGTGGTTAAAATGGTTTGTTCATGTA
TCAATATGGTTTCATTACAAAAGCATAATTTTTGAATGAAGAATAGTACATTGCAGAATGATAGTAGAATTTGAT
CTGATACCATTTATGTAACACTTGAAAATAGGCAAAATAATGGTGTATATTGTTTATGGATACTTATATGTGGAA
TAATTGTTTTACAATATACTCAGCTTTATACTGATGGATGTGATAAAGTTTGGGGTGGTGGCTATCTCTGGAAAA
CAAGGAAGAAAAATTGGATTGGAGAGTGCTAAAACAGAGATATCACTCTGACTTTTTTTCATTACATAAGAAATA
GCTAGATCTATTGAGTTATATAGAAATTCACTGTTACCAACTACTCTTTTATAGGTATATAAATATTAGATAATG
CAAATTATTTAAAAATAAAATGTATTTTATATAGGAATCAAATTTAATATATTGGTTTGAATATTTTATAGCATT
ATTTATGGGTTAAGCCAATTAAATATGGGCAAGTATCTGTAGAAACATAAAATTTCAGAGTTGCATAAACTGCTG
GCTTCTTAATGATTTGTATTTAATCTCAATAGTTCCATAAGTTAATAATGCAATAGTACTTTGATTTAAGAGTTA
TGTATACAACATTCTCAGCTAAAATCCCTATACGTACTTTTTTTTTTCCCT[AG]*GATCCAATGAGTTCTACCTACA*
*TAGAGGAACTGGGTAAAAGAGAATCCACACTTCCTCCAAAATATAAGGAACTTCTGAAT*[GT]AAGTTAAACAGTTA
TGTATTTACACCTTATTGTTTTCTCTTTGGAATTATAATTTTTATCACATTAATATATCCAATTATTTTAACTTA
GATAAAATAAGGGGCTTGTGAAACTATCATTACTCTGAAGCTCACCGTATTAGTTTGATGGGGCTGCCATGTCAG
AGTGTTACAGATTGGATGGCTTAAACAACAGAAACTTACTATCTCACAGTTCTGGGGGCTCGAAGACTGGAATCA
AGATGTGGGCAGAGTTGGTTCTGTTTCAGGCCCCTCTGCTTGGTCTCCACATGTGGATACCTCCGTGTGGAATAA
CTCTACATCTTCTTTCCATGTGTACATATCTGCATGTCGTCTTTTCTCTATATGGATCGCTGGGTCACTTCCCCC
TTTTATAGGAACACTGGTCATATTGAAATAAGACTGATCTTAATGTTGTCATTTCACCTTAATTACCTCTGTAAT
TAAATTCAATACCACTTCATGGCAAATAGATGGGGAAACAGTGGAAACAGTGGCTGACTTTATTTTTCTGGGCTC
TAAAATCACTGCAGATGGTGATTGCAGCCATGAAATTAAAAGACGCTTACTCCTTGGAAGGAAAGTTATGACCAA
CTTAGATAGCATATTCAAAAGCAGAGACATTATTTTGCCAACAAAGGTCCATCTAGTTAAGGCTATGGTTTTTCC
AGTGGTCATGTATGGATGTGAGAGTTGGACTATAAAGAAAGCTGAGCGCCGAAGAATTGATGCTTTTGAACTGTG
GTGTTGGAGAAGACTCTTGAGAGTCCCTTGGACTGCAAGGAGATCCAACCAGTCCATCCTAAAGAGATCAGTCCT
GGGTGTTCATTGGAAGGACTGATGCTAAAGCTGAAACTCCACTACTTTGGCCACCTCATGAGAAGAGCTGACTCA
TTGAAAAGACTCTGATGCTGGGAAAGATTGAGGGCAGGAGGAGAAGGGGACAACAGAGGATGAGATGGTTGGAT
GGCATCGCCAACTCGATGGACATGGGTTTGGGTGGACTCCGGGAGTTGGTGATGGACAGGGAGCCTTGGCGTGCT
GAGGTTCATGGGGTCGCCAAGAGTCAGACACGACTGAGCGACTGAACTGAACTGAAAGGCCCCATCTTCAAATAG
AGTCCCATTCTGAGGTTTTGGGGGATGGGACTTCAGCATGTGAGTTTGGGGAGGATACAGTTCAGCCCATCCCAT
TCACTGAGGTATGCATTTTGCTGACTGTAAGGATTAATCTTGCCTTCTCAGCATCATCAAACTAATATTTGTTTC
[AG]*AAAGAAGAAGGGATCGCAGGGCCTCCTCCAGACTCCTTG*[GT]GAGTTTACATAAATGTCTTCCAAGATCAGAT
TTAACATTTTTCATATCTTTGGTTGGGGGAATAGTTATCAATTCTGTATTTTTGGATTATGACTATAGTGATCTC
TGAATCAGATGAAGTTTCCATCTATTCAAAGGAAGAGGGTGGGGATGGGGGTCATTTCAGTGCTTGTTTATTTCC
TAATTAGTTCTTTTTTGAGGGAAAGAAGAATGGGACAAGAAAGTTTTAGGACAGAATAAATATTATTAAAAATAA
GATGAGAATATCCTACCAGCATAATAACAAGTACGTTGAGAGAAACAGAAAAATAATATGCACTGAGCATCCAAT
TTCCTCCCAAACATAGGCTTTCATCTGAGTTATTTCATTAAGTATCTCCTTTGGTAGTCAAAGACTTGCACGAGT
GCATTCACCATTTGCTGGGTTTGTAATCTGTTCTGTCACTTAAATGGTTCCCATATGTGACCCGTCATGCTGCCT
GTTTCTTT[AG]*AAACCCCTGGGGCCCAATGATGCCATCGATGCCTTGTCATCCGACTTCACCTGCAGTTCCCCTAC*
*AGCTGATGCAAAGAAAACTGAGAAAGAG*[GT]ATGGTTTTAATGCCCTTAGGGAAGCTTGTTAGAAACTACCTCCC
ACTTTAAGACAACAACTTTTTTTTAAACTTCATTTTTCACTTCACTGCGTCTTCATTGCTGTGTTCGGGCTTTC
TCTAGTTGGGGCAAGCGAGGCCTGTTCTCTAGTTGCGATGTGTAGGCTTCTGCAGGGGGCTTCTCTTGTTGCTGG
GCCGGGGCTCTAGGTGCACAGGCTTCAGTTGT

FIG. 6D

```
TGTGGCTCGAGGGCTCTAGAGCACAGGCTCAGTGGTCTTGGCGCACGGGCATGGTTACTCCAATGCATGTGGGAT
CTTCCCTGGCCAGGGAGCGAACCTGTGTCCCCTGCATTGCAAGGCGGCCTCTTAACCGCTGGCCACCAGGGAAGC
CCCAAGATGCCAAGGCTTTTTACTTCTGGTTCTTACCGTTTGGTTCATATGTTTCCTTCATCTGCCAGTCAAACC
TTCTTCTGTATTTTATTTTTCAGAAATCTACAGAAGAGGCTTTAAAAGCTCAGTCAGCTGGGGTGATCAGAAGTG
CTGCTCCACCCCAAGAGAAAAAAAGGAAAGTGGAAAAGGTATCAATAATTACTTCTTTGAACTTCAGCACGGTGC
CCTGGATAGCAGTTTGGTTTCCTGAGGCTGATCCAGCTGACTGGGGGGAGGTCTCAATAGTGCATTATACCCGT
AGACCTCCTTTACTCCCCTCAGGCCTCGGGCCTGCGTGGCATAGTGAAACCAGTCAGGCTTATGTTGGTCGGGCA
GGCCTTCTCTGTTTCTACAGATGCTTATGGGTGATTTTGGCACATGTGCCTTGGTTGTGGGAAAAGACTGTCTCA
CTGTTACATTACACAGAAGGGCAGGACCCCAGAGACACCACTCTCTGGGGACATCAGATCTTTGACTTGATTTTC
TAAAGGGCCTAGAGTCCTGTGACCCTCAAAGGGAGCGTTTCTGCAGTTACTCTGTTCACCTTGACCACAGTCAGC
TATAACCTGCTTCTCAGGAATCCTGAAAGGCGGCCCTGCAGCTCTGGACTGGATGAGAAGACCTGCCCTGTCTGC
AGATCGCCCAGATACTGCAGGGAGGAGTTTTCTGTGGGTGCTGCTCTGCCTCTGGCTCGTGGAGTGGCCAGTTTA
TTTTTTATCTGGAGGAGCAGAGAGCACCACACCCCTGAGTGTGGGAATTCCTACAGCTGTGAGCCACTTCAGGGC
CCCCTGCTTCCTGGGCTCCGCTGGGCTACAGGACAGGGTTATCAGAGTCATTTTTAAGGGACCTAAGTTTAGAAA
AAGAAACACAGTACTTTGATACGAGTATTTTACAATTATTACTCTACGTGCACCTCTCGCCTCCTAAGAGGTGAA
GTGCACACCCGTACAGGAGCCCCGTTACTGTGCAAACGGGTCCTACCCCATGTTTCCTGTCACCGGTAAGTTCTT
ATTTCTTTCTCCTTTTTTTGCTGGGTTTCAAGTAGCACTGCCTTCCTAGAGTCCTTCCTCAAGCCACAGCTCATT
CCTAGAGATTTACTGACAAAATGTGAATGTCATGAAGAAGTAGGTGGCTTATCGAGGTTGAGGAGAGCGTCTCGT
TTTTCATGTACAGAATTCTTTGCTTCTCCGCAGGATGCCATGACTGAGCACGCCCTGGAGGCCCTGTCAGCCTCC
CTGGGCACCCGGAAGCCGGAGCCGGAGCTCGACCCCAGCTCCATTAAGGAGGTCGATGAGGTACTGACCTGGGGG
TTCACGTACAAAGCCTGTTAGTCTGCAGCTTACAAGGTTACGAAACTAATGCCCAACATATGTTTAGAACTTTTG
TACCACTTTTGTTTTTATTAGAGATCTCAAATGAACTGTGCTTTGTTCTGCTGTACTTTCAGGGTCTGGCTAATT
CAGGTATTTTATTGCCAGGGAGTTAACAACCAGGAAGGATATTTGAGTGTTTGTCTTATAAACCATCTAGAATTG
TCATACTTCAAATGAACGACTAATCTCCTTTGCCAATTCTTAAGTGACACCTGGCTAAACAAGATAACATAGAGG
TGGTGGCCTGATGAGAAACAGGTTGTCTGCTCGTATGGAAATTAGAAATCTGTCTTTGCAAAAAGGTTCTAGGTG
CTTCTATTTATAAAGAAAGAGAGGAGATGGCTGCAGATGGGGGTGGGAGATCCTTTATATAACTCTGGGGAAAAG
TGTTGAAACCTTGTTGCCAATTAGAATAAAATCAAGCAATAATTGCTTTATAACTAAAAGGAATGCACGTTTAGA
GTATGGAGCTGGGGAGTTGCTCCTGTTTGGTAGAGGAGTTTTCATGTTAAGTTTCAGTTTTTAAGGGATTGCTGA
GGAGTCCTCTTGGGGAAAAGAGGAGGGGAAGCACAGGGATGTCCTGGGGCCACCCTTGGCCAGGCAGTGGTGGG
GAGACCCTCCGGAGCGCCCGCCTCCCAGCTCAGGTGGGACCTGGTGGCTGTCGCTGTCACAATGCTGCAGCCTCT
GCTGTCACTTCCTGTTCCGGGTCTCCGGAGGAAGGTGGGTCTCCGTCACTTTCAGCAGCTCCCCCGTCTGGGACC
ACCCGGTCCCCAATGGGCCAGTTTCTATCGTCAACCTTTTTGGAGGACTCACTGGGTGCCGTATGGCACGAAAGG
CTTTACGAAGGCGAAGGCAAGGGAGCGGGAGAAGCCGCCTTTGTCCTCCAGGACCAAGTAATGTACAGGGAGAAG
GGGAACTTGGATTGCAGCAGGGTGCGAGGGGGCACAGCAT (SEQ ID NO: 5)
```

FIG. 6E

```
ACCACAGTTCAAAAGCATCAATTCTTTGGCACTCAGCTTTCTTTATAGTCCAACTCTCACATCCATACGT
GACTCCTGGGAAAACCAAAGCTTTGACTAGATGGAACTTTGTTGGCAAAGTAATGTCTCTGCTTTTTAAT
ACCAGGGAATATGTTAAATTTCCTCTAGAAAGCTAGCAAACTCTTAAAATTTAAACAAAAAGAACAGTTC
CTTTTCACTCTTTCCACTAGTTTTCCTTTTAAATTATATATAAAGTATGAAGATTTTCTAACCCTCTGGA
TCCTTACATTGAGTTTTAGTACCTGATCATGAATTCACTACTTTGGTTAGTCTGCTGTGATAACCCCATA
AAGATTGATATGGTATAGGAGTCCATGGCCACTCCAGCACATTCTACGCCAGGGGATGCTTCAGAGAGGA
GGTCCATGCCTGCTTGTCGTTCTCATAAATAATGTACCATGGCATATTTATTCTGTAGTGATACCTCATT
ATTAATCTCCCCAGATTCTAGGGCTTCGCTGGTAGCTCAGTTGGTAAAGAATCTGCTTGCAATGCAAGAA
ACCAGGGTTCTATCCCTGGGTCTGCAAGATCCCTTGGAGAAGAGAATGGCAATCCACTCCAGTACTCTTG
CCTAGAAAATCCCATGGACAGAGGAGCCCAGCGGGCTACAGTCCATGGGAGCTGCAAAAGAGTCAGACAT
GAGTTAGCGACTAAACCACCACCATTTTTAGTGCTGTTAACTAGTCTGGAACTATGTCAATTCAGGGATG
TTTGTTTTCATTGCCTATTGAATACAGACCACAGTGCAGACATTTAAGATATATAAAGATCAAAGAGGAA
TAGAAAGGTATCTAGCTGTGCATATGACTCACTGTTCACAAGCCCAAGTCGGGGCACGGTCCTATATGGG
TGACTCTTCCATGAGGACTGTTTTATAGCTGGAGACCTCACAGATCCCTGAACTGGGGAGAACTACGGTG
TAATAGGATGTCCACTATATCCTGAAATAGAATATAACTGGAAACATTTTTAAAAAAAATCCTTTCATCC
CTTAATGACGGCTATTATTCTATAGAAAATAAAACTATAATACCAAAGCCTAGAAAAAGTACCTGGCTT
ATTAAAAGTGCTCATTAAATATTTTAAAATTAATCAACTAACTAAGCATTCAATGGAGAACCACGATCTT
AGGCTGAGACGTAGGTGGGAGCAATAAGGTGAGCTAGAATCAGCTAAATACCACCCACCCCACAAACACG
CACACATACATACACACTTTTGTGCCCAGTAGCTCCTTGGCTTGTGATTTAAATCCATGTCTTGATAC
TGATACAGATTATTACATAGCATGAAACTTCACATTACCCACCAGTAACTTAAAATGTAGACGTTCCGTC
CTGAAAGCCACTGATCTGCTGCGGCAGTGCACTTCTATGTACGTGCATTCGGTTGCTCGTGGTTCAGTAA
TCCAGTGAATCTTGGTGTTACTGAAGGGAGTTCTTGTAAAAGAGGTAAAACCAGTTATCCATGTATCAAC
CAGATTTGTGATGGGATGTCTCTCCCATTTCTCATCTGTTTAACACTGAACGAGTTTAACACTCTTGAGC
ATTGTTTTTTTTTTTCTCCCCCTTAGATAAGTACCTCATTGAGTATGACAGATGAAGGCTGTAAAATCA
TTGCAACTAACTTGTGCACTCTTCTTAACTTTCTTCCAAGAATATTTATTTAATTTTCTCTGCTGGTCTT
TACAAATCAAGAGAGCTAGGTAAGGGTTCTTAAAGAAGTAGCCCCGTTTTACAGCTGAAGAAACTGAGGC
AAAGAAAGTCTGGGTGGCTTCCCAGGGTCACGGAGACAGGGCAGGGACGCCTCCCCGGGACTCCTGGCTG
GCTTGTTTTTCCTCCACCTCCAGTCTCCCTACACCACCTCCTCCCGGCCGCTCACTAGGCCCTTTAATCT
GATTGGGTCTTCTCCTCAACACCCATGGAGTACATAAAGTGATGTCTTATTTTACCTGTATTATCCAATT
TTTTTTTTTCCTCTCCACTTTCTTT[AG]GCAAAAGCCAAAGAAGAGAAAGTAAAGAAATGTGGTGAAGATG
AGGAAACAGTCCCATCGGAGTACAGATTAAAACCGGCCACA[GT]ACGTTGCTCACCTCGTTGCGTGCCAGC
GGCTCGCTGCTCCTGCCCATGTGTCCCGTGGCGCCCTGTCTCCCCAGGAGGCTTCAGGGCATGTCTGG
CCAAGTTCAGATAACAACTCTGGAAACCCTGAAACTTTTATTTTCTGTCCTGAACAGTTGAACCCTTTAA
AAGAGGGTTTCCTAAGTAGCGACCATGTGTGGTCACTAAAATTCCCACAAATTCAAGTGTTTCAGCTATT
AACCATACTTGACATAGATCCTTAACCTTAAAGTGGAAGGAATAATTTGGAGTTTATATTTTCTCTAACT
GCCAATGGATAAAAGCACATAGATCTTGTAAGTGGTAGAGAAACATATAATGATTTACCAGTGTCTTCAG
TGAAAGTGGGTTTGGTTTGGTGTGAGGAGACTGGACTTATCCCTGTAATTATATTTGTCATTTATCTTTG
AAAGAATGCACATAAATGTATGATGGGAAATAGTTGTAATGCTTATATATGGAAAGTATAAAGTATTTTA
AGAAATATTCTAGAATGTGAATGTCCAAACAACTAAAACAGTTTTA (SEQ ID NO: 6)
```

FIG. 7

TCACTCAAACATATCAGAAAAAGACAGTCTCTTCTCTCATATCCTGGAATTTCAAAAACAAACTTAATGGAATAA
GAAAGCAAAATTTTTTGTTTCATTTTAAATGAATTTTCAATTTCATTCAC AG *GATAAAGATGGAAAACCACTCTT*
*GCCAGAGGCTGAAGAAAAACCCAAG* GT GAGGAAATAAGTTTTTTTCTGATACTTAAAAAAAAAATACAACTGTAA
GATATAAACAGATAATTTTCATAGACCAGATCTCACTGTGGAGACTCATATGCCAGCCTAGTATTAAGGAGAAAG
GAACCTTTGACAGCAGCATTTGGCCATTTCACGCATTTTAATGATTATTTACCTCATGAATTATTACCTATTATA
AGTTTATAGGTGATATTCATTGTACATAGGAGCTGATATCAAGAGGGCCCTCAAATTAGGTCATTAGCATTTACT
TTGATCCTATTCTTATCATCAAATGCTCTGATTCTACACTACCTTTACTTAATTTGGTATTAGCCAGCATAGTGA
CCTGTCATGATGATACTAAGCAACTACATTTATTAGTCACTTACTGTGTGCCTGACACCACACTAAATGGTGTTT
GTGTGTTAGCATTTTGAGAACTCGCTGAATGAGGAAGGCACTATTATTATCCCCACTTGACAGGTGAGGAAATTA
AGACATAAAAGGATCCTGTAAATAGCCCAAAGTCAAATAGCTAGCAAGTAGCAAGGCCAGGGCTCAAAACTCAGC
CTGTCCCTCTCTGGGGCCAAGCTTCTGAATTACATGCCATCTGTCTGTCTTAGATTAGGGCATGTGGAGATTTTG
ACCAATTACAGTAAATAAATAATACTACTTCACCAGAAGGAACTAGGGATAACAGAACTTTCCTGCCAAACCCAC
GTTCTCATAGAAAGGGAACATATGATCTATGTTTCCTCTGGCTTATTCATTACGGAAGTCAATAGGAAGTAGAAA
AAGCAATCACATAAAAAAAACCATGCAGCTCTCACAAAATTACTTTGAAATTGAAGTATCAGGAAAACTTTTAGC
TGAATAAACCTTTAACATTTTTTATGGTACTCGGTGTTCAGTATTCATTACTTGTTGTGTGACATTTATCTTATA
TTGATAAATGAAATGTATGCCCTGTATAAATTAGCTTTGGGTTTTAGATCCTAAAATGCAACCTAATATATGTTA
ACTAGAAAACTTTTTCTCTAGGAAAGAATTTTTTCTTCTATCAAAATAAAAAAAAAATATTTTTTTTCATACTA
TATAATATTCCTTATATTAC AG *CCCCTGAGTGAATCAGAACTCATCGATGAACTCTCAGAAGATTTTGACCAGTC*
*TAAGTGTAAAGAAAAACAATCTAAGCCAACTGAAAAAACAGA* GT ATGTTTCTAAAACTTAAAATCTCCAGTTTT
GGTCGTTTTTCAGTGTTTGTCTATCATCTTGAAAATGCCAGGACCAAACGTATTTTAACAGGAAGCAGCTGATGA
AAAGGCCTGTTTTGCCATATTTTTTCACATGCTGTGTTCATCTTGCCTGTTTATGGATGTGCTTTGTTTTCCCAA
GCTGACGCTGATACTCTTGCAGTTTAAGTCCTGTAATCAAGTATTCCGTTCAGGAGAGCCTTCACACCAATGCTT
TTCTTTCCCTTCTTGCTTCTGTAACTGACCTACTTAAAGCTGTCATCACTCATCACCTCAAGACGGCCGTGGCCT
CTGTCTTTGGTCTCCTTCCAGCCCACCCCATGTGTCCACTGGCATTATTCTTTCTCAGCATGTTTGTAGCCACAA
CATCCCCCTGTTCCAATGCCAAGAGCTTCCCAAAAGAGTTCCTGCTTGTTTATTTGGGTCTGGAGAAGGAAATGG
CAACCCACTCCAGTGCTCTTGCCTGGACAGTCCCATGGACAGAGGAGCCTGGCGGGCTACAGTCCACGGGGTCGC
AAGAGTCGGACACGACTGAGCGACTAAACACCACCACCACCAGCTTCCTTCCCTACCAAGATGTGTCCCCCATCA
CTAAACTCTGATAGTAAGTACTTATGTATCTTCAAGCTTTTCTCATGTGGTTCTTTCTGCTTGGAATAACCTCTC
CAAATTCTAGATCAGCTAAAATTGTAGTCAGCCCTAAAAGGCTCTGCTAAAATATGGCCTTTGTCTCCCGCATGT
CCCTCCCCAAACCTTACCACACTTCCAACTCTTAAGAAGCAGAATACAACACGCCAGGGAAGTCTGTCATGCTTT
CTTTTTATATCCCTGTTGGGACATTTGTTGCAAACAAGCTTTTAGCTGCTTTGGTCTTTACTTCTCACATGTGTA
CATATTTTTACATAGTAAATTTCTTGAAAGAAGAGATCATACACTATTAATGATCATCTGGTAAGCACCTTGCAT
ATAGGATTTGCTTCCATAAATGTCTGGAATAAGAGCAACCTGTTTGAAATTTTACTCTTGTGACAAAATGATAGT
GACTCTCAAACTTCAGTGTGCATCAGGATGACTGGGAAGGTTTATCAAAGTACAGATTACTGAGCCCCACCCCCA
GAATTCTTGATTTAGTATGTTAAGGTGGGCATACGAATTTGAATTTCTAACAAGTTCCCTAGCAGTGCTGAGGT
TGGTGGTCGCAGGACCTCATTTTGAGAACCCCCAGGATAGTCTTACCACCTTGCATTTGTACCTAGCTATTTACA
ACTGACAGGGTGCTGTTAGATATATGAACATGATATATTTAAATATTGCATAATTGCAATATATATATATATATA
CTACAGCTATATAATATTATGTTGTATAACATTATGTATTATATGATGGCAAATCATCTAAATAATGACAGTTGA
TAACAATCTTTGCGCTTACTGTGTTCCCACGTACTATGCAAAGCACTTAGCGTGTTTTGTCTCATTAAAGGCCTT
GAGATGTAGGTACTGTCATTGTTCTCATTTTGCAGATGTGGAAACTGTGTCTCAGAGAGGTTAAGTAACCCACCT
AAGGTAAGAGGTAAAACCAAGTGACGTAGTGGTAGCTGCAGAGGTTTAACGTACCTTGAGTTATTCACTGCTCAA
GATCCTTAGGCATTCAAGAAATCATGCTCACAGCGGGTAGGGTAGCAGACCGTATTGTTGGTTCATTGTTGTCC
CATTTTAATAACTGGGTATTTCAGAAGTCCTTCGTTGTGCCTGATTCTTTCTGC AG *GCATCCCCGGCCGCTGCCC*
*CTGTACCCGTGGCAGAGGACGTGCCTCGGACCTCTATGTGTTCCGTGCAGTCGGCTCCGCCCACAGCAGCTCCA* G
T GGTGAGTGACCCTCTGGGCCTTGGGAAATGTCTTGAGAAAGCAGTGTTCTTCCTCCCCTGCCCTTCCTCCTGTA
TTACCAATGTATTACCTTGTTCTAGCAAGATAAAAATTAAATCTTAGATAGCTCTATTATCCTCCAGGGAGGATA
ATACAGCTCCAGGGAGGAGCTGGAAACTCAGGCTAGATTTAAGGTTTCCACTATTTCAGGTGGTTTTGTTTTTA
ACCTCTTGACATGCTTTCTAGCTCCTCAGCTACTGTGGATAATCATGCTTCTTCACTTTCTTGTGTCTTTCAAGC
TGATTTGGAGCCCCACCAACAGCCAGAAGCACTTTTATTGACTGTCCTGATGGAAAGTCTGCACCTTTATCAT
CAGTTCAGTCACTCAGTTGTGTCTGACTCTTTGCGACCCCATGGACTGCAGTATGCCAGGCCTCCCTGTCCATCA
CCAATTCCCGGAGTTTACTCAAACTCATGTCCATCACGTCAGTGATGCCATCTGACCATTTCATCCCCTTTTCCT
CCTGCCTTCAATCTTTCCCAGCATCAGGGTCTTTTCCAATGAGTCAGTTCTTCGCATCAGGTAGCCAAAGTATTG
GAGTTTCAGCTTCAACATCAGTCCTTCCAGTGAATATTCAAGACTGATTTCCTTTAGGATGGACTGGCTGGATCT
CCTTGCAGTCCAAGATATTCTCAAGAGTCTTCTCCAACACCACACGTCAAAAGCATCAATCATTTAGCATTCAGC
TTTCTTTGTAGTCCAACTCTCACATCCATAC

FIG. 8A

```
ATGACCACTGGAAAAACCATAGCTTTGACTCTACAGACCTTTGTTGGCAAAGTAATCTCTCAGCTTCTCAATATG
CTGTTTAGGTTGGTCATAGCTTTTCTTCAAGGAGCAAGTGTCTTTTAATTTCATGGCTGCAGTCACCATCTGCAG
TGATTTTGGAGCCCCCCAAAAATAGTCTGTCACTGTTTTCATTGTTACCCCATCTATTTGCCATGAAGTGATGGG
ATCAGATGCCATGATCTTAGTTTTGTGACTATTTTAAGCCAACTTTTTCACTCTCCTCTTTCACTTTCAACAAGA
GGCTCTTTAGTTCTTCCCTTTCTGCCGTAAGGGGTGGTGTCATCTGTATATCGGAGAAGGCAATGGCACCCCACT
CCAGTACTCTTGCCTGGAAAATCCCATGGATGGAGGAGCCTGGAAGGCTGCAGTCCATGGGGTCGCTGAAGGTCG
GACACGACTGAGCGACTTTACTTTCACTTTTCAATTAAATGCATTGGAGAAGGAAATGGCAACCCACTCCAGTGT
TCTTGCCTGGAGAATCCCAAGGATGGGGGAGCCTGGTGGGTTGCCATCTATGGGGTCGCACAGAGTCAGACACGA
CTGAAGCAACTTAGCAGCAGCAGCAACAGCAGCATCTGTATATCTGAGGTTATTGATGTTTCTCCCGGCAATCTT
GATTCCAGCTTGTGCTTCCTCCAGCCCAGCGTTTCTCATGATGTACTCTGCATGTAAGTTAAATAAGCAGGGTGA
CAACATACAGCCTTGTTGTACTCCTTTTCCTATTTGGAACCAGTCTGTTGTTCCATGTCCAGTTCTAACTGTTGC
TTCTTGACCTGCATACAGATTTCTCAGGAGGCAGGTAAGGTGGTGTGGTATTCCCATCTCTTGAAGAATTTTCCA
CAGTTTGTTGTGATCCACACAGTCAAAGGTTTTAGCGTAGTCAATAAAGCAGAATTAGATGTTTCTCTGGAACTC
TCTTGCTTTTTCCATAGTCCAACAGATGTTGGCAATTTTATCTCTGGTTCCTCTGCCTTTTCTAAATCCAGCTTG
AACATCTGGAATTTCTCAATTCATATACTGTTGAAGCCTGGCTTGGAGAATTTTGAGCATTACTTTACTATCGTG
TGGGATGAGTGCAATTGTGTGGTAGTTTGAACATTCTCTGGCATTGCCTTTCTTTGGGATTGGAATGAAAACTGA
CCTTTTCCAGTCCTGTGGCCACTGCTGAGTTTTCCAACTTTGCTGGCTTATTGAGTGCAGCACTTTCACAGCATC
ATCTTTTAGGGTTTGAAATAGCTCAACTGGAATTCCATCACCTCTACTAGCTTTGTTCATAGTGATGCTATGGCC
CACTTGACTTCACATTCCAGGATGTCTGGCTGTAGGTGGGTGATCACACCATCATGATTATCTGGGTCATGCAGA
TCTTTTTTGTACAGTTCTGTGTATACATAGAATTCTGTGAATACACAGAAGAACACAGAAGAACCTTTATCATCA
TGACTCCTTTTTTCTCCCAACTGAATGGTGACAGATGGACTCACTTCCTTTCCCTTTCTTCTTTTTGTGTCTCTG
ACTTTTTGACTTTTGTATGAAGTGTGATATTTAACTGGTTGAATCTGTGTTCTTCTGTTTTCATTAGCAAGTAGA
TTCTGACTCAGAGGATACCAGCTGATGGAACTATGTTTCCTTACTATAGACTTAGTGAATCTACAGGCTAAATAA
CTATCTTCTAGATTCTTTGCAGTATCTTCTCATTAAATATTCATGAGGACACTGTGAAATCTGTTCTGATCATGT
CTCTCTTATTAATGAGGAAAATGAACTTTGAATGGACCTTGAGCAATTCACTTCACCCTTCAGAATCTCAGCTAG
ATTTAAAATAGGGTCCTGCACTCAGTCCCCCTCAAGCCTAGTGTGGATATGGGCCAGGTCTGACACTCACAGCTC
AGTTGGATCATTCTCCTGTGGAAAAATTAAAGTGGGTGAAGAAACTCCTCTCCTGGTGGAACTTGGAAAGGCTTG
CATGTGGAGGACAGGATCCTGCTGAGAAGTGGGAACAGCACTGTTTCCTGGGGAGACCAGTGAGCCCAGGTCAGG
CCAGCACAGAGGTGTGGAGCCCTTGGGATACTGGGGTCTGTGCATTTAGTTGTTTGAGAGAAGAGGGCCTTGGGG
AAGGTGTGGGACGTGTGTCCTGGGTACCCCGAGTGGGTGCTTCCTGCCAGGGAATCCTGGGTGCCATCGGCAAAT
CCCGTCACAGCCTTCCTCCTGCCTTGGACAGGACGTGACCTCCTTTTTGGCGTGGGAGATTCTCAGGGTACCCTC
CAAAAACTATGAGGTTGTGGGAGTCAAGCCACAGGCCAGAGTGGTAAAGAACAGAAGTGGGAGAGAGAATCTTGG
CAGAGACTGTGCAGGGAGTAGGCACAGAGTCAGTGACTGGAGTCAAAAAGACAGTAGCCAACATTCCAGTGCAGA
ACTCTCGTACCTAAACATGGCCACTACCTGTCGTCCTGAGTGTGACTGCCAGGGCTTAAGAGCAAGTTAGCTCCT
TTCCAACTTTACCTTGACTGTAGAGACTCAAGCATTGGAGAGCGGGAAAAAAAAAAAGAGCCATTCTCTTACCC
CCTCTCCTGGGCCTCTACTCCACCAACTCTGGTTACCACGGTTGCGGAGTTTCTCACCACTGAGGTCAGTTGGCA
TTTCTGGGGTTGTGACGCCCACGGGAGCCAGAAACAATAGGCGCAGAATGTGATAAAGGTCAGAGAACTCCAGAG
AGGCTGGAGGATGAACGAGCAAAAGCAGACAGTAAGCCAGGAGGGCGGGGATGAGTGTCTGCTGTCTGCATTCTT
GTGGTAGAAAAGAAAGTTTCCGGAGATTTGAGTTCTAGTTCTGAACTTGACAATGGAGATAGAAGCTTTTGTCC
GTAGTCCTGTTTCTAGATCCATTAGTTATTAAGACTGCTGCTTCTCCTAGCTCTTCTAATGCTGTTTCACTTATT
TCTTGAATCAGAGGACACAGAATAAGGCAGCGTTGGTTTCCAAAGATTCTGCAGCAGAGACTAGAAAACAAAAGT
GTGAGCAAGTGACTGGGATCAGGTAGCAATGAGATTGTTTGGCTAAGACTTGGGGACCCCAGCAACTCTTGGTTA
CAATCCCAAGCAGGTTGAAGACATCAGGGGTGTTGTCCCTGGGGGGAAAAAAATCTATGGAGTTTCCAACCACT
CAGTTCAGTCCAATTGCTCAGTCGTGTCCAATTCTTTGTGACCCCATGGACTACAGCACTCCAGGCCTCCCTGTC
CATCACCAACTCCCAGAGTTCACTCAGACTCATGTCCATTGAGTCAGTGGTGCCATCCAGCCATCTCATCCTCTG
TCGTCCCCTTCTCCTTCTGCTTTCAATCCGTCCCAGCATCAGGGTCTTTTCCAGTGAGTCAGTTCTTCGCATCAG
GTAGCCAAAGTATTGGAGTTTCAGCTTCAGCATCAATCCTTTTCCAATGAATAATCTAACCACTAGATGGTGATA
AATCCCTTCCCACTTAACTGCCCTTTATTCCCTGGTGATCTTTTGTGGTGCAGCTTAGCAGCAGAACAAGTTTTC
TTACTTAGGAGGGTAGCTAAGCTATAGAAAACAGAAAGACGCTTTTACTCCAATATGTACTCCATGTGAGGTCAT
ATATCTTTTACGATAAGAATAATCTTTGAGACTGTTTAATTCAGGAGCCTTTACTTTGGATCAAGACCAACTGTG
GGAAATTCATCAATTCTGCAACCCACACAGTAGAAACAATAGTTTAGTCAATGGTACTTATCCTTGATATGCATG
ATGTGTTCAGTTTTATATTCTTCATTAAAAATAAGCCTGACCAGCACCTGCTAAATTGATTTAAGTGCTGCTCAC
GTATGGATCGTGACCTATGGTTTGAAAAAGCCAGCTCAAGGCAATGGCACCCCACTCCAGTACTCTTGCCTGGA
GAATCCCATGGACGGAGGAGCCTGGTAGGCTGCAGTCCATGGGGTCACTAAGAGTCGGACACAACTGAGCAACTT
TACTTTCACTTTTCACTTTCATGCATTGGAGAAGGAAATGGCAACCCACTCCAGTGTTCTTGCCTGGAGAATCTC
AGCGACGGCGGAGCCTGGTAGACTGCTGTCTAT
```

FIG. 8B

```
GGGGTCGCACAGAGTTGGACACGACTGAAGCAACTTAGCAGCAGTAGCAGTCCTATCTTTTAGCCCAAACATAAT
TTATTCTTTATTTTCCCTTTATGCCATTTACATTCTGTGTTCATCCAGTTTTGTTTTGTTTTTTTTAATAACAC
TGTGTCCGGTGTTATTACTGTATCTTAGGGAGCATGTTTCATTTTCATCAGCTGGACCACAGGCAGACTGATCTC
ACTGTATCACTCAGGTTAGTAGGTCACACAGACCGTCATCTGAACTGGCGTGAGTCCACTCTGACCAGTAGAAGC
CACACAGAGAACGCAGGCTTCTGTGCCTACAGGCTCAGCCAGAGTCATCGCCTCCAGGGCAGGTCTGGCTGTTTC
AATGGGAAAAACGTCCTCTCGAGGGCTTTTCTGGGCCTCTTTCCTGTGCCATCTCTAGGACAGTTGCCTGAAGAT
CATGTCTTTTTCTTCTTTCCTGGCTTTCGGCTTCTCCGTGGTCCTCCCCATTCAGTGAACTGCCTTATTCCTGAA
CCAGAGTGCTGGTTAGATCTTATAAGCTTCTCAGTGCCAGCTCACAAATTGCACACTCTTAATGTTTAATGTAAG
AAGCTTGCCCTCATTTTTAACACGTCAGGTTTTTTAAACCTAGATTCTAATTCCGTAGATTTTCCAAATTATTAA
AAGATGACCTGTGCTTCTTATCTAGGCCTGAAAGAAGGATGTGCTCATCTGAGTTGTTCGTTGTAGTCTCTTTTA
AAAGGCATGGTTAACCATCTACTTAGTATACCCGCTGCTGTGCTTTC AG AAGGGCATGGTGCCAGACGATGCTGT
TGAAGCCTTGGCTGGAAGCCTGGGCAAAAAGGAAGCAGATCCAGAAGACGGAAAGCCTGTGGAGGATAAAGTCAA
G GT AATGGCAGCTCAGAAACTTCTAGAAAGGAGCTATCATTGGAGCTATGATTGGTCACCCCAACTCCCCAAATA
AATCAGTTTAAAAAAAAAAAATTCCTGCAGCACATGGCCGGCTGGACCCCTCTGTTACGATGCATGTCCTGCTTA
ATAAGTGAAGCAGAGCGAGCGCCAGTGTTTAGGTGTGGCAGTGGGTGGCCGGCGTACAGAGATCGGGCTTCTGAG
TCTCATGTTGTCCACCCGGTTTCCATTGCCAAGGACCAAGGCGGGAAGTGGTACTGCCTGCCGCTCCTCACAGCT
GCCCCTTAACCCGGCAGGCTGAAAACAGTGGTCTCTGAGCCTGCTAACCCAGGAGGATACAGCGTCAAAGATACA
GTTGCTGTGGGAACCTCACAGTGGAGTCACTGACCTCGGATTTAGTCACTCAGGCATCCACTTTATCAGAGAACG
AGGTACTAACACTGAAAACGGTTTAATTTTTATTC AG GAAAAAGCCAAAGAAGAGGATCGTGAGAAACTTGGTGA
AAAAGAAGAAACGATTCCTCCTGATTACAGATTAGAAGAAGCCAAG GT AAACAGGCCGGGATCTTTTTTTCTAAC
TCATTTTCATTCATATTGAATTTCATATACATAAAGAAGGGACATGGAACAGACCTGGGATATAAAAGTCATGTT
TCTTAGTATTTCAAACATCAAGTAGTATTACTTAACTCACATCCTGTTAGCACACCCACTGTAAAGCTAAAATAT
TTGTCAGTGGCCTGTCACTCCTTCCTTAGGGGAAAGAAGTCTAAGATTTTCTTGTCTGATACGTGGTTTGTTACA
ATACCAGAAATAAACAAAACTCAGGAAATCTTTATATGGATAGATAGGAAAACCAAAGGAAAGTAAAGTCGCTCA
GTCGTGTCCGACTCTTTGTGACCCCATGGACTGTAGCCTACGAGGCTCCTCCGTCCATGGGATTTCCCAGGCAAG
AATACTGAAGTGGGCTGCCATTTCCTTCTCCAGGGGATCTTCCCAACCCAGGGATCGAACCCAGGTCTTCCGCAT
TGCAGGCAGACGCTTGACCGTCTGAGAACCAATTACTTCCTAAAGAAGGATTTACAAAACTTAGATAAAGTTGAA
AAACAGCCCATTTGACATTGTATTATAGTGAGCAATATGGCCTTCCTTGGTGGCTCAGATGGTAAAGAATCTGCC
TGCAATGCAGGAGACCCAGGTTCAATTCCTGGGTCGGGAAGACCCCCTGGAGGAGGAATGGCATCCCACTCCAGT
ATTCCTGCCTGGAGAATTCCCATGGACAGAGGAGCCTGGCAGGCTACAGTCTATAGGGTTGCAAAGAGTCAGACA
TGACTGAGCAACTCAATATAGCCAGTGATAAATTGACCCATTTCCTTTATTTTGAGTATACAGATTGTACAGAAT
AAGTGATATGGGAGAGACCACTACTTAAGAGAATATTCTACCAGACTTTATGAATAATGCAGGAAAATCAAATTG
ATACTCTTTGTATTCATCGATTTGCACTAGTCCATTTATGTGGCAAAGATAGGAACTATACTGAGCGCTCTCCCT
GATCGAAAGTTTATTATGCTGGGTCCCTTTAGTCTGCTTCCTTTCTGCATTTCACAATTCAGTCGAAACCATGGC
ATTTCTATTTGTTTGGGCTTGTATGTTTATAAGGTTCTTAGACCACGTGGCCCGTAAGTAGCTGTCACATTCGAT
AAAGCTGGTCAAGTGCCTGTAACTCTCTTTAGAGTAGGAGGTTGGAGGTTGGTTACTTTCTCTCTCCCTTTGCTG
GATTTTCATCGTAACTTCTAAGAACGTGGCCAGTTAGCTTTCCTGACCACTTTATTCTGTGGTTGTCTCATCCTC
AACTATGGATCTCACCCATTATGAATTACCTATGGCTTCATAACATGTCCAGGTGCTGCTTGATTTCGGGGTTAA
ATCTTGTGTTGTTCTTCAACTGCTCCCATCAGGCCTCCTCAGGAGAGTCAGCTCCCAAGGTAGACTGCAGGTGT
CCCCTTCCAAACTTGGGATGATCTCAGTGTGAGTGTGGAACAAGTGTGCCCCCTGTCCCCACTCCTGTGTGCCCC
TTGGGAGATTTGCTGCCTTGGCAGCTAAGGGGTGGCAGAGAGCGCACCCTGGGCTCTGTTCCCCTCCTAACTGGA
CAGTGATTAGAAGGTCCATGAGGACGCAGAGGACGTGGAAATGGGGGAAAGCACTTTGAGAAAAGGGAAGCTGGT
GATACTCTTGACCTCTGCATCTCCTCTAATGTTAAAGCAAATGAAAACCACCTTGATCAGTGTATCAGGGGAACT
GTGCAGTTGACCCTGGAGTGACACGGGTTTGAATTGCCTGGGTGCACTTCTGTTGGACTTTTTTCACTAGTAAA
CACTACAGCATCTCACCTTCTGTGGTTGACTGAATTCACAGATATGGAATTGAGGATACTGAGGGCCAGGTGTAA
ATTACACATGGATTTTTTCAGCTGCTTGAGATGTCCGTGCCCTAACCTCTGCAGTTATCCAAGGGTTAACTGTGT
GTACAAACAGAGAATCTTGTGCTTACACATTTTTGCATGTGTAGATAAATGGGATTTTACCATTTATTTATAAAT
CACCTTTTACTAAAGAGCCCCAAATGCTTTATTTTGTCCCATTACTCAGAAGTGGCACTTAGGGTCATTTGAAGG
TTGGCATCATCTGAACTGTAAGTTTTGAGCATCATACCCCTAGGGTGAGTTTTCCCAGTGCTTGGTATCGGTGCT
TGGCACAGAGTCGGTGCACAGTGGTTGGATGCACTGCCTCTAAAGTTACCCGGCTTTTCCCAGGCAACTCGTGCA
AAGCCCCCTCCCCAGGCCAGCGAGGGTCTCATCCCCGTGTTCCCTCTGTGTCCTGTGCACGCTGTGCCACACACC
ACAGTAGCCATTGTCCGTGGGCTTCTGGAGTTGGCAAGCCCCATTAGCAGCCCCCACGCCTAGGGGATGTCTGTC
AGCTGTTTCTTGACATGAGCTCATGAGAGCCTATTTCCTGGTGAGAGAATCTGTTTCCTGGAATGAGGAATCGAC
TTCATAATGTACATCATCAGCTATAACCTATCAACCTCTGATGCTATTTACAGAGTGCACACTTAGAATACATGT
GAAATGACTCAATGCCATGTTTTTCTCCACC
```

FIG. 8C

TGCAC AG GATAAAGACGGAAAACCACTGCTGCCAAAAGAGGTCAAGGAACCGCTCCCA GT AAGCAAGCCAGTTT
TTCTCTGAGTGTATCTTTCTCCTTTAGTCCTGATGGTTAATTTAGGAAGGGCAGAGCTTTCTGTGTAATGAGCTG
ATCAGCATATATGCAGTGACAGTACTTTGGAGAGGAGACTGACGAGGTAGCGTTTGCTGACACGTCTCCTGGTTC
TTTGC AG CCCTTGAGTGAAGACGTCCTCCTCGATGCTCTGTCCAAGGACTTCACTGTCCCCTCAGACACATCATC
GCCT GT AAGTCTCCTGAGAGTCCTGGTTTTAGTGCCTCACTTTTTAGGGTAGCAGAAATAAGTGGAAACCTGTGA
CTTAGAATCCGACATGAGAGATGAGGAAACAGTCATGAAATTAGCGGCCCTCAACCCATTGTGGCCATTAAAGAT
GTATTCCATCAGGAAATATGGTCCAGCACACTGGATGTTTTCAACAGTGTAACTAATAGAGCCAGTGGCCGTGCA
CTCTGTCAAGTATATGCATGGAAAGAGAATTTAAAACGGAGCTGTCCAATATATTTGAAAAATAAATGCGTAAAG
ATATGGAAAAAACTGAAAAGCATTTTATTTTTAGGGAAGATTAAGCCAACTAAGTGCCAGGATTTATTATACAGT
AATGTTAAAAAGTAAAGTTCTGATTCAGAAAGTGAAGCCAAAAGCCAATGGGAAAATAACCCATCGATGACAGAT
TTAGTATATCTTTAAAGTGAGAAACGTCATTATTTCAGAAAGATTCTAAAATAATATACTACTTAACATTAAGAA
AAAATGATACAACTGAAACCTCATCCTGTGTGCCAAATATTAAAGCAATAGTAGCACTTATTCTGGAGAAGGCAA
TGGCAGCCCACTCCAGTGTTCTTGCCTGGAGAATCCCCGGGACAGGAGAGCCTGGTGGGCCGCCGTCTATGGGGT
CGCACAGTCAGACACGACTGAAGCGACTTAGCAGCAGCAGCAGCAGCACTTATACAGAATTAAAAATAGGATAAG
TATCTAATTTAGGCAAGCAAGGCTACTGGAGACAGGCATACCCATTCACTGCTTTTAGCAGCATGATTTTCTAGC
AGCTTTTAAAGAGAAGTTATTTGGCGCAATATAGCTAGCACCATACAGAGAGAGAGCCACTTCTAAAATTTACTC
AGAGCAACTCATTACAAAGAGCAAAGCTAAAACACTTCCATCAGCCTAAATGTGCAACAAGAAATGTATAAGCCA
TAAAACTCTTAAATACTTAGCTTATTGAATATTTAGGATAATAAGCAGGAAGAGAAAATAGGAAAGTGTATAAAA
TAATGCTTGGAGTAGAAAGTAGAATAAAATGGCTCTTAAGCTGCTGTGTTGCTGTGCTTCCATTCGGATCAAGAG
AACAACCATCATAAAGCTGTCCCGAGGGTTTTATTTAAGTAATGGCATTGTGGGCATAATTTGCTACAACATATT
ACGGGTCAAATCTTTTTTCGTGATTGTTTCTTACAAA AG CAATTTGAAGATGCTAAACTTTCAGCTGTCGTCTC
TGAAGTGGTTTCCCAAACCCCAGCTCCAACCACCCAGGCAGCCGGTCCACCCCCCAGCACTGCG GT AAGCAGCAT
GGCTTATAAGTACTTGGTTTTTGAGCAGCAACTAGAGGGTCAACAAAATTGTTACCACAGTCACCTTCTGTTTCA
GAAGAGGTAAGACTGGCAAGATAGGGAGATGACAGAGATTATCTAAAATGATTAAATAAAACAATTCCTGTGAAA
GTATTTTACACACACTGAAGGAGCTTAATATATTGTTGCCTTATTAGAATTGAAGTGCAATAATGCATATTGTGT
ATATATTCAGATTTTTTTAATTGTTTCGCTTTCTTGACAATGTTTCCTTCCTTTATATTTTTTCTGATACATGCT
GTAAGTACTACTCATTATTTAACCTCAAGTTTACTTTAAGGAATTGTTCAGTGTTTGAGCTTCTCTCTGCCCACC
AAATCACAGATTCCTGGTAGAAAAGCATTGTTTTCCTCCCAGTCATACCAGTAAAAACTTGTCATTTTCATGCTA
GTAATGGAAAAACCTCAGTGTCAATATCGTTTTAATTATTTACATGTTCTGAGGCAAGACTGTGGGACCAAAGCT
TTTCCTGACTTCCTTGATTAATTTTCTTTACAATACCAAATTATACATGATGCAGGAGACCACGGCACATCAAAA
GATAAAGAGATTGCCCTAAACCAAACCCCCAGCTCCTTGGGCTGAGATAGAAGTGCTTTATGAGCTAGTTGGAGA
CGAAGTAGCTTGAGTGAAGTCAGCTAGGCTCCCTTGCCTTTTGATGTAGCATCAAAGCTTGCTTCCTGCTGCACT
CTGAGATTCTGAGTGAATTTTCCTCCTGTTGGGTCAGTCGTGGGATCATCTGAAAATATCCAGAGGCACAATGAC
AAAGCCCAGATCTGGCTGTGGGCGGCGCCACCATTCGCTGCTATAATCCTGGGCGCTCATGAAGCAGTTAAAACC
AGTAAAATGCCCTCTCTCCATGTGTCTGTGTGTATGTCTGCACACACACCCACAGTGACAAAAGTCCCTGTGCAA
CAGAAGGAAGACTCATTAATAACCAGGCTGCCGTTTACACTTCAGTTCTTAATACTCGGATTTTAGGAGTCCCTA
GAATAGTGATCGAGGCTGTTAAGAAACATCCACAATCAAAAAACCTTTTTGGCCTTCCACAGTATGTTTTAGAAT
GATCCCTTTCCCATCACTTCCTCCGTCAGAGTTTTTAGTTTTTGTTAATATTTTATTTGAAGCTGTCATTAAAAC
TAGGTATAAAGCTTTATTTACAACAATACACTTGGGAATCAGAGAGTAAACTTAGTGATTTTGTGGGGAACATAA
TGTTACATGTATTGAAGGCATCATAAGACTTCTAGAAATCGGGCCAAGAACCCCATCTTTTTAGGAAGGACCTAT
TTTCTAGGAAGAAAAATGCATCTAGGGGTGGGGAGGGTAGACAGGTGCAGAGAGGTGCTGAGTGAAGCGAGGGAC
AAAGAGCCGGCGTCTCTGCCACCTGCCCCCTCCCTGGGGAAAACCCACGAGCTTACGGAAGTCTCAGAGGCACTG
TTGGGGCTGCAGGTGACCTAAGGTGGCTAACCAGTGACTAATTCAGATTTACTTTTT AG CAGCGTGACAACAAAG
AACTTGACGATGCCCTGGATCAACTTTCTGACAGTCTCGGCAAAGACAGCCTGATCCAGATGAGAATAAACCCG
TAGAGGATAAAGTCAAG GT ACAAGAAAAAGTCATTTAAATTGAAAGTTTTTATAGCCCTCTTTTTTTGGGGGGG
AGGGGGGTATTAGTTCTAAAAGCTCTTGTAGGTCTTCACAGACCCGTTCAACTTCAGCTTCTTCAGCGTTACTGG
TTGGGGCATAGGCTCACCGTGATATTGAATGGTTTGCCTTGGAAACGAACAGAGATCATTCTGTCGTTTTTGAGA
TTGCATCCAAGTACTGCATTTCGGACTCTTTTGTTGACCATGATGGCTACTCCATTTCTTCTGAGGGATTCCTGC
CCACAGTAGTAGATATAATGGTCATCTGAGTTAAATTCACACATTCCAGTCCATTCTAGTTTGCTGATTCCTAGA
ATGTCGATGTTCACTCTTGGCATCTCCTGTTTGACCACTTCCAATTTGCCCTAACATTCCAGGTTCCTATGCAAT
ATTGCTCTTTACAGCATCGGACTTTGCCTCTATCACCAGTCACATCTACAACTGGGTATTGTTTCTGCTTTGGCT
CTGTCCCTTCATTCTTTCTGGAGTTATTTCTCCACTGATCTCCAGTAGCATATTGGGCACCTACCAACCTGAGGA
GTTCCTCTTTCAGTATCCTATCATTTTGCCCTTTCATACTGTTCATGGGGTTTCAAGGCAAGAATACTGAAGTGG
TTTGCCATTCCCTTCTCCAGTTTTCATTCCAATCCCAAAGAAAGACAATGCCAAAGAATGCTCAAACTACCGCAC
AATTGCACTAATATCACACGCTAGTAAAGTAA

FIG. 8D

```
TGCTCAAAATTCTCCAAGCCAGGCTTCAGCAATATGTGAACTGTGAACTTCCAGATGTTCAAGCTGGTTTTAGGA
AACGCAGAGGAACCAGAGATCAAATTGCCAACATCTGCTGGATCATGGAAAAAGCAAGAGAGTTCCAGAAAAACA
TCGATTTCTGCTTTATTGACTATGCCAAAGCCTTTGACTGTGTGGATCACAATAAACTGTGGAAAATTCTGAAAG
AGATGGGAATACCGGACCACCTGACCTGACTCTTGAGAAACCTATATGCAGGTCAGGAAGCAACAGAACTGGACA
TGGAACAACAGACTGGTTCCAAGTAGGAAAAGGAGTACGTCAAGGCTGTATAATGTCACTCTGTTTATTTAACTT
ATGTGCAGAGTACATCATGAGAAATGCTGGGCTGGATGAAGCACAAGTTGGAATCAAGATTGCTGGGAGAAATAT
CAATAACCTCAGATATGCAGATGACACCACCCTTACGGCAGAGAAGGCGATGGCACCCTACTCCAGTACTCTTGC
CTGGAGGGTCCCATGGATGGAGGAGCCTGATGGGCTGCAGTCCATGGGGTCGCAAAGAGTCGGACATGACTGAGT
GACTTTACTTTCACTTCTTACTTTCATGCATTGGAGAAGGAAATGGCAACCCACTCCAGTGTTCTTGCCTGGAGA
ATCCCAGGGACAGGAGGAGCCTGGTGGGCTGCTGTCTATGGGGTTGCACAGAGTCGGACACAACTGAAGTGACTT
AGCAGCAGCAGCAGCAGCCACCCGTATGGCAGAAAGTGAAGAGGAACTAAAAAGCCTCTTGGTGAAAGTGAAAGA
GGAGAGTGAAAAAGTGGGCTTAAAGCTCAACATTCAGAAAACGAAGATCATGGCATCTGGTCCCATCACTTCATG
GGAAATAGATGGGGACACAGTGGAAACTGTCAGACTTTATTTTTGGGGGCTCCAAAATCACTACAGATGGTGATT
GCAGCCATGAAATTAAAATACGCTTACTTTTTGGAAGGAAAATTATGACCAACCTAGATAGCATATTAAAAAGCA
GAGATATTACTTTGACAACAAAGGTCTGTCTAGTCAAGGCTATGGTTTTTCCAGTGGTCATGTATGGATGTGAGA
GTTGGACTGTGAAGAAAGCTGAGCGCCGAAGAATTGACACTTTTGAACTATCATGCTGGAGAAGACTCTTGAGAG
TCCCTTGCAAGGAGATCCAACCAGTCCATCCTAAAGGAGACCCGTCCTGGGTGTTCATTGGAAGGATTGATGCTG
AGGCTGAAACTCCAATACTTTGGCCACCTCATGCGAAGAGTTGACTCATTGGAAAAGACCCTGATGCTGGGAGGG
ATTGGGGACAGGAGGAGAAGGGGATGACAGAGGATGAGATGGCTGGATGGCATCACTGACTCGATGCACATGAGT
TTGGGTGAACTCCGGGAGTTGGTGATGGACAGGGAGGCCTGGCGTGCTGCGGTTCATGGGGTCACAAAGAGTCAG
ACACGACTGAGCGACTGAACTGAACTGAACTGATAGCCCTGACTTGCCTGCAATCGGTCTTCCCTAGTGGCTCAG
CTGGTAAAGAATCCACCTGCAATGCAGGAAACCTGGGTTTGATCCCTGCGTTGGAAAGATCCCCTGGAGGAGGGA
ATGTTAACCCAGTATTCTTACCTGGATAATTCGTCATTGACTTGATGGACATGAGTTTGAGTAAACACCAGAAGT
TGGTAATGGACAGGGAAGCCTGGCATGCTGCAGTCCATGGGGTCGCAAAGAGTTGGACATGACTGAGTGACTGAG
AATAATTACTTAAAAGCTTATTTCAGTTTAAAATACAAGTAGAAAATTCATAGGTGTGGAATGACAAACAGAAGC
ACTGGGTTTGCTTTTTTTCCATCAACTGGAAATCTGTTGACATTGTTGCTCTAAGTTACTTATAAAACTTAGAGG
GACTATGTTTGCCTCAGAAATATCCAATAAATGCTGAATGCTGCATTTTCGAATGTGCTAGATGAAGGTAGAAC
AGAATAGTAATTCTGTATGTTCAATGTTTAC[AG]GAAAAAGCCAAAGCTGAACACAGAGACAAGCTGGGAGAAAGA
GATGACACCATCCCACCTAAATACCAACATCTTTTGGATGACAACAAGGAG[GT]AAATGAAGGTGGTGTCCAGGTT
GGATCTATACTCCAAAGCTTTTGAGATTCAAACCTCACTTGAACAGAACACTGTAACAATAGCATAAAAATGTAA
CATGACTGACACATTTAATCTGTCCCCACTGAGCAGGCTGTCTAGAATTCTGTTTAATATTTATTTGAGCCAGTA
TCCTTGCATGTTTACTGTGCTGGGCACTGTGGCGTAGAGAGAATTGAAGAATGTTCCATCACTCGCTGATGCTTA
ACAGTGATTCCGAGGCAGGTACACAGAAGAATTCTCTGCAAGAAAGGCTGTAATAACAATGAATGATATTTGTA
ATCTTACCTGACACAGAGTCTCTCTGTTGAAGCAGAACAGAAAAAGAGCTAGGATGGAAATAATTCATGGGGCAA
ATACGATCCAAGGCCTGCTGTCTCTCTTTCTTCCCCAACACCACCACCACCGGTGCTGTTGAGAACGAAGACCGG
CAAAACCATATTTCCAATTGAAAGCTCTGTTGCTCTATCTCAGTACAGCAACAGTATCGTCAAGAAGTTTATCTG
TCTTTGTGTCTCTCCTGGTCAGCCTGCTGTGTTCCCTGCCCCTTCCTGTTTGGCTTCTAGATATTAAATAACCCT
TTCCAGATCTGTTCATCAGATAAAAACAAGGAAGTCCAAATGACAGTTTCTGTCTCTGCACTGATGATTTGTGAA
GGGTTTGACTGTATAGAATACTATCAGCTTCACTGTCTTCTGTTACAGAAATCAGTTCCCCTCGCTTGCATTCAG
CAGTCATGACAGCGCTTGTACACCCTGCTAGAATGCCCCTGCTCTGATGGTCCCATCTGACCCTGTTGTGTTCTT
TGGGAAATGTGTTCATTAGTGTCCTGGCCTTTGCCGATGGGAAAATCCCTGATGAGTTGTCCTTGGAATCCTCAC
TGAAAAAAATCACCTACAGACCATTTCAGTGCCTCAAATCCTTTTGAAGTGTAATAAGCTGTAGTGGATACATA
TATAGTAAAACAGCAAATAAGACATAAAAACACAAGTTACCTTTTGTGATGTTTAACTAGAGTTAAGCAGTGAC
AGAGTTGCTAAAATAGTATTTCTTTCACTTCCAGGAACAGATTCATCCTTTGCGTTTTCCCCAAGGCTATTGAAA
TAGTTATGAGATAGTCATTAAGCAAAGCTGGTGAAGAGATAATACGGACCCAGGTTTATCAGTTATGCAAAGTAT
ACAGTTGTCCCTTGGTATCTAGGGGGGTTAGTTCCAAGACCCCCAGAGACCAAAATCTGAGGGTACTTTAGATC
ATCTCTGCATTACTCAGAATACCTAATACAGTGCAAGTGCTACATAAGTAGTTGCTAGCATGTGGCAAATTCAAG
ATTTGCTTTTTGGAAATTCCTAGAATTCTGTATCCCCAAATAGTTTCAATCTGCTGGTTGGTTGAATCTGCCAAT
GCAGAAGCCACAGATGCAGGGGATGACTGAACTCCACTGGATAAAGATCATGTAAATACTGACTTACACCTGAG
TAAAACCTTTACAATTTGTTTAACCAACGGTCTGCTTTGTTTCTA[AG]GGCACACCCGGGAAGCCAAAGGCATCAG
AGAAGCCCAAGGCATCAGAGAC[GT]AAATATCATAGCTGTGTATTTCCAGAAACAATTTTTTTAACCTCTAGCTGCAG
CTTTCACATTTTAGAAATCTAAAATTCAGTGAATGCCTACCTTGTGCTTGGTCTGATGCCAAGGCATGTATATTA
TATATTATTTCTGTCTTCCCAAGAGCCACTCAACATAGGCAGTTCCATTTTCCAGATTAGAACATCATAGCTCAG
AGAATACTCAGCACCTTGTATAACAGAGTGGAAGAAATGGAGCTGTCAAGATTTTCCTGTTGTAAGATCTCTTT
TATAATAGTTTGTTAGGAAAAGAATGCAGCA
```

FIG. 8E

```
AGGCTTTCTTTGAACACATTTTCAGGGCTGTGGGGAAATAACCCACAAAGCATCTTTCCCTTGCTTCTCCAAAAA
GCAAATCTTGATGGTTATTTCTGTTGATATCTCAGAAACCTGCAGGTGCCCAGGACCCCATTGATGCCCTCTCAG
GGGACTTTGACAGCTGTCCCTCGACTACAGAAACCTCGACAGACACACCAAAGGTACTGGGCTTTTTCTTCTTGG
CTTTTGTTTTTAATGTATCTCTGTACAAACAACACACACACACATTATATAATTTTTATACCGTAAAATAAACTGA
TTAATGCCCTAGGAAACTTGAAAAAAATTCTATTTCTCCCCAAACACCATTATTTGGTGTTATTTCTTGTCTTTT
TGCATATGTAGGTTTTACATAATTATACTTAGATTCTATATATATATTATATAGAATATATATATTATATATAGA
ATATTCTATATTCTCTACTTAGATTCTATATATAAAACATTTCTTAAGAGTATATCATAAATGTTTTCCATGTTG
CTTTATAAGCTCCATTGCCACCATTTTTGATTGCCACACTATATTGGCTTGTAACAGTACGACTTTATCTGTGGT
CATTTAAAAGGAGAGCAGTCCCTCACTGTATACACCATGCCCCTTGCCCTCTGGGCTTTCCTCCCCTTTTCTGCC
CTGAGCAGCTCTCCTCCTTACCCCTCAGAGACCAGTTCAAGCATCAGCTGCTCCAGGAAGCTCTCCCTGTCTGCT
TCTCCCTTCCCAGGTCAGGGGCTTCTCCTCTGCCATCCCTGCGTTGTGAGTTACCTGTCCCATGGGCCTCACTCC
ACTGAGCTGTGGGCTTTAGATAGCAGTCATGTGTCTGGTAGCTCTGTGGCCAGCATCAGCAAAATGCCTGGTGCA
TAGCAGAGGAGATCGAATGTGAATGGGGAAAAAGTGTAATCCACCAAATAGGAGGAAAAGTGAAATGAGTGTCC
TCCGTTGTTATTTTCAGAATAAAATGCATGTGGTTTCAGCGGGTATTAAACATATTTCCCAGTCACTGAATTGCG
AGTCTTCCCTATCTTGCGTGATTTAATTTCTAGATCACATCAGTATCCTATTTCTCAACTCCTAGAACCTCATCA
ATAATGCCTTTTTGGTGAATGGACTTTACTTTTGTATGTGACTGGCCCTAGCTCACTCTGGTTGCTTCCACTGTT
AGATTATTCTTCCATAATTCTGAAAGCAGTGTCCTCTTGGCACATAGAAACCAGTCCTGATAGAACCAGGCTCTA
TTTTGATAAGCAAAATACAGTCTGAGTGCATCGTGAAAATTGGCAGGGCGTCAACGTGAGTCGCCTTTTCCTCAT
TTTTTTTCCCTTCTTACCTCCCACTTTGAACACCTGTGTGTACATTCACTGTGGTTCAAAAAGTCATGACTGTGAA
ATACTCAATTTTTCATTATTTAAACTGGAGATTCCAGGCTCCTAAAAAGAAGAGTCTGGATCGATTTGCTTGCAG
CAGCAGTTAATTGCTAGATGGAGTGTTGACTGCAGCAGCTTCATTACATCTCCTCTGCTCTAGGACAAAGACAAG
AAGCCTGCTTCCAGTGCCGAAGCACCTAGGAATGGCGGGAAAGCAAAGGATTCCACAAAGGTAAGTTCAAAGCTC
GGTCGTGTCCGACTGTTTGTGACCTTCATGGACTGTAGCCCGCCAGGCTCCTCCATCCATGGGATTTTCAGGCA
AGAGTACTGGAGTGGGTTGCCATTTCCTTCTCCAGGGCATCTTCCTGACTCAGGGATCCAACCAGGGGCTCCTGC
ACTGCAGGAAGACTCTACCATATAAGCCACCAGGGAAGCCCCCACCAGAGCAGTAAATAGATGACAAATGAGCTT
GGCAATTACAGGGAACGGCACGTTCTTAGTCATTTACTTTCTGCTTGGGGTCTATTTAGAATAAGACCATTTTTA
AGTACTATCTATACCTTAGAACATCTTGCCAAAGAAACTGAAGTTTTAAAGATTTTTTTTTAATTATTTATTTT
AATTGGAGGTTAATTCCATTACAATATTGTAGTGGTTTTTGCCATACATTGACATGAATCAGCCATGATATATAT
TATTTTTTAAAGTAATCGATACTTAAGTATCAATATTACTTATCAATAATCAGTATTCAGTAAGTATCAACTTAC
TGAAGGAACAAAGATTCGGAACACAATTGAAGCGTGCTGCATTGCCAGCCCTTGTCACACAAAGTCCCAGTGTCA
GCTGTGCTGGTCTGGGGTGAGCGGAGGCCCTCTCCCTTCATCAGCCCCAAACGCCTTGCACTCCCTTGTTGCTAC
TCTCCCCTACCGTGTGCAGAAAGCCTCGCCTTCTACTTAAAGAGAAAACTGAGGGTGCCTTGCAGGAAATAACCA
AGACCCCTTCCTATCTTCCTCCTAATAAACCCACTCTCCCCTCCTTGTCTGCAGCCCCTTCTCTCTCTTTCTCAA
GGGGTCACTAACTCTCTCCAGGCCTCCCTGGTTGCTCAGCTGGTAAAGAATCCACCAGCAATGCAGGAGACCAGG
GTTTGATCCCCAGGTTGGGAAGATCCCCTGGAGAAGGAAAAGGCTACCCATTCCGGTATGCTGGCCTGGAGAATT
CCATGAACTGTGTAGTCCATGGGGTCCCAAAGAGTCAGTCCTGAATATTCACTGGAAGGACTGATTCTAAAGCTG
AAACTCCAATACTTTGGCCACGTGATGCAAAGAACCAACTCATTGGAGAAGACCCTGATGCTGGGAAAGATTGAA
GGAGCGGGGAGAAGGGGACAACAGAGGATGAGATGGTGGGATGGCATCACCAACTCGATGGACATGAGTTTGAGT
AGGCTTCGGGAGTTGTGATGGACAGGGAAGCCTGGCGTGCTGCAGTCCATGGGGTCGCAAAGAGTCGGACATGG
CTGAGCAAGTGAACTGAACTGTCTCCAGTATCTCTGTCTCAATTCATCTCCTTTGTAGCACAAACATATTCAAGC
TCTTCAACAACTCAAAGCCCTATTCCCTCCATCCCTTCACCTCCTTGGAAGATCTGTCTGTGACCCCTGCTCCCC
CTCCTTGGGCTCCCCCTGAGAACAGCAGTGACATGCTGGTTGCTGTACTGTTTCCTTATCAGCCCTTAGTTTGCT
TGTTCTCTCGGGGTGTGCTTTGGGACGTTAGATTTGATGCTGTAATGACTGAGACTTCGGACGGGTGAATATTT
TATAACTTCACCTGCCCAAAGACCCAGACTAACACTTCCTACCTCACATTTCCACTTGGATAAACATTGACAGTA
TAGATCCGTATACATTATTAGATCAAGTCTAAATCGCCACCAATTATTAAGAAAAAAGTCAACAGTTTGATTACG
ATGTTAGTCATCATAACAGCAAATTAAGACATGTTAAAATATGTGTGCGTGGCAAAGGAGATGACACCACCAGAG
AATGTAGTTTCTGTAAATCTTGGAACAGGAAAGTAGTATAGAGAACTAGAGAAGCTCTTACAGTCTCTGAGATCC
AATATACTCATATTAAATACTAGTAGTCTTTCCTCCCAAGTGGTACCTCATTTTTCACATTGTTATAGAAAGCAG
AACTGAGACTAATGAGCAGATCTGGTTTCTTAGAGCTGGGCGTTAATGCAGCATGGCACTTTGAAAGTTTCCTAT
TATTAAAATGACTCAAACTGTGGTTAGGAAAGGGATGGAAGTTGGATTGGATAAACAACTTCTGGGTCCCCTCCA
ATTCTAAAACCATAGTATTCAAATGGTTATGACTGTTAATTCCAATTATAACGAGAAATAAAAGATACAGGTCCA
GAAACAATAATCCAGCTGCATCCAAACTCTTAAAAAGCAAGATAGTGAGTTCTGGTTCAAGGTGGTGATGCAGAA
AAGATCAGCTCGCCTCGTACCATGGAAACACCAGATCTACAGCTGCATACACAACAATTTCCTCTAGGAAAAAAC
TCCTACAGTGATATGAATGACTCCTATCCATCAGGCCAATAAAAGAAGGCCAGCATTAAAGAAGGTAGAAGAGGC
TGGGACAGACTCTTGACATAAATCCAGTCCC
```

FIG. 8F

```
AACACAGTCAACTCACCGTCAGAAGGAAACTCAAAACTCAGAGCTTCTCCTGAGGAGCAAATCAGGTTGAACCCC
CAAGGCAGCACCCCAACATTTAAAGACCACCTGAGAAATGAGCACACAAAACCTCTAGCTTTGGGAAGCCAATGG
AGTTTGTGTCCAGAAGGCCATAGCAAACTGAGGAAAGCTTCTTCAAGAGCTCATGAGCTCAGACGCACCCGCCCC
CCCAACCAAGCAATCAGAGCTACAGTTCTTAGCCGGCCACTATCCCCAGAGTGCTGCACAGACCACAGACCAAAA
CACGCCCCAGCTTTCTGTGTAAGAGGCCTCCTTGCTTGTCCTGAAGCTCCGGTGTGAAGCAGGCTTCCGATTT
GGCAGAAGATGCCCAGATGTGCTCTTAGGAGACATCAGCTGGGTGCTCACCACCACTGAGCTATTTCTCCATCTC
ACTCCAGGCCACCAGTATCTCCCAGAAAGGGGCTTTGACGCTTACCTAGACGCCAAATTTTGTAACTGCCCCC
CAGAGGGATACTTCCTGATCACCTGCTGTGGCCCTTCAAGACTATTATGTTTGTATATTGAACCAATGAAGATAA
AATAGGCTGCTTACAGTGTTTGGAGATAATCAAGAGTCAGGGCAGGGTTAACAGTAAAGTTCATCTGCTACACG
AGGCTACTCCTTCAAGACTGGAAGAGGTGGCTGTTTTATCTAATGCACACAGACCAACACAGAGAGTCAAAGAAA
ATGAAGAAATGGAAGAATACATTCCAAACGATTAAAACCTCAGGATAGAAACCTTAATGAAGCGGTTTACCTGAT
GAGTTCAAAGTAACAGTCATAAAGATGCTCACCAAACTTGGGAGAAGAATGGATGAACACAGTGAGAACTTCAAC
AAAGATATAGGAAAAATACAAGAAAGTAACAGATAGTCACAGAGCTGAAGAAGACAGTAACGGAACCAAAAAACA
CACTGGAGAGGTTCAACAGCAGACTAGAAGCAGAAGTACGGATCCAGGAACTCAAGGACAGAGCAGGGACTCA
CCCAGTCAAAGCAGCAAAAAAAGATAGCCAAAAAGACTTATCAGACAATATCACGCAGACCCACACAGATGAAC
ATTTGCATTATAGGAGTCCCAAAAGGAGAAGCAAGAGAGAAGAGACCAAGAACTTATTGACATAAATAATGGCT
AAAACCTTCCCTAACCTGAGGAAGGAAACGGACATTCATAACCAGGAAGCCCAGATGCTTTCAAATAAGAAGAAT
CCAAAGACACCCACACCAAAGACACATTAAAATGTCAAAAGTTAAAGACAAGGAGGAATTTGAGTATACCAAA
AGAAAAACAACTTTTTACATACAAGGGGCCTCTGTTAAGACTCTCAGCAGATTTTCAACAGAAATTTTGCAGGCC
AGAAAAGGAGTATCATGATATATTTTCAAAGTGCTGAAAGAAAAAAACGCCAAGGATATTCTCTTCTTAGAAAAA
CTGTCATTCAGGAAAAAATTTTCCCGATAAGCAAAAGCTAAAGGAGTTCATCACCATTAAACCAGTTTTACAAG
TAATGTTAAAAAGACTTCTTTAAGCTGAAAAGGGTGCTAATTAGTAATGGGAGAACAATCAAAGTACAAATCTCA
CTGGTAAAGGTTAATATACAGCAAAATTCAGAATAATTTAATGTAAAGGTGGTGTATTAATCACTGATAAAGCTA
GTAGGAAATTTAAAAGACAAAAGTAATTTAAAAAACAGCTAACTATAATAAGGGATACACAAGATTAAAAAGACA
TAAAATGGACATCAAAAACAAAACATGAGGGTGATGAGTAAAACTGTAGAGCTTTGGAATGCATTTAAACCTAAG
TGATTGTCAACTTAAAATATAACTGTAACCCTTATGGTAACCACAAAGTAGCTGCACGAAAACCTTTGGTAGATA
AACGAAAGAGAAAGGAACCTACTGTAGGAAATCATCAAATCACAAAAGGAGAGAGCCAGAGAAAAGAGAGCAAAG
AAACTACAGAACAGTCAGAAACAGTTCACAGAATGGCAATACGTACACACTTATTAATAAATACTTTGAAAATAA
TGAGCTGAACTCCCCAGAATACAGAGAGGCAGAATGGATTAAAAAAACATGACACATCTATGTATACTGCCTATA
AGAAACTCGCTTCAAATTTAAAGACAGACTGAAAGTGAAGAGATGGAAAAATAAGCCTTGCAAGTGGAAACCAAT
GATGTTGGCCTTCAAACAAAAATGAAAGTCTAGAGTAAAACATTTAGAATCACTTAAGGTTATTTTTAGTTTAT
AAACTTCAAGGGGAAGAATTCAGTGTTTGGACTAAATAAAATACTCAAAAGGACTATCTTATTTTCCCCTGCTA
ACTGCCATCTTTTACCTTTTAAATCTGAAAAACATTTTTCCTCATAAAGCTCTTCTGGTTGATCAGTTTGGGGT
ACTCAATACAGAAAATAAAGAACTCATTGATGGTTTTTGCTTGTCCTTTT[AG]GCAAAGGAGGAAACTTCCAAGCC
AAAAGCTGATGGAAAAAGTACAAGTTAAAGTTCACACTATTTG[GT]AAGTTGGGTGTTTGTCACAAATGAAGACCA
CTGTACCTTCTACCAGCCCGTGTGTTATAGGTGAGAGAAACTAAGTCCATTTCTTGAGTATTTCATGTTCTCTTT
ATGCTATTGGCAATGAAAGGGACACTGAAATCTGTAGAGTAATTCCCTGAAAAGCAATAAATGGTGCTTCCAGAA
TGTTTAAAAACATTAATCTTGTAATTAAAAGCTCTTTAAAATATGAGGCCAGGCTTTTAAACAAAATGACCATCT
AAGTCTAGTTGACTCTTTGAAACCCAAATGCTCATGACTGCAGGTTACTGTGGCAAAGCAAAATTGACAAGTTAC
ATCTTATGGTGAAATGGCCTTACGATCTAGATATTACCCGAAACACTTGTGGGGTGAGGAGAAGTGCACGCCTAC
GGTCTGACGGTAATTGCAGGGTTTTGAGAATAGGGCAAAGGAAAAGACTGATAACTTGTGATCATCTTAGTTTTA
GAAAGTAAAGCCCTGTGTTTGATTCTACTTTACAGTAACCGAAGAGCTGGTTTGGATGAGGGAGACTCTGACATC
TGTCTTGAGAGCTAGGCCCTTATTAATGTCAAAGAGAAGAGGCCTTATTCTAAATGACAAAGCATATAACTACT
CGCTGCAAAAAAATCTAAAAGAAATAACAATGTGGATTAAATTGGATTGGCTCTCTCACCGTGATTCACTTTCAT
TTCCTGTAGAGGAAGGTATACTGATTAGAACTGCTCCAAAGATTTTCTCCAAAAAAAAAAGTTCTTCTTCTAATT
TTCTACTCTAATATCTGCTTAAAGTAAATGCCTCCTTAGATTTATTATGCCTGTAATAAGAAAATAACCTAGCAA
ATGGTTCACTGGATTTTCTTCTTTGAATTTTTCA[AG]GTATCTGCATATAAAATCTTCAGCGGGTAGATGGTGACT
TCTGAAGAAGAAAGGCTTTGATAACAGAAACAATTTCTGGGTGGCTTGGAGACAGTGGTATTTGCTGAGTCTTT
TGACCTCCTAAACATTGTCTGTTATTCTTTTCCTGAAAAGAAACTGAATTTGTCTGGTTCACCTGTGTTATTCTA
CTGAGTATTGATAAACTTTAAATTTTTAAAAATTGCCTTCAGTTGGGAGAGAAAGGAACTTTATATTTCTAAGAG
ATACATTTGATAGTTTCTTAAAGCAGCACACAAAAAAGGAAAAACCTTTGCAAACTTTTGCACATTCTCCCCACA
GTGCCTGTAAATCTCATTAGTATTTTCGATTTGCACTTATTTTTGTTGTTAGCATTTGGAAAACGATGCCTCACG
TGTTCTTCAGTGTTCTGATTTCTCATGACCCCTTTCCTCTTAGACTTGTGGACTGTGTTTGATGTTTCTTTGGGT
TGTTGTTTATAAGTCAGTCATAAAATACTGTGCATTGGGCACATGTCTCCTCTTGAGCTGCTAATCGTAGAGACC
CTGGACAGACCAGGAAGCGCCGCACCCCCCT
```

FIG. 8G

```
TTCAGGTTGAACTTCTCTTTGCCAGAGGTTAGGACTTCCGCACCTTGTCCGCAGAGACCCAGCGGGACTTGACTC
AAGTCAGAAGAGCAAAACGCAGACTCTGTCACTGCATAGCAAGTTTCAAGAATAACAAAACCTAATGCTTAGAAT
ACTCACATGGCTTGATCTCTGCCACAGTACTGCCTTAAGCTGGGCTTGCCATCCTCTCTCTGTGAAACCGAGCAG
CCGCTGTTAGCGCAGAGCCATTGCCACGTCAGTCTTGCGCTGTACAGCATGTGGCTTAATGGAAGTTGGGTTTAT
TGCCAAAAACAAAAACAAACTTCTGCTTAAAAATAAAGAAAAAAGATCTTTTTAACATTAAAAAAAATAATCTGT
TTTTTTTTCCCCCATAGCCATTTAAGAACTAGGGAGGGTCTGATATCCGACAACTTGGAAAGGTTTCTCATATTT
TTCTGAATGGTTGATGAACATAGCACTGATGAAATTAAATTATCAAAATCCCATCTTCATTTTCTGATAGTGAAC
GCAGGAAAAGATATCAGGTACACATCATAAAACTGATTTGGAATTCCTGCTTTCAGAGAGTACAGCCTTCCTTAG
CATCTGTTTAAACTATTTCTTAGGACTTGGCAATTTCACTAAAAATTAGTAGTATCACTGATACTGTCTAATGGG
GTAGGAGGCAAGCAAAATAACAATACTATTCATAATGGGTATCCAATTCTATTAATACTAACAATTCTCTTTAAA
AATCATGCATATGCCTGAGATTGCAAACTTCATCCACTTCAAATGCTCTGTCTTCATCTCATGAGAGGTAAAGGC
ATTATTAGTCTAAATCTGGGAAAGATAAGCCAGGATTATGGTAATTTAAACAGACCTTTTCAAGGCACTAACAAG
AAAATAAACACTTTTCCTGAGGGATTTTAACTATGTGTCTGTAAGTAGTACAAAGTTGTTTTAAAAAAAATGAAA
CCTTTGACATTGACAGATGTGTTTGCAAAGATATGACTCCAGTATTACTAATTTACATGCATATATCAAGTGTTT
TTTTAATTACATACCAAATCCAGAGATTTTAAGAAATGCCTGTAAAAGTAAACATTTATTTAAGGTTCTCTGAAT
ATGCCTTTTGTTTATTCAAAATGTCTTCAAGACTTGGGTGTCTGCTGGTAATTAATGATGAACTGAGTAAGCTAC
AGGATCTAAATCAGTCCTTTTTACCCATCTAATTCACAGTAAATAATTGCAAATACTTGCTTAGAGGTAAATAAC
ATTTTTTATTACCAAAAAGGGTTTTGCACATTGTTGCGGTGATGTGTGTCTCTTTAGAAAACGGACTTCTCCAAA
AGCAAATGAAAATAGGTTCCTCAGGTGACCAAAACGGAAAACCACTATGTCCATGTTTCATTACTCAAGATACAA
GATGCAATTAAAGGAAAGTATTTTACATTAAAATCTTGGCTTTGTATGTTTTTTAGAAGGAAAACACCTGGGGGG
TAGAAATGACCAGTGATTTCTGTTTTTTCGTTCTTAAACCATGAAGTCAGGCAGTATATATAAAAATGGAATTAT
AAACACATTTATGTCCTGAAAAGACCTTCTATTCCATAGTGTGTTAGAACACATTGACATTTTTCATATCCTATT
CCTTTATCTTAAGTTTTGCAATATATTAAACTCATAAAAGATTTCAACTCCAACAACACCATACCTGGTCTTCGC
TTAGGCTGATATAAGCAAGTCGTTTCCATTTCACAGTAGCTTACATTTAGTAGAGTCTGCAGTGCTCACTCGGAG
AAGGCAATGGCACCCCACTCCAGTACTCTTGCCTGGAGGATCCCAGGGACAGAGGAGCCTGGTGGGCTGCAGTCC
ATGGGGTCACTAAGAGTCAGACATGACTGAGCGACTTCACTTTCACTTTTCACTTTCATGCACTGGAGAAGGAAA
TAGCAACTCACTCCAGTGTTCTTGCCTAGAGAATCCCAGGGACGGAGGAGCCTGGTAGGCTGCAGTCCATGGGT
CACACAGAGTCAGACACAACTGCAGCGACTTAGCAGCAGCAGCAGCAGCAGTGCCCACTGGCAATAAACAACAAG
TTATTTAGGGATTATAAACCAGACCATCTCATCCTCTGTCAGCCCCATCTCCTCCTACCTTCAGTCTTTCCCAGC
ATCAGGGTCTTTTCAAATGAGTCACTTCTTCAACGGTTGGATGGCATACCGACTCAATGGACATGAGTTTGAGT
AAATTCCGGAAACTGGTGA (SEQ ID NO: 7)
```

FIG. 8H

```
   1 atggcatttgcaagctggtggtacaagacgcatgtcagtagaaaa
     M  A  F  A  S  W  W  Y  K  T  H  V  S  R  K
  46 accagtggatcgccttccaagtcaggagaaaagaaaggatcagat
     T  S  G  S  P  S  K  S  G  E  K  K  G  S  D
  91 gagaaaaaagcaacaagccttgggagcagtcagctctccagaact
     E  K  K  A  T  S  L  G  S  S  Q  L  S  R  T
 136 caggctgg tgaaaaagccc c ggtccccaaggtaactacttcctct
     Q  A  G  E  K  A  P  V  P  K  V  T  T  S
 181 gcgtcagccagcaagtcttccagtatgaatcccacagaagccaag
     A  S  A  S  K  S  S  S  M  N  P  T  E  A  K
 226 gctattccaggcagcaaacagctggaaggaccgcattctcctaac
     A  I  P  G  S  K  Q  L  E  G  P  H  S  P  N
 271 aagaaaagacacaaaaaacaggctgtaaaaacagaacctgagaag
     K  K  R  H  K  K  Q  A  V  K  T  E  P  E  K
 316 aagccacaatcatctaagccatctgtggttcatgagaaaaaaacc
     K  P  Q  S  S  K  P  S  V  V  H  E  K  K  T
 361 caagaagtaaagccaaaggaacacacagagccaaaaagcctaccc
     Q  E  V  K  P  K  E  H  T  E  P  K  S  L  P
 406 aagcactcatcagatacaggaagcaagcatgctcctaaggaaaaa
     K  H  S  S  D  T  G  S  K  H  A  P  K  E  K
 451 gccgtttccaaatcaagtgagcagccaccatcagagaaatcaaca
     A  V  S  K  S  S  E  Q  P  P  S  E  K  S  T
 496 a t accaaagaccaa t c c caggacaagatctccggtggtggaaag
     I  P  K  T  N  S  Q  D  K  I  S  G  G  G  K
 541 agcactgttcctgctgctgctgctgcagcatctgccgaaccagct
     S  T  V  P  A  A  A  A  A  S  A  E  P  A
 586 gacaagaataaagaaaataaattgttaacatcggccgtaccagct
     D  K  N  K  E  N  K  L  L  T  S  A  V  P  A
 631 gaatctaaaccaagtaaaccatctggaaagtcagacatggacact
     E  S  K  P  S  K  P  S  G  K  S  D  M  D  T
 676 gctctggatgacttaatagacactttaggagaacctgaagagatg
     A  L  D  D  L  I  D  T  L  G  E  P  E  E  M
 721 aaagaagataacacaacatataccggaccggaagtgtcggatcca
     K  E  D  N  T  T  Y  T  G  P  E  V  S  D  P
 746 atgagttctacctacatagaggaactgggtaaaagagaatccaca
     M  S  S  T  Y  I  E  E  L  G  K  R  E  S  T
 811 cttcctccaaaatataaggaacttctgaataaagaagaagggatc
     L  P  P  K  Y  K  E  L  L  N  K  E  E  G  I
 856 gc g gggcctcctccagactccttgaaacccctggggcccaatgat
     A  G  P  P  P  D  S  L  K  P  L  G  P  N  D
 901 gccatcgatgccttgtcatccgacttcacctgcagttcccctaca
     A  I  D  A  L  S  S  D  F  T  C  S  S  P  T
 946 gctgatgcaaagaaaactgagaaagagaaatctacagaagaggct
     A  D  A  K  K  T  E  K  E  K  S  T  E  E  A
 991 ttaaaagctcagtcagctggggtgatcagaagtgctgctccaccc
     L  K  A  Q  S  A  G  V  I  R  S  A  A  P  P
1036 caagagaaaaaaggaaagtggaaaaggatgccatgactgagcac
     Q  E  K  K  R  K  V  E  K  D  A  M  T  E  H
1081 gccctggaggccctgtc t gcctccctgggcacccggaagccggag
     A  L  E  A  L  S  A  S  L  G  T  R  K  P  E
1126 ccggagctcgaccccagctccattaaggaggtcgatgaggcaaaa
     P  E  L  D  P  S  S  I  K  E  V  D  E  A  K
1171 gccaaagaagagaaagtaaagaaatgtggtgaagatgaggaaaca
     A  K  E  E  K  V  K  K  C  G  E  D  E  E  T
```

FIG. 9A

```
1216 gtcccatcggagtacagattaaaaccggccacagataaagatgga
      V  P  S  E  Y  R  L  K  P  A  T  D  K  D  G
1261 aaaccactcttgccagaggctgaagaaaaacccaagcccctgagt
      K  P  L  L  P  E  A  E  E  K  P  K  P  L  S
1306 gaatcagaactcatcgatgaactctcagaagattttgaccagtct
      E  S  E  L  I  D  E  L  S  E  D  F  D  Q  S
1351 aagtgtaaagaaaaacaatctaagccaactgaaaaaacagaggca
      K  C  K  E  K  Q  S  K  P  T  E  K  T  E  A
1396 tccccggccgctgcccccgtgcccgtggcagaggacgtgcctcgg
      S  P  A  A  A  P  V  P  V  A  E  D  V  P  R
1441 acctctatgtgttccgtgcagtcggctccgcccacagcagctcca
      T  S  M  C  S  V  Q  S  A  P  P  T  A  A  P
1486 gcgaagggcatggtgccagacgatgctgtcgaagccttggctgga
      A  K  G  M  V  P  D  D  A  V  E  A  L  A  G
1531 agcctgggcaaaaaggaagcagatccagaagacggaaagcctgtg
      S  L  G  K  K  E  A  D  P  E  D  G  K  P  V
1576 gaggataaagtcaaggagaaagccaaagaagaggatcgtgagaaa
      E  D  K  V  K  E  K  A  K  E  E  D  R  E  K
1621 cttggtgaaaaagaagaaacgattcctcctgattacagattagaa
      L  G  E  K  E  E  T  I  P  P  D  Y  R  L  E
1666 gaagccaaggataaagacggaaaaccactgctgccaaaagaggtc
      E  A  K  D  K  D  G  K  P  L  L  P  K  E  V
1711 aaggaaccgctcccacccttgagtgaagacgtcctcctcgatgct
      K  E  P  L  P  P  L  S  E  D  V  L  L  D  A
1756 ctgtccaaggacttcactgtcccctcagacacatcatcgcctcaa
      L  S  K  D  F  T  V  P  S  D  T  S  S  P  Q
1801 tttgaagatgctaaactttcagctgtcgtctctgaagtggtttcc
      F  E  D  A  K  L  S  A  V  V  S  E  V  V  S
1846 caaaccccagctccaaccacccaggcagccggtccacccccagc
      Q  T  P  A  P  T  T  Q  A  A  G  P  P  P  S
1891 actgcgcagcgtgacaacaaagaacttgacgatgccctggatcaa
      T  A  Q  R  D  N  K  E  L  D  D  A  L  D  Q
1936 ctttctgacagtctcgggcaaagacagcctgatccagatgagaat
      L  S  D  S  L  G  Q  R  Q  P  D  P  D  E  N
1981 aaaccgtagaggataaagtcaaggaaaaagccaaagctgaacac
      K  P  V  E  D  K  V  E  K  A  K  A  E  H
2026 agagacaagctgggagaaagagatgacaccatcccacctaaatac
      R  D  K  L  G  E  R  D  D  T  I  P  P  K  Y
2071 caacatcttttggatgacaacaaggagggcacacccgggaagcca
      Q  H  L  L  D  D  N  K  E  G  T  P  G  K  P
2116 aaggcatcagagaagcccaaggcatcagagaaacctgcaggtgcc
      K  A  S  E  K  P  K  A  S  E  K  P  A  G  A
2161 caggaccccattgatgccctctcaggggactttgacagctgtccc
      Q  D  P  I  D  A  L  S  G  D  F  D  S  C  P
2206 tcgactacagaaacctcgacagacacaccaaaggacaaagacaag
      S  T  T  E  T  S  T  D  T  P  K  D  K  D  K
2251 aagcctgcttccagtgccgaagcacctaggaatggcgggaaagca
      K  P  A  S  S  A  E  A  P  R  N  G  G  K  A
2296 aaggattccacaaaggcaaaggaggaaacttccaagccaaaagct
      K  D  S  T  K  A  K  E  E  T  S  K  P  K  A
2341 gatggaaaaagtacaagttaa  2361   (SEQ ID NO: 8)
      D  G  K  S  T  S  *         (SEQ ID NO: 9)
```

FIG. 9B

DNA   C/C  T/T  T/T  T/T  T/T  T/T  C/C  T/T  T/T  T/T  C/T  C/C  T/T  T/T  T/T  T/T  T/T
Ladder

SEQUENCE LISTING

```
<160> NUMBER OF SEQ ID NOS: 21

<210> SEQ ID NO 1
<211> LENGTH: 16143
<212> TYPE: DNA
<213> ORGANISM: Bos taurus

<400> SEQUENCE: 1
aactgtctga aacacagcac cgcagagagc agtgaccccg aggctcacat tgtcaatgcc      60
atggcagggt taacaggttt tcttctgtca gatcttcaca aactggcagc aaccacaggc     120
agacaatcac tgcagaggag gagcctttc tagtctggct tataacattt cacttcaagc     180
ttgttataat tcacagcccc aaaccaggaa gtgctcttta agatgaacca aagacaaaag     240
caatctggcc tcctcgcaaa cgaaattcaa cagcctcctg aaaggcaatg gggtttaaat     300
ttaggactgt tcttcggttt tgattggaac ccaagacttg ttccacatga aacatcattg     360
cactttcaaa acaagtaaag ccgcacaaaa cacacccagg cccgtgtgtg tacacacaca     420
cacacacaca cacacacaca cacacacaca cacacacaca atcacaacac acggagtcac     480
acacagacca atttgtttct gcaatccgct tcctcatcca gagggtccag gccccgggcc     540
atctgagttg gtaaattctc ctcctagtta actcagagca gattgcagaa atgctgtcta     600
attcttgaga ttcttaggga gtggggcttg agatgtagac ggggccacgc cccggttccg     660
```

```
ctctccttgc acaactgcaa gccaagtcta ggcaagtcgg ggggaaaacc ccgccatctc    720
cagcccctcc tctctgcgac ccactggggc accaaggcga cctcgggtgg ggtggggtgt    780
ccctgggaga agatacggga cccagggtgt gagttgcaaa caggcagccc cgggctgctg    840
ccgcccgggc gctgccaact gcaggcagga aggggagggc cctgcccggc aaggggagc     900
tctcgcgggt cggggctggg tcggaaaagc tgcctcacag gcgcgcccgc cagcccctcc    960
gcgccctcgc tccctcccag cgctccccgg ctccagcctc ccttccaggc tccgccgcgc   1020
ccgcccggag gcagcgctcg caccggcctc gccatgtccc agccgggccc gaagcccgcc   1080
gcctccccgc ggccccggcg cgctgcccgc cacacccagg aggtgagtgg cgctcctacc   1140
gccggggttg agcgcgggga ggatctcggg gccccccgaa gcctcgggtc caccttcaga   1200
ggagggttag ccttcctggc cttctgtccc tgggcgccac ccctcccagg cccggagaaa   1260
catctggaga gagacggtg tggactcaga acctgcctct gggcaggtga ccggaggggc    1320
ccgcggatgg ccctgggtcc cggccaagtt cactgggcgc ggcgcaagcc acattggagt   1380
gggcttccct ggcggctcag ctggtgaaga atccgcctac aatgcgggag acctgggctc   1440
gttgggttgg gaagatcccc tggagaaggg aactggctcc cagtatcctg gcctggagaa   1500
ttccctgcac tggatagtcc atgggtggca gagtcaggac acgactgagc gacttttgct   1560
cacttgtcac tcatgcgttg ggaaaagttg gtggatgaga caggggtggg tgagaagcgg   1620
ataagggtaa aaggagaatg aaattcattt gggaccccc gggattccgg agtctgtaag    1680
atcagcagaa aagtctggtc ttccgcccag tcagggctgc agggcgtggc tgcctggagc   1740
aataacactt cttccctaag cagctttgag ccaaaccggc agggcggggc ggggcggggc   1800
ggggcggggg cggggagggg cggggagagg gcggggtcag cccgagggc ggggtctggg    1860
taggccccgc ccagctgtct tgcccacccc ctgacagcct aggtgcttac agagttagtc   1920
ccagtcaggt ctgcggcagg tggagtgcga acccgtggcc ctttgctgcg ctgcacccgt   1980
gtcctcgccg ggtccctcgg gtctctcgct gcgtctctcg gaacacatcc atcgtcgcca   2040
tggcatttgc aagctggtgg tacaagacgg taaataggag tgatcgtccc tgggcaggac   2100
tgggaaggga atgtgctctg tcttcctggg ctgtaggcga ggtcactgtt cagattttcg   2160
ggcgagggtt ggggagcagg ttgtgacctc ctctcagacc ttcaggggag gctccgggag   2220
aggctgagac ccaccctgct gtggaatgtg ggagccagct cggacgtaca cgtgctagtc   2280
ggcgtgagtt caggctcaca agttgaatgg catagggatt gttgctggac gaattctgcc   2340
ctcggacgcg gattcctgga tgaacgcgga ctcagaaagc gctcagctct agagtttgtt   2400
tttaactcat aagtaaagca caaaactttc agaggcgtgt tgttgggcgt gtattttcca   2460
gcgccaagta gacaggtaac taagatagtg gggtggggca aggaaaaaaa tcccaaaact   2520
ccaaggaaca taaacaactg agatcaagac ccttgttgag aatgagagag agagagggag   2580
actctatact ttattgcttg gatcggggc aaagatgttc catttattta atgcactgaa    2640
tgcttgtcca actatgtaag tgtgatatcc agtcaagctg gtacttgtaa tgttttgaac   2700
caggaagcat gctttaatat taggatgctt tccaaaataa taacaataca cataagtctt   2760
gttgacagaa aggatagaaa tatttatatc ccattgattt atgatgagag ttggaaaaaa   2820
gaagtatacc cttctctttc atcatgtggt actgggaaca acaagagtgt tgtaatcaga   2880
cactcttag aaggaaacct tgtactggaa ccagtaaaat gtccctttc atcccgtggc    2940
cattcactga gcatctacta tgtgtcagac tcagtgttag cctcaaagtg gaaaatggac   3000
```

```
agaattcttg ttctctttt tcaaccggtt tccacatcta taaaacgtgg gtgataatag    3060
gtaccacata agggttgctg aagacttaat tcctgaataa aagtaccata cccatacatc    3120
gctgctgctg ctgctgctgc ttctgctgct gctaagtcgc ttcagtcgtg tccgactctg    3180
tgcgacccca tagagggaag cccaccaggc tcccccatcc ctgggattct ccaggcaaag    3240
aacactggag aaaatttcca ttttccttga gatgtttctt catgaatgct tccttgtaca    3300
ttttctgggt ttttttgaat gtagcatctt attgatgtgc taagagcaaa agtttacttt    3360
gagtcattat cgtcttaagc tctgaactac tgttattgat atttgcagat aattcatatg    3420
gtgcattttg ataagaacat gaattatctg caaatatcaa taacagtggt tcagagctaa    3480 catcacttt cttccaaatt catgattctt caaggaaat tatgcctgga ttattgggat    3540
gaaaatagtt taaaggtatg ttttaaccc tattatgttt aggcacagtc tgacatcttt    3600
gctgaaacct ctcttataat tcagtgtcag aactattcta aattttcttt ttctgctagt    3660
aggaacctcc tagaatcagt aacctgccag tgatgaagcg ctaacttttc cccaaccaga    3720
gctggtcaaa tatagtgtga gccacatatg tgattttaaa ttttctagta attacattag    3780
ctgacagagg aaattaaaac gacatatttt aattagccca ctatattcca aatggtacta    3840
tttcaacatg gaatcaatgt gcaaatcatt gggatattgt aaattttctt tttcattttc    3900
ttcaaaatct ggtgtgtatt ttacacttag agcacatctc agttaacacg acatatttca    3960
agtgcttaat aggcatgagt ggctaatgac tactgtattg gacagtatag ctctagacat    4020
tggtttctaa ccactttcct ttggtggctg tgagggatg accacagcca ttttgagaat    4080
taaatgaaag tcgtggacca ctttcccaca acaaaatgta cacacataca gaagaccatc    4140
tataatccct taaagacccg tggagccaat ttatatatgt gtacacac atatatatga    4200 tttatattat atgctattaa atataacatt tatgcagttt attaatacaa aaattttata    4260
caaaaacacg atataataca tatctgcata tatgtatatc atgcttcagt aagtcctata    4320
attaaaatgt ctttactgag atcctttaat tactgaaaaa gattgtgaat gagctaactt    4380
taaaaattta ggcagaataa ggtaaaataa ttgaagggtg tatcttttgt tttattttgt    4440
ttaagggatt gccacctata aagccaatca aagaaacgct tcagtatata ttttcccagt    4500
gaataccatc agtattatga atctgatctt ttgaagaact atgtggtttt agtaaaaaaa    4560 aaaaaaaaa aaatttacaa agctagattt gaaggacatc tgatgacctt cataatgatg    4620
aagcatgacg gagagtaaat tttgttggct gacaccagta atcatattcc tgagtcataa    4680
gttgactcta ttagaccgtg ttaattaaag atgtttcttg gcctaattag acccattggt    4740
ccaacggcag agtcatctag gagcagtcat ttgggaggcc ccgccattgt gaccagcctg    4800
ggaagagtgt cacaaacctt ccctggcagg acagaccact tggctgcagc gacttttaag    4860
aataaggaat gtaaattata gattctgcaa aaagggcaca gcaccaccac cttctgcctc    4920
gcccccaacc cgcccctcaa cccatcccc gcctctgtct ctgaattggt tgcttccca    4980 ttgcagataa gacttaagag tacacctgat gatattattc tttaatccat tttgatactt    5040 cccagaaaatt taattgtata atactttt aaagaatgac gtagcttgcc gctggtggta    5100
taaatggtgg gtggccactg gaggttccca ggtgaactag tgggtaatta gttctgagta    5160
gactgtctca atggagtata aaacctctaa gcaaaccatc tttgttttgt tttttccttg    5220
aggttttaaa aaaaattta ttgtggtaac atacagcaaa tgtgccgtct ttaccattta    5280
tagctgtaaa gttcagtgga agtaaatatt cataattctt gtgcgactat cactaccatc    5340
tagcttcaga acaattttta tcttgcagaa ctgggactct atactcatta aacaataaat    5400
```

```
tctcattcaa ttttcatatc tacatttaaa cgcatggtac tatattccag tatctgtgtt    5460
ccttatcatt tttattgtat tatgaaagca tttaacctga aatgtaccct tttaacaaat    5520
ttttaagtat acagtgcatt attgttcact gtaggtacaa tattgtacag cagatctctg    5580
gagcttattc attttccttg accaaaactt tatgcctgtt gatcagtaac tctgaattct    5640
cctctcccct cagtccctgc cagccatcat tctactttct gtctctatga ttttgactat    5700
cctaggcacc tcacatcagt ggagttttat agtatatgcc ttttgtgac tggcttattt     5760 cactggactt ccccggtggc tcagatggta aagcgtctgc ctacaatgtg ggagacctga    5820
gtttgatccc tgggttggga agatcccctg gagaaggaaa tggcaaccca ctccagtatt    5880
cttgcctgga aaatcccatg gacgaaggac cctcataggc tacagtccat ggggtcacaa    5940
acagtcggac aggactgagc gacttcacta atcccctcaa gattcatcca tgttaaagca    6000
tatatcaaaa ttttcttcct tttaaggctg aaatacacac acacacacac acacagagta   6060
ttgtgctcat ccatacaact actgtggaaa acagtaaggt ggttcctcaa aaaacggcca    6120
tccacggaag caacccaagt atacttgacg acgtctctca ggtcctatag gctctgtttg    6180
tcgttgctgt actagtcact cagtcgtgtc tgactctttg caacctcatg gactgtagcc    6240
cgccaggctc ctctgtccac tggattctcc aggcaagaat cctggagtgg gttgccatgt    6300
cctcctccag gggatcttca acccagggat caaacctaga tctcctgcat tgcaggcaga    6360
ttctttacca tctgagccac ttgggacacc ctgcgggctc tatttacttt aatcattttc    6420 cttctctgttc ctcagactgt ataatttcag ttgtcctatt tttgattgca atgattcttt   6480
cttcagcctc ctcaagtctg cctttgaatc cctctagtga tttttttcat ttcagttatt    6540
atatgtctcc actctataat tttttttttgg tttctttta gatgatatat tttttattgg    6600
tatttccatt ttgtttatgc attggtttct tgactgtctc cacacttgct ttagttcttt    6660
gagcatcttt aaggcagttg ttttaaagtt tttatctagt gtatctacta tcagctctta    6720
gggacagttt ctgttttta tttgtttttt gttttctcc ttgattgggc aatacatctc      6780
tgtttctttg catgctttgt gatttctttt tttttttttt tggttgaaaa ctggacattt    6840
gaatcattga aagttttgga aatcaaattc tcttctttcc ctagggtttg ctgttttgtt    6900
tttggtaatg atgggatctt tttgtgccaa ggttcagcca aaagtgtaca ctgaagagct    6960
tctcaggtct tttctgattc tgcacctttc cctgggcgtg agcaatctgt gatcagaata    7020
cagatctgca gtatttggag ggcagagtcc ttttgcatgc tccagggcac acttgcatga    7080
gctgtgtgcg cacacttgct gtgagttgtg tgtgctcagt cactcagtcc tgtctgactc    7140
tgtgacccca tggactacag cctgctcagc tcctctgaca actggattt ccaggcaaga     7200 atactggagt gggttgtcat ttcctcctcc aggagatctt cccaacccag agatcaaacc    7260
cacgtctcct gagtcttctt tacccctgag ccacctgagc tgtgaattgg ggacgaggaa    7320
tgggcagctg ctgctgagca gagctaaaat ggatgcaaat taaccaaaac ttaccattta    7380
aatgttcccc tggaagttgc aagtctttga tagactccag aacttacagt agttacatca    7440
gacagattct gccagggaga atttgttcca gatcagggga tggattcctg gtacctctta    7500
cttcatcttc ccagaatctt ccctttaaac tgttttaagg attgaaatcc tgttaatgtg    7560
attctaaacc tctattcttc aagttgtctc attttctttt cataaaaaat gacccagaaa    7620
gctttgcagc taccataaag aaaaaatatc cagtgtcttt cacttaagag aagtgtgaaa    7680
ttacttgatc caatgagtac catctatgta agttgcttcc tcagatggga gcgtcattta    7740
```

-continued

```
actccagaaa ataaagggtc tatggttagt tttcctaaaa tttatggaat tccttctgac   7800
tctggagaac ttacagaata taaaagtgct ttggtaaagg ccaaagatgt tcacagttgc   7860
ttatagccca cctactatgt gtcatgtgtt gaacagggtg ccctggacac aaaaattgtg   7920
ctgatggtcc attcctggtc ttctcttgcc tttctcatag ataaaaatca caagcacagc   7980
ctaaagacta gtacaaaagt agcagagtag ctattgaaat tctcatggcg tcgtctttga   8040
ctcagaggaa attaaaaaag ccttactaca gtggaacccc taagctaaac aaggcagaaa   8100
ggcaatcaat gttacttctg aaaactgggc aaaagaagg tgcacccta cactgccacc    8160
tgggcatatc caccagaatg ttaaaatgtt agagaaaagc aaagggagtt cagggaaaca   8220
tgaggatttc agaattatac atatgttgct gctgctgctg ctaagtcgct tcagtcgtgt   8280
ccgactctgt gtgaccccat agatggcaat ccaccaggct cccccatccc tgggattctc   8340
caggcaagaa cactggagtg ggttgccatt tccttctcca atgcatgaaa gtgaaaagtg   8400
aaagggaagt cgttcagttg tgtccgactc tttgcgaccc catggactgc agcctaccag   8460
gctcctccat ccataggatt ttccatgcaa gagtactgga gtggggtgcc attgccttct   8520
ccatatacat atgcatttaa accttaattt gcgtcttctt ttttatgaga ccccaaaga   8580
agcttatcct gtatttctat agtttaataa caaatgtttt cagagaagca gaaagatacc   8640
atgcatcaca cctttcattt cctttcttta aataattatt cccctataa aacctagcac    8700
acagcagctg ctcactgatt attttttag taaatgaatt cttcctctca tactagcctt    8760
ctccattatt tgggttttt cagtattaaa agcaagtaaa aatggctagg atattccctt    8820
tgtgtgactc tgttgttgtt caactgctaa gttgtatcca actcttttgc agccccatgg   8880
attgcagcct gccaggctcc tctctccctg ggatttccca ggcaagaatc ctggagtggg   8940
ttggcatttc cttccccagg ggaatcatcc cttcccaggg attgaaccca tgactcctgc   9000
attggcaggt ggattcttta ctactgagtc tccagggaaa ccctttgtgt aactttaggg   9060
agatacaagc tctcaagaag attcaaaaaa ttttttaaact tttttttta gcacagaggc    9120
agagagaata atataacacc ctcctcttgt acccatcacc ttctataatt atcagcgtaa   9180
cactgtgcct atcctgcctt atctatctta ctagaagccc caccaacaca cacacacccc   9240
acaccgttga agtattttat agcatgggaa ttgcacaata agtgctatcc ctgtgaccag   9300
cttggtgttt gttgtgtgaa aaactgagtt ctctgttccc tgtgtacttt gtttcctcat   9360
ctgtactatg gaaatgtgag actaacgtga cacagtgtcg tgaggtaggc aaagtactaa   9420
acataaactt agcagatgac tctcgctcct ttgtacttac ggccagttaa aatctaaatt   9480
ccctgctata ttatttatag ccttagaaaa tgaaagctta aacctctgtt tcttctcata   9540
ttcattttat tgtctcataa ttcagcatgc cagtgaaaaa gaagggagtg aagtgacctt   9600
tattgtgttc ttaaaatgaa cgagccaatg gaccagactc ctcattaaca gtggactggg   9660
ctcctcctca cttgttttgt acgtaagcca gcccctgggg taggcatcat gacctgcatt   9720
ttacaaggag aaaacagaaa gtttaaatca ttggctcaaa gtctcatagc attgcagacc   9780
cacattcttc ctgtcttatc cgagtttggg gaatggaatg gaatgcaggg agctggttgc   9840
caggtaacag aaaaggccgg aaagccaact ggggtggatg aggcaacaca ggggttagaa   9900
atctaggaag ctgctaccat tcctagactg aggggaagc aggatcacct tgcagaagct    9960
gaaaccactg ctggcctgtc ctgcaggagg ctcccatgga ggcagccatc acacattcct  10020
actacaccaa ctgaccgggg tcagggcagg gagtccaccc tagggcaagc aggtccactt  10080
cggcctgcac cagggagcct gttttaaagc aaaaccagct ttccatcttg agccttatgt  10140
```

```
ttgttggctg aacagtctta ttttagaaag cagaatacat ggaaaaataa attttttaagg   10200 gactttgcag gaaatccagt ttgcatattg tctgttaatt tttcaagcta ttctgttttt   10260
cagctttaaa aaaagtcttt tacctagtct actaacctga aaagagcaaa agtacttccc   10320
aaggaatgtt agaggtttgt ggaaatgcag tcatcagtca agaattgttt gtcggaccgc   10380
tgccacggta ctaggaaaaa aaatttaatc taccatctgg ctgagcaggc aaaatacaca   10440
tttatgaagt aatcagtgag caggagcgta tataataaag tgctgattgg tttgctttac   10500
taagaaaata gagacttaca tgcaacatga agatctgatg tgccattagc aggacaaggc   10560
tcagaactag tcaggaaatg ctgggttgaa cacagggcac tgggttcctg ccttgagcag   10620 ttggttttacc caggaggccc tgagctgccc tggcctgtct gacttgggga agctcccatg   10680
ggtgctgact cagtggggtg attggaggag tagaaacctc cacttcctga catggtgccc   10740
acagagctcc tctccaagca gtggtttcag tcctagccgg gtgttagttt cagctgggga   10800
agttcaggga tgtacatctg tccccagcat caccctggat aaactaaatc tgaatcccca   10860
gactctagct taagtgtttc caaaagtgct tgggcacttg tgacctgcac tgaaagacga   10920
gttgttgttc ggtcactaag tcttgtctga ctctttttga caccatggac tgccacacac   10980
taggcttccc atcctttacc atctcccctga gtttgttcaa gctcatgtcc gttgagtcag   11040
tgatgccatc caatcatctc atcctctgtc gcccacttct tctcctgccc taagtccttc   11100
acaacatcag ggtctttttcc aatgagttgg ccaaagtact ggagcttcag ctttagtatc   11160
aacccttcca atgaatattc aggggttggtt tcctctagga tttactggtt ggaatctcct   11220
tgcagtccaa gggactctca agagtcttca acaccacagt tcaaaggcat ctattctgtg   11280
gtgcacagcc ttctttctgg tccaactctt acatctgtgc atgactactg gaaaaaccgt   11340
tgcattgact atacagtcct ttgtcagaaa agtaatgtct ttgcttttta atatgctgtc   11400
taatttggtc atagcttttc tttcaaggag caagtgtctt ttaatttcat ggctgcagtc   11460
accatctgca gtgatttttgg agccccctaa aataaaatct gtcactgtta ccattttttcc   11520 ccgtctattt gccatgaagt gatggaaccg gatgccaaat tttagttttt tcggatgttg   11580 aatttttaagc caactttctc actctccaca ttcaccttca tcaaaagact ctttagtttc   11640
tctttgcttt ctgccattag tggtgtcatc cgcatatctg aggttattgg tatttctccc   11700
gacaatcttg atttcagctt gtgattcatc cagcctggta tttcacatga tgtactctgc   11760
atataagtta aataagcagg gtgacaatac atagccttga catactcctt tcccaatttt   11820
gaaccagtcc attgttccat gtccagtttt aaccattgct tcttgacctg catacatgtt   11880
tctcggaggt caggtaagat ggtctggtat tcccatctct ttgatatgct gtctaggttt   11940
gtcatagctt ttcttccatg gagcaaccta cagctaaatg aaggcttttt gatccttagg   12000
gagcacccct accccaccct cccccagcaag cctttgtctc tgtgtgcagc agtggtgcag   12060
ggagggagct aagcggtgtg caccaggctc cagagggccc tgggattacg tatcattact   12120
tcttgatttt gccatagctg tctctggaca tgcaaacatt gatctccgtc agcattcccc   12180
aaattgcaga aggaagatct tccagctgtt ttcacataat ctttattatt ttcttaaaca   12240 gcttttatttg gatataattc ataatttacc tttaaaatac acaattcagt attttttaata   12300 ttttaatatt ttattattga aagtgaaagt gaaagttgct cagtcatgtc cgactctttt   12360 caacccccatg ggctatacag tccatggaat tctccaggcc aaaatactgg agtgcgtagc   12420 cttctcttc tccaggggat cttccccacc cagggattga acctaggtct cctgcatgtt   12480
```

```
ggcggattct ttaccagctg agccacaagg gaagccccat tttattatta actcagtatt    12540
attattttat tagtactgag tacagagttg tccaagcatc actttaagat cattttacaa    12600 tgttttttgtc acccttaaat gaaactcagt accttttttgg gggggttta aatctaacag   12660 aggcatttca gaagcacact agttttttgat gctctttcac agctgagctt aggcttgcag   12720
aagctcaatt tttgtctgtc ttccttctct tcttatatgt gtagaagttc gagcttcagc    12780
tcatcctgtg acacataccc ttgtctctga gtgtgtcagg gtgtatctgg gttgccctgg    12840
ggaggcgacc ccaaatgctg cagagccaaa gcctggcgct ggcatacgtc cttagctggg    12900
tgggagcaca gtgccaagct tcatggctcc ttgctcctgt tgatttcctg agacgtttgt    12960
gagattgcta gggcagaaaa ttgtatgcat attaatgctg tcttctagaa tgaggacaaa    13020
ggacagctat gcttaccaaa tatatagcaa tgccaggagg tggaaacagg ttggaaaatt    13080 cttttttgaag caagaccaaa aaacccttta tctgatatttt tctctgcctc taaactcctg   13140
tcactcttgt tctttcacgt gttttcatct tagctcctgg cttccggggc cgtatcctct    13200
gagtgaaatg tctcctactt taggaccagc atcctgcact tcctgtcttt gctcccgtcc    13260
agctcctaaa acatcctaaa acaggatgac actttggtat tgtgtgtctg attaatttca    13320
cacacacaca aaaagaaaca gttttagaat aggaaggttt tatctgggtt ttgttgatttt   13380 tttttttttt gagttgtttt ccttttagag cattggattg agactttctt gacgggcatc    13440
aaaagttttc agctagctta accagcccag tctctggctt ccagactata acccacacat   13500
gtagctgaca tgtagtgtga ctgaggagga tcttacgttt cacattctat ttctttatca   13560
ataaaatgag ctgccagttg tgtctctttt ttactgctat ggcagtcaag gagaccacag   13620
agaggaaatg cccagtgctg ggctcacaaa ggagatgctt agaacatgtt agtttctttc    13680
cactcttaca gaaaagtcct tcctggatat ttcaggtttg tggttcagtc ccttttccat   13740
gtttctctca gctcatcctg acccaccaac tacatgtagt gatagtagac gaaggtttct   13800
ttcttcactc tttgagatac ttgctgcagc ttcctaagct ggatcaaatc tgaaatgtat   13860
aattttcaaa catttatttc atcagcagaa tggaaagtat gtggaaagta cacagttatt    13920
ccatgaatgt agaaatcagg cactttgaat ctctctcaat gaaaagatat aactgatttt    13980
gtatcattaa taagctactg aatgggggttc cctggtgact cagatcgtaa agaatccgcc   14040
tgcagtgtgg gagacctggg ttcgatccct gggttggcaa gatcccctga aggagggcat    14100
ggcaacccac tccagtattc ttgcctggag aattccatgg acagaggagc ctggcgggtt   14160
acagtccatc ggattgcaaa gagctggaca cgacttagcg actaagcaca gcacagcacc    14220
agctactgaa tatgaataag cgccatttct tggtcagggc aatgattcac ttataaagtt    14280
tccatttact ggaaattgaa tggcattagg taattcttat taattctatt agagtttgt    14340 tagagtgagg atgtattgta attatagagg gaaaagtcct cagtttaagg acatgcttga   14400
taaaatgttt aggggtaaag tctcaggata tcttcaattt actttcaaat gctggtacat    14460
atgcaaatat atgtagatca tgtgtctgtc cataatatat gatgagatgt cagtatatgg   14520
caacaatagt taatagttgt tgactctcag tgatgggact atggatattt ttcttttcaac    14580 ttttctgtat gttagaaaat ttttataata aaaagccagg ttaaaaaaac tagaaaaaat    14640
ataatcctga tagttactaa aaaatgtcat ttcactatgt gattttttatt tatattatta    14700 tacttactct attgagagca aatctttctt tgaagttaaa aaatgacaat tcttatagta    14760
cataattttt ataatttgtc attacaaattc aacattttaa aaagcatttt cttttttaaa    14820
acctcatttc gtaaaacata tatttataat agacatttta agcaaaaaaa gcatttgtta    14880
```

```
tatatttata tatatccctc tcaaactatt atttggaaac tatgtaattg tgagagattt   14940
tgagcatttc agtggaagca agtaactgat gatgttggtt aatctggagg actgcaattt   15000
tgaaatacca gggaatcaac tttataaacg ttttatagta agatatctat ctacctttat   15060
tttaaagaga aaaggctgtc tgcatgtttc ctgtagggta gatcgtaatg tatgtttccc   15120
acctgagcaa gaaccgaaat gggaccttgc ggagagcatg gagccttgcc caagacaaga   15180
gcgagttgtg tgtctgtatt ctcatttcta aaatggaact tcacacgtgg tgctagtgca   15240
aagcatccgc ctgccaatgc agaagactca ggagatgcgg gttcagtccc tgggttggga   15300
agatcccctg gaggaggaaa tggcaaccca ctccagtatt cttgcctgaa gaatcccatg   15360
gagagaggag cctggtgggc tacagacctc ggggtcacaa agagtcggac gcgactgagc   15420
gagtaagcac atttctaaaa tggagtaatc atacttccta aaagtaaatg aggctgtatg   15480
ttcagtgtgt atgctcaaac agtgggtatt gttgtgacta gatattacct atatctaacc   15540
tgaaaaatat atagaattgg tgataaaaat gaatttgata tcatggttct aaatttacca   15600
gttctgaaag gagacaaatt gaataaattt gtgtcatgta gacccatccc tctcaaattc   15660
tctctccaaa cactgaataa ttcttctctt ttgctcacct attattctta aagcttatca   15720
atggccatct agctctgaca tatatatgtg ggcttttaaa tggctcttgt ttttcaaga   15780 ttcattaatt actcaatagc tattgctctc aactgtggac aaaactcttt tttttaaac   15840 acacaccaca tcttctttat tcatcatctg ttgatggata caggttgctt ccatgtcttg   15900
acaattgtaa ataatgttgt aaatgtaaac atgaacattt ttgtcgttgc taggttgtgt   15960
ccacctcttt tgtgacccta tggaatatag cccgctatac tcctctgtct gtgcttccct   16020
tgtagctcag ttggtaaaga atcttcctgc aatgcaggag atctgagttc aagtcctggg   16080
tcgggaagat cccctggaga aggaaatggc aacctgctcc agtattgcct ggaaaatccc   16140
atg                                                                 16143
```

<210> SEQ ID NO 2
<211> LENGTH: 13144
<212> TYPE: DNA
<213> ORGANISM: Bos taurus

<400> SEQUENCE: 2

```
gtctactatc actacatgta gttggtgggt caggatgagc tgagagaaac atggaaaagg     60
gactgaacca caaacctgaa atatccagga aggactttc tgtaagagtg aaagaaact    120 aacatgttct aagcatctcc tttgtgagcc cagcactggg catttcctct ctgtggtctc    180
ctcgactgcc atagcagtaa aaagtgtcc cacccagcag ttcatgatag ggataacgtt    240
tccttctcca gggggtgggc aaactcttga ctaggtcatc tgggtgaaac aagccctgta    300
gagagcttca ttaaccaagc tactgcaatc tgcctgcttt tctgtgggca gaaattcatg    360
agaggtttct gtttgggga aagttttcca tttgtgaaag tgatttattt ctagttttta    420
tacaaagaac tactgcacat gtctaatatt gcttagcctt tttattttac aaaaatatct    480
gttgatatga tttaaagaaa tattatcttg ttttatttat catagtatgt gtgatatagt    540
tggtaagtca tgtccaactc ttttgatccc acagagtata gcctgtcagg ctcctctgtc    600
cactggattt cccaagcaag gatactggag tgggttgcaa tttctttctc cagggaatct    660
ttccaaccca gggatcaaac ccaggtctcc tacattgcag gcagattctt taccgactga    720
gccatcaggg aagctcttat catagtatag agacaataga tttgctgtca gaaaccagc    780
```

```
tttgcaagct tttctcattt actgggtgta tcttttgtg aaaagcgcat cacatgactt      840
ttattcttaa ttttttttaa tccatgaact caggtgagca tctttttttg tatcagataa      900
aaatatatat gaaagttcct gtaagtaata aaaaatgata aacattatta ttactattat      960
tactgttatt gccattcttt ttaatttgaa taacttgagt gacatgcata tccaggtttt     1020
gattccactt tagggaacat gatggggttt tatgtttcaa tgtaactaaa gatgattggg     1080
ctaagaccca atagtgagct tttcattttc ttatatttag gttccttttc ccactttctt     1140
gcatatccca cttgtataag aaataaattct ttatccctaa ttttcaggaa cataaaatat    1200
tttcatttct caaaaaaatt caagaatgag aacttccctg atggtccagt ggttgggagt     1260
ctgcctttca gtgcaggggg tgagggtttg atccctgatg ggggaaataa gatcccacat     1320
actgtggggc gactaagcac caccccagca actagagagg ccacacacct cacctgagac     1380
ccaatgccac caaaaataaa taaaataaat attttaaaa gtacaataat gttcatggct      1440
tcttttatct tatcaaacca aatagcgtgt aaactacttg acgcttttat ataccacata     1500
aaaatacttc cttgccaacg caggagatgt cagagaagca tgcgaattgg ctccctgggt     1560
tgggaagatc ccctggagga gggcatggca atcccctcca gtgttcttgc ctggagaatc     1620
ccatggacag aggagccttc ctggctgcag tccatagggt cgcaaagagt cagacatgac     1680
tgaagcagcc caccatgcat gcaaaaatac tcccattcat caccagtgtt cttgtgagaa     1740
aaataattct gatttaggac ataatgaaat cctaaagcca taaataatga acgttggagg     1800
tatggggttc ccaatgcacg ctttatcttt ctgttttggt aagtagacag aactccagag     1860
aatttcctcc cttgagttta tgctgaactg aggcttaagt aatggcttca gctcaacatg     1920
gtcctcagac atctcatctc catgaggaac caaatgtcgc ctatgctggc aatttgggct     1980
ttgaaattcc aggaggcatt tgtaggaga cgagatgccg ccttggcacc accatcagat      2040
ctatgtctgg ttaattacag acttactttc tgcatcccaa ataaatgtct atagcttccc     2100
tttatttttg aaggccacct atgtcaatgg agaattatta acagttctca ggaggaagat     2160
taaaggtgtc cttgttttta cagtctgtgt atttagccct ttgggattaa agtcactatt     2220
atataatctt gtatcacctc cctctattaa atgttatctc ttttaatatt tttacagcat     2280
gtcagtagaa aaaccagtgg atcgccttcc aagtcaggag aaaagaaagg atcagatgag     2340
gtaatttcta caatactgaa ttttcatttt ctcctgtttt taaattgtga attctatcat     2400
gaaataaata atgaggtagc aaatatctcc tactaaaatg ttggcaaatt tagttttaac     2460
taagagctgc ttcaatgctg taagtggaaa tcattaaaat aaataaagtg ttcctcagag     2520
aggaactatt tcctccagaa atagttttca tttaggagaa ctcagttatt tagggtgttg     2580
tctctatagg aattggtgaa tcttaactgt ttttctgtt ttttttttt tttttaaca        2640 aaaacataca gaagggaaac caaatgctac tgttgaaaag gaaatctttt tttatgagag     2700
tcattgtgaa aggagaacag tgataaccta gactaaacca gtcattcagg ttcacaaaca     2760
aaagggagag aaaaagacta ttttttatttg gttccatcct gtggaaatac tagtggaagc    2820
aagcctcact ttcagatggg ttgtctttga gtccgtgaat ttctcctttc actgaacgat     2880
accccattat gttcactatc agcatcgtct ggtctccatg aatgggtcgt gtgaaagtgc     2940
tagcctctga gagggtccta ggcttgcttc cttttgctgc ttttacatt ttaaatctca      3000 atggaatatt catcttcatt cagtagaaat aattatcatc attcatccca gtttgtaaaa     3060
gagccaggtc ctgaaaggta cctggaaatt taaaaagcat agagtaacca ttttggtttt     3120
tctctcttat taacatgctt ccagaaatct agcttctctt tctgcttatt ttctgcagtt     3180
```

```
ttgaaatagt ccatatattt ctgtatattc agtatgaagg gagccattat gactagatct    3240
tgctatgaat tctgcacgaa ggtttagtcc tcagctgtct actattgttt ccattaccaa    3300
cacccaagtc aatataattt agattatttc ttaccatgca aatctgcagt gaatattttt    3360
gtttccatgg aagaaaattt tctttacaaa gtaaaaataa acttttatta aggttttatc    3420
ctggctctta gttaaattat ttaaactttt tttccatgag aacaagccaa cttttactag    3480
catgaagatc tatgtaccta atatcactca gttccctat caatccttct ctttaaatat    3540
cttcccagat aagttatcta ccaaataggt ttcctgttga ataaagagac aactatagtg    3600
tctctttatt gtccagatca ggaaataatg ttttagatg ttattcttta tgttaatatt    3660
aatcaagttg aaaacatttg cacaagaaag gaaatcttcc agttcaatca agtggatagt    3720
gacctaattc taagaatcct agatcttaga ggattattct caacaattac gttttatgt    3780
ggaagcttaa atgttatgtc ttgaatgtac agatatcatt ggttaaggca gcagctgctc    3840
ccccagtgtt agatctcttt taatatctgg actataaaat gcctcatttt cattttata    3900
aagggcttgg gaaaattgat aaggagtcct gttatcagta caatcagagg agaattcaag    3960
acttctgtgt ctgtgtgatg actgtgcttg cagttctttg aaagtgaaag gctgagcttc    4020
catctcagga gaagaagaa agaatttttc ttttctttat cagcagttga agcaagtctg    4080
actttgtttc ataacacgtc tgggaaattc agattcacag ctcttgcgtt tgtgccagaa    4140
cctggtcatc tgggtctgtt ctgctccacc ccagctggct gacagagagg agagccaggc    4200
ttcgccctgc tcccgtgaca taaatcactg cagaggttca gatagcctga gactgaagac    4260
tgcttattat ctcgccaaat ctgcccgta tctatttgat agggtggacg gatgtgtaag    4320
ttgaatcatc tagtggtcta gttatatttc taatgtagtc tgtctccaag gagtctctca    4380
ttccgtatgt catggatgac atattatggc cctggagaca attcaaggaa atcatccgtt    4440
tggcattatt tttactctat gttcgtgatt ataaaaccac gtgcagtctg gacttgtcat    4500
ctgccctgcc taccatctac aaccagttac tatcgtcttc agattactag ggaaagattt    4560
cctaaaactg attctttcgc acaaatgctt tcttatctgc tgttctgttg aacaagaagt    4620
aagattaaga agcttattgg gggggtttgg ttatccattt tcaaactagc atctacctcc    4680
aaagagtaaa cagcttgttg tccccaagca tatgcaaaca tactggttaa gcttccaagg    4740
actaagccag gcctttgaaa taaagtcagt ttgaaaatgt gctttctctg ctcagggata    4800
cttctccagt gcctttcatt tggaggtgca agaaaaaggg tacagagaag gcttcggga    4860
agatttaacc aggattgaaa atgattagga tcagacaaga accattatga tattgtcata    4920
ggcaaaacta cctggggatg aatgcagctg tgtgaatttc agagttctttt ctcttctgct    4980
gccataaatg gttttatttt atcttgaata ttactcctat acacccacta agtgatccta    5040
ggatgtctgc agttatttta atagactatt gcaactaaaa tatcatttgt catgttgcat    5100
ttgcagtata aatgcttgag gatggagttg agtaagtttc tttgaaaatg tatgttttgt    5160
tttttgtgac aattgttaag aacttaagtt cttctcaggt gtagaggaac tgtaagacca    5220
aaagttgaat ggactaaaaa aaccaaagat aaaatgacta cagagtagga aagagaaaaa    5280
tgaaaacatt tagcagcacc tttaaataca gtggaacaaa gttgtctttc caaacctgca    5340
atcacatcta tttaaagtgt tgactgaca catctgacca ccctggggga gtgtgagcat    5400
cttagcagca tatttccgtg acgtcctgag aaatagaatt taagacatgg gatgcacacg    5460
atctcacaga gcctgtttta aggacttcag atttaatgat ggatatattt ttataggtaa    5520
```

```
agaaagggag atgtatagag tctaaactgc tccttgaagg tatttgataa attctctgta   5580
ccataacagc tttcgtggta ttcttccctc agtgtgttta cctctcctgc ttctaaagtc   5640
catgaattac tccaacattt taaaatttct ttctaacata tttttttctct tgatgagatt  5700
agtctttttt aattgcaaaa gtaatatgta cttgtgaaaa gcaaaagtat ttaccctgtc   5760
ttaccactta agttatcact gctgctacaa aattttgtgt gtactctcaa atcattgtga   5820
tgatattata tgttcatagt tattatatat actgattttt gtagcttta aataatgatg    5880
cagctcttac atatcattat agaaacgtat ttcaatatgt ttcttctaaa gaaaatttag   5940
aaggtatcaa caattttaaa gaaataaaca ctgtcatcta gaattccagc cctacagaaa   6000
tggccactat ttctatcttt gagtattttc cttcatcttt tttctatgtg tgttcatgtt   6060
agtcacttag tcttgtccta ctctttgcga tcccatggac cacagtccac caggctcctc   6120
tgtctatgga attctccagg caggaatacc gggatgggta accattccct tctccagagg   6180
atcttcccga cccagggatc taacctgggt gtcttgcatt gcaggcagat tttttaccat   6240
ctgaggcacc agggaagcca tattttatgt ttaagctgag ataacaaagg aacattacta   6300
gactaaaagg gcctagacta aagatgataa acaatgtgct ttgtgataga taaatatttt   6360
ccaattgaga gaagtcatca ttgtgtgtgg cttttaaata catggggttt tccaggtggc   6420
gctagtggta agaatctacc tgccaaagca ggagatgtaa aagatgctgg tcccaccgag   6480
ttgggaagat cccctggaga agggaatggc aacccacttc agtgttcttg cctggagaat   6540
tccacagaca tggagcccac cagaggagcc tggtgggcta caacccatga ggtcgcaaag   6600
agtcggacat gaccgagcga ctaacacttc cacttttaaa tacatagaaa atcgtattta   6660
agtaccttgg catttcacat aatatttaat ctggttatta ttttgtgctg tgtgtttgag   6720
agaggaaaac aagtttcttg ttaacaagtt ttctgggaca gtgttccggc caacaagtga   6780
taaagccgtc cttagcaaat tctggaaaag tgccacagca aatgttattt taaggggtgt   6840
taagtcatta caatctcttg tccactttaa ttgtggggac ttgattgtgc tggacaagtt   6900
catgtcccag tgccaagaag gaggcaactc tgaaaacgtg ccccaagggc agtccccgtc   6960
tgtcttacct ggagatccag aactctgctg ggtgtccgat ttgaaaggct aaactcacta   7020
aaggaagttc caaatccctt tcaattgca gtttccaatt ttttttttta attctaaatt    7080
tttattattt tccaattaac taaaatattt ttaagataat ttattttca atgaaggcat    7140
atggatggtg attttctgca tctgtgtgga tctaagcatg cttttctgct ggcctcacac   7200
aaggtgctac tacaaaattg tacgttttgg ggtaacagtt ctgttcccctt aaaatattct   7260
acctgtttct ccatagtttt ctgactttt gtgctataga aaagatgtct gagggagcct    7320
aattgttatt tattttaga gaacttgttt ttcctgcttt ggtgtatttg tgatttcttt    7380
ttcttttatt cttacaattt taaaaattgc caggatgtgc ctacatgtgt gttttttctat  7440
taatttttc ctagagtgtc tattatgtag ttatcggtc tatttcagtt tcttttaaa      7500
catacatata gttctgagat cagacattca ttaggcacct gcctcagttt tctctttgac   7560
cttcaccttt gtattctgct agagtttctg aactttatcc cccatatttt tatttctgtc   7620
atttaaattc tgctccttga aacttccaat acaggtttaa attttgcctt ttccctgtt    7680
gcattgtacc cctctctaat ccagtcttcc tgccctctct ctctgtttca ctctgttatt   7740
ttcccatctc catcttctct gtgtctgtgg ctctctacct ggctttcacg ggggcaatgc   7800
catctcgttt cctattaagg atgcagacag tcttctgaaa ttttcttctt gtagtgtatc   7860
attttatgag atttactgtc tcagtcttca ggaaaacggc atctttcttg actgttttcc   7920
```

```
ttcttctcac ttatctgatt aaatgtcttt ttttggaact caggcaaggc ctaggaggcc    7980
aaagtttttc tgcaaaccag aggcagtgga ggatgtggtg agtgggtggg aggtggcctt    8040
tcccgggaag cctccacagg gtcctgctca gttactgtca gggtggagat tttacctcag    8100
ttttggcaat tccctgactt cctttgttgt tgagtcaaat tccagcctct tctgtgagaa    8160
gatgattaga aaactgctgt cgagattatt ttgtagtagc cattcccgga gtggtctcct    8220
aatgactctc tttcacgtct tgaatccagt ctccccttt ctagcctcct tcgggtataa    8280
cctgtgaagt aggccttcac tgcggactct gttctgttta ttaactgtgt gtagctcctc    8340
atgagtttca ccagaagggc ttgaggtgta gggcttcggg agcattccat gtcgcctctt    8400
ttctggaatt tctctgactg gtttccggtg cgtgggcctc gttctgtgcg tgtgtcgtca    8460
tgacgtgctt taggtactgc ttgcgtctca gcgcctgata cttgtgtacg cacgtaatag    8520
agtttgtatt ttcttatgtg gagcctgcca tatgggtctt cgccagccat ctatggattt    8580
aaggtcaaaa cctatggtta gaataccagc cattatgtag ccattcaaac agcctgttta    8640
tcggaagaca tgttttcagg ttgaattctg agaaaaacac agggagtttc tcaaattcag    8700
gacaaaaatt ctttgccgtc ttgagaccac tgtaagagca tcttcttct catgtgccgt    8760 gggagcgctg aaaagctccc cagttagccc gcccccagtc cacagtgcct aaagaggcag    8820
cacgctgtag ttgctgagag caggccctgg agtcccagtg tgtggacttg tccccagctc    8880
tgcaacctcc tagctgggtg ttcttaggca gattcctttg cctccctaag ggtacctttc    8940
tcatgtgtcc atggagacag cgataggttc tacatgagtt aatgtgaaga tcaatgagac    9000
caagcaaatg aagtgtctag aacagtgcct gggacatgcg acggtgttag ctgctatcat    9060
ggttattatt attactactg ttattacttt tactagccaa tgaggagaac ttgtttggca    9120
ataaaggtaa gccccttata gctttagagc caggactcaa attctttgt tgactatata    9180 ttgccaagcc tttcccatta aaaaggaag gaagtttggt agttcattaa gcttagtagt    9240 cttctttgt ttcaaaacaa ctctgttaac acccaaaaat atatgccagt tgctagaaaa    9300
tacagtccct ctgtaaccaa gaacatgaaa ataatttgct gttaaattaa gaatctgtga    9360
tatacaaaat gttatctaag tagtagtgag tgactaataa aaatagttat tattgcactt    9420
cagagtaatg agcctaactg cgtaagatct taggtcctac caaaattgtc tctgaagact    9480
ataccttata gcatagggaa ttagaataaa agttaaaaaa aaaatcaaag gaattgaata    9540
gaagttacat ttcttggctt tagaatagat cttaagtcct ggaaacccga gggacaaatc    9600
aattaaatat taatcctgaa atacactgtt ttaacattta tattttttc agtcttctct    9660 ctagacttta ttagcttcta aaagataatg gaatgactga ttcagaaggg aggatgacct    9720
aaaattgtgc ccacagcaag aaacctttat catttaagga ctgaatatgt atgattcttg    9780
tcataaagtc agtaatattt tatcatatac caatgtacat aataacttgt taagaccttc    9840
caaaaacagt tcacttgtga agtcaaaatc tcttagcaag ttgacatcat aaattagtct    9900
tttatatttc aatccacatt attacagaac ccttagtaaa tgtatagagc gctgttcatt    9960
tcagttcagt tcagttgctc agtcgtgtcc aactctttgt gaccccatgg actgcagcac   10020
gccaggcctc cctgtccatc accaactccc agagtttacc caaactcatg tccattgagt   10080
cagtgatgcc atccaaccag ctcatcctct gtcatcccct tctcctccca ccttcaatct   10140
ttcccagcat cagggccttt tcaaatgagt cagctcttca catcaggtgg ccaaagtatt   10200
ggagtttcag cttcagcatc agtcgttcca atgaacactc aggactgatt tcctttagga   10260
```

```
tggactggtt ggatctcctt gcagcctaag ggaccctcaa gagtcttctc caacaccgca   10320
gttcaaaagc atcaatttgt tagtatcata aaaatttatt ttaaactttg ttcctcatct   10380
cctaggacat tacatgagat tatgcaatat ttctcaagtt taagcatgcc tatgaatcac   10440
ctggacatag tatgaaaaat tcagactcct gggcccagat cagggtgaga tcaggctttc   10500 ggtattttc ccagtcactc aggtgactct tctgacggtg gtcttctgag cactttcga    10560 gtaacacaga taattcttac agatctcata atgcagttcc tggaaaatat gagcttttct   10620 tcctttttt cctttctcat ttccttttct ttttgaaatg cctgcccacc ccacccatc    10680 cctcagccgt ctcctgtctc catgtcctgg ggacagcgtg gctctgaagc acattgaggg   10740
cactgtggtt tcaaggagtc attggaccag atggggaggc tttggttgca agggagaaat   10800
gcagaaatgc aaaccctatt tcttcctact tctcctagga cctcgttcct taactcttcc   10860
ctcattcctt ttgttattgt tgtttttgag tcactaagtc gcatcccatt cttttttttt   10920 tcttttact ccttatttaa tgactcctct ttagacgaca ttttagttta gtcttcctca   10980
tcatgaacta ttttaaaata tttcgtttga agctgctcaa gcttccattc catcttcctt   11040
tttaaccctc actgccaaaa ttcttggttg aaattattga agaagcgagt agggagaaag   11100
aagagagaaa ccaaaagcaa atgttaataa atggctgcct gaagtaggta ggaaggagac   11160
accagtgaac gagtcaaaga agcagaaaca aaggggtgg gggagcctgg atgttgccgg    11220
gtcatgggtc ggaaggctgg aaggagcacc taggctgagg atagacccgg gactgggagc   11280
tgagggagct ttcttgtttg gagactggga tatcgtcggt tcacttgaga gctgtttctg   11340
ttacgagcca gaggctgctg agtcagtgga gattcggcac cgatgactct tttcctccag   11400
tgtacgtgca tttatagtga gcatcagata aacaaaaga aaagaaaaag tttaaatcag    11460
tgtttattta cacagaaaga gataagtgtt gccatgtgtc acatggtaca gatttcttgg   11520
attgcttgcc aggtgtttat aggtaaatgg attcatttat caattgacca atatcaaata   11580
agaaagacat tatttgggaa gagctcagga atgaattcta cacatatgtt tatcttaatc   11640
attaggactg tgggcttcgt ggttggtttt tcacgttaag gtgggcaccc ctgttctctt   11700
tctttttcaa atcaagtctc tgattcctaa gcgatctaat ttgagctcaa agtacgtaat   11760
gtttggactt cagcaccttc cagaaatata tcactctgaa gtctgcaaag tacagtttca   11820
aagaaaacac tttttttaca ggaaacagag agctaaagtg atctcatgtt cacattccaa   11880
ttttggtttc acttagtgct tgggataaaa attacttctc tgaatgcaat attgttactt   11940
ttttttttcc tgcttacctt cttaaaacac tgagtttact cagtcaagtc tgaaaccatg   12000 catctcttc ccagaaaaat gaaagctgac aagaaagttg aatgactaat ttttaaaata    12060
ttgcatttaa aaataatga gggttccttg taccagctat atgatgagag attgctgaac   12120
tatttgttag ataggatctg gtgatacctg cctaacttta aaataggat tcaggggaca    12180 cccagtggtt aaaaggagga aattcctcct gaggtgcagt gttcagttag aataagtatt   12240
tcttgtctca gcagtcaaaa tgttgataca ttgctgattt tgtctttctg aataagcata   12300
tgttagctgt atgtgtgtgc tttaagaaga aagggacttg gttttgacat ttatatgaat   12360
tttcttcaag tatttgaaaa cttacaaatt ataaggttag aaatgttaga aatgtgatta   12420
aacttttctt ttaatgaaga cacaataata ttaataaatg agaaataagc aacccagagt   12480
cataaataag aaaaacaatt aaaatttttt gacccagaaa ttccagttct agaaattttt   12540
ttcaaataca taatcagagg tgtacttgat gcctgtgtac aaagtattca ccatagcttt   12600
atttacagtg ataacaaact agagaaacaa acatacagct ttaatgaact ggtgacgtta   12660
```

| | | | | |
|---|---|---|---|---|
| acagcacaaa | aatagtgagt | aaggtatctt | taacaccatg | ctttcaagaa catttaacaa | 12720 |
| tggaggaaaa | tgtttatgat | aggtaaaaaa | cgatgataaa | agaccagtaa ttccatgtat | 12780 |
| ttaacaaatt | gtgtatattt | tgatttgcat | aaaaatagaa | aaataactga atgtggttgt | 12840 |
| cttgattggc | aagatttcga | gtaatttgta | ttctcttctt | tatacttttc tctttattct | 12900 |
| aaacttttt | ttttcattag | agggagaaga | ataataaaca | gcatagataa taaaaggata | 12960 |
| atggaagaaa | atgttgtaac | aatgatcaaa | gctaaatctg | tgaatctatc tgcttagacc | 13020 |
| ttaaagggag | aaatgtttta | tgtgccttt | tcctttggaa | ccttcaagag atgtttccag | 13080 |
| agtaaagctg | ctgctgccac | cctttgtgtg | tgtgtgtgtg | tgagtgtgtg tgtgtgtgtg | 13140 |
| tgtg | | | | | 13144 |

<210> SEQ ID NO 3
<211> LENGTH: 11057
<212> TYPE: DNA
<213> ORGANISM: Bos taurus

<400> SEQUENCE: 3

| | | | | |
|---|---|---|---|---|
| actcccaact | tcatctcctc | agcccagaca | gacagacagc | caccgcataa tccaacagct | 60 |
| ggaagctccg | cgggcagtag | acggtggcaa | tcacagggca | tccctggttt gttttccctc | 120 |
| tctggggac | cccgtccttg | ctgactggtg | tccagcatct | ggaaaccgct gtagcatata | 180 |
| gtggtctagg | gttttcttta | gttatttaag | gcagaaacac | tccttccttt ttaatctcaa | 240 |
| tttacttaca | taagactgtc | atcagtgtaa | aagggaaaca | aacctgtgtt tgccaggagg | 300 |
| ctgtggccca | gcttacaaac | cgaagttcct | tcttttactg | tgaagggatt tgagttgtga | 360 |
| cagttttctc | atttatacgc | ctggtcactg | acttgcttct | ttgttcattt agcaatgcgc | 420 |
| ttgagtgttc | tgcaggtatt | ttactaatat | tgaaatgtgc | cacaaaggct gttgaaatcg | 480 |
| cctatcccat | atcctgtcct | gacacccgtg | agtacctcag | aaggaggctt gccactccca | 540 |
| gaaacactga | ggtcatgttt | attcctgcgg | atcttgatga | cgctggatca ccctcccaca | 600 |
| cacacactca | cacaccgtgt | gaggcctagg | ggagcgaggt | ccagaggggc cggcatctgt | 660 |
| cacagctgac | gcacgagcac | caggacctgc | tgctctggct | ctggaaggcc acactcatca | 720 |
| cggaagcctt | tcagcattga | ccccggaagt | gatccccagg | tccctcagc tagcagttat | 780 |
| cgggctcccc | aggcggcgct | agtggtaaag | aaccagccta | caatgcagga gacttaagag | 840 |
| acatgagttc | agtccctggg | tcgggaagat | gccctggagg | agggcatggc aacccgcttc | 900 |
| agtattcttg | gcctggagaa | tcccatggcc | agaggggcct | ggtgggctag tccatggggt | 960 |
| cacaaagagt | cagacatgac | tgaagtgact | taccgtgcac | agcagttatt gagtaatcac | 1020 |
| agtatctctg | agtgtgggct | tagatgcact | gtatatataa | tttcatatca tctccagagt | 1080 |
| tcctgtaaga | ccagtcacag | gacatgttct | caccagtcag | aatcactggg tacagtactc | 1140 |
| actgtattga | aaaaaattag | ttctgctctg | aaggctgctc | ttgttcaacc taacaaagct | 1200 |
| taaaagcaaa | cctcaaaagg | atcaaatttt | tccaggtaa | tagaatcatg accagtcctt | 1260 |
| aaaaaaaaa | aaaatcactt | tcttttcaat | gaaaaaacta | ttcttctatt atataaatgg | 1320 |
| gcttccctgg | tggctcaggt | gatagaaaat | ccgcctatga | tgtgggagac ctgagttcaa | 1380 |
| tccctgggtt | tggaagatcc | cttgaaggag | agcatggtaa | cccactccag tattcttgcc | 1440 |
| tggagaatct | ccatggacag | aggagcctgg | agggctgcag | tctatgggt tgcaagagt | 1500 |
| cggacatgac | tgagtgacta | agcacatgta | ttatatagat | aacaaagctc caaaaaaatt | 1560 |

```
ctcagcagcc actaagaccc attatgagtt aaaattagat gcacaggggt tgccctgggt    1620
tgatgagtct gtcccagtgc cactggttca aggccttggg cctctctctc ccccagagca    1680
gcaatttcta acctgtgagc cacagacttc aggccacact tcatttcata cagtcctctc    1740
agtctctctc tgagatacaa ataggattat tttcattgct caggtgagaa agtgagtgtt    1800
taatagtgct cataaacttg accgaggtct catagttggc atttggttgc agccaggatt    1860
ttcctgccac atgtatcaaa gagcaggacc attattctag aggatttggc acttttctgt    1920
gtagagccat caggtctcag gctggcatga ggcctcactt aaggggcctt tcctgagatt    1980
ttagaagata gtgacacagc agctttgcct ggctctcgga atttcattgt tactttgaaa    2040
acttgaattc ttattttgag acttgagttc tgattcattc aataaaaact tttgttatga    2100
accacaacag acatccaaga aatgcatgcc gttaattcct ttcatgtcct cctgcaacag    2160
cggacaggat ggatgtaatc tgtgcgttct ttatccatct tgtctgctca agacgaggtg    2220
ccgttttatg gatctcctgg ccggcagact ctgaacttct ttcgagatgg gagaggcagc    2280
ttctagcaga aggtgtggat tcatggtcca tggaaacagg gtctatgtct tctcaggagt    2340
ctgcacctga gcaggaaaaa atcacacaaa ttccctataa atggaccgga cctgatgacc    2400
tggagtcaga gtccagtaga ggcagatctg gcatggatgg tgacacttct gtcaactgtt    2460
tttaagactg aggccctatg acaggctggc ctgccaggaa gggtgactca gccttagacg    2520
aggggcagac tgttcctgac catttccttt ctataaaact taagtaaaac agagacgtgc    2580
tcgtaaatgt tagaaggaat gcggttgaat ggcaagggag aatctgttca gtggcctcga    2640
agaaaaatta gttgaactca aactttgaat tgtcctggta ccggtgttct cacgtaacag    2700
cttaatcgtg tagagaccag agcgtgtctg tgtgtgaaga caaagacaga atcctacagg    2760
agtgagcttg ttgcgagttt tcccttactg tgagtaaatg aattccattc tatccagggg    2820
tagacccagc cctgtcagag ctgtgaatgt gcagacctag ctgggtgaga atgtgtccag    2880
ggccagactg cgatttctaa ggactgatgc tcatggttgg ggggagagag ggggtgagga    2940
tgaggaagac tgcacaagtt aagttcacgc tgacgtgaag ccaagggact ttgagaactt    3000
ttcccgtgga gacaagaaag actcccaagg actagatggt aggtacccag agaaggcagg    3060
aagccagcca aggcctgcaa gaaactggtg gtcccagccc acctgactgt gggtctgtca    3120
tgaacccacc gcttcggact cagcatcttg gttcagcatc ctgtatcacc ttgttccatg    3180
cttgctggtg cccacgttgc ttcagcggca gcaacttccc tctgttcctc cagctagcta    3240
aacccagccc aggaccctta tccgtgccgc cctatccacc tcgagtgcct cccttccccc    3300
gtgccgcact ttatgcttga tttatttata ccagatctca gtcaaatgtc acttctttgt    3360
ctatcctgtc taaggaaccc ttagccagtt actctctgtt acatgaccct gttttattat    3420
ctttacaaca ctcttcactc tctgaaacca tcttgatttt tattgactta tttagagtcc    3480
aagtcctctt actggaatgt aagcagtaca ggagtaagac ctgttttgtt caattggtca    3540
ttatatcacc actgcctaga ggaggaccag gcttctagcc agggttcagt aaatgtccag    3600
tgagtaaagg gatggtggtg atgggtggtt tagtcgctaa gttgtatcca acacttgcga    3660
ccccatggac tgtagcccgc caggctcctc tgtccgtggg cttctccagg caagaatact    3720 ggagtggggtt gctgtttcct tctccagagg ggtcttcctg acccaggaat cgaacctggg    3780
tctcctgcat tgcagacaga ttctttacca aatgagctac aagggaagcc cggagtaaag    3840
ggatgcatga agtcaaatac agctgaagag agaaccacgt catgtatgtg tggttcacag    3900
tgaaaacaat gtgtaacaat acaaatctga gaataagggg tttgtgctgt ggtatatgtg    3960
```

```
tgcatatcta agcttttgtg ctgtgtttca agtgcctgac attgttaaga gctctataaa    4020
tattacataa tggaagatca tttttttacaa attctactcc tgtttcagct aaactaaatt    4080
ggtcctttgt aaactagata attcagttgt ctcaaagaac aaagcaaggt catacccaca    4140
ggaaagctga gatacccatc ctcagttgag ttaaaagata ctgaatttaa taataatttt    4200
aaaattacct tttaaagtaa acgttaagtt tatacacagg taaaataaaa atcattatgt    4260
atgttaaatt tatattaaaa aaaaaggcat gtgtatcaag ttattttttaa cttaatggtt    4320
ttgtaactca gccaaaagtt tttaattttt gtgggcaaat cttagctaac gggtgaagta    4380
gaattcattt acagataagt ctgggtctgg tatgtgcatt ctgatgtgag aattgaagct    4440
gcagttagtg caggattgca acgtgacctt ccctgattac agctgggacc acaagttaat    4500
agctggagca gtggacagtg attggacttt gccaggcttc agtctcctca ctggaaatga    4560
ggaggttgaa atggaaaatg caagtataat gaataacccc aatgctatat gcttgtcttc    4620
ctttcttata tccaaccccct tacacggaat ccatgttatg cactatgatt atcagaagct    4680
gcttggctcc tctgtccatg gtattctcca ggcaaaaata ttggaatttg gtagccattc    4740
tcttctccag gggatcgtct ccacccaggg atcaaaccca ggtctcctgc attgcaggca    4800
gattctttac catctgagcc accagggaag ccctctttaa ttctatcaca tttatctagg    4860
atttttttct tcctctggtt gatggtagtg catgaatgct gggagagac tacttagttt     4920
acagttgata ctttggagtc tggggcccct gcagaggcct ctgaagaccc tcagacaccc    4980
attaaaacgt gtccaccctg ttgattcagt gggcaccctg cagggctctg agaatggcca    5040
accagtggac acatgaccat tggactttga ggacagcaag ctgagtttca tcttttctac    5100
ttgctaagac agtatttgcc ctgaagggaa acaaggcttc agctcaaact tcagctcaaa    5160
ttgtggcaga cagtttcaca aaattaagca atataaattt tgctgaatat cttctaaatg    5220
ttaaagaatt caaccaaatt cttctcaatt atatattttt caaaaagtgt ccaaagttgt    5280
gtgtaagtgg aaatgtaact ctttacagtg ttatatatca cctaatcggc atgataaccc    5340
ctcctatgta ttcaatgctt atagtacatg cttcatgttt tatagatact ggatcataat    5400
ctcgccatgt tgcattataa actttatatg cttgcttctc tgaaatacat aagtaaaatt    5460
cataagtaaa agatacaaga tatcaagtcc ttgtggagaa agcaactgta tattttatct    5520
tccccccttg tttattatcc atttgtcact taagtagtta tatgccactg ccgctgctaa    5580
gtcgcttcag tcgtgtccaa ctctgtgcga ccccatagac ggcagcccac caggctcccc    5640
tgtcactggg attctccagg caagaacact ggagtgggtt gccatttcct tctccaatgc    5700
atgaaagtaa aaagtgaaag tgaagtcact cagtcatgtc tgactcttag caaccccatg    5760
gactgcagcc caccaggctc ctctgtccat ggagttttcc cgtcaagaga actggagtgg    5820
ggtgccattg ccttctccaa gtagttatat aagaaaataa aaaaaaaaaa gaactcttaa    5880
ccccacgatc agaaaataac cccacataaa cttcagagat catactatgc atgttacttt    5940
ataatgtggc ttttctttat gtaaaatata agttaagtat tttcatttaa tgcagtgttc    6000
ttctaaacat gatctttaaa caaccacatg acatttcatc ctgtagctgt tcatagcatg    6060
acctcttatg tgggaggcag tgtaggtagg tgagagaata aggtctgaaa tagacatttt    6120
gcttttttaca agctgtgacc acggccaagt tatatactca ccccattcct ccatctcctt    6180
acccataaaa tggggataac aatagtaaca gccttatatt gtgtaatttt aagattaact    6240
aacttgttat acatgataca tgttacatat ttatcatgtt atatgatgtt atacacgtta    6300
```

```
cacatgatga tgcttagagc acttacaata gtactgtaat atattgtatt attagagcat    6360 tatttttatta ttatctataa tttagttatt ctgatggaac aattacctga tacacattga   6420
gtaagaactc aatgtgcagt gaaaatgaag tgaaagtcgc tcagttgtgt ctgactcttt    6480 gagacccat ggactataca gtccatggga tctccaggcc agaatactgg agtgggtagc     6540 ctttccttc tccagggatc ttcccagccc aggaatcaaa ctgggttctc ctgcattgca     6600
ggcagattct ttaccaactg agctatcagg gaagcccta tggagtgggt agcctttccc     6660
ttctccaggg gatcttccag cccaggaatc gaacctaggt ctcccacatt gcattcggat    6720
tctttactgg ctgagccaca agggaagccc aagaatactg aagtgggtag cctatccctt    6780
ctccagcgga tcttcctgac ccaggcatcg aactggggtc tcctgcattg taggcagatt    6840
ctttaccaac tgagctatca gggaagccca agaactcaaa taatttatta ttatgcatca    6900
ttgtattcta acttcaaaaa gcaaaaaaca gtataggtaa taaaggactc aataaacatt    6960
cattattacc tatattgtgt tttgcttttt gaagtcagaa taccgtgatg aatatctgtg    7020
aaaaaaaaaa ggcttttgct cttgtactat tatttcccta agataagttt cttagacata    7080
ggattgcatc cttgctgctg agtcaccctc tgcagcctgt gctaacgcct gctctgcagc    7140
gctcagggta agagagaaag aacgcaccct gtcccagtga gtgatgctgt tctgggaatg    7200
catggcagtg gaaaatggca cctggccatg tgaggagttc ggcagtttc caaaaccatt     7260 gactattgaa caattgcaat ttactcaatg cactctttct ttttaatatt tatatagtct    7320
tcaggctaag atataacaaa ttaaaaactt gtttcacttt ttgtgtgctt agcattgagt    7380
atattagtct gaattttgct tgaaaagata cttgtattga cagaaaaatt tgcggttgac    7440
cacactgtta aggtatcttc ccccatcgaa gctaatattt tcttttttt tttttcaga     7500 aaaaagcaac aagccttggg agcagtcagc tctccagaac tcaggctgat gaaaaagccc    7560
tggtccccaa ggtcagtcat ttcctggaca tgaaaagaca cctactttac agatgtatca    7620
ctagtggggg gtgggacttg tagggaaaac agacatgtca aatatgtcac tgaaaatgga    7680
acaaagtatc atttctgggc aggtggggga ggtacaaagc aacaggcata acatttctta    7740
ataaggattg atgatttaag acctaataaa gacatttgtg ttattattct tactggcatc    7800
taatagtaag agtccaaaaa tattaatcat tattctaaat gtttataaat aatatttgat    7860
ttttgcacat attatgagta gaaatatagt tttttcattt cttcagaaaa taattcaaat    7920
tatctttatg agtattaagc atagcaggtt cttgctaaat gtgctgtgta attatcttat    7980
gttatctgtc acaaccttat aattattatt cctttatact tgaggaaacc tggggtcaga    8040
gaggttaagt aaccttgaca agatcacaaa gccagtaaga tggaggtagg gttcaaaccc    8100
aggcttccag ttcacaaaag atcctggacc ttttaaagtc tgaccaagcc ttcttcggca    8160
atataacact accaagtttt gcagcttata aaaaccactg aaatttcatc tttcaagata    8220
agctgtaact ccaatttaag ctaatagttt ttaatatata agtaaaagc tatctatgct     8280 ccttccactt cagctggtga tcttccagta tgtccaggat tatccaaacc ttaacctgtt    8340
tcgggattgc ctatatgact actgaaaata agcctttttt tcccattgaa actggtagct    8400
ctcctgtgga gggctgtgga cttcctcatt catgtatgtt acttgcttgg tgaagagtgc    8460
atattttaga gcctcctgga gcctcagctg ctgtccaaac cccttataag tatccaaact    8520
aaaacccagc tgagacatga gaagaggctg ggccagggta tctctgctgc cattgccctt    8580
gttagtcctc atactctctt gtttggaggt ctccaactaa aatatatttt ctagacatgt    8640
cctatctttt gtaatattat gacttttatt taacttgcac ttaagttatg cctctaaaaa    8700
```

```
tttgaagctt cattagttca gtctctcagt cgtgtccgct ctttgtgacc ccatggactg   8760
cagcatgcca ggcctccctg tccatcacca actaccggag tttactcaaa ctcatgtcca   8820
tcgagttggt gatgccatcc aaacatctaa tcctctgctg tcccttctt ctccggcttt    8880 caatctttcc cagcatcagg gtcttttca gtgaaaagac tggttctttg catcaggtgg    8940
ccaaagcttc attagccaga cctcaatctc aagagatttt tagtgaatca tttgtaaatg   9000
gtttctagag ttgtcattac ctaaactctt ggagtttcag tacattgtcc agatctcctg   9060
cctgggaagg gcctttattc atttcattca ttcaaactct tggagggtca gtccattgtg   9120
gaaaatcaca cttaggtatt tttgtttcct ttatttcctg cccacccgct ccttgaattt   9180
agtggtaaga agcagtccct tttacatttt ttttctaccc aggagtatca tacactcatt   9240
tctaggtaga attcttgtga agaatttggc aattctcctc aaaccttgcc cctgcctcag   9300
gaagctgtgg gagggagtgt agctaggagg cagagacatt tagccacaca gtgactgatt   9360
tagtatttac tggcagactt gtaattctct ccttggcttc tcccatccca ttcttctatt   9420
gttctttatc actgtggttt cctgactgga gttccttcac caatttcctg aatattgttt   9480
tttccaggat ttaattcttc attccttcct ttttatatct ttaaccctta cagagtatta   9540
gaaatacata tatatataca cttatatatg tgcataatat atatacttat atatgtgcat   9600
acatatatat tatatatata tataatatat atatactttc ttagttttt aactttgtct    9660 tttgatacta gattgaaagt cctcagtatc atcatcactt aaaaatgacc attcccatgc   9720
atcatttaat agcatttgtg acccttgaa gcctttatt acacaataaa ttatcacaac     9780
acacaggcaa atgatattct cccgacacat aacatgacaa tagtagatat aattggtagt   9840
gagaattagt tctggttttc ttgattctgg acacattcaa ctcaaagtaa gtgacaattt   9900
tacttattaa gaaaaacttc agttcagttc agttcagtcg ctcagtcgtg tccaactctt   9960
tgtgacccca tgaattgcag cacgccaggc ctccctgtcc atcaccaact cccggagttc  10020
atcgagtcag tgatgccatc catccatctc atcctctgtc gtccccttct cctcctgccc  10080
ccaatccctc ccagcatcag agtctttcc aatgagtcaa ctcttcgcat gaggtggcca   10140
aagtactgga gtttcagctt tagcatcatt ccttccaaag aaaaacttag tctgtattaa   10200
aatttcagta tggcaatagc accccactcc agtactctta cctggaaaat cccatggaca   10260
gaggagccgc aaagagttgg acaggaatga gccacttcac ttcactttca cttttcactt   10320
tcatgcattg gagaaggaaa tggcaaccca ctccagtgtt cttgcctgga gaatcccagc   10380
gacggcggag cctggtggac tgctgtctat ggggtcgcac agagtcagac acgactgaag   10440
cggcctagca gcagcagcag cagcagcgag ctgtatatag ctgtatatta gagactggtt   10500
accatgtatt gcagaaatgt tttatgagaa ttcttacaaa atcagtagtt atgtgtacaa   10560
ataatatcac ttctgccata cagtcctggg tttggaggtc caaaatactt aagtggcata   10620
gatatttcta attcaaaatc attatttaa ggtgtttagt gcttaaaatt ggagaaggcg    10680 atggcaccc actccagtac tcttgcttgg aaaatcccat ggatggagga gcctggtagg   10740
ctgcagtcca tggggtcact aagagtcaga caggactgag ctacctcact ttcactttc    10800 actgtcatag attggagaag gaaatggcaa cccactccag tgttcttgcc tgagaatcc    10860 caggaacgga ggagcctgat gggctaacct ctatgggtc gcacagagtc agacacgact    10920
gaagcgactt agcagcagca gcagcagcag tgcttaaaat tgaatttta taaattaata    10980 atgaggtcta atgaggctat agaaattaga ctcttactaa ataaatagct ggggtccata  11040
```

-continued

| | |
|---|---|
| atcagtcatg cagttgt | 11057 |

<210> SEQ ID NO 4
<211> LENGTH: 23250
<212> TYPE: DNA
<213> ORGANISM: Bos taurus

<400> SEQUENCE: 4

| | |
|---|---|
| cttgaatatt tcggttactg tttatcgcct tttgccctcc agggaggagt ctgttttgcc | 60 |
| ctccagttct gatctgctaa gttgcttcag ttgtgtccga ctctgtgcga ccccatagac | 120 |
| agcagcccac caggctcccc catccctggg attctccagg caagaacact ggagtaggtt | 180 |
| gccatttcct tctccaatgc atggaagtga aaagtgaaag tgatgtcact cagtcatgtc | 240 |
| cgactcttag agaccccatg gactgcagcc ttccaggctc cttcgcccat gggattttcc | 300 |
| aggcaagagt actggagtgg gatgccattg ccttctccga gttctgatct acttgagtct | 360 |
| atttcccaga gctgtgccta ctcttctgtc tggtataata ccttagaaat aatgccctgg | 420 |
| caatttatg agcgcctaga atgtgcaggc gttttaccca cattatctca aatacatgca | 480 |
| gccctgcaaa ataggtatta taggctccat tttatatatt tggaaaagtt aagacccaaa | 540 |
| gtcacagagc tagtaatggg gaaagctgac atttgaacaa aattctctaa gtttccaagt | 600 |
| cgatgttcct tctgaaaata atacaaacaa aaattagaat gatattttgt tgttgttgtt | 660 |
| cagtcgctca gtttatctga ctctttgcga ccccatggac ggcagcatgc caggcctccc | 720 |
| tgtccatcac caactcctgg agcttactta aactcatgtc cattgagtca ataatgccat | 780 |
| gcaaccatct catcctctgt cgtccccttc tcccgcatct ttcccagcat cagggtcttt | 840 |
| tccaatgagt tggctcttcg agtcaggtgg ccaaagtatt ggagcttcat tttcagcatc | 900 |
| agtccttcca atgaatattc aggactgatt cctttagga tggactggtt ggatctcctt | 960 |
| gcagtccaag ggactctcaa gagtcttctc caacaccaca gttcaaaagc atcaattctt | 1020 |
| tggtgctcag cttcttat agtacaactc tcatatccat acatgaccac tggaaaaacc | 1080 |
| atagctttga ctagatggac ctttgttggc aaagtagtgt ctctgctctt taatacgctg | 1140 |
| tctaggtttg tcagctttc tttcaaggag caagtgtctt ttaattcat gcctgcagtc | 1200 |
| accatccata gtgatttttgg agaccaagaa aattgtcact gtttccattg tttcccatc | 1260 |
| tgtatgccat gaagtgatgg aactggatgc cttgctctta gtttttttgaa tgttgagttc | 1320 |
| taagccattc tccactttca ctttcatcaa gaggctcttt ggttcctctt tgctttctgc | 1380 |
| cataagggtg gtgtcatctg catatctgag gttattgagc acttaattac caggcagcaa | 1440 |
| tagacttaga aggtctttat ttcctatgga agaaaaatca agcagaaact aaagatcaga | 1500 |
| gtgtttaagt agcttgccca agattattta ctatgtagca cacccaaaat ttgaaccccat | 1560 |
| ttggagtgat tacaaaggtt ttacccactg gacaacacca tgtactgaac tttcatggga | 1620 |
| gtgttactct cagttcagtt cagttgctca gtcgtgtcca actctttgcg acccccatgaa | 1680 |
| tcacagcacg ccaggcctcc ctgtccatca ccaactccca gagttcactc aaactcatgt | 1740 |
| ccatcgagtc agggatgcca tccagccatc tcatcctctg tagtccccctt ctcctcttgc | 1800 |
| ccccaatccc tcccagcatc agagtctttt ccaatgagtc aacttttcgc atgaggtggc | 1860 |
| caaagtactg gagtttcagc tttagcatca ttccttccaa agaaatccca gggctgatct | 1920 |
| ccttcagaat ggactggttg gatctccttg cagtccaagg gactctcaag agtcttctcc | 1980 |
| aacaccacag ttcaaaagca tcaattcttc ggtgctcagc tttcttcaca gtccaactct | 2040 |
| cacatccata catgaccaca ggaaaaacca tagccttgac tagacagaca ttgttggcaa | 2100 |

```
agtaatgtct ctgcttttca atatgctatc taggttggtc ataactttcc ttccaaggag    2160
taagcatctt ttaatttcat ggctgcaatc accatctgca gtgattttgg aacccaaaaa    2220
ataaaatctg atactgtttc cactgttccc ccatctattt cacatgaagt ggtaggacca    2280
gatgccatga tcttcatttt ctgaatgttg agttttaagc caacttttc actctcctct     2340 ttcactttca tcatgaggct ttttggttcc tcttcacttt ctgccataag ggtggtgtca    2400
tctgcatatc tgaagttatt gatatttctc ccggcaatct tgattccagc ttgtgcttct    2460
tccagcccag tgtttctcat gatgtactct gtatataagt taaaaaaaca gggtgacaat    2520
atacagcctt gatgtactcc ttttctattt ggagcttgtc tattgctcca tgtccagttc    2580
taactgttgc ttcctaacct gcatataggt ttctcaagaa gcaggtcagg tggtctggta    2640
ttcccatctc tttcagaatt taacacagtt tattgtgatc cacacagtca aaggctttga    2700
catagtcaat aaagtagaaa taggtgtttt tctggaactc ttgcttttc agtgatccag     2760 cagatgttgg caatttggtc tctggttcct ctgccttttc taaaaccagc ttgaacatct    2820
ggaagttcac aattcacgta ttgctgaaac ctggcttgga gaattttgag cattacttta    2880
ctagtgtgta agatgagtgc aattgtgcgg tagtttgagc attctttggc attgcctttc    2940
tttgggattg aatgaaaac tgacctttc cagtcctgtg ccactgctg agttttccag       3000 atttgctggc atattgagtg cagcactttc gcagcatcat ctttcaggat ttggaatagc    3060
taaactggaa ttccatcacc tccactagct ttgttcgtag tgatgctttc taaggcccac    3120
ttgacttcac attccaggat gtctggctct aggtgagtga tcacaccatc gtgattatct    3180
tggtcgtgaa gatctctagg tgagataaaa ccaaggtaaa gagttaaaag taagtatggt    3240
taaaagggac ttccaccatg actcatatgg taaagaatct gcctgcaatg caaaagaccc    3300
agcttccatc cctgggtcgg gaagatcccc tagagaaggg aatggcaact tactccagta    3360
ttcttgcctg gagaattcca ttgacagaga acccggcag gctacagttc atgaggttgc     3420
aaagagtcag ccacgattga gtgactaaca ctactacact gctgtggtta aaggaggtg     3480 gaggacaaag cagggtgtag gttaactagg ctcaaacttc ctgtttcttt tctttctagg    3540
taactacttc ctctgcgtca gccagcaagt cttccagtat gaatcccaca gaagccaagg    3600 tatgagagt cttcaagggt caacttgggt gaaagcctc attttgtaaa gcaaaatgaa       3660
tagagacttt gacagatagc ttgtgtgtcc taggagactt acactatgga agtaaatatt    3720
ttcttcttaa ttaatgaggg tctttgaaaa ctcagctttc ctttcagtat ttgcctcaaa    3780
caccatctat atacttatac aggattttag aatatctaga aaagtgtagt ccgtgagagt    3840
tcttttggtt ctagccttga gttttttaaa ttgtaaaaaa gtatctctaa gtacattat     3900 caagatctag atagaaatat aaattcttaa tttcttacta aaacggtttt attatcctaa    3960
ccatttaaaa cgaaatccaa gaatgagaaa gtttacacta aatgaacata gaaagaagtg    4020
acacagactc tggttatttc agatgctttc tgaagttttt ttctgacatt tgagtcatgt    4080
gggtcaccat cttattgata aactgtggtt gagctcttgg ggtgtattct gataatttct    4140
tggaatttca gaattagaaa taaaagaatg gcctgcagtg ggattgccac atagaataat    4200
aagcctactt ctaaagagtt gactgagcga cctaaaccct ctcaccgact taccatgact    4260
cgaactgagt ttctcgggaa tgttctaggt tggaagatta aagaggaagc attttctcaag   4320 atgctctcaa ctaattctta tgagctaata ttcttcagtg cctgtaggag ctaccccagc    4380
tccattatta tcaaattgcc cttgtttaaa attaccaaca cacttttgct ttgtgttttc    4440
```

```
cttgttactt tactgtccca agtagaatcc tatgccataa tttaatactg gcaccataat    4500
gtagtactgt ttagtaatcc tgtggcatca tcttgaactg tatttaaagg agattgaaac    4560
tatcttgaaa cacgctgtca aactctaagc cctatccaa tgtcatttag cactcatttt    4620 tattttaaa tgtaaaatta tgttttatt tagtaattaa tttcttaatt ttttcaaaat    4680
acatgttatc tgattcgtga ttaaccacct attaggtgtc actacttatt tataccaaag    4740
tgaagtgaag tcgctcagtc gtgtctgact ctttgtgacc ccatagactg tagcctacca    4800
ggctcctctg tccatgggat tttccaggca atagtactgg agtggattgc catttccttc    4860
tccaggctga tctttaaaat gatcttaaga ctatagaaaa aaacatttag ccctgcccc    4920 cgaaaaattc tcattgaact tagagtccgt gaaaattaaa gtaaggagat aaaaaggaga    4980
gccagaaata tgagatttcc tttttcttat tattttggtt cacatttgac atgatgcctc    5040
attataattc atccctgctg acactcagct taagggccga tgcttatttc aagtgtgtcc    5100
tgttttccag agtaaatgtc agcaaatgct tcagccattg cgagcgtgaa tcatgagaat    5160
tcttggcact cctatagacg tggactgagg ggagagagag aggaaagtag gagagggaag    5220
aaagggagga acaaaactaa gatgcgccag tcgatgactc agaaccactc ttggccttaa    5280
ttctctgtcc ttggtggatt tcagtcatac tgttctcatt aatcatctta tcttcgtgtg    5340
cttctttaat tttttttaat tttaattaat tttatttaat ttaatttgta ttttatattg    5400
tagtaggctt cccaggtgac tcagtggtaa agaatctgcc tcccaatgca ggagctgtag    5460
gcttgatcct taggtcagga agatgccctg gagaaggaga tggcaaccca ctccagtatt    5520
cttgcctgga taatcccata agagggata atcccacaga ggagcctggc gggctgcagt    5580
ccgtggggtc acaaagagtc agacacaact gagcgaccga gcagccacac ccacagttga    5640
tttacagtgt tatgttagtt tatggtgtgc atactttttc catttattgc agaatattga    5700
gtagagttcc ctgtactata cagaagatcc ttgttggtta tctatttaa atactagtgt    5760 gtatatgtca atcccaaact cccagtttat cccccctcct ttccccttta ataaccataa    5820
gcttcttttc tgtttctgtt ttgtaaataa gttcttttgt atcatttttt taagattccc    5880
catgtaagag ataccatgct atttgtcttt ctgtgtctga attagttcac ttagcccagt    5940
aatctccagg gctatccatg ctgccacaaa tggcatcatt tcattctttt taatggctga    6000
gtaatattca tatatatata tatattttaa tccattcatc tgttgataga cttataggtt    6060
gcttccatgt gttggctatt gtaaacagtg cttcaatgaa cattggaata cacgtatcct    6120
tctgagcaat ggttttctct ggacctgttg ccaggagtgg gatgacttga tcttatggtg    6180
gttctttgct tagttttcta aggaacctcc atactgttct ccatcgtggc tgtaccaatt    6240
taacattccc accaacagta tgggagggct ccctatctca caccctctct ggcatttagt    6300
gtttgtagac tttttgatga tggccattct gactggagtt aggtgatatc tcattttagt    6360
tttcatttgc atttctctaa taattagtga tgttgcacat cttttgatgt tcctcttggc    6420
ccatttgtgt gtcttcttta gagaaatggc tatttaggtc ttcccatttt ataacttttt    6480
tttttttaat attgagttgt gtgagctgtt tgtaaatttt ggatattaat cccttgtcag    6540
tcacatcatt agcaaacatt ttctcctatt ctgtaggttg tcttttcact tgtttgtgg    6600 tttttttaa tgtgagaaag cttttaatta ggccccattt gtttattttc attttactc    6660 ccattattct gggagatgga tccaaaaata tattgctgtg atttatgttg aaatgtgttc    6720
tgcctatgtt ttcctctgag agtttttatac aagtatctgg tcttgtattt gggtcttcag    6780 cccatttga gttaattttt tgtatgaaat tacagaattt tctagcttaa ttctttcaca    6840
```

```
cgtagctgtc caattgtcct ggtaccactt tttgaggaga ctatcttttc tccatggtat    6900
agtcttgcct cctttgttga gattaattga ccataggtac atgagtttct ttccagaatt    6960
tctatcctat tctgttgatt tgtatttctc tttttatata tttctgtttt tatagttatt    7020
tggtgattgt agctttgtag tatagactga agtctggggg cctgattcct ccagctccat    7080
ttttcttttt ctagattgct gtggctattt gggttctttt gtttctccat acaggtttta    7140
aaattttttg ttctaggtct gtgaaaaatg ccgttatttt gtagagattg cattgagtct    7200
gtagatggcc ttgggtagtt gagtcatttt gacaatattg attcttccaa tgcaagaacg    7260
tggtgtatct tcccatttgt ttatgtcatc ctcagtttct ttcatgagtg tcttacagtt    7320
tttgaagtac agatcttctg cctcgtgaag taggtttatt cctaggtatt ttattctttt    7380
cgatgtgatg gtaaatggga ttgtttgctt aatttctcct gatcttttat tgttgatgtc    7440
ttgaaatgca acagttttct ctgtgctgat tttgtatcct gcaactttac tagattcatt    7500
gctgagctct agtagttttc tggaagcatc ttttggattt tctacataca gtattgtgtc    7560
actatgccaa agcctttgac tgtgtggatc acaataaact atggaaaatt ctgaaagaca    7620
tgggaatacc agaccacctg accttcctct tgagaaacct atatgtaggt caggaagcaa    7680
cagttagaac tggacatgga acaacagact ggttgttcca tgtccaaata gaaaaggag    7740 tacgtcaagg ctgtatattg tcaccctgct tatttaactt atacgcagag tacatcatga    7800
gaaatgctgg gctggaagaa gcacaagctg gaatcaagat tgccaggaga aatatcaata    7860
acctcagata tccagatgac accacccta tggcagaaag tgaagagcaa ctaaaaagcc    7920
tcttgatgaa agtgaaagag tagagtgaaa aagttggctt aaagctcaac attcagaaaa    7980
tgaagatcat ggcatccagt cccatcactt catgggaaat agatggggaa acaatggaaa    8040
cagtgtcaga ctttattttg gggggctcta aaatcactgc agatggtgat tgcagccatg    8100
aagttaaaag acactcactc cttggaagga aagttatgat cagcctagat agcatattca    8160
aaagcagaga cattactttg ccaacaaagg tccgtctagt caaggctatg gttttttcctg   8220 tggtcatgta tggatgtgag agttggactg tgaagaaggc tgagcaccga agaattgatg    8280
cttttgagct gtggtgttgg agaagactct tgagagtccc ttggactgca aggagatcca    8340
accagtccgt tctgaaggag atcagccctg ggatttcttt tggaaggaatg atgctaaagc    8400 tgaaactcca gtactttggc cacctcatgc gaagagtgga ctcattggaa aagactctga    8460
tgctaggagg gattggggc aagaggagaa ggggatgaca gaggatgaga tggctgcacg    8520
gcatcactga ctcgatggac gtgggtctca gtgagctccg ggagttggta atggacaggg    8580
tggcctggcg tgctgtgatt catggggtcg caaagagtcg gacatgactg agtgactgat    8640
ctgatctgat ctgattgaaa caaaatgtct agatgtgaga cagctactaa ggtcaggaac    8700
acacactaac agaaatacaa taatggactc tcctcatcag aatccagggg tgcagtggga    8760
atcacagctc atggatatgg caggaatgtt ttttttttaat taatttttttt attgaaggat    8820 aattgctttta cagaattttg ctgttttctg tcaaacctca acatgaatca gccataggta    8880
tacatatatc ccaaatcaag cagctgaact ttctttcagc ttaaatcctt ttcacaattg    8940
aacaaccagt ccatgctaaa ggaaatcaat cctgaatgct cattggaagg actgatttga    9000 agctgaaaact ccaatacatt ggccacccaa tgggaagaac tgactcattt gaaaagaccc    9060
tgatgctggg aaagattgag ggcaggagga aaggggacg acagaggatg agatggttgg    9120
atggcatcac caactgaacg ggcatgagtt tgaataaact tcgggagttg gtgagggaca    9180
```

```
gggaggtctc gtgtgctgta gtccatgggg tcgcaaagag tcagacacaa ctgagcgact    9240
gaactgaact gaactgaaat tgtatgaaat gctcatctca agcattttga atgtaagcaa    9300
ttttgcagcc tcgtaattgg ggtagagcag tttcttcccc tgtgatacct cttttgtgca    9360
gcatagtcgt acccacacaa agccacaaac acctcctgta acaaaaatgt gactagtgca    9420
cctccctcgt gctaacactc ttctgggccc tgaggaaaga tcagtgagca aaagagacaa    9480
agtcaccact gctctattag tcagacttgg cttaacaggt cagctttact gtgtgtgatt    9540
cccagagtca gggcttcaga gttgatctaa cctgtcgtga ttcctggctc tgtgtgacca    9600
taaacaagtg tttatatatc tctctttata gacactatat atgtgtatat acatatatat    9660
tatacactat atatgatata tatcatatat atggtatata tatattatat ataccata    9720 tattatatat gctatatata atatatatac catacattgt atatactaca tatataattt    9780
attatatatg tgctatatat aatactatat attatactac tatatataat atataatact    9840
atatattata tacactatat atgtatataa atatatatat ttatcacatc caatctatgg    9900
tgattcctgg ctctgcatga tcatgaagac gtgtgtatat agaagttcat agtagacatg    9960
tactgaataa aacactgcat aaatcgtaac cattatattt atgagcattt gttgaaaaaa   10020
ccccttcttc aaagatgttg ccatttaaag gagagctgct aagtcgcttc agtcatgtcc   10080
gactctatgt gaccccacag acagcagccc accaggctcc ccgtccctgg gattctccag   10140
gcaagaacac tggagtgggt tgccatttcc ttctccaatg catgaaagtg aaaagtgaaa   10200
gtgaagtcgc tcagtcgtgt ccgactctgt gggaccccat agacagcagc ccaccaggct   10260
ccccgtccct gggattctcc aggcaagaac actggagtgg gttgccattt ccttctccaa   10320
tgcatgaaag tgaaaagtga agtgaagtc gctcagtcgt gtccgactct gtgggacccc   10380
atagacagca gcccaccagg ctcctcgtcc ctgggattct ccaggcaaga acactggagt   10440
ggattgccat tttcttctcc aatgcatgaa agtgaaaaat gaaagtgaag tcactcagtc   10500
atgtctgact cttagcgacc ccatggactg cagcctacca ggctcctccg tccatgggat   10560
tttccaggca agtgtactgg agtggggtgc cattgcctcc tccgttaaag gagagcaata   10620
tcccccaaat actaatttaa gagctgaaat ttcaccccag agagagagag agaaacggac   10680
gggtttgtga gggcgggaat gcggaggtgc caccacagag cacggggtgt tgctgggtgg   10740
ccctgttctg agagggcaag actgccaaga cctgtgagga agtgcgcttc agacaggttg   10800
tgaaagggag tgttgaaaga gtggaagaga aaaacttgag caaggagatc caaagcctca   10860
taaagacagc ctaaaatgtg aactcaatca cacagagaga aggaagccct tcttcctaag   10920
aatgttgtgg agacacaacc tgagtaaagg tggttaactc tttctagcct agatgctcaa   10980
atcagagttc agatttgcaa gaggcatttc ctggtacagg aagaaactgc gaaaggtctg   11040
aatcatttct gagctgggtc tttatgcctg tgtccagcat tctgcctcct gggtgtattt   11100
gttggctaag tctgccataa caacagctag ggctggctta gaacaactga aatgtattct   11160
gtcttagttc tggaggctga agcccaaaag cggcgtgttg gcagggtctc agtcctttg    11220 cagatgcctg tctcaggtct ctctccagct tctggtagtt tctcagcttt cagcagcata   11280
actccagtct gcacacaatg tctacactgt gtgtgcatcg gtaccccaat ttttctttt    11340 tatgacatcc atcatcctgg attagggccc atctaatgac cttatttac ctttctatt     11400 tctataaaac cctatctcca ataaggtca aattctgttg tatggggtta agattccaat    11460
gtaccttttt tggagggaca cagttaaact cataacacag aaaaaaggaa acagacctca   11520
tcattaaagt actattggtt tgaatagtac aaagtgaagt gaagtgaagt cgctcagtcg   11580
```

```
tgtctgactc tttgcgaccc catggactgt agtctaccaa gctcctccat ccatggaatt   11640
ttccagacaa gcattctaga gtggcctgcc atttccttct ccagggatc tttccaaccc    11700 ggagatcgaa cccaggtctc ctgcactgca gacagacgct ttaccatctg agccaccagg   11760
aaagccccaa tagtacaaag caataacgta tttgcgaatt catatcaagt aaaaatccta   11820
tagaagcaaa cgagttttac aatgcaatga agcttctttg caagaaggct gttttacca    11880 cagaactacg ctgtgttgat ttgaataaca agtcatgctt aaagcaagat ctcctgttat   11940
ccatactttt agagtctgaa ctgggtctaa ttaacaaaca gtgttatgaa accaaaaggg   12000
tacttttgac cctgcggata cagagaactg ggctgttagc agagtagagt ttcctttaca   12060
gttctctgtg tgtaactggg cagcaacaaa ccaccctcca ctaatcgcat tgcagacatg   12120
acggctgcac cagcagaaaa gtcaggccac tttacagaaa caaaaatcat ccaagtctca   12180
aaagtattcc agaaagaggt ggcaggacac gggacaaaca tatagcccct gtcctgccgt   12240 cttttctgg aatagttttt cagtattcaa aaaacttttt acctgcttgt tagttcatag     12300
cagagaggct tcaacttcac cctcccaatt gtaatcacct ttgtaagttt tataaaatag   12360 ttcaaaaat aagaataatg ttttatatt ttaaaataat ttgagtgtaa gctggactta      12420
atgacttgct tccgaagaat agcgtataag aagggagaga ctagaactcc tcagtggagg   12480
aacccagcaa acaccacctt acttaagtga tggagatcac catcgctagt gacagagcat   12540
gtggatatca ttgtaccttc aagaggacgt gatgagaagc cactcactac tgtagtattc   12600
ttcccccaga cccacagccc cagcctactc accagaaaaa catcagataa cgtcaaattg   12660
agggacgttc tacagaacac ctgaccaata ctcctcaaaa ctgtcaaagt catgaatgcc   12720
tgtcaagaaa agactgaaga gctgtcacag tgcacagagg agtctgagaa gatgtgacga   12780
tagtgtgaga tcctggatta cagcctcaaa cagaaagagg acattaatga gataactggt   12840
gaaataaagt ctggggtttg gtgaacagta atatactaac taatgttggt ttcttagctt   12900
tgatgaatgt gtcacataag atggtgacat taggacaact gaaactggga actttatact   12960 accttttgcag cttttttcta actctaaaat tattacaaaa taaaattta ctagaaaaat    13020 gatttcctat tttaacaaga attttctgag aataaacacc cctaaaaatt tgaaataaac   13080
ttttatttgt aatcaccatg tttaaaggtt taaagtataa cttccagtcg cacatttact    13140
gcttgaagga ggtaaccaac atactacctg aatctgccag gtaacaaaag cactcctgtg   13200
gtgagtatct cttccaaaat ccttgaagga gcagcaaata taagtgggta aacagaagtt   13260
taagtggaag acctgtactc cagaaggatc ctaaagtgtt cttttgaaat tcatagatac   13320
ccatcgtgat gaaatagatt tgttttaaag gaagtatttt tttaaaaac agcttaatcg    13380 aaatatcttt cacatactac acaattcact caatttaact atgcaattca gtggttttta   13440
gtatattcac gaacatggaa agcactagtc aattctagga ttttttttta tcacctcgaa   13500
aagaaacccc aaacccttta gctatcaccc ttctgtcata gggcttccct ggtagctcag   13560
ctggtaaaga atccacctgc aatgcaggag accccagttc tattcctggg tcaggaagat   13620
cctctggaga aaggatagac ccactccagt attcttgagc tttcctggtg gctcagctgg   13680
taaaaaatcc acctgcagtg tgggagtgga agacctgggt tcaatccctg ggttgggaag   13740
atcccctgga gaagggaacg gctacccact ccagtatgct ggcgtggaga attccattga   13800
ctgtatagtc cacggagtca caaagagtca gacacaactg agcgactttc actttctcct   13860
gtccttacaa ccttctctcc ccaccagcca acccagaaca gttgctaatc aacttttgt    13920
```

```
ctctatagat ttgcatattc tgagcatttt gtgtaaaagg aatcatatat gacctttgat   13980
gactggctag ccatattatt tttataatct ccagatgtac tctgaagaac agatagttaa   14040
ggtaccttgg aaaattcact gttatcatta cagatattga atcacccatt ttgaaatata   14100
atctcaattc ccaacccaca agatatatgt agccatccac attccactcc ccaggccatt   14160
atcagtgtct gtatgtagca agaataacc ttagcatagt ggttaggcac ccacatcagg    14220
aagcgagacc tccagattca aatgctaggg ctgtcactta gcagctctgc aacccagggc   14280
aaattattca gtttctctgg gccttagtct cctcatctgt agcatggggg aagtaacggt   14340
ccctacgtca taagggtgaa acgagcaaat atgacctagt gtggagagcc attcggcgca   14400
aatagtacca ctgagtgttt agacagtact gctgacttcc tgatcttatg tgatcagaga   14460
cggtttcagt cataagcgtc tttttaaatt acccagtcca ctccttttcat cttttgaaga  14520
cggaagttta gcttggaaag actcaacagt gcattcttac tcattccata aatatttttt   14580
gaggacatag tctgtgccag ggagagtctc aagtgttgtg cataagattg aaatggtctg   14640
tttcatcatg gagtctagtg gaggatatgg ataagcaggc aaaaggtgaa tcagagaaca   14700
ttaatataca cctttaggag gaattgcatc atggcagaag gaaacaaggg ggattagaac   14760
aaaagaacat ctggttgatt tctgaagtgt ttatagaaga actttctgag caggggttg    14820
ggggaacgta gttaaagtaa gatacagaga gaaaggattt taaagatgtt ttgctgagtg   14880
ttcagattct gtgcccactc aggcaccttc aactgcagtg aagattgaaa tgcttttagt   14940
tcctttggga gcactgagcc actatttctt taaatataag ccaaatttag gattgagccg   15000
tgtcctgggc tgcagtgctg gggaaggtta gagccttggg gatgggaagg caggagtatt   15060
tcagaaggaa agtgagtgaa gggagcaact gggaagagcg ggcgtccccc aggacctgaa   15120
ggcaggaagg caaggctgga gaatggtggc ctgaatgtac aaggttgcag atagggctgc   15180
ctgggacagg accatcctgc aggtcctggg aggccatgtt aagggatcac ccccattggc   15240
accgaggaac cagcagggac cgtaaacaag aaaaggaatg actcacacat ggatcgttag   15300
ctgttggccc acaagcatag tgcactaact gtgcaaactg agccctttt aggaacccgt    15360
actctcagga tggaaggttg caaacttact ttttggggaa actagccagg aaacttcggg   15420
aaattagcaa ggaaggcaga agaagctgaa ggcttagagc ttcggggcaa acaaaggatg   15480
tcttctaccc acctcctcac ctgctgctgg acctaaagag caatctttt gtttgtttgc    15540
ttgtttaat actacgagac aaacctagaa aaaaaaggt tattttctct ttatttctac     15600
ccgttcttag caataacagt ggtaaaattg ttgtttccat gtatctagat actagtattg   15660
acagcatggc tgctctgtga acaaggtgt tcctctcttt tgccttcttg aagacaaact    15720
caactgtaaa aggaggaaaa ttttaattaa atgggttatg ctttcaaacc taatgttctg   15780
ttatatagca gtttgacagc acatatttgc aacatttatt ctctcctcca ttcttttgc    15840
aaagttctat ggtgctacat agccttgagg ggtgtagcag atgtgataaa ctacctgaat   15900
tccgcccagg gatgaaagag ccctacccag gttcctaccc cagctccttg gagtgctgcc   15960
agctggtaac cctcatcagc ccccttaggg gttcccacca cttaaaggag acacccccc    16020
cccttcctta aagtcacact ccctcccccct tcaactgcat ctaaggactg gttgatgcag  16080
gcttattaag gctcagctct ctcttgccaa ccctggacat ctctaaaggg taccacatct   16140
tcgtcattcc ctgcaggatt atgtgagact tctgccaggt ctgcactcca gctcaacttc   16200
ttcctttgcc catctttcct taccttaacc aggtattgag cccaagagga gtccctaata   16260
tctccctgga aactcagccc tctgtgttcc accgagacaa gaagcagaac attgtgtcca   16320
```

```
gctgaagaac aaggcctgag ggtatatgcg ggtgtcttac tcccttcaat tcagttcagt    16380
tgctcagtca tgtccaactc tttgcaaccc catgaaccac agcaccccag gcctccctgt    16440
ccatcactaa ctcctggagc ttactcagac tcatgtccac tgagtcagtg atgccatcca    16500
accatctcat cctctgttgt ccccttctcc tcctgccctc aatctttctc agcatcaggg    16560
ttttttcaaa tgagtaagct cttcacatca ggtggccaaa gtattggagt ttcagcttca    16620
acatcagtcc ttccaatgaa caccgaggac tgatctcctt taggatggac tggttggatc    16680
tccttgcagt ccaagggact ttcaagagtc ttctccaaca ccacagttca aaagcatcaa    16740
ttctttggtg ctcagctttc tttatagtcc agctctcaca tccatacatg accactggaa    16800
aaaccatagc cttgactaga cagacctttg ttggcaaagt gatgtctgac tccctggagg    16860
gacgtaaagg ctgggaagta aaacctgaga tcccctgtac aggtgtgtgt atgattcaag    16920
ttcttgtttg gtagtagtga aaactaaaag ctatctcatc tgctcttgat tctctttcct    16980
gtcttcctcc tctgaccctc caatcttcca ttctttctcc ctcccctcc tcatctgcca    17040 ttcacgcaca agcccggggt gagctgagaa gcaaggtgtc ttagtccatt caggcaacta    17100
taacaaaaca ccacagactg cagggcttag gaacaacaga aatgttttt ctcaaagttc    17160 tggaggccag aagtctgaaa tcagagtgcc agcctggttg ggtgagggcc tcttccaagt    17220
ggcagacttc ttgttgcatt ttcataagat ggaaaggaca aggggctct cacagggata    17280 ttgcataagg gcattaattt cattcatgag ggctgtgtcc tcaggaccta acactttgga    17340
aggtctcacc tactaacgcc accagcttgg acactggcat cccaatttag gaatttgagg    17400
ggacacagac attaaggcaa cggcaagcct cctgtggtct aaacatcgac tcctccaggt    17460
cagcactccc atttccttta tgcacagaac ttcagggctt ccctggtggc tcagctggta    17520
aagaattcgc ctgcaatgca ggagacctgg gtttgatccc tgggttagga agattcccct    17580
ggagaagaga atggctaccc actccagtat tctggcctgg agaattccat ggattgtata    17640
gtccatgagg tcacagagag tcagacacga ctgagtgact tccactttc acttttcac    17700 ccctgacggc attcttcaag ataattcaag acagaagcag gaagctccta ctcagataca    17760
tgtttgttaa aagggaaagg agactctgag agcctttgaa tatttacta ctcagtcttt    17820 gctggtgtgc gcgcatgttt attttctggt ttacttaggc aaacattact atggagtgga    17880
gcaaacttgg ctgtgaatgt tgaaatggcc aacaggacag gcacgtttca gtagcatcag    17940
agggcacttg aatgccagcc agaagatcca ggttttcagg ggtaaattcc cctccggggg    18000
tgtagaaaga aataccatcc aaagtgaagg gcactgtgca tcccttcgaa aaatgctctg    18060 cctccttta agttttacc caccagctgc gttaccaaaa acctctcagc tgtcagagcc    18120
aatggacact ccctgctttg tctgacccaa cttttgagtg aggttttata ctatggggtg    18180
gagaaggcac tggcaaccca ctccagtact cttgcctgga aactcccatg acgaggag    18240 cctggtaggc tgcagtccat ggggtcgcta agagttggac atgactgagt gacttccctt    18300
tcattttcca ctttcatgca ttggagaagg aaatggcaac ccactccagt gttcttgcct    18360
ggagaatccc agggacggag gagcctggtg ggctgccatc tatgggtcg cacagagttg    18420 gacatgactg aagcgactta gcagcagcag cagcagttat actatggagt ggggcttccc    18480
tgttagctca gctggtaaag aatccacctg caatgcagga gaccccagtt tgattcctgg    18540
gtcgggaaga tctgctggag aaggagtagg ctacccactc cagtattctt gggcttcctt    18600
tgtggctcaa ctggtaaaga acccacctgc agtatgggag acctgggttc catccctggg    18660
```

```
ttgggaagat cccctggaga agggaaaggc tacccactcc agtgttctgg cctggagaat   18720
tccatggact gtatagtcca tgggattgca aagagtcaga cacgaccgag cgactttcac   18780
ttcccttccc ttcatttaca ccgggggtca gcctttcctt tcagaaggcc ctcctccctg   18840
aatcttaggg ctcacttttc caccatcttc cttctgctcc ttgcctgcac cttctcaggc   18900
tgccctggtt tcttctctgg acatcatcct gcctttattt ttcttcttca tgcatttcct   18960
gatgaaaagt gatggaggag gggagtggtg aggctgggga ggagatacaa tgtggagatt   19020
gttcagagca ggtttcaact caagtcagag atgagggaag gatgcagccc tgagctctct   19080
cctgtcccca gaccacctgt ccctcagtca gaaagagaag cccctccagg gaaccaacaa   19140
ggctcttagg ctgtctctgc tggcagctgc cctcatcgca tggtcattgt ggattcattc   19200
gtctgtcttc cctactagat tctgagatcc ttgagctcct gttgcctccc cagagcctga   19260
catagagcag gcatcctgtt acagactaaa taaaggaata aaacagagcc atgtgtccag   19320
gctctattgc aacctcactt tactgtgcat taagggcttc cctcattagc tttcccagtc   19380
tttcaatctg ggaaagactg agggcaggag gagaaaggga tgacagagca tgagatggtt   19440
ggatggcatc actgacatga tggacatgag tttgaacaaa ctccaggagt tggtgatgga   19500
caggggagac tgttgtgctg tagtccatgg ggttgcaaag agttggacaa gactaagtga   19560
ttgaactgaa cagaactggt tagcttagac agtaaagaat ctgcctgcaa tgcagaagac   19620
ccaggttcaa tccctgggtt gagaagatcc cctggagaag ggaatggcaa cccactccag   19680
tattcttgcc tagagaactt tgtgaaaaga ggctacagac catggaatca caaacagttg   19740
gacatgactg agcaatgaat cacttact gtgcattaca aagaccttgt ttttacaaa   19800
ttgaacattt gcagcaacct tccttggatc aagtctatca atgctatttt tctagcagca   19860
tttgctcata tcatgtctca tattttgca aattcaccaa tttacagact ttttcattat   19920
tattatagtt atggtgatct atgatcattg atctttgatg ttaacatgat aattgatttt   19980
ggtttatatt tttaaattaa tacatataca ttactttttt agaaatgttg tttattgcac   20040
acctaatgga tacagtgtaa acataacttt tatctttagt tcagtcagtt cagtcagtca   20100
tgtccaactc tttgtgaccc catggactgt agacgcaagg cttccctgtc catcaccaac   20160
ttccagagct tactcaaact catgtccatt gagtcagtga caccatccag ccacctcatc   20220
ctctgtcatc cccttctcct cccaccttca atcttcccca ccatcggggt cttttccaat   20280
gagtcagttc ttcacatcgg gtggccaaag tactggagtt tcagcttcaa tatcagtcct   20340
tccatgaat atttaggact gatttccttt aggatggagt ggttgatctt gcagttcaag   20400
ggattctcaa gagtcttctc caacaccaca gttcaaaagc atcattcttc aaaatcatca   20460
atcagttgtg gatgtgactt tgatggaag taaagtgtga tgctgtaaag agcaatattg   20520
cataggaacc tggaatgtta ggtccatgaa tgttagttcc agctttcttt atagtccaac   20580
tctaacatcc atacatgact actggaaaaa ccatagcttt gactagatgg acctttgttg   20640
gcaaagtaat gtctctgctt tttaatatgc tatctaggtt ggtcgtagct tttcctccaa   20700
gaagcaagca tcttttaatt tcatggctgc aatcaccatc tgcagtgatt ttggagcccc   20760
cccaataaag tctgtcactg tttccattgt ttccccatct cttcgccatg aagtgatggg   20820
accgaatgcc atgatcttag ttttctgaat gttgagtttt aagccaacta tttcactctc   20880
ctttttcact ttcatcaaga ggctctttag ttcctcttca ctttctgcca taagggtggt   20940
gtcatctgca tatctgaggt tattgatatt ctctcagca atcttgattc cagcttgtgc   21000
ttcatccagc ccagcgtttc tcatgatgta ctctgcatag aagctgaata agcagggtga   21060
```

```
caatacacat ccttgacgta ctccttttcc tatttggaac cagtctgtag ttccatgtcc   21120
agttctgact attgcttcct gacctgcata cagatttctc aggaggcaga tcaggtggtc   21180
tggtattccc atctctttca gaattttcca cagtttgttt tgatccacat agtcaaaggc   21240
tttagcatag tcaataaaac agaagtagat gttttctggg agtttcttgc tttttcaatg   21300
atccaatgga tgttggcaat ttaatctctg gttcctctgc cttttctaaa tccagcttga   21360
acatcaggaa gttcatggtt catgtactgt tgaagcctgg cttcgaggat tttgagcatc   21420
actttactag tgtgtgagat gagtgcaatt gtgcggtagt ttgagcattc tttggcatag   21480
tctttctttg ggattggaat gaaaactgac cttttccagt cctgtggcca cttctgagtt   21540
ttccaaattt gctggcatat tgagtgcagc actttaacag caatcatctt ttaggatttg   21600
aaatagctca gctggaattc catcacctcc actagctttg ttcatagtga tgcttcctaa   21660
ggcccacttg acttcacatt ccaggatgtc tagctctaga tgagtgatca ccatcatg   21720 gttacctggg tcatgaagat cttttttgta tagttttct gtgtattctt gccacctctt   21780
aatgtcttct gcttctgtta ggtccatacc atttctgtcc tttattgtac ccatctttgc   21840
atgaaatgtt cccttggtat ctctaatttt cttgaagaga tctctagtct ttcccattct   21900
attgttttcc tctatttctt tgcattgatc actgaggaag ctttcttat ctctccttgc   21960 tattctttgg aactctgcat ccaaatgggt atatctttcc ttttctcctt tgccttttgc   22020
ttctcttctt ttctaagcaa ttttttaaggc ctcctcagac accatttgc cttgctgcat   22080 ttctttgtct tggggatggt cttgatccct gtgtcctgta caatttcagg agcctccgtc   22140
catagttctt caggcagtct gtctatctga tctaatccct tgaatctatt tctcacttcc   22200
actccgggag tttgtgacgg acagggaagc ctgacatgct gtagtccata gggttgcaaa   22260
gagtcggata tgactgactg aactgaactg aactgatccc cactttcttc taaccacatc   22320
ccaccagcca gtcagccagc tcaagcctgc tttcccttcc tatagtcccc caaacccaca   22380 gaacccaaa ttcccaaagt gcgtttgtat ttattcaccc actgtgtgtc tttcaatgcc   22440
acccaaatga tcatgggtta caaatgctat atgacttcag ctaaactgtg aagtccctgg   22500
agggcaggaa atacgtattt taacctttat atcgctccgt ctacagtcct tttcatcgtg   22560
ctttacatgg aagcctttca aatatgacac tagccagttt aagctcagtt ttattttat   22620 ttttggttgt gctgggtctt cactgctgcg cacaggcttt ctctagttgg acgagggca   22680 ctactctgtt gtggtgcgtg ggcttctcat ctctgcggct tctcttgctg tgaagcacag   22740
gctctaggtg cgtggcttca gtagctgcag cctgtggact cagtagtcat ggcacaaggg   22800
cttacttgcc ccgtgtagca tgtgaaatct tcctggacca gggaccaaac ctgtgtcccc   22860
tgcattgaca ggcagatcat tatccactgt accaccaggg aagtcccaag tccaatttca   22920
atactccatt aaaaaatgac tcagacttta atgggaactg ttctttcaga gtcagaataa   22980
tgtactcggg gatactgaat ctaggccctt taggatcctg ggagaggtgg ttccaattcc   23040
tgggcctgga ggtagggcca ttatatcact cctttcattt tatgtttgct taaattactg   23100
taggtgtttg gtcacaatca taaaagcatt tttcaggttt atgacatatt ttcttcatt   23160 gtgaatgtaa ctgatgccat caatcagttt ttcttgaatg ggcaatcata ggccccatat   23220
tcaagttgat tcaaattatg tataagttgt                                    23250
```

<210> SEQ ID NO 5
<211> LENGTH: 18916
<212> TYPE: DNA

<213> ORGANISM: Bos taurus

<400> SEQUENCE: 5

```
acactcactc cttggaagga aagttatgat cagcctagat agcatattca aaagcagaga      60
cattactttg ccaacaaagg tccgtctagt caaggctatg gttttcctg tggtcatgta      120
tggatgtgag agttggactg tgaagaaagc tgagcactga agaattgatg cttttgaact     180
gtggtgttgg agaagactct tgagaatccc ttggactgca aggagatcca accagtccat    240
tctaaaggag atcagccctg agtgttcttt ggaaggaatg atgctaaagc tgaaactcca     300
gtactttggc cacctcatgc gaagagttga ctcattggaa aagagtctga tgctgggagg     360
gattggggc aggaggagaa ggggacgaca gaggatgaga tggctggatg gcatcaccaa      420
ctcgatggac atgagtcgga gtgaactccg ggagttggtg atggacaggg aggcctggtg     480
tgcggagatt catgggatcg caaagagtcg gaaacaactg agtgaccgaa ctgaactaag     540
tgtgggaaga tgcaagaacc tgggctcacc tgcaaacaag gcatttgta ggtcttcttt      600
tccaatttgt attctttta tttcttttc ttctctgatt gccatgtcct agacttccaa       660
aactatgttt aataaaagtg gtaaaagtag acatctttgt agtgttcctc atattagagg     720
aattgctttc agcttttcac tgttgagtgt gttgttagct gtaggtttgt catatatggc    780
ctttattatt ttggggtatg ttccctccat gcccactttg ctgttttcc cttgatgctt      840
tcaatatttt ctccttgtct ttaatttttg ccaatttgat tgtgatattt gtttagtttt     900
ttgtggctgc tggtgtttga tttttgttga tggctgttca gcggttactt gtgattttag    960
tgtgtccgtg agagctcatg tcctcccact ccaccatctg tctccacctc ccttcatata    1020
cttctggtat ttggcttata acatttatac tagcctcctc ctggggattt ttggaaattg    1080
tatgagcata tttctataaa tattttgagc ttttagagaa aaggtgttaa tgcaaggtga    1140
agcctgtatc aaatctttgt caggttcggc acctttaaaa tgagagtcag tctggctgtg    1200
gcagtatgtc tgggtctcag gtctctctct tgtccctcat acttgttagg cacactgctg    1260
tgtgtagggt gaaaggtcag atcattgttc ataaggggag atcccttaga gattatgtat    1320
agtggacact ggagcccagt ggcttggctt ttattcctgg ttccatgctg gctatgatat    1380
tggaaaactc ctcctaactt aattttaaac ttaactgaac ttaattttta ctttatgtta    1440
gcgtacagtt gattgacaat gttgtgttag tttcaggtgt acagcaaaga gattctttgt    1500
gtcatgaaat ggggatgatg gtggtgatga taataatgat actcaccata cctttcttac    1560
aggaatattg tgaggactcc gagagtttag aacagtccct tgtactgagg ggctatcaat    1620
aagcgttagt tattattgtc atcattacta tgttcatcag cctcactgcc accaaaaata    1680
aactaaagag atgtgttagt gattactgat taaaatgtat atttcattag aacctgcttg    1740
attctgtgat tatacattct ttcttgtgat tatacattct taattgtatt gtagagttct    1800
tccatgctaa atattgccat aacgccagat tacaaattag aagctattga tagactcaaa    1860
ccactacagt accagctggc ttattttcct tgttaatcat ttaatagatt acatttgcat    1920
aaactaaaaa aaagcagtgt tgcaagtata gaaactcatt aacaaggatc cagtttgaaa    1980
cgaaccaaaa ttttaaattt taaaaacatt tctttgttca tgaactttgt ttccttccca    2040
aagcaatgtg tgctggcata aaagtgttgt tatgtgaaga gcacatgtac cttcattact    2100
gaagcataag acctgataaa ttaagaggag ttttaatcag tgtcttcaga taatatagta    2160
aaatatagaa gttgtgctg ataccaccaa gcacataaaa aggaaagaaa tagcaggaag     2220
catcaggctt catttttaat ctcttctttt gagaagttca taaactgttt catcaagttt    2280
```

```
tattcttgtt tttatttcct ccctatatgg agaagggatg tatgcactta aggaattgtc    2340
tttttgatac aggtaacttt ggattgggtg aaactgtcaa atactccact aaagaacctg    2400
aatcacagcc agctcttcag aagcattcct caaactttag atttgatcac agatttttat    2460
tgtgcaacaa agaatctatg cactgtttga tcaaactgtc ataatattgt gcagacagca    2520
tttcagaaaa cttttgataa aacctttagc tttgttaatt cgtgttgctt acttgactgt    2580
cagataaaat aaagtcacac ttggggctgt gctcttatat taggctattc caggcagcaa    2640
acagctggaa ggaccgcatt ctcctaacaa gaaaagacac aaaaaacagg tgatgtggtt    2700
cattgtacca gggaacacgt atgtttacta atggtcactg cagctgccta gcacgagcta    2760
ataatttcag ttcaccatct tctgtaacgc tttggcccat cacagaattc tagtaggctt    2820
agttacccat cactcacatt ctggcactaa aaataaactt cactgcttcc tatgttctca    2880
acactgtcag catcccattc ttttacctca tcagctgaaa cctgtgctga atattccact    2940
cataaagagg tcaaacatgt taatggcttt gagggatgag ggttttttatt ttcatttatg    3000 tgttagctac aatgttcatg gtaataaatc tctacatatc tgtaatactc gcagaagtaa    3060
aatgcagatt gccatctcag tcgtaagagc tgactgttaa ttgatgtgct tctatctaaa    3120
gagttgcaat tccgggaatt ccctggcagt ccagtggtta ggactctctg cttcccctgg    3180
aggggacaca gatttgaccc ctggttgggg aaccaggatc ccagaagcca tgtggcatgg    3240
ccacataaat agcagttcca attccaagaa aagcataata atcttaactc acaacactta    3300
cattgatcaa tacataaaac ttatctttta gctcccttag ttgaagaaaa tatatgataa    3360
actttataaa ctctgtttat ttttccttcc cttcttttc tttcttttgc atttaggctg    3420
taaaaacaga acctgagaag aagccacaat catctaaggt aaatgattta agtcgactaa    3480
tgaattattg ggattctttg aaataataat gaatagctaa ttttctacat tgattactga    3540
atggtaaaaa aaaaaaaaaa atggtcagct aactaatttt ggattcccct tttgatcatg    3600
attatataga gtgtatataa aataattata atgttatcta tatatatata ttgttaagat    3660
gaataatatt ttataaatga aaacagttta cttcagaaag catttgttc aaatctaggt    3720 cttcgttata gctgaagtaa ttaaaaagaa aaaaaaaac agaaacaaag gacaagagac    3780
aaagggtaat gagtatctga ttaatgatga gacatggagg acaaaggtgt ctattgaacc    3840
cggcacctag ataactaaag atgacagcct ctcctcagag gccctgggtt taccgtggtg    3900
gtctcacctc cgtcggtgga ctacttgtca gttgctcagg atacagctct cacttgccct    3960
tgggaacggc ttcccttcct ttcctgatgc gtggctgtct agactgaaag ccgattcccg    4020
tctgtgtgga gacggacccc ggaatgtctg caggtgggc aagtgtctct cttctgaaag    4080
gtgctgtgcg ttccttctct caagcacact tgagcagttg ctcagatacg attgcaaggt    4140
ttcctgtcgg aaagcacaaa cgtggttttgg gctggagtac tttaagtgca ggcagggggtc    4200 ggggcgccag ggtcatctgg gtaaaagatg acgcttatgt gattctgtgt aagacctctt    4260
ggtggcccct atagacgtat aattcagcag ctggtggaag ttgtcttcta ttccaaattt    4320
aaatgttttt ggttacccag cctcaagaga attgggtttc tggtgatacc tgtcttctct    4380
acttgtaacg cagaaaagat catataaatc atttaactga aaaaaatata gtgttcatct    4440
cctatgaaag gagttttttt tttaattaat tttaatttct agagtaggat cccctataa    4500 acaaactcag tgttcagagt gatcttttttg atgtttctgt ggatggactt gcagttacca    4560
aatgatctac atgaattgtg agaaacagcc tataatgtag atacatacct gtgtgaaaaa    4620
```

```
tcattccaga tgaaatacta cattttccat tattttttta ataattattg ttttcagact    4680
gttgctagga ttattatcaa ccagacacca acagccattt ctctccctag gcctttctca    4740
agagaggcag aatggtctaa ttgggatctt tgtttctgag cttatttgca aaacaaaaac    4800
aatggcctag aatgtaattg caattttatc ttttgaaatt gacagccatc tgtggttcat    4860
gagaaaaaaa cccaagaagt aaagccaaag aacacacag aggtaagtaa tcattattag    4920
gacttgatat cataagatga agccttttt tttttcccct tattttgtg aaggataaaa    4980 ttttgaactc tcatctttca acacttaagt cctacctaga atggcagtta tttgtttttc    5040
tgttaaaacg gcacctctgt gtggcatcag caggtattgc aatttgcttg tgtgattctt    5100
gctgaatttg gagggaagga attgcattgt ttcaaatttt ctacccaaag tgaaatttgt    5160
cacatgtaaa tcatactaat ttaaattctc acaattgact acataaaaca caagtgttat    5220
gaattgcttt ctactcctca gagaaagta gcaatatgtg tcatattatt aaccccatgg    5280
ggtgtatgcg tgttttcagc caaaaagcct acccaagcac tcatcagata caggaagcaa    5340
gcatgctcct aaggaaaaag ccgtttccaa atcaagtgag cagccaccat cagagaaatc    5400
aacaaaacca aaggtaaata aagcagacag atgaaagaaa gaaagaaaga aagtgaagtc    5460
tctcaatcgt atccaactct ttgagacccc atggttcccc caggaaccta ccaggttcct    5520
ctgtccatgg aattttccag gcaggagtgc aggattggat tgccatttcc ttctccaggg    5580
gatcttcccg acccagggag tgaacccagg tctcctgcat tgcaggcaga tgttttacca    5640
gacggataga tgggaaaacg ctaatgtcag ctagggaata agacacagat cctctaccta    5700
cactgatgtg tgtaggtgac tcttcggagc tatgccaaat gtatctagta tagtcaagat    5760
ttggtgctgt cacttccctg tgttgcaaa taggcttgag gggacctggg actatgtaag    5820
gcctgaggag ggcatcagac gggtctgggg gatgttccgc cacgcccctgt cactgcccag    5880 cagtactcag ttgtgacctt gagggagcag gctccggtgt cttacagaga ggaagctggg    5940
agttgaggct gcctcctgca cccctcttct tgtggcagtt tagttgccaa gtcatgtctg    6000
acgcttgctg tagcccacca ggctcctctg tccatgggat tctccaggcc aggccactgg    6060
agtgggtcac catttccttc tctaggggat cttcccaacc cagggattga atccgggtct    6120
cctacatttc aggtagatga tttaccaact gagctatgag ggaagccctc tccttatggg    6180
ctgtgggaat tcagatgccc tgcgtgatct gctccttacc tggaggtctt agagttttat    6240
ggctcttact ggagacatca acttacagag ccaaaaaaat cagaaatata gtgtatttcc    6300
agaactaaca ggagtcatat ataagaagaa taaaatctat gagaaggact tcttcgttat    6360
gagctcctgg aagaccgtgt atcttgtata caacatgcct tgtatcagga ttgccgtgtg    6420
gcccactgac tgcagccact tgtgtatgtt atttggctta ctggaattaa aatgaatttt    6480
aattagctgc taacaattac agtcagaata gttcatataa aatgccaatt tctagcttct    6540
cttgaaaaac tggaatcgct ggcagcagtg ggccccatg gcaacacctg actggcgtcc    6600
ttacagcctg gtgtgagcct ccccggccca cctcacctgc gtggcctctg taggctctgg    6660
cgtccagctc tgtgtgcccc gccttgcatc atgtccagca gaagctagtg accattccc    6720 tacaagatgc tcactagggg aaacgggctc cctggtaaca tttgaaatgt tgatcttga    6780 aaatggtcat tcaaagttaa cttagttctg tcgatctttt agaccaagtc acaggacaag    6840
atctccggtg gtggaaagag cactgttcct gctgctgctg ctgcagcatc tgccgaacca    6900
gctgacaagg tgagcacacg tgaaagatac ggcgtgtgcg tgggccctga cgcttgtcag    6960
gtctgtttat gagaaacatg ctcagcgaag accccttctc cctggggttgg cctctgttta    7020
```

```
accattcagt gttccagcgc cgtcataccc aaataacctg tcattcggta aaactgaaca    7080
cgtcgtgtgt gacatttgat gaagaggagc gtgcgtctaa aggatagaga agagagcaag   7140
gcaccaaaaa tgaatttaaa attcctgtat tcagtacagt taccgggcac ctgccatgtg   7200
taaggcctcg tgtcaatacc aagaaaatta aaatgcaggt ggactcagac cctgccagca   7260
ggatttatag gtttgaaatg aagcagataa aactgccgtg agcatttgaa ttagcattac   7320
tctcagcgtt tcatatgaac actaccgtcc tgaagcaagt aaaccatgtg cggtcacagc   7380
acctacatga attgataggg gaggttttcg acggggtctc acaagccctc tcaggagtat   7440
atgtgccctg ctggcaaatt atgggcagct tcgcgagatc ctttgaaggg actagcccga   7500
gagtgtaaga caagaaatgg tctgctggtt ctactcagag caatacagag ttagcagttg   7560
gttagtaatc agtttggaag tcatcttgtc ccagaattgc tagtacttat ttctcttaaa   7620
gccacaggta actaattgca gtaacaataa gatggaaatg aaagcaaaaa aaaaaaaaag   7680
taacatgttt attttcctgc ttctcaaaat gggaactgtt atcccctgc aggctagatg    7740
gtaaggaaag tcataggata aaagtatggc ccagtctccc tgaaacatct gttttttctta  7800
gattttgaaa aggataaagc atgcttattt ttctccaaac taatgcagat accaggtggc   7860
atgatggcaa aatttacatg aactttaaat ggaaatactc aaattttaaa ctgttttgtt   7920
tttcccagca gacccccctg tatgtccctt gagactcccc ctccctaccc cagggtacac   7980
ctcactctct tgtgttgatg agagatactt agatgctaca gatggaaaag tggatagctt   8040
aaaggtggag gattggatct cttggaatag atttaaaatg cactcaaaat ttgaaaatgt   8100
atgccacact ttatttagcc agggttatct ataaaatcaa acagtaaagt caggcaaggt   8160
ttatatggga ttctgctgtg cattggcttg tgctggggct tggggcaaat tatttcactt   8220
ttctttgcct ctaatttgtc tcctagaaaa tgaggttgat aagatctgct ttttctttt    8280
cagtccacac tgtgtgtaaa gcactgtgga ctgtggtctg gctctgcagg acattgagct   8340
gcaggctggc ctctcttttt ttggatgtgc tgtgctcagt catgtccagc tgtttgtgac   8400
cccatggact atagcccacc aggctcctct gtctcctctt gcctggagaa tccaggcaag   8460
aatactggag tgggttgcca tttcctcctc cagggcttct tctggaccca ggaatcaagc   8520
ccaagtctct tatagctcct gcattggcag gcgggttctt taccactgag ccacctgggt   8580
atccctggcc cctctaatgt gcctggggct gcattcaggc agattgaaac aggcccccac   8640
agggagctgt tgtgggagac agggattctg tctgatttgg agaacccggg aggactttga   8700
gtgcatatag tctgagtaag tcattaaagg aaagctggga ttgcaggctt gcaaacaaaa   8760
caagagagaa aaatagaagt gtgatctgag tgcaaagggc attccagtgt gcgtgaagca   8820
caggagacat gagtgggagt gtaagaccag aaagacaggt cgaggcgctg ctgaggagca   8880
cactgagatg cattaatccc atggtaatga taatagctgg cccacgtaaa cactggggat   8940
cagaggacag atggagcgat gtgatgggat taaaaccagg ctgcaggagg attaagtgac   9000
ttcaacggct acgatgagac agcatagaga ttggaaagag ggaggctggt caggggctgt   9060
tctggggagc cgaagtcagc ctgaattaga gctaggatag aatcagtgag tagggagcaa   9120
ggcaggaggt gttgcagagg tgcaagctaa gagttggaca cgactgagcg acttcacttt   9180
cactttccac tttcatgcat tggagaagga aatggcaacc cactccagtg ttcttgtctg   9240
gagaatccca tggacggaga agcctggtag gctgcagtcc atggggtcac acagagtcgg   9300
acacgactga agccacttag tagtagtagt agtaagatct cagatgaccc agggcctcag   9360
```

```
tgtctgaatg gactaggttg gcaaccctaa ggtgagacaa gagagccggg tatcactgct   9420
aggtttgtgc cagtgcagag tcagcaccca tgaggcgagc atcttcttaa gcggggagcc   9480
cggccctggt taccactgac gggtggacag aggtcagaag gagggaatt ggtggaggtg    9540
gaaaacggat gcctgccttt ggacaggctg aagtttctga ggtgtcccga gagaggtgat   9600
tcgaacatcg ctttggagcc caggtgacga tggagaagga gaagcgggct gggggagag    9660
agtgacactg agtgaacacc tgcgcaaggc tgtggatgaa tcgaggaact gaattcagtt   9720
gccaggactt gggttcaccc tggtgcctcc acagtatctt taatacaaca atcacagcaa   9780
ctgcttatgt agtacttcgg aagagcttag catgtgccca accaccagct ttctcactgt   9840
gatcgattaa ttagttgaac cctcacaacc ctctgcagta ggtgcattga ctgccctggt   9900
tctcacacac gaggatacag aggttcagaa ggagacgtga cctgctggca gcctcctgga   9960
gccagtgtgt gttgggggct gatgtgcaaa cccagagcat ctgagcctgt acgctccgcc  10020
tccaagctct gctgcgtgga tttcagagac cttcaaataa gacagttttc tattgtcttc  10080
aacccaatga cctcaccatt tagttcctgc ctggccccga aagcatctgg cccctgatcc  10140
tagagaatga ttgcctgggc ccagcagcac agtagaaaca cacagagtgt gcggggcgag  10200
gagcaaagca gaagatttgc cagacggggc agagaacaga ggccacaggt gccagtgtgg  10260
aaccagggtg gtgctgtgag agataagagt caggagacgg gtgctgggca gaggaatgga  10320
gggaagatta tgatgtctgg gtaaaggcat ggaaatcgca ggttagaaag ttgtcagcag  10380
ttactgacag agcaactgac gcagtggtgg aagggcatt catttcacgg aaatgaaaga   10440
aacagtgtgt gatgatttga caaaacaagg ggtgtggagg tcttgatgtg tgggtacaaa  10500
gactgagaga acagcgccta gaagcagtgg ctgccttgtg ataagaaaga attcatgagc  10560
attgcaaaga ctagctgtgg gtcctgggag aggcagccaa gagcaatgaa gagatgggta  10620
gacctggatt catatcctag tgctatcctt tactgagtga cctgagaagt gactcagcct  10680
ctctgagcct tgtttgttgc atcgctaaat gagattaata tcattgttat tattacttct  10740
gctgttctga aaagtatata acacgtatag tgtctggcac agagcagatg tccagtgtat  10800
gagcgatatt atttatgtta cagcgtattc attttcaagt atgtaatatt attaagcttg  10860
atgaaagtat atgaggagtt tttatctctt tctcaacccc accagaataa agaaaataaa  10920
ttgttaacat cggccgtacc agctgaatct aaaccaagta aaccatctgg aaaggtatga  10980
agacagcagg gcatttttgc ataggtattt cttcacagtc tctgtgtttg tcatgatccg  11040
atttctcgag ggcaaacaat atgaggtgag gttagcttaa aggaccttt taatgaattg    11100
ttgtttgaag ctaatgaaac tgggttggaa gtgtgacttt cttcatgtat gtctataaca  11160
ttttatattg taaccctctg ttctgaaaac tccaattata tatcgaggag tttacattcc  11220
agtttccctc ctgcaaatgt actttcttta aacagaggtt taaggaatc taaagaatgc   11280
caggcacttc tttattctga aatttccatt tgaatcaccc cagagctaac agaccccaga  11340
ttctattaca cagtctggtg agttcctgaa gttgtagtag atatatggta gttgcaaaaa  11400
aaaaagtaag cgatcatttt taagctgaat taaatagtaa agggtctttc ttcaacttgt  11460
tattttcccc tttgaaagca gcttagtctt cacaatgaat cattaaaaaa taataataat  11520
aacaagttgt tttatttatt tggccatact gtgagacatg tggaacttct ctcaccagga  11580
atggaaccct tgccttgcaa tgccccctg ccgtggaagg gtggagtctt aaccactgga   11640
ctataggggga gtctcacaa tgtatgattc ttaacctcaa aaatagggtg gagtcactgt  11700
ttcttttacc atttaagcc catatcgaca gaataaactg tcgcttctta taaatttaac   11760
```

```
atcccttca  ggaaatttct  atttgtaaac  atcctcagac  aagcaagtga  acagaaaacc   11820
acaaatgaat  aaaagagcac  agggcaatcc  gttcatgaga  tgcattttat  ttggaagagg   11880
tggaaacaac  tgataaaaaa  aaccaagcat  ctttcctctt  tcatatagca  acatggtcat   11940
cattctttgc  attttgtttt  cttctttctt  ttgactatcg  gtacagtggt  ctggcagcca   12000
taatgaacca  tatgcttgtt  ccctagtta   ataatgctgc  ttattttgct  gctgctgcta   12060
agtcgcttca  gtcgtgtccg  actctgtgcg  accccataga  cggtagccca  ccaggctccc   12120
ccgtccctgg  gattctccag  gcaagaacac  tggagtgggt  tgccatttcc  ttctccaatg   12180
cgtgaaagtg  aaaagtgaaa  gtgaagtcgc  tcagtcgtgt  ccgactccta  gcaacccat   12240
ggactgcagc  cgaccaggct  cctctgtcca  tgggattttc  caggcaagag  tactggagtg   12300
gggtgccatt  gccttctcca  ataatgcct   ttagacttac  tgaaattgtg  attcttactt   12360
gaatgtggct  ttctatcttg  ccaacctaga  gtctgtactc  tgggacttta  ataagttcta   12420
ttacaggcca  gattttaacc  attttgatag  ctgaagaact  tttggtgttt  gctattttc   12480
tacatagaat  ttcttttgat  gattaaaatg  tcaaagtgaa  ggatgtgcag  caagtagcat   12540
ttacatatct  gctctgtttt  ccagtcagac  atggacactg  ctctggatga  cttaatagac   12600
actttaggag  aacctgaaga  gatgaaagaa  gataacacaa  catataccgg  accggaagtg   12660
tcggtacgtg  accttgatgt  ctctaaagat  tcgtacctag  tgagtaagag  ggctggtagg   12720
tcatggccct  gatgcacgca  aggatgcacc  gtgttctgtc  acttgaagag  aaagaggatg   12780
ctgttagcgt  ccgtggtagc  aaatgaacat  gagtgttgtg  gttggaaact  gtcccaggga   12840
gctatgcaag  ctgtgctgat  cagcaaaccc  cgattgcttg  tttcttctga  gactacagct   12900
gggatgtact  ctgttgagtc  acaaagactt  actttctgtc  ttcgaggttt  acatcctcat   12960
ggtttccaga  tatttccatc  ctgtgacttg  agcttattct  gacgtctaga  tattttctgc   13020
ccgcagttca  tttctactcc  tgattcataa  aaagcaattg  tatattcttt  ggtattaaga   13080
aagatgttcc  atagattgga  agaaaatatt  gcaacagaca  caacaaagga  cttgtttcta   13140
gagtttatga  agaattttg   aaagtgagaa  aaaacaatcc  agtataaaat  taggagaaaa   13200
tttgaccagt  agacacatga  aagtctccct  agtaattggg  aaaatgatac  taaaacgcag   13260
agggatagca  cttcacactt  acctgattgg  cagaagtgta  gacgtctgac  acgtgacaga   13320
ggctgtggtt  gtcacctgaa  tataagcatt  ccctctaacc  agcacttcca  tgtctagaca   13380
gattcccggg  aggggggcct  tgcacagtgt  gtaaggagtt  ataagaacag  gtgaaacatt   13440
tggaaataat  tgcattcaac  aggaaacaag  atgatgacaa  gtggaatgct  ttatagtggt   13500
taaaatggtt  tgttcatgta  tcaatatggt  ttcattacaa  aagcataatt  tttgaatgaa   13560
gaatagtaca  ttgcagaatg  atagtagaat  ttgatctgat  accatttatg  taacacttga   13620
aaataggcaa  aataatggtg  tatattgttt  atggatactt  atatgtggaa  taattgtttt   13680
acaatatact  cagctttata  ctgatggatg  tgataaagtt  tggggtggtg  gctatctctg   13740
gaaaacaagg  aagaaaaatt  ggattggaga  gtgctaaaac  agagatatca  ctctgacttt   13800
ttttcattac  ataagaaata  gctagatcta  ttgagttata  tagaaattca  ctgttaccaa   13860
ctactctttt  ataggtatat  aaatattaga  taatgcaaat  tatttaaaaa  taaaatgtat   13920
tttatatagg  aatcaaattt  aatatattgg  tttgaatatt  ttatagcatt  atttatgggt   13980
taagccaatt  aaatatgggc  aagtatctgt  agaaacataa  aatttcagag  ttgcataaac   14040
tgctggcttc  ttaatgattt  gtatttaatc  tcaatagttc  cataagttaa  taatgcaata   14100
```

```
gtactttgat ttaagagtta tgtatacaac attctcagct aaaatcccta tacgtactttt  14160 ttttttccc taggatccaa tgagttctac ctacatagag gaactgggta aaagagaatc   14220
cacacttcct ccaaaatata aggaacttct gaatgtaagt taaacagtta tgtatttaca   14280
ccttattgtt ttctctttgg aattataatt tttatcacat taatatatcc aattattta   14340 acttagataa aataagggc ttgtgaaact atcattactc tgaagctcac cgtattagtt   14400
tgatggggct gccatgtcag agtgttacag attggatggc ttaaacaaca gaaacttact   14460
atctcacagt tctgggggct cgaagactgg aatcaagatg tgggcagagt tggttctgtt   14520
tcaggcccct ctgcttggtc tccacatgtg gatacctccg tgtggaataa ctctacatct   14580
tctttccatg tgtacatatc tgcatgtcgt cttttctcta tatggatcgc tgggtcactt   14640 cccccttttta taggaacact ggtcatattg aaataagact gatcttaatg ttgtcatttc   14700
accttaatta cctctgtaat taaattcaat accacttcat ggcaaataga tggggaaaca   14760
gtggaaacag tggctgactt tattttctg ggctctaaaa tcactgcaga tggtgattgc    14820
agccatgaaa ttaaaagacg cttactcctt ggaaggaaag ttatgaccaa cttagatagc   14880
atattcaaaa gcagagacat tattttgcca acaaaggtcc atctagttaa ggctatggtt   14940
tttccagtgg tcatgtatgg atgtgagagt tggactataa agaaagctga gcgccgaaga   15000
attgatgctt ttgaactgtg gtgttggaga agactcttga gagtcccttg gactgcaagg   15060
agatccaacc agtccatcct aaagagatca gtcctgggtg ttcattggaa ggactgatgc   15120
taaagctgaa actccactac tttggccacc tcatgagaag agctgactca ttgaaaaaga   15180
ctctgatgct gggaaagatt gagggcagga ggagaagggg acaacagagg atgagatggt   15240
tggatggcat cgccaactcg atggacatgg gtttgggtgg actccgggag ttggtgatgg   15300
acagggagcc ttggcgtgct gaggttcatg gggtcgccaa gagtcagaca cgactgagcg   15360
actgaactga actgaaaggc cccatcttca aatagagtcc cattctgagg ttttggggga   15420
tgggacttca gcatgtgagt ttggggagga tacagttcag cccatcccat tcactgaggt   15480
atgcattttg ctgactgtaa ggattaatct tgccttctca gcatcatcaa actaatattt   15540
gtttcagaaa gaagaaggga tcgcagggcc tcctccagac tccttggtga gtttacataa   15600
atgtcttcca agatcagatt taacatttt catatctttg gttgggggaa tagttatcaa    15660 ttctgtatttt ttggattatg actatagtga tctctgaatc agatgaagtt tccatctatt  15720
caaaggaaga gggtgggat gggggtcatt tcagtgcttg tttatttcct aattagttct    15780
tttttgaggg aaagaagaat gggacaagaa agttttagga cagaataaat attattaaaa   15840
ataagatgag aatatcctac cagcataata acaagtacgt tgagagaaac agaaaaataa   15900
tatgcactga gcatccaatt tcctcccaaa cataggctt catctgagtt atttcattaa     15960
gtatctcctt tggtagtcaa agacttgcac gagtgcattc accatttgct gggtttgtaa   16020
tctgttctgt cacttaaatg gttcccatat gtgacccgtc atgctgcctg tttctttaga   16080
aacccctggg gcccaatgat gccatcgatg ccttgtcatc cgacttcacc tgcagttccc   16140
ctacagctga tgcaaagaaa actgagaaag aggtatggtt tttaatgccc ttagggaagc   16200
ttgttagaaa ctacctccca ctttaagaca acaactttt ttttaaactt catttttcac    16260
ttcactgcgt cttcattgct gtgttcgggc tttctctagt tggggcaagc gaggcctgtt   16320
ctctagttgc gatgtgtagg cttctgcagg gggcttctct tgttgctggg ccggggctct   16380
aggtgcacag gcttcagttg ttgtggctcg agggctctag agcacaggct cagtggtctt   16440
ggcgcacggg catggttact ccaatgcatg tgggatcttc cctggccagg gagcgaacct   16500
```

```
gtgtcccctg cattgcaagg cggcctctta accgctggcc accagggaag ccccaagatg    16560
ccaaggcttt ttacttctgg ttcttaccgt ttggttcata tgtttccttc atctgccagt    16620
caaaccttct tctgtatttt attttcaga aatctacaga agaggcttta aaagctcagt     16680
cagctggggt gatcagaagt gctgctccac cccaagagaa aaaaggaaa gtggaaaagg     16740 tatcaataat tacttctttg aacttcagca cggtgccctg gatagcagtt tggtttcctg    16800
aggctgatcc agctgactgg gggggaggtc tcaatagtgc attatacccg tagacctcct    16860
ttactcccct caggcctcgg gcctgcgtgg catagtgaaa ccagtcaggc ttatgttggt    16920
cgggcaggcc ttctctgttt ctacagatgc ttatgggtga ttttggcaca tgtgccttgg    16980
ttgtgggaaa agactgtctc actgttacat tacacagaag ggcaggaccc cagagacacc    17040
actctctggg gacatcagat ctttgacttg attttctaaa gggcctagag tcctgtgacc    17100
ctcaaaggga gcgtttctgc agttactctg ttcaccttga ccacagtcag ctataacctg    17160
cttctcagga atcctgaaag gcggccctgc agctctggac tggatgagaa gacctgccct    17220
gtctgcagat cgcccagata ctgcaggag gagttttctg tgggtgctgc tctgcctctg     17280
gctcgtggag tggccagttt atttttatc tggaggagca gagagcacca caccccctgag    17340 tgtgggaatt cctacagctg tgagccactt cagggccccc tgcttcctgg gctccgctgg    17400
gctacaggac agggttatca gagtcatttt taagggacct aagtttagaa aaagaaacac    17460
agtactttga tacgagtatt ttacaattat tactctacgt gcacctctcg cctcctaaga    17520
ggtgaagtgc acacccgtac aggagccccg ttactgtgca aacgggtcct accccatgtt    17580
tcctgtcacc ggtaagttct tatttctttc tcctttttt gctgggtttc aagtagcact     17640
gccttcctag agtccttcct caagccacag ctcattccta gagatttact gacaaaatgt    17700
gaatgtcatg aagaagtagg tggcttatcg aggttgagga gagcgtctcg tttttcatgt    17760
acagaattct ttgcttctcc gcaggatgcc atgactgagc acgccctgga ggccctgtca    17820
gcctccctgg gcacccggaa gccggagccg gagctcgacc ccagctccat taaggaggtc    17880
gatgaggtac tgacctgggg gttcacgtac aaagcctgtt agtctgcagc ttacaaggtt    17940
acgaaactaa tgcccaacat atgtttagaa cttttgtacc acttttgttt ttattagaga    18000
tctcaaatga actgtgcttt gttctgctgt actttcaggg tctggctaat tcaggtattt    18060
tattgccagg gagttaacaa ccaggaagga tatttgagtg tttgtcttat aaaccatcta    18120
gaattgtcat acttcaaatg aacgactaat ctcctttgcc aattcttaag tgacacctgg    18180
ctaaacaaga taacatagag gtggtggcct gatgagaaac aggttgtctg ctcgtatgga    18240
aattagaaat ctgtctttgc aaaaaggttc taggtgcttc tatttataaa gaaagagagg    18300
agatggctgc agatgggggt gggagatcct ttatataact ctggggaaaa gtgttgaaac    18360
cttgttgcca attagaataa atcaagcaa taattgcttt ataactaaaa ggaatgcacg     18420
tttagagtat ggagctgggg agttgctcct gtttggtaga ggagttttca tgttaagttt    18480 cagttttta gggattgctg aggagtcctc ttggggaaa agaggagggg aagcagaggg      18540
atgtcctggg gccacccttg ccaggcagt ggtgggggaga ccctccggag cgcccgcctc    18600
ccagctcagg tgggacctgg tggctgtcgc tgtcacaatg ctgcagcctc tgctgtcact    18660
tcctgttccg ggtctccgga ggaaggtggg tctccgtcac tttcagcagc tccccgtct    18720 gggaccaccc ggtccccaat gggccagttt ctatcgtcaa ccttttttgga ggactcactg   18780 ggtgccgtat ggcacgaaag gctttacgaa ggcgaaggca agggagcggg agaagccgcc    18840
```

-continued

| | |
|---|---|
| tttgtcctcc aggaccaagt aatgtacagg gagaagggga acttggattg cagcagggtg | 18900 |
| cgaggggca cagcat | 18916 |

<210> SEQ ID NO 6
<211> LENGTH: 2706
<212> TYPE: DNA
<213> ORGANISM: Bos taurus

<400> SEQUENCE: 6

| | |
|---|---|
| accacagttc aaaagcatca attctttggc actcagctttt ctttatagtc caactctcac | 60 |
| atccatacgt gactcctggg aaaaccaaag ctttgactag atggaactttt gttggcaaag | 120 |
| taatgtctct gctttttaat accagggaat atgttaaatt tcctctagaa agctagcaaa | 180 |
| ctcttaaaat ttaaacaaaa agaacagttc cttttcactc tttccactag ttttcctttt | 240 |
| aaattatata taaagtatga agattttcta accctctgga tccttacatt gagttttagt | 300 |
| acctgatcat gaattcacta ctttggttag tctgctgtga taaccccata agattgata | 360 |
| tggtatagga gtccatggcc actccagcac attctacgcc aggggatgct tcagagagga | 420 |
| ggtccatgcc tgcttgtcgt tctcataaat aatgtaccat ggcatattta ttctgtagtg | 480 |
| atacctcatt attaatctcc ccagattcta gggcttcgct ggtagctcag ttggtaaaga | 540 |
| atctgcttgc aatgcaagaa accagggttc tatccctggg tctgcaagat cccttggaga | 600 |
| agagaatggc aatccactcc agtactcttg cctagaaaat cccatggaca gaggagccca | 660 |
| gcgggctaca gtccatggga gctgcaaaag agtcagacat gagttagcga ctaaaccacc | 720 |
| accatttta gtgctgttaa ctagtctgga actatgtcaa ttcagggatg tttgttttca | 780 |
| ttgcctattg aatacagacc acagtgcaga catttaagat atataaagat caaagaggaa | 840 |
| tagaaaggta tctagctgtg catatgactc actgttcaca agcccaagtc ggggcacggt | 900 |
| cctatatggg tgactcttcc atgaggactg ttttatagct ggagacctca cagatccctg | 960 |
| aactggggag aactacggtg taataggatg tccactatat cctgaaatag aatataactg | 1020 |
| gaaacatttt taaaaaaaat cctttcatcc cttaatgacg gctattattc tatagaaaaa | 1080 |
| taaaactata ataccaaagc ctagaaaaag tacctggctt attaaaagtg ctcattaaat | 1140 |
| attttaaaat taatcaacta actaagcatt caatggagaa ccacgatctt aggctgagac | 1200 |
| gtaggtggga gcaataaggt gagctagaat cagctaaata ccacccaccc cacaaacacg | 1260 |
| cacacataca tacacacact tttgtgccca gtagctcctt ggcttgtgat ttaaatccat | 1320 |
| gtcttgatac tgatacagat tattacatag catgaaactt cacattaccc accagtaact | 1380 |
| taaaatgtag acgttccgtc ctgaaagcca ctgatctgct gcggcagtgc acttctatgt | 1440 |
| acgtgcattc ggttgctcgt ggttcagtaa tccagtgaat cttggtgtta ctgaagggag | 1500 |
| ttcttgtaaa agaggtaaaa ccagttatcc atgtatcaac cagatttgtg atgggatgtc | 1560 |
| tctcccatttt ctcatctgtt taacactgaa cgagtttaac actcttgagc attgtttttt | 1620 |
| ttttttctcc cccttagata agtacctcat tgagtatgac agatgaaggc tgtaaaatca | 1680 |
| ttgcaactaa cttgtgcact cttccttaact ttcttccaag aatatttatt taattttctc | 1740 |
| tgctggtctt tacaaatcaa gagagctagg taagggttct taaagaagta gccccgttt | 1800 |
| acagctgaag aaactgaggc aaagaaagtc tgggtggctt cccagggtca cggagacagg | 1860 |
| gcagggacgc ctccccggga ctcctggctg gcttgttttt cctccacctc cagtctccct | 1920 |
| acaccacctc ctcccggccg ctcactaggc cctttaatct gattgggtct tctcctcaac | 1980 |
| acccatggag tacataaagt gatgtcttat tttacctgta ttatccaatt ttttttttc | 2040 |

```
ctctccactt tctttaggca aaagccaaag aagagaaagt aaagaaatgt ggtgaagatg      2100
aggaaacagt cccatcggag tacagattaa aaccggccac agtacgttgc tcacctcgtt      2160
gcgtgccagc ggctcgctgc tcctgcccat gtgtcccgtg gcgccctgtc tgtcccagg       2220 aggcttcagg gcatgtctgg ccaagttcag ataacaactc tggaaaccct gaaacttta       2280 ttttctgtcc tgaacagttg aacccttaa aagagggttt cctaagtagc gaccatgtgt       2340
ggtcactaaa attcccacaa attcaagtgt ttcagctatt aaccatactt gacatagatc      2400
cttaacctta aagtggaagg aataatttgg agtttatatt ttctctaact gccaatggat      2460
aaaagcacat agatcttgta agtggtagag aaacatataa tgatttacca gtgtcttcag      2520
tgaaagtggg tttggtttgg tgtgaggaga ctggacttat ccctgtaatt atatttgtca      2580
tttatctttg aaagaatgca cataaatgta tgatgggaaa tagttgtaat gcttatatat      2640
ggaaagtata aagtatttta agaaatattc tagaatgtga atgtccaaac aactaaaaca      2700
gttttta                                                                2706

<210> SEQ ID NO 7
<211> LENGTH: 30913
<212> TYPE: DNA
<213> ORGANISM: Bos taurus

<400> SEQUENCE: 7
tcactcaaac atatcagaaa aagacagtct cttctctcat atcctggaat ttcaaaaaca       60
aacttaatgg aataagaaag caaaatttt tgtttcattt taaatgaatt ttcaatttca       120
ttcacaggat aaagatggaa aaccactctt gccagaggct gaagaaaaac ccaaggtgag      180
gaaataagtt tttttctgat acttaaaaaa aaaatacaac tgtaagatat aaacagataa      240
ttttcataga ccagatctca ctgtggagac tcatatgcca gcctagtatt aaggagaaag      300
gaacctttga cagcagcatt tggccatttc acgcatttta atgattattt acctcatgaa      360
ttattaccta ttataagttt ataggtgata ttcattgtac ataggagctg atatcaagag      420
ggccctcaaa ttaggtcatt agcatttact ttgatcctat tcttatcatc aaatgctctg      480
attctacact acctttactt aatttggtat tagccagcat agtgacctgt catgatgata      540
ctaagcaact acatttatta gtcacttact gtgtgcctga caccacacta atggtgtttt     600
gtgtgttagc attttgagaa ctcgctgaat gaggaaggca ctattattat ccccacttga      660
caggtgagga aattaagaca taaaaggatc ctgtaaatag cccaaagtca aatagctagc      720
aagtagcaag gccagggctc aaaactcagc ctgtccctct ctggggccaa gcttctgaat      780
tacatgccat ctgtctgtct tagattaggg catgtggaga ttttgaccaa ttacagtaaa      840
taaataatac tacttcacca gaaggaacta gggataacag aactttcctg ccaaacccac      900
gttctcatag aaagggaaca tatgatctat gtttcctctg gcttattcat tacggaagtc      960
aataggaagt agaaaaagca atcacataaa aaaaaccatg cagctctcac aaaattactt     1020
tgaaattgaa gtatcaggaa aactttagc tgaataaacc tttaacattt tttatggtac      1080
tcggtgttca gtattcatta cttgttgtgt gacatttatc ttatattgat aaatgaaatg     1140 tatgcccctgt ataaattagc tttgggtttt agatcctaaa atgcaaccta atatatgtta     1200
actagaaaaa cttttttctct aggaaagaat tttttcttct atcaaaataa aaaaaaaata     1260
ttttttttca tactatataa tattccttat attacagccc ctgagtgaat cagaactcat      1320
cgatgaactc tcagaagatt ttgaccagtc taagtgtaaa gaaaaacaat ctaagccaac      1380
```

```
tgaaaaaaca gaggtatgtt tctaaaactt aaaatctcca gttttggtcg tttttcagtg    1440
tttgtctatc atcttgaaaa tgccaggacc aaacgtattt taacaggaag cagctgatga    1500
aaaggcctgt tttgccatat ttttttcacat gctgtgttca tcttgcctgt ttatggatgt    1560
gctttgtttt cccaagctga cgctgatact cttgcagttt aagtcctgta atcaagtatt    1620
ccgttcagga gagccttcac accaatgctt ttctttccct tcttgcttct gtaactgacc    1680
tacttaaagc tgtcatcact catcacctca agacggccgt ggcctctgtc tttggtctcc    1740
ttccagccca ccccatgtgt ccactggcat tattctttct cagcatgttt gtagccacaa    1800 catcccctg ttcaatgcc aagagcttcc caaaagagtt cctgcttgtt tatttgggtc      1860
tggagaagga aatggcaacc cactccagtg ctcttgcctg acagtccca tggacagagg      1920 agcctggcgg gctacagtcc acggggtcgc aagagtcgga cacgactgag cgactaaaca    1980
ccaccaccac cagcttcctt ccctaccaag atgtgtcccc catcactaaa ctctgatagt    2040
aagtacttat gtatcttcaa gcttttctca tgtggttctt tctgcttgga ataacctctc    2100
caaattctag atcagctaaa attgtagtca gccctaaaag gctctgctaa aatatggcct    2160
ttgtctcccg catgtccctc cccaaacctt accacacttc caactcttaa gaagcagaat    2220
acaacacgcc agggaagtct gtcatgcttt ctttttatat ccctgttggg acatttgttg    2280
caaacaagct tttagctgct ttggtctttta cttctcacat gtgtacatat ttttacatag    2340
taaatttctt gaagaagag atcatacact attaatgatc atctggtaag caccttgcat     2400
ataggatttg cttccataaa tgtctggaat aagagcaacc tgtttgaaat tttactcttg    2460
tgacaaaatg atagtgactc tcaaacttca gtgtgcatca ggatgactgg aaggtttat    2520 caaagtacag attactgagc cccacccca gaattcttga tttagtatgt taaggtgggg     2580
catacgaatt tgaatttcta acaagttccc tagcagtgct gaggttggtg gtcgcaggac    2640
ctcattttga gaaccccag gatagtctta ccaccttgca tttgtaccta gctatttaca     2700
actgacaggg tgctgttaga tatatgaaca tgatatattt aaatattgca taattgcaat    2760
atatatatat atatactaca gctatataat attatgttgt ataacattat gtattatatg    2820
atggcaaatc atctaaataa tgacagttga taacaatctt tgcgcttact gtgttcccac    2880
gtactatgca aagcacttag cgtgttttgt ctcattaaag gccttgagat gtaggtactg    2940
tcattgttct cattttgcag atgtggaaac tgtgtctcag agaggttaag taacccacct    3000
aaggtaagag gtaaaaccaa gtgacgtagt ggtagctgca gaggtttaac gtaccttgag    3060
ttattcactg ctcaagatcc ttaggcattc aagaaaatca tgctcacagc gggtagggta    3120
gcagaccgta ttgttggttc attgttgtcc cattttaata actgggtatt tcagaagtcc    3180
ttcgttgtgc ctgattcttt ctgcaggcat ccccggccgc tgcccctgta cccgtggcag    3240
aggacgtgcc tcggacctct atgtgttccg tgcagtcggc tccgcccaca gcagctccag    3300
tggtgagtga ccctctgggc cttgggaaat gtcttgagaa agcagtgttc ttcctcccct    3360
gcccttcctc ctgtattacc aatgtattac cttgttctag caagataaaa attaaatctt    3420
agatagctct attatcctcc agggaggata atacagctcc agggaggagc tggaaactca    3480
ggctagattt taaggtttcc actatttcag gtggttttgt ttttaacctc ttgacatgct    3540
ttctagctcc tcagctactg tggataatca tgcttcttca cttttcttgtg tctttcaagc   3600 tgatttggag ccccaccaac agccagaagc acttttattt gactgtcctg atggaaaagt    3660
ctgcaccttt atcatcagtt cagtcactca gttgtgtctg actctttgcg accccatgga    3720
ctgcagtatg ccaggcctcc ctgtccatca ccaattcccg gagtttactc aaactcatgt    3780
```

```
ccatcacgtc agtgatgcca tctgaccatt tcatcccctt ttcctcctgc cttcaatctt   3840
tcccagcatc agggtctttt ccaatgagtc agttcttcgc atcaggtagc caaagtattg   3900
gagtttcagc ttcaacatca gtccttccag tgaatattca agactgattt cctttaggat   3960
ggactggctg gatctccttg cagtccaaga tattctcaag agtcttctcc aacaccacac   4020
gtcaaaagca tcaatcattt agcattcagc tttctttgta gtccaactct cacatccata   4080
catgaccact ggaaaaacca tagctttgac tctacagacc tttgttggca aagtaatctc   4140
tcagcttctc aatatgctgt ttaggttggt catagctttt cttcaaggag caagtgtctt   4200
ttaatttcat ggctgcagtc accatctgca gtgattttgg agccccccaa aaatagtctg   4260
tcactgtttt cattgttacc ccatctattt gccatgaagt gatgggatca gatgccatga   4320
tcttagtttt gtgactattt taagccaact ttttcactct cctctttcac tttcaacaag   4380
aggctcttta gttcttccct ttctgccgta aggggtggtg tcatctgtat atcggagaag   4440
gcaatggcac cccactccag tactcttgcc tggaaaatcc catggatgga ggagcctgga   4500
aggctgcagt ccatggggtc gctgaaggtc ggacacgact gagcgacttt actttcactt   4560
ttcaattaaa tgcattggag aaggaaatgg caacccactc cagtgttctt gcctggagaa   4620
tcccaaggat gggggagcct ggtgggttgc catctatggg gtcgcacaga gtcagacacg   4680
actgaagcaa cttagcagca gcagcaacag cagcatctgt atatctgagg ttattgatgt   4740
ttctcccggc aatcttgatt ccagcttgtg cttcctccag cccagcgttt ctcatgatgt   4800
actctgcatg taagttaaat aagcagggtg acaacataca gccttgttgt actccttttc   4860
ctatttggaa ccagtctgtt gttccatgtc cagttctaac tgttgcttct tgacctgcat   4920
acagatttct caggaggcag gtaaggtggt gtggtattcc catctcttga agaattttcc   4980
acagtttgtt gtgatccaca cagtcaaagg ttttagcgta gtcaataaag cagaattaga   5040
tgtttctctg gaactctctt gcttttttcca tagtccaaca gatgttggca attttatctc   5100
tggttcctct gccttttcta aatccagctt gaacatctgg aatttctcaa ttcatatact   5160
gttgaagcct ggcttggaga attttgagca ttactttact atcgtgtggg atgagtgcaa   5220
ttgtgtggta gtttgaacat tctctggcat tgccttttctt tgggattgga atgaaaactg   5280
accttttcca gtcctgtggc cactgctgag ttttccaact ttgctggctt attgagtgca   5340
gcactttcac agcatcatct tttagggttt gaaatagctc aactggaatt ccatcacctc   5400
tactagcttt gttcatagtg atgctatggc ccacttgact tcacattcca ggatgtctgg   5460
ctgtaggtgg gtgatcacac catcatgatt atctgggtca tgcagatctt ttttgtacag   5520
ttctgtgtat acatagaatt ctgtgaatac acagaagaac acagaagaac ctttatcatc   5580
atgactcctt ttttctccca actgaatggt gacagatgga ctcacttcct ttccctttct   5640 tcttttttgtg tctctgactt tttgacttt gtatgaagtg tgatatttaa ctggttgaat   5700
ctgtgttctt ctgttttcat tagcaagtag attctgactc agaggatacc agctgatgga   5760
actatgtttc cttactatag acttagtgaa tctacaggct aaataactat cttctagatt   5820
ctttgcagta tcttctcatt aaatattcat gaggacactg tgaaatctgt tctgatcatg   5880
tctctcttat taatgaggaa aatgaacttt gaatggacct tgagcaattc acttcacccct   5940 tcagaatctc agctagattt aaaatagggt cctgcactca gtcccctca agcctagtgt   6000 ggatatgggc caggtctgac actcacagct cagttggatc attctcctgt ggaaaaatta   6060
aagtgggtga agaaactcct ctcctggtgg aacttggaaa ggcttgcatg tggaggacag   6120
```

```
gatcctgctg agaagtggga acagcactgt ttcctgggga gaccagtgag cccaggtcag    6180
gccagcacag aggtgtggag cccttgggat actggggtct gtgcatttag ttgtttgaga    6240
gaagagggcc ttggggaagg tgtgggacgt gtgtcctggg tacccgagt  gggtgcttcc    6300 tgccagggaa tcctgggtgc catcggcaaa tcccgtcaca gccttcctcc tgccttggac    6360
aggacgtgac ctccttttg  gcgtgggaga ttctcagggt accctccaaa aactatgagg    6420
ttgtgggagt caagccacag gccagagtgg taaagaacag aagtgggaga gagaatcttg    6480
gcagagactg tgcagggagt aggcacagag tcagtgactg gagtcaaaaa gacagtagcc    6540
aacattccag tgcagaactc tcgtacctaa acatggccac tacctgtcgt cctgagtgtg    6600
actgccaggg cttaagagca agttagctcc tttccaactt taccttgact gtagagactc    6660
aagcattgga gagcgggaaa aaaaaaaaag agccattctc ttaccccctc tcctgggcct    6720
ctactccacc aactctggtt accacggttg cggagtttct caccactgag gtcagttggc    6780
atttctgggg ttgtgacgcc cacgggagcc agaaacaata ggcgcagaat gtgataaagg    6840
tcagagaact ccagagaggc tggaggatga acgagcaaaa gcagacagta agccaggagg    6900
gcggggatga gtgtctgctg tctgcattct tgtggtagaa aaagaaagtt tccggagatt    6960
tgagttctag ttctgaactt gacaatggag atagaagctt ttgtccgtag tcctgtttct    7020
agatccatta gttattaaga ctgctgcttc tcctagctct tctaatgctg tttcacttat    7080
ttcttgaatc agaggacaca gaataaggca gcgttggttt ccaaagattc tgcagcagag    7140
actagaaaac aaaagtgtga gcaagtgact gggatcaggt agcaatgaga ttgtttggct    7200
aagacttggg gaccccagca actcttggtt acaatcccaa gcaggttgaa gacatcaggg    7260
gtgttgtccc tgggggggaa aaaaatctat ggagtttcca accactcagt tcagtccaat    7320
tgctcagtcg tgtccaattc tttgtgaccc catggactac agcactccag gcctccctgt    7380
ccatcaccaa ctcccagagt tcactcagac tcatgtccat tgagtcagtg gtgccatcca    7440
gccatctcat cctctgtcgt ccccttctcc ttctgctttc aatccgtccc agcatcaggg    7500
tcttttccag tgagtcagtt cttcgcatca ggtagccaaa gtattggagt ttcagcttca    7560
gcatcaatcc ttttccaatg aataatctaa ccactagatg gtgataaatc ccttcccact    7620
taactgccct ttattccctg gtgatctttt gtggtgcagc ttagcagcag aacaagtttt    7680
cttacttagg agggtagcta agctatagaa aacagaaaga cgcttttact ccaatatgta    7740
ctccatgtga ggtcatatat cttttacgat aagaataatc tttgagactg tttaattcag    7800
gagcctttac tttggatcaa gaccaactgt gggaaattca tcaattctgc aacccacaca    7860
gtagaaacaa tagtttagtc aatggtactt atccttgata tgcatgatgt gttcagtttt    7920
atattcttca ttaaaaataa gcctgaccag cacctgctaa attgatttaa gtgctgctca    7980
cgtatggatc gtgacctatg gtttgaaaaa agccagctca aggcaatggc accccactcc    8040
agtactcttg cctggagaat cccatggacg gaggagcctg gtaggctgca gtccatgggg    8100
tcactaagag tcggacacaa ctgagcaact ttactttcac ttttcacttt catgcattgg    8160
agaaggaaat ggcaacccac tccagtgttc ttgcctggag aatctcagcg acggcggagc    8220
ctggtagact gctgtctatg gggtcgcaca gagttggaca cgactgaagc aacttagcag    8280
cagtagcagt cctatctttt agcccaaaca taatttattc tttattttcc ctttatgcca    8340
tttacattct gtgttcatcc agttttgttt tgttttttt  taataacact gtgtccggtg    8400
ttattactgt atcttaggga gcatgtttca ttttcatcag ctggaccaca ggcagactga    8460
tctcactgta tcactcaggt tagtaggtca cacagaccgt catctgaact ggcgtgagtc    8520
```

```
cactctgacc agtagaagcc acacagagaa cgcaggcttc tgtgcctaca ggctcagcca    8580
gagtcatcgc ctccagggca ggtctggctg tttcaatggg aaaaacgtcc tctcgagggc    8640
ttttctgggc ctcttttcct gtgccatctct aggacagttg cctgaagatc atgtcttttt    8700
cttctttcct ggctttcggc ttctccgtgg tcctccccat tcagtgaact gccttattcc    8760
tgaaccagag tgctggttag atcttataag cttctcagtg ccagctcaca aattgcacac    8820
tcttaatgtt taatgtaaga agcttgccct cattttaac acgtcaggtt ttttaaacct    8880
agattctaat tccgtagatt ttccaaatta ttaaaagatg acctgtgctt cttatctagg    8940
cctgaaagaa ggatgtgctc atctgagttg ttcgttgtag tctcttttaa aaggcatggt    9000
taaccatcta cttagtatac ccgctgctgt gctttcagaa gggcatggtg ccagacgatg    9060
ctgttgaagc cttggctgga agcctgggca aaaaggaagc agatccagaa gacggaaagc    9120
ctgtggagga taaagtcaag gtaatggcag ctcagaaact tctagaaagg agctatcatt    9180
ggagctatga ttggtcaccc caactcccca aataaatcag tttaaaaaaa aaaaattcct    9240
gcagcacatg gccggctgga cccctctgtt acgatgcatg tcctgcttaa taagtgaagc    9300
agagcgagcg ccagtgttta ggtgtggcag tgggtggccg gcgtacagag atcgggcttc    9360
tgagtctcat gttgtccacc cggttttcat tgccaaggac caaggcggga agtggtactg    9420
cctgccgctc ctcacagctg cccctctaacc cggcaggctg aaaacagtgg tctctgagcc    9480
tgctaaccca ggaggataca gcgtcaaaga tacagttgct gtgggaacct cacagtggag    9540
tcactgacct cggatttagt cactcaggca tccactttat cagagaacga ggtactaaca    9600
ctgaaaacgg tttaattttt attcaggaaa aagccaaaga agaggatcgt gagaaacttg    9660
gtgaaaaaga agaaacgatt cctcctgatt acagattaga agaagccaag gtaaacaggc    9720
cgggatcttt ttttctaact cattttcatt catattgaat ttcatataca taagaagggg    9780
acatggaaca gacctgggat ataaaagtca tgtttcttag tatttcaaac atcaagtagt    9840
attacttaac tcacatcctg ttagcacacc cactgtaaag ctaaaatatt tgtcagtggc    9900
ctgtcactcc ttccttaggg gaagaagtc taagattttc ttgtctgata cgtggtttgt    9960
tacaatacca gaaataaaca aaactcagga aatctttata tggatagata ggaaaaccaa    10020
aggaaagtaa agtcgctcag tcgtgtccga ctctttgtga ccccatggac tgtagcctac    10080
gaggctcctc cgtccatggg atttcccagg caagaatact gaagtgggct gccatttcct    10140
tctccagggg atcttcccaa cccagggatc gaacccaggt cttccgcatt gcaggcagac    10200
gcttgaccgt ctgagaacca attacttcct aaagaaggat ttacaaaact tagataaagt    10260
tgaaaaacag cccatttgac attgtattat agtgagcaat atggccttcc ttggtggctc    10320
agatggtaaa gaatctgcct gcaatgcagg agacccaggt tcaattcctg ggtcgggaag    10380 acccctgga ggaggaatgg catcccactc cagtattcct gcctggagaa ttcccatgga    10440
cagaggagcc tggcaggcta cagtctatag ggttgcaaag agtcagacat gactgagcaa    10500
ctcaatatag ccagtgataa attgacccat tcctttatt ttgagtatac agattgtaca    10560
gaataagtga tatgggagag accactactt aagagaatat tctaccagac tttatgaata    10620
atgcaggaaa atcaaattga tactctttgt attcatcgat ttgcactagt ccatttatgt    10680
ggcaaagata ggaactatac tgagcgctct ccctgatcga aagtttatta tgctgggtcc    10740
ctttagtctg cttcctttct gcatttcaca attcagtcga aaccatgca tttctatttg    10800 tttgggcttg tatgtttata aggttcttag accacgtggc ccgtaagtag ctgtcacatt    10860
```

```
cgataaagct ggtcaagtgc ctgtaactct cttagagta ggaggttgga ggttggttac   10920
tttctctctc cctttgctgg attttcatcg taacttctaa gaacgtggcc agttagcttt   10980
cctgaccact ttattctgtg gttgtctcat cctcaactat ggatctcacc cattatgaat   11040
tacctatggc ttcataacat gtccaggtgc tgcttgattt cggggttaaa tcttgtgttg   11100
ttcttcaact gctcccatca ggcctcctca ggagagtcag ctccccaagg tagactgcag   11160
gtgtccccttt ccaaacttgg gatgatctca gtgtgagtgt ggaacaagtg tgcccctgt    11220
ccccactcct gtgtgcccct tgggagattt gctgccttgg cagctaaggg gtggcagaga   11280
gcgcaccctg ggctctgttc ccctcctaac tggacagtga ttagaaggtc catgaggacg   11340
cagaggacgt ggaaatgggg gaaagcactt tgagaaaagg gaagctggtg atactcttga   11400
cctctgcatc tcctctaatg ttaaagcaaa tgaaaaccac cttgatcagt gtatcagggg   11460
aactgtgcag ttgaccctgg agtgacacgg gtttgaattg cctgggtgca cttctgttgg   11520
gacttttttc actagtaaac actacagcat ctcaccttct gtggttgact gaattcacag   11580
atatggaatt gaggatactg agggccaggt gtaaattaca catggatttt ttcagctgct   11640
tgagatgtcc gtgccctaac ctctgcagtt atccaagggt taactgtgtg tacaaacaga   11700
gaatcttgtg cttacacatt tttgcatgtg tagataaatg ggattttacc atttatttat   11760
aaatcacctt ttactaaaga gccccaaatg ctttatttg tcccattact cagaagtggc    11820
acttagggtc atttgaaggt tggcatcatc tgaactgtaa gttttgagca tcatacccct   11880
agggtgagtt ttcccagtgc ttggtatcgg tgcttggcac agagtcggtg cacagtggtt   11940
ggatgcactg cctctaaagt tacccggctt ttcccaggca actcgtgcaa agcccctcc    12000
ccaggccagc gagggtctca tccccgtgtt ccctctgtgt cctgtgcacg ctgtgccaca   12060
caccacagta gccattgtcc gtgggcttct ggagttggca agccccatta gcagccccca   12120
cgcctagggg atgtctgtca gctgtttctt gacatgagct catgagagcc tatttcctgg   12180
tgagagaatc tgtttcctgg aatgaggaat cgacttcata atgtacatca tcagctataa   12240
cctatcaacc tctgatgcta tttacagagt gcacacttag aatacatgtg aaatgactca   12300
atgccatgtt tttctccacc tgcacaggat aaagacggaa aaccactgct gccaaaagag   12360
gtcaaggaac cgctcccagt aagcaagcca gttttctct gagtgtatct ttctccttta     12420
gtcctgatgg ttaatttagg aagggcagag cttctgtgt aatgagctga tcagcatata    12480
tgcagtgaca gtactttgga gaggagactg acgaggtagc gtttgctgac acgtctcctg   12540
gttctttgca gcccttgagt gaagacgtcc tcctcgatgc tctgtccaag gacttcactg   12600
tccccctcaga cacatcatcg cctgtaagtc tcctgagagt cctggtttta gtgcctcact  12660
ttttagggta gcagaaataa gtggaaacct gtgacttaga atccgacatg agagatgagg   12720
aaacagtcat gaaattagcg gccctcaacc cattgtggcc attaaagatg tattccatca   12780
ggaaatatgg tccagcacac tggatgtttt caacagtgta actaatagag ccagtggccg   12840
tgcactctgt caagtatatg catggaaaga gaatttaaaa cggagctgtc caatatattt   12900
gaaaaataaa tgcgtaaaga tatggaaaaa actgaaaagc atttattttt tagggaagat   12960
taagccaact aagtgccagg atttattata cagtaatgtt aaaaagtaaa gttctgattc   13020
agaaagtgaa gccaaaagcc aatgggaaaa taacccatcg atgacagatt tagtatatct   13080
ttaaagtgag aaacgtcatt atttcagaaa gattctaaaa taatatacta cttaacatta   13140
agaaaaaatg atacaactga aacctcatcc tgtgtgccaa atattaaagc aatagtagca   13200
cttattctgg agaaggcaat ggcagcccac tccagtgttc ttgcctggag aatccccggg   13260
```

```
acaggagagc ctggtgggcc gccgtctatg gggtcgcaca gtcagacacg actgaagcga    13320
cttagcagca gcagcagcag cacttataca gaattaaaaa taggataagt atctaattta    13380
ggcaagcaag gctactggag acaggcatac ccattcactg cttttagcag catgattttc    13440
tagcagcttt taaagagaag ttatttggcg caatatagct agcaccatac agagagagag    13500
ccacttctaa aatttactca gagcaactca ttacaaagag caaagctaaa acacttccat    13560
cagcctaaat gtgcaacaag aaatgtataa gccataaaac tcttaaatac ttagcttatt    13620
gaatatttag gataataagc aggaagagaa aataggaaag tgtataaaat aatgcttgga    13680
gtagaaagta gaataaaatg gctcttaagc tgctgtgttg ctgtgcttcc attcggatca    13740
agagaacaac catcataaag ctgtcccgag ggttttattt aagtaatggc attgtgggca    13800
taatttgcta caacatatta cgggtcaaat ctttttttcgt gattgttttc ttacaaaagc    13860
aatttgaaga tgctaaactt tcagctgtcg tctctgaagt ggtttcccaa accccagctc    13920
caaccaccca ggcagccggt ccaccccccca gcactgcggt aagcagcatg cttataagt    13980 acttggtttt tgagcagcaa ctagagggtc aacaaaattg ttaccacagt caccttctgt    14040
ttcagaagag gtaagactgg caagataggg agatgacaga gattatctaa aatgattaaa    14100
taaaacaatt cctgtgaaag tattttacac acactgaagg agcttaatat attgttgcct    14160
tattagaatt gaagtgcaat aatgcatatt gtgtatatat tcagattttt ttaattgttt    14220
cgctttcttg acaatgtttc cttccttat atttttttctg atacatgctg taagtactac    14280
tcattattta acctcaagtt tacttttaagg aattgttcag tgtttgagct tctctctgcc    14340
caccaaatca cagattcctg gtagaaaagc attgttttcc tcccagtcat accagtaaaa    14400
acttgtcatt ttcatgctag taatggaaaa acctcagtgt caatatcgtt ttaattattt    14460
acatgttctg aggcaagact gtgggaccaa agcttttcct gacttccttg attaattttc    14520
tttacaatac caaattatac atgatgcagg agaccacggc acatcaaaag ataaagagat    14580
tgccctaaac caaaccccca gctccttggg ctgagataga agtgctttat gagctagttg    14640
gagacgaagt agcttgagtg aagtcagcta ggctcccttg ccttttgatg tagcatcaaa    14700
gcttgcttcc tgctgcactc tgagattctg agtgaatttt cctcctgttg ggtcagtcgt    14760
gggatcatct gaaatatcc agaggcacaa tgacaaagcc cagatctggc tgtgggcggc    14820
gccaccattc gctgctataa tcctgggcgc tcatgaagca gttaaaacca gtaaaatgcc    14880
ctctctccat gtgtctgtgt gtatgtctgc acacacaccc acagtgacaa aagtccctgt    14940
gcaacagaag gaagactcat taataaccag gctgccgttt acacttcagt tcttaatact    15000
cggattttag gagtccctag aatagtgatc gaggctgtta agaaacatcc acaatcaaaa    15060
aacctttttg gccttccaca gtatgtttta gaatgatccc tttcccatca cttcctccgt    15120
cagagttttt agttttttgtt aatattttat ttgaagctgt cattaaaact aggtataaag    15180
ctttatttac aacaatacac ttgggaatca gagagtaaac ttagtgattt tgtggggaac    15240
ataatgttac atgtattgaa ggcatcataa gacttctaga aatcgggcca agaacccat    15300 cttttttagga aggacctatt ttctaggaag aaaaatgcat ctaggggtgg ggagggtaga    15360
caggtgcaga gaggtgctga gtgaagcgag ggacaaagag ccggcgtctc tgccacctgc    15420
cccctccctg gggaaaaccc acgagcttac ggaagtctca gaggcactgt tggggctgca    15480
ggtgacctaa ggtggctaac cagtgactaa ttcagattta cttttagca gcgtgacaac    15540 aaagaacttg acgatgccct ggatcaactt tctgacagtc tcgggcaaag acagcctgat    15600
```

```
ccagatgaga ataaacccgt agaggataaa gtcaaggtac aagaaaaaag tcatttaaat  15660
tgaaagtttt tatagccctc ttttttgggg ggggagggg gtattagttc taaaagctct   15720
tgtaggtctt cacagacccg ttcaacttca gcttcttcag cgttactggt tggggcatag  15780
gctcaccgtg atattgaatg gtttgccttg gaaacgaaca gagatcattc tgtcgttttt  15840
gagattgcat ccaagtactg catttcggac tcttttgttg accatgatgg ctactccatt  15900
tcttctgagg gattcctgcc cacagtagta gatataatgg tcatctgagt taaattcaca  15960
cattccagtc cattctagtt tgctgattcc tagaatgtcg atgttcactc ttggcatctc  16020
ctgtttgacc acttccaatt tgccctaaca ttccaggttc ctatgcaata ttgctcttta  16080
cagcatcgga ctttgcctct atcaccagtc acatctacaa ctgggtattg tttctgcttt  16140
ggctctgtcc cttcattctt tctggagtta tttctccact gatctccagt agcatattgg  16200
gcacctacca acctgaggag ttcctctttc agtatcctat cattttgccc tttcatactg  16260
ttcatggggt ttcaaggcaa gaatactgaa gtggtttgcc attcccttct ccagttttca  16320
ttccaatccc aaagaaagac aatgccaaag aatgctcaaa ctaccgcaca attgcactaa  16380
tatcacacgc tagtaaagta atgctcaaaa ttctccaagc caggcttcag caatatgtga  16440
actgtgaact tccagatgtt caagctggtt ttaggaaacg cagaggaacc agagatcaaa  16500
ttgccaacat ctgctggatc atggaaaaag caagagagtt ccagaaaaac atcgatttct  16560
gctttattga ctatgccaaa gcctttgact gtgtggatca aataaactg tggaaaattc    16620
tgaaagagat gggaataccg gaccacctga cctgactctt gagaaaccta tatgcaggtc  16680
aggaagcaac agaactggac atggaacaac agactggttc caagtaggaa aaggagtacg  16740
tcaaggctgt ataatgtcac tctgtttatt taacttatgt gcagagtaca tcatgagaaa  16800
tgctgggctg gatgaagcac aagttggaat caagattgct gggagaaata tcaataacct  16860
cagatatgca gatgacacca cccttacggc agagaaggcg atggcaccct actccagtac  16920
tcttgcctgg agggtcccat ggatggagga gcctgatggg ctgcagtcca tggggtcgca  16980
aagagtcgga catgactgag tgactttact ttcacttctt actttcatgc attggagaag  17040
gaaatggcaa cccactccag tgttcttgcc tggagaatcc cagggacagg aggagcctgg  17100
tgggctgctg tctatggggt tgcacagagt cggacacaac tgaagtgact tagcagcagc  17160
agcagcagcc acccgtatgg cagaaagtga agaggaacta aaaagcctct tggtgaaagt  17220
gaaagaggag agtgaaaaag tgggcttaaa gctcaacatt cagaaaacga agatcatggc  17280
atctggtccc atcacttcat gggaaataga tggggacaca gtggaaactg tcagacttta  17340
tttttggggg ctccaaaatc actacagatg gtgattgcag ccatgaaatt aaaatacgct  17400
tacttttttgg aaggaaaatt atgaccaacc tagatagcat attaaaaagc agagatatta  17460
ctttgacaac aaaggtctgt ctagtcaagg ctatggtttt tccagtggtc atgtatggat  17520
gtgagagttg gactgtgaag aaagctgagc gccgaagaat tgacactttt gaactatcat  17580
gctggagaag actcttgaga gtccttgca aggagatcca accagtccat cctaaaggag   17640
acccgtcctg ggtgttcatt ggaaggattg atgctgaggc tgaaactcca atactttggc  17700
cacctcatgc gaagagttga ctcattggaa aagaccctga tgctgggagg gattggggac  17760
aggaggagaa gggatgaca gaggatgaga tggctggatg gcatcactga ctcgatgcac  17820
atgagtttgg gtgaactccg ggagttggtg atggacaggg aggcctggcg tgctgcggtt  17880
catggggtca caaagagtca gacacgactg agcgactgaa ctgaactgaa ctgatagccc  17940
tgacttgcct gcaatcggtc ttccctagtg gctcagctgg taaagaatcc acctgcaatg  18000
```

```
caggaaacct gggtttgatc cctgcgttgg aaagatcccc tggaggaggg aatgttaacc    18060
cagtattctt acctggataa ttcgtcattg acttgatgga catgagtttg agtaaacacc    18120
agaagttggt aatggacagg gaagcctggc atgctgcagt ccatgggtc gcaaagagtt     18180 ggacatgact gagtgactga gaataattac ttaaaagctt atttcagttt aaaatacaag    18240
tagaaaattc ataggtgtgg aatgacaaac agaagcactg ggtttgcttt ttttccatca    18300
actggaaatc tgttgacatt gttgctctaa gttacttata aaacttagag ggactatgtt    18360
ttgcctcaga aatatccaat aaatgctgaa tgctgcattt tcgaatgtgc tagatgaagg    18420
tagaacagaa tagtaattct gtatgttcaa tgtttacagg aaaaagccaa agctgaacac    18480
agagacaagc tgggagaaag agatgacacc atcccaccta ataccaaca tcttttggat     18540 gacaacaagg aggtaaatga aggtggtgtc caggttggat ctatactcca aagcttttga    18600
gattcaaacc tcacttgaac agaacactgt aacaatagca taaaaatgta acatgactga    18660
cacatttaat ctgtccccac tgagcaggct gtctagaatt ctgtttaata tttatttgag    18720
ccagtatcct tgcatgttta ctgtgctggg cactgtggcg tagagagaat tgaagaatgt    18780
tccatcactc gctgatgctt aacagtgatt ccgaggcagg tacacagaag aattctctgc    18840
aagaaaaggc tgtaataaca atgaatgata tttgtaatct tacctgacac agagtctctc    18900
tgttgaagca gaacagaaaa agagctagga tggaaataat tcatggggca aatacgatcc    18960
aaggcctgct gtctctcttt cttccccaac accaccacca ccggtgctgt tgagaacgaa    19020
gaccggcaaa accatatttc caattgaaag ctctgttgct ctatctcagt acagcaacag    19080
tatcgtcaag aagtttatct gtcttttgtgt ctctcctggt cagcctgctg tgttccctgc    19140
cccttcctgt ttggcttcta gatattaaat aacccttttcc agatctgttc atcagataaa   19200
aacaaggaag tccaaatgac agtttctgtc tctgcactga tgatttgtga agggtttgac    19260
tgtatagaat actatcagct tcactgtctt ctgttacaga aatcagttcc cctcgcttgc    19320
attcagcagt catgacagcg cttgtacacc ctgctagaat gcccctgctc tgatggtccc    19380 atctgacccct gttgtgttct tgggaaatg tgttcattag tgtcctggcc tttgccgatg     19440
ggaaaatccc tgatgagttg tccttggaat cctcactgaa aaaaaatcac ctacagacca    19500
tttcagtgcc tcaaatcctt ttgaagtgta ataagctgta gtggatacat atatagtaaa    19560
acagcaaata agacataaaa acacaagtta ccttttgtga tgttttaact agagttaagc    19620
agtgacagag ttgctaaaat agtatttctt tcacttccag gaacagattc atcctttgcg    19680
ttttccccaa ggctattgaa atagttatga gatagtcatt aagcaaagct ggtgaagaga    19740
taatacggac ccaggtttat cagttatgca aagtatacag ttgtccttg gtatctaggg     19800 ggggttagtt ccaagacccc cagagaccaa aatctgaggg tactttagat catctctgca    19860
ttactcagaa tacctaatac agtgcaagtg ctacataagt agttgctagc atgtggcaaa    19920
ttcaagattt gcttttgga aattcctaga attctgtatc cccaaatagt ttcaatctgc     19980
tggttggttg aatctgccaa tgcagaagcc acagatgcag ggggatgact gaactccact    20040
ggataaagat catgtaaata ctgacttaca cctgagtaaa acctttacaa tttgtttaac    20100
caacggtctg ctttgtttct aagggcacac ccgggaagcc aaaggcatca gagaagccca    20160
aggcatcaga ggtaaatatc atagctgtgt atttccagaa acaatttttt taacctctag    20220
ctgcagcttt cacattttag aaatctaaaa ttcagtgaat gcctaccttg tgcttggtct    20280
gatgccaagg catgtatatt atatattatt tctgtcttcc caagagccac tcaacatagg    20340
```

```
cagttccatt ttccagatta gaacatcata gctcagagaa tactcagcac cttgtataac    20400
agagtggaag aaaatggagc tgtcaagatt ttcctgttgt aagatctctt ttataatagt    20460
ttgttaggaa aagaatgcag caaggctttc tttgaacaca ttttcagggc tgtgggaaa     20520 taacccacaa agcatctttc ccttgcttct ccaaaaagca aatcttgatg gttatttctg    20580
ttgatatctc agaaacctgc aggtgcccag gacccattg atgccctctc aggggacttt     20640
gacagctgtc cctcgactac agaaacctcg acagacacac caaaggtact ggcttttt     20700 ttcttggctt ttgttttta tgtatctctg tacaaacaac acacacacac attatataat     20760
tttataccgt aaaataaact gattaatgcc ctaggaaact tgaaaaaat tctatttctc     20820 cccaaacacc attatttggt gttatttctt gtcttttttgc atatgtaggt tttacataat   20880
tatacttaga ttcatatatat atattatata gaatatatat attatatata gaatattcta   20940
tattctctac ttagattcta tatataaaac atttcttaag agtatatcat aaatgttttc    21000
catgttgctt tataagctcc attgccacca tttttgattg ccacactata ttggcttgta    21060
acagtacgac tttatctgtg gtcatttaaa aggagagcag tccctcactg tatacaccat    21120
gccccttgcc ctctgggctt tcctcccctt ttctgccctg agcagctctc ctccttaccc    21180
ctcagagacc agttcaagca tcagctgctc caggaagctc tccctgtctg cttctccctt    21240
cccaggtcag gggcttctcc tctgccatcc ctgcgttgtg agttacctgt cccatgggcc    21300
tcactccact gagctgtggg ctttagatag cagtcatgtg tctggtagct ctgtggccag    21360
catcagcaaa atgcctggtg catagcagag gagatcgaat gtgaatgggg aaaaagtgt    21420 aatccaccaa ataggaggaa aagtgaaatg agtgtcctcc gttgttattt tcagaataaa    21480
atgcatgtgg tttcagcggg tattaaacat atttcccagt cactgaattg cgagtcttcc    21540
ctatcttgcg tgatttaatt tctagatcac atcagtatcc tatttctcaa ctcctagaac    21600
ctcatcaata atgccttttt ggtgaatgga ctttacttt gtatgtgact ggccctagct     21660
cactctggtt gcttccactg ttagattatt cttccataat tctgaaagca gtgtcctctt    21720
ggcacataga aaccagtcct gatagaacca ggctctattt tgataagcaa aatacagtct    21780
gagtgcatcg tgaaaattgg cagggcgtca acgtgagtcg ccttttcctc attttttcc    21840 cttcttacct cccactttga acacctgtgt gtacattcac tgtggttcaa aaagtcatga    21900
ctgtgaaata ctcaattttt cattatttaa actggagatt ccaggctcct aaaaagaaga    21960
gtctggatcg atttgcttgc agcagcagtt aattgctaga tggagtgttg actgcagcag    22020
cttcattaca tctcctctgc tctaggacaa agacaagaag cctgcttcca gtgccgaagc    22080
acctaggaat ggcgggaaag caaaggattc cacaaaggta agttcaaagc tcggtcgtgt    22140
ccgactgttt gtgaccttca tggactgtag cccgccaggc tcctccatcc atgggatttt    22200
ccaggcaaga gtactggagt gggttgccat ttccttctcc agggcatctt cctgactcag    22260
ggatccaacc aggggctcct gcactgcagg aagactctac catataagcc accagggaag    22320
cccccaccag agcagtaaat agatgacaaa tgagcttggc aattacaggg aacggcacgt    22380
tcttagtcat ttactttctg cttggggtct atttagaata agaccatttt taagtactat    22440 ctataccta gaacatcttg ccaaagaaac tgaagtttta aagattttt ttttaattat     22500 ttatttaat tggaggttaa ttccattaca atattgtagt ggttttgcc atacattgac      22560 atgaatcagc catgatatat attatttttt aaagtaatcg atacttaagt atcaatatta    22620
cttatcaata atcagtattc agtaagtatc aacttactga aggaacaaag attcggaaca    22680
caattgaagc gtgctgcatt gccagccctt gtcacacaaa gtcccagtgt cagctgtgct    22740
```

```
ggtctggggt gagcggaggc cctctccctt catcagcccc aaacgccttg cactcccttg    22800
ttgctactct cccctaccgt gtgcagaaag cctcgccttc tacttaaaga gaaaactgag    22860
ggtgccttgc aggaaataac caagacccct tcctatcttc ctcctaataa acccactctc    22920
ccctccttgt ctgcagcccc ttctctctct ttctcaaggg gtcactaact ctctccaggc    22980
ctccctggtt gctcagctgg taaagaatcc accagcaatg caggagacca gggtttgatc    23040
cccaggttgg gaagatcccc tggagaagga aaaggctacc cattccggta tgctggcctg    23100
gagaattcca tgaactgtgt agtccatggg gtcccaaaga gtcagtcctg aatattcact    23160
ggaaggactg attctaaagc tgaaactcca atactttggc cacgtgatgc aaagaaccaa    23220
ctcattggag aagaccctga tgctgggaaa gattgaagga gcggggagaa ggggacaaca    23280
gaggatgaga tggtgggatg gcatcaccaa ctcgatggac atgagtttga gtaggcttcg    23340
ggagttggtg atggacaggg aagcctggcg tgctgcagtc catggggtcg caaagagtcg    23400
gacatggctg agcaagtgaa ctgaactgtc tccagtatct ctgtctcaat tcatctcctt    23460
tgtagcacaa acatattcaa gctcttcaac aactcaaagc cctattccct ccatcccttc    23520
acctccttgg aagatctgtc tgtgacccct gctccccctc cttgggctcc ccctgagaac    23580
agcagtgaca tgctggttgc tgtactgttt ccttatcagc ccttagtttg cttgttctct    23640
cggggtgtgc tttgggacgt tagatttgat gctgtaatga ctgagacttc gggacgggtg    23700 aatatttat aacttcacct gcccaaagac ccagactaac acttcctacc tcacatttcc    23760
acttggataa acattgacag tatagatccg tatacattat tagatcaagt ctaaatcgcc    23820
accaattatt aagaaaaaag tcaacagttt gattacgatg ttagtcatca aacagcaaa    23880 ttaagacatg ttaaaatatg tgtgcgtggc aaggagatg acaccaccag agaatgtagt    23940
ttctgtaaat cttggaacag gaaagtagta tagagaacta gagaagctct tacagtctct    24000
gagatccaat atactcatat taaatactag tagtctttcc tcccaagtgg tacctcattt    24060
ttcacattgt tatagaaagc agaactgaga ctaatgagca gatctggttt cttagagctg    24120
ggcgttaatg cagcatggca ctttgaaagt ttcctattat taaatgact caaactgtgg    24180 ttaggaaagg gatggaagtt ggattggata acaacttct gggtcccctc caattctaaa    24240
accatagtat tcaaatggtt atgactgtta attccaatta taacgagaaa taaaagatac    24300
aggtccagaa acaataatcc agctgcatcc aaactcttaa aaagcaagat agtgagttct    24360
ggttcaaggt ggtgatgcag aaaagatcag ctcgcctcgt accatggaaa caccagatct    24420
acagctgcat acacaacaat ttcctctagg aaaaaactcc tacagtgata tgaatgactc    24480
ctatccatca ggccaataaa agaaggccag cattaaagaa ggtagaagag gctgggacag    24540
actcttgaca taaatccagt cccaacacag tcaactcacc gtcagaagga aactcaaaac    24600
tcagagcttc tcctgaggag caaatcaggt tgaaccccca aggcagcacc ccaacattta    24660
aagaccacct gagaaatgag cacacaaaac ctctagcttt gggaagccaa tggagtttgt    24720
gtccagaagg ccatagcaaa ctgaggaaag cttcttcaag agctcatgag ctcagacgca    24780 cccgccccc caaccaagca atcagagcta cagttcttag ccggccacta tccccagagt    24840
gctgcacaga ccacagacca aaacacgccc cagcttctg tgtaagaggc ctccttgctt    24900
gtcctgaagc tccggtgtga aagcaggct tccgatttgg cagaagatgc ccagatgtgc    24960
tcttaggaga catcagctgg gtgctcacca ccactgagct attttctccat ctcactccag    25020 gccaccagta tctcccagaa aagggggcttt gacgcttacc tagacgccaa attttttgtaa    25080
```

```
ctgcccccca gagggatact tcctgatcac ctgctgtggc ccttcaagac tattatgttt   25140
gtatattgaa ccaatgaaga taaaataggc tgcttacagt gtttggagat aatcaagagt   25200
cagggcaggg tttaacagta aagttcatct gctacacgag gctactcctt caagactgga   25260
agaggtggct gttttatcta atgcacacag accaacacag agagtcaaag aaaatgaaga   25320
aatggaagaa tacattccaa acgattaaaa cctcaggata gaaaccttaa tgaagcggtt   25380
tacctgatga gttcaaagta acagtcataa agatgctcac caaacttggg agaagaatgg   25440
atgaacacag tgagaacttc aacaaagata taggaaaaat acaagaaagt aacagatagt   25500
cacagagctg aagaagacag taacggaacc aaaaaacaca ctggagaggt tcaacagcag   25560
actagaagca gaagtacgga tccaggaact caaggacaga gcaacgggac tcacccagtc   25620
aaagcagcaa aaaaagata gccaaaaaga cttatcagac aatatcacgc agacccacac   25680
agatgaacat ttgcattata ggagtcccaa aggagaagc aagagagaaa gagaccaaga   25740
acttattgac ataaataatg gctaaaacct tccctaacct gaggaaggaa acggacattc   25800
ataaccagga agcccagatg cttcaaata agaagaatcc aaagacaccc acaccaaaga   25860
cacattaaaa tgtcaaaagt taaagacaag gagaggaatt tgagtatacc aaaagaaaaa   25920
caacttttta catacaaggg gcctctgtta agactctcag cagattttca acagaaattt   25980
tgcaggccag aaaaggagta tcatgatata ttttcaaagt gctgaaagaa aaaaacgcca   26040
aggatattct cttcttagaa aaactgtcat tcaggaaaaa aattttcccg ataagcaaaa   26100
gctaaaggag ttcatcacca ttaaaccagt tttacaagta atgttaaaaa gacttcttta   26160
agctgaaaag ggtgctaatt agtaatggga gaacaatcaa agtacaaatc tcactggtaa   26220
aggttaatat acagcaaaat tcagaataat ttaatgtaaa ggtggtgtat taatcactga   26280
taaagctagt aggaaattta aaagacaaaa gtaatttaaa aaacagctaa ctataataag   26340
ggatacacaa gattaaaaag acataaaatg gacatcaaaa acaaaacatg agggtgatga   26400
gtaaaactgt agagctttgg aatgcattta aacctaagtg attgtcaact taaaatataa   26460
ctgtaaccct tatggtaacc acaaagtagc tgcacgaaaa cctttggtag ataaacgaaa   26520
gagaaaggaa cctactgtag gaaatcatca aatcacaaaa ggagagagcc agagaaaaga   26580
gagcaaagaa actacagaac agtcagaaac agttcacaga atggcaatac gtacacactt   26640
attaataaat actttgaaaa taatgagctg aactccccag aatacagaga ggcagaatgg   26700
attaaaaaaa catgacacat ctatgtatac tgcctataag aaaactcgctt caaatttaaa   26760 gacagactga aagtgaagag atggaaaaat aagccttgca agtggaaacc aatgatgttg   26820
gccttcaaac aaaaaatgaa agtctagagt aaaacattta gaatcactta aggttatttt   26880
tagtttataa acttcagggg gaagaattca gtgtttggac taaataaaat actcaaaaag   26940
gactatctta ttttcccctg ctaactgcca tctttttacct ttttaaatct gaaaaacatt   27000
tttcctcata aagctcttct ggttgatcag tttggggtac tcaatacaga aaataaagaa   27060
ctcattgatg gttttttgctt gtccttttag gcaaaggagg aaacttccaa gccaaaagct   27120
gatgaaaaaa gtacaagtta aagttcacac tatttggtaa gttgggtgtt tgtcacaaat   27180
gaagaccact gtaccttcta ccagcccgtg tgttataggt gagagaaact aagtccattt   27240
cttgagtatt tcatgttctc tttatgctat tggcaatgaa agggacactg aaatctgtag   27300
agtaattccc tgaaaagcaa taaatggtgc ttccagaatg tttaaaaaca ttaatcttgt   27360
aattaaaagc tctttaaaat atgaggccag gcttttaaac aaaatgacca tctaagtcta   27420
gttgactctt tgaaacccaa atgctcatga ctgcaggtta ctgtggcaaa gcaaaattga   27480
```

```
caagttacat cttatggtga aatggcctta cgatctagat attacccgaa acacttgtgg    27540
ggtgaggaga agtgcacgcc tacggtctga cggtaattgc agggttttga gaatagggca    27600
aaggaaaaga ctgataactt gtgatcatct tagttttaga aagtaaagcc ctgtgtttga    27660
ttctacttta cagtaaccga agagctggtt tggatgaggg agactctgac atctgtcttg    27720
agagctaggc ccttattaat gtcaaagaga agaggcctta ttctaaatga caaaagcata    27780
taactactcg ctgcaaaaaa atctaaaaga aataacaatg tggattaaat tggattggct    27840
ctctcaccgt gattcacttt catttcctgt agaggaaggt atactgatta gaactgctcc    27900
aaagattttc tccaaaaaaa aaagttcttc ttctaatttt ctactctaat atctgcttaa    27960
agtaaatgcc tccttagatt tattatgcct gtaataagaa aataacctag caaatggttc    28020
actggatttt cttctttgaa tttttcaagg tatctgcata taaaatcttc agcgggtaga    28080
tggtgacttc tgaagaagaa aaggctttga taacagaaac aatttctggg tggcttggag    28140
acagtggtat ttgctgagtc ttttgacctc ctaaacattg tctgttattc ttttcctgaa    28200
aagaaactga atttgtctgg ttcacctgtg ttattctact gagtattgat aaactttaaa    28260
tttttaaaaa ttgccttcag ttgggagaga aaggaacttt atatttctaa gagatacatt    28320
tgatagtttc ttaaagcagc acacaaaaaa ggaaaaacct ttgcaaactt ttgcacattc    28380
tccccacagt gcctgtaaat ctcattagta ttttcgattt gcattatttt ttgttgttag    28440
catttggaaa acgatgcctc acgtgttctt cagtgttctg atttctcatg accccttttcc   28500 tcttagactt gtggactgtg tttgatgttt ctttgggttg ttgtttataa gtcagtcata    28560
aaatactgtg cattgggcac atgtctcctc ttgagctgct aatcgtagag accctggaca    28620
gaccaggaag cgccgcaccc cccttttcagg ttgaacttct ctttgccaga ggttaggact    28680
tccgcacctt gtccgcagag acccagcggg acttgactca agtcagaaga gcaaaacgca    28740
gactctgtca ctgcatagca agtttcaaga ataacaaaac ctaatgctta gaatactcac    28800
atggcttgat ctctgccaca gtactgcctt aagctgggct tgccatcctc tctctgtgaa    28860
accgagcagc cgctgttagc gcagagccat tgccacgtca gtcttgcgct gtacagcatg    28920
tggcttaatg gaagttgggt ttattgccaa aaacaaaaac aaacttctgc ttaaaaataa    28980
agaaaaaaga tctttttaac attaaaaaaa ataatctgtt ttttttttccc ccatagccat    29040 ttaagaacta gggagggtct gatatccgac aacttggaaa ggtttctcat attttttctga   29100 atggttgatg aacatagcac tgatgaaatt aaattatcaa aatcccatct tcattttctg    29160
atagtgaacg caggaaaaga tatcaggtac acatcataaa actgatttgg aattcctgct    29220
ttcagagagt acagccttcc ttagcatctg tttaaactat ttcttaggac ttggcaattt    29280
cactaaaaat tagtagtatc actgatactg tctaatgggg taggaggcaa gcaaaataac    29340
aatactattc ataatgggta tccaattcta ttaatactaa caattctctt taaaaatcat    29400
gcatatgcct gagattgcaa acttcatcca cttcaaatgc tctgtcttca tctcatgaga    29460
ggtaaaggca ttattagtct aaatctggga aagataagcc aggattatgg taatttaaac    29520
agaccttttc aaggcactaa caagaaaata aacactttc ctgagggatt ttaactatgt    29580
gtctgtaagt agtacaaagt tgttttaaaa aaaatgaaac ctttgacatt gacagatgtg    29640
tttgcaaaga tatgactcca gtattactaa tttacatgca tatatcaagt gttttttttaa   29700 ttacatacca aatccagaga ttttaagaaa tgcctgtaaa agtaaacatt tatttaaggt    29760
tctctgaata tgccttttgt ttattcaaaa tgtcttcaag acttgggtgt ctgctggtaa    29820
```

-continued

```
ttaatgatga actgagtaag ctacaggatc taaatcagtc cttttaccc atctaattca     29880 cagtaaaataa ttgcaaatac ttgcttagag gtaaataaca ttttttatta ccaaaaaggg   29940
ttttgcacat tgttgcggtg atgtgtgtct ctttagaaaa cggacttctc caaaagcaaa    30000
tgaaaatagg ttcctcaggt gaccaaaacg gaaaaccact atgtccatgt ttcattactc    30060
aagatacaag atgcaattaa aggaaagtat tttacattaa aatcttggct ttgtatgttt    30120
tttagaagga aaacacctgg ggggtagaaa tgaccagtga tttctgtttt ttcgttctta    30180
aaccatgaag tcaggcagta tatataaaaa tggaattata aacacattta tgtcctgaaa    30240
agaccttcta ttccatagtg tgttagaaca cattgacatt tttcatatcc tattccttta    30300
tcttaagttt tgcaatatat taaactcata aaagatttca actccaacaa caccatacct    30360
ggtcttcgct taggctgata taagcaagtc gtttccattt cacagtagct tacatttagt    30420
agagtctgca gtgctcactc ggagaaggca atggcacccc actccagtac tcttgcctgg    30480
aggatcccag ggacagagga gcctggtggg ctgcagtcca tggggtcact aagagtcaga    30540
catgactgag cgacttcact ttcactttc actttcatgc actggagaag gaaatagcaa     30600
ctcactccag tgttcttgcc tagagaatcc cagggacgga ggagcctggt aggctgcagt    30660
ccatggggtc acacagagtc agacacaact gcagcgactt agcagcagca gcagcagcag    30720
tgcccactgg caataaacaa caagttattt agggattata aaccagacca tctcatcctc    30780
tgtcagcccc atctcctcct accttcagtc tttcccagca tcagggtctt tcaaatgag    30840 tcacttcttc aacggttgga tggcatcacc gactcaatgg acatgagttt gagtaaattc    30900
cggaaactgg tga                                                      30913
```

```
<210> SEQ ID NO 8
<211> LENGTH: 2361
<212> TYPE: DNA
<213> ORGANISM: Bos taurus
<220> FEATURE:
<221> NAME/KEY: CDS
<222> LOCATION: (1)..(2358)

<400> SEQUENCE: 8
```

```
atg gca ttt gca agc tgg tgg tac aag acg cat gtc agt aga aaa acc      48
Met Ala Phe Ala Ser Trp Trp Tyr Lys Thr His Val Ser Arg Lys Thr
1               5                   10                  15 agt gga tcg cct tcc aag tca gga gaa aag aaa gga tca gat gag aaa      96
Ser Gly Ser Pro Ser Lys Ser Gly Glu Lys Lys Gly Ser Asp Glu Lys
            20                  25                  30 aaa gca aca agc ctt ggg agc agt cag ctc tcc aga act cag gct ggt     144
Lys Ala Thr Ser Leu Gly Ser Ser Gln Leu Ser Arg Thr Gln Ala Gly
        35                  40                  45 gaa aaa gcc ccg gtc ccc aag gta act act tcc tct gcg tca gcc agc     192
Glu Lys Ala Pro Val Pro Lys Val Thr Thr Ser Ser Ala Ser Ala Ser
50                  55                  60 aag tct tcc agt atg aat ccc aca gaa gcc aag gct att cca ggc agc     240
Lys Ser Ser Ser Met Asn Pro Thr Glu Ala Lys Ala Ile Pro Gly Ser
65                  70                  75                  80 aaa cag ctg gaa gga ccg cat tct cct aac aag aaa aga cac aaa aaa     288
Lys Gln Leu Glu Gly Pro His Ser Pro Asn Lys Lys Arg His Lys Lys
                85                  90                  95 cag gct gta aaa aca gaa cct gag aag aag cca caa tca tct aag cca     336
Gln Ala Val Lys Thr Glu Pro Glu Lys Lys Pro Gln Ser Ser Lys Pro
            100                 105                 110 tct gtg gtt cat gag aaa aaa acc caa gaa gta aag cca aag gaa cac     384
Ser Val Val His Glu Lys Lys Thr Gln Glu Val Lys Pro Lys Glu His
```

-continued

```
            115                 120                 125
aca gag cca aaa agc cta ccc aag cac tca tca gat aca gga agc aag    432
Thr Glu Pro Lys Ser Leu Pro Lys His Ser Ser Asp Thr Gly Ser Lys
        130                 135                 140 cat gct cct aag gaa aaa gcc gtt tcc aaa tca agt gag cag cca cca    480
His Ala Pro Lys Glu Lys Ala Val Ser Lys Ser Ser Glu Gln Pro Pro
145                 150                 155                 160 tca gag aaa tca aca ata cca aag acc aat tcc cag gac aag atc tcc    528
Ser Glu Lys Ser Thr Ile Pro Lys Thr Asn Ser Gln Asp Lys Ile Ser
                165                 170                 175 ggt ggt gga aag agc act gtt cct gct gct gct gca gca tct gcc        576
Gly Gly Gly Lys Ser Thr Val Pro Ala Ala Ala Ala Ala Ala Ser Ala
            180                 185                 190 gaa cca gct gac aag aat aaa gaa aat aaa ttg tta aca tcg gcc gta    624
Glu Pro Ala Asp Lys Asn Lys Glu Asn Lys Leu Leu Thr Ser Ala Val
        195                 200                 205 cca gct gaa tct aaa cca agt aaa cca tct gga aag tca gac atg gac    672
Pro Ala Glu Ser Lys Pro Ser Lys Pro Ser Gly Lys Ser Asp Met Asp
210                 215                 220 act gct ctg gat gac tta ata gac act tta gga gaa cct gaa gag atg    720
Thr Ala Leu Asp Asp Leu Ile Asp Thr Leu Gly Glu Pro Glu Glu Met
225                 230                 235                 240 aaa gaa gat aac aca aca tat acc gga ccg gaa gtg tcg gat cca atg    768
Lys Glu Asp Asn Thr Thr Tyr Thr Gly Pro Glu Val Ser Asp Pro Met
                245                 250                 255 agt tct acc tac ata gag gaa ctg ggt aaa aga gaa tcc aca ctt cct    816
Ser Ser Thr Tyr Ile Glu Glu Leu Gly Lys Arg Glu Ser Thr Leu Pro
            260                 265                 270 cca aaa tat aag gaa ctt ctg aat aaa gaa ggg atc gcg ggg cct        864
Pro Lys Tyr Lys Glu Leu Leu Asn Lys Glu Gly Ile Ala Gly Pro
        275                 280                 285 cct cca gac tcc ttg aaa ccc ctg ggg ccc aat gat gcc atc gat gcc    912
Pro Pro Asp Ser Leu Lys Pro Leu Gly Pro Asn Asp Ala Ile Asp Ala
    290                 295                 300 ttg tca tcc gac ttc acc tgc agt tcc cct aca gct gat gca aag aaa    960
Leu Ser Ser Asp Phe Thr Cys Ser Ser Pro Thr Ala Asp Ala Lys Lys
305                 310                 315                 320 act gag aaa gag aaa tct aca gaa gag gct tta aaa gct cag tca gct   1008
Thr Glu Lys Glu Lys Ser Thr Glu Glu Ala Leu Lys Ala Gln Ser Ala
                325                 330                 335 ggg gtg atc aga agt gct gct cca ccc caa gag aaa aaa agg aaa gtg   1056
Gly Val Ile Arg Ser Ala Ala Pro Pro Gln Glu Lys Lys Arg Lys Val
            340                 345                 350 gaa aag gat gcc atg act gag cac gcc ctg gag gcc ctg tct gcc tcc   1104
Glu Lys Asp Ala Met Thr Glu His Ala Leu Glu Ala Leu Ser Ala Ser
        355                 360                 365 ctg ggc acc cgg aag ccg gag ccg gag ctc gac ccc agc tcc att aag   1152
Leu Gly Thr Arg Lys Pro Glu Pro Glu Leu Asp Pro Ser Ser Ile Lys
    370                 375                 380 gag gtc gat gag gca aaa gcc aaa gaa gag aaa gta aag aaa tgt ggt   1200
Glu Val Asp Glu Ala Lys Ala Lys Glu Lys Val Lys Lys Cys Gly
385                 390                 395                 400 gaa gat gag gaa aca gtc cca tcg gag tac aga tta aaa ccg gcc aca   1248
Glu Asp Glu Glu Thr Val Pro Ser Glu Tyr Arg Leu Lys Pro Ala Thr
                405                 410                 415 gat aaa gat gga aaa cca ctc ttg cca gag gct gaa gaa aaa ccc aag   1296
Asp Lys Asp Gly Lys Pro Leu Leu Pro Glu Ala Glu Glu Lys Pro Lys
            420                 425                 430 ccc ctg agt gaa tca gaa ctc atc gat gaa ctc tca gaa gat ttt gac   1344
```

```
                Pro Leu Ser Glu Ser Glu Leu Ile Asp Glu Leu Ser Glu Asp Phe Asp
                        435                 440                 445 cag tct aag tgt aaa gaa aaa caa tct aag cca act gaa aaa aca gag       1392
Gln Ser Lys Cys Lys Glu Lys Gln Ser Lys Pro Thr Glu Lys Thr Glu
        450                 455                 460 gca tcc ccg gcc gct gcc ccc gtg ccc gtg gca gag gac gtg cct cgg       1440
Ala Ser Pro Ala Ala Ala Pro Val Pro Val Ala Glu Asp Val Pro Arg
465                 470                 475                 480 acc tct atg tgt tcc gtg cag tcg gct ccg ccc aca gca gct cca gcg       1488
Thr Ser Met Cys Ser Val Gln Ser Ala Pro Pro Thr Ala Ala Pro Ala
                485                 490                 495 aag ggc atg gtg cca gac gat gct gtc gaa gcc ttg gct gga agc ctg       1536
Lys Gly Met Val Pro Asp Asp Ala Val Glu Ala Leu Ala Gly Ser Leu
            500                 505                 510 ggc aaa aag gaa gca gat cca gaa gac gga aag cct gtg gag gat aaa       1584
Gly Lys Lys Glu Ala Asp Pro Glu Asp Gly Lys Pro Val Glu Asp Lys
        515                 520                 525 gtc aag gag aaa gcc aaa gaa gag gat cgt gag aaa ctt ggt gaa aaa       1632
Val Lys Glu Lys Ala Lys Glu Glu Asp Arg Glu Lys Leu Gly Glu Lys
    530                 535                 540 gaa gaa acg att cct cct gat tac aga tta gaa gaa gcc aag gat aaa       1680
Glu Glu Thr Ile Pro Pro Asp Tyr Arg Leu Glu Glu Ala Lys Asp Lys
545                 550                 555                 560 gac gga aaa cca ctg ctg cca aaa gag gtc aag gaa ccg ctc cca ccc       1728
Asp Gly Lys Pro Leu Leu Pro Lys Glu Val Lys Glu Pro Leu Pro Pro
                565                 570                 575 ttg agt gaa gac gtc ctc ctc gat gct ctg tcc aag gac ttc act gtc       1776
Leu Ser Glu Asp Val Leu Leu Asp Ala Leu Ser Lys Asp Phe Thr Val
                580                 585                 590 ccc tca gac aca tca tcg cct caa ttt gaa gat gct aaa ctt tca gct       1824
Pro Ser Asp Thr Ser Ser Pro Gln Phe Glu Asp Ala Lys Leu Ser Ala
            595                 600                 605 gtc gtc tct gaa gtg gtt tcc caa acc cca gct cca acc acc cag gca       1872
Val Val Ser Glu Val Val Ser Gln Thr Pro Ala Pro Thr Thr Gln Ala
        610                 615                 620 gcc ggt cca ccc ccc agc act gcg cag cgt gac aac aaa gaa ctt gac       1920
Ala Gly Pro Pro Pro Ser Thr Ala Gln Arg Asp Asn Lys Glu Leu Asp
625                 630                 635                 640 gat gcc ctg gat caa ctt tct gac agt ctc ggg caa aga cag cct gat       1968
Asp Ala Leu Asp Gln Leu Ser Asp Ser Leu Gly Gln Arg Gln Pro Asp
                645                 650                 655 cca gat gag aat aaa ccc gta gag gat aaa gtc aag gaa aaa gcc aaa       2016
Pro Asp Glu Asn Lys Pro Val Glu Asp Lys Val Lys Glu Lys Ala Lys
                660                 665                 670 gct gaa cac aga gac aag ctg gga gaa aga gat gac acc atc cca cct       2064
Ala Glu His Arg Asp Lys Leu Gly Glu Arg Asp Asp Thr Ile Pro Pro
            675                 680                 685 aaa tac caa cat ctt ttg gat gac aac aag gag ggc aca ccc ggg aag       2112
Lys Tyr Gln His Leu Leu Asp Asp Asn Lys Glu Gly Thr Pro Gly Lys
        690                 695                 700 cca aag gca tca gag aag ccc aag gca tca gag aaa cct gca ggt gcc       2160
Pro Lys Ala Ser Glu Lys Pro Lys Ala Ser Glu Lys Pro Ala Gly Ala
705                 710                 715                 720 cag gac ccc att gat gcc ctc tca ggg gac ttt gac agc tgt ccc tcg       2208
Gln Asp Pro Ile Asp Ala Leu Ser Gly Asp Phe Asp Ser Cys Pro Ser
                725                 730                 735 act aca gaa acc tcg aca gac aca cca aag gac aaa gac aag aag cct       2256
Thr Thr Glu Thr Ser Thr Asp Thr Pro Lys Asp Lys Asp Lys Lys Pro
            740                 745                 750
```

```
gct tcc agt gcc gaa gca cct agg aat ggc ggg aaa gca aag gat tcc   2304
Ala Ser Ser Ala Glu Ala Pro Arg Asn Gly Gly Lys Ala Lys Asp Ser
            755                 760                 765 aca aag gca aag gag gaa act tcc aag cca aaa gct gat gga aaa agt   2352
Thr Lys Ala Lys Glu Glu Thr Ser Lys Pro Lys Ala Asp Gly Lys Ser
    770                 775                 780 aca agt taa                                                       2361
Thr Ser
785
```

<210> SEQ ID NO 9
<211> LENGTH: 786
<212> TYPE: PRT
<213> ORGANISM: Bos taurus

<400> SEQUENCE: 9

```
Met Ala Phe Ala Ser Trp Trp Tyr Lys Thr His Val Ser Arg Lys Thr
 1               5                  10                  15

Ser Gly Ser Pro Ser Lys Ser Gly Glu Lys Gly Ser Asp Glu Lys
             20                  25                  30

Lys Ala Thr Ser Leu Gly Ser Ser Gln Leu Ser Arg Thr Gln Ala Gly
             35                  40                  45

Glu Lys Ala Pro Val Pro Lys Val Thr Thr Ser Ser Ala Ser Ala Ser
     50                  55                  60

Lys Ser Ser Ser Met Asn Pro Thr Glu Ala Lys Ala Ile Pro Gly Ser
 65                  70                  75                  80

Lys Gln Leu Glu Gly Pro His Ser Pro Asn Lys Arg His Lys Lys
                 85                  90                  95

Gln Ala Val Lys Thr Glu Pro Glu Lys Lys Pro Gln Ser Ser Lys Pro
                100                 105                 110

Ser Val Val His Glu Lys Lys Thr Gln Glu Val Lys Pro Lys Glu His
            115                 120                 125

Thr Glu Pro Lys Ser Leu Pro Lys His Ser Ser Asp Thr Gly Ser Lys
    130                 135                 140

His Ala Pro Lys Glu Lys Ala Val Ser Lys Ser Ser Glu Gln Pro Pro
145                 150                 155                 160

Ser Glu Lys Ser Thr Ile Pro Lys Thr Asn Ser Gln Asp Lys Ile Ser
                165                 170                 175

Gly Gly Gly Lys Ser Thr Val Pro Ala Ala Ala Ala Ser Ala
            180                 185                 190

Glu Pro Ala Asp Lys Asn Lys Glu Asn Lys Leu Leu Thr Ser Ala Val
            195                 200                 205

Pro Ala Glu Ser Lys Pro Ser Lys Pro Ser Gly Lys Ser Asp Met Asp
    210                 215                 220

Thr Ala Leu Asp Asp Leu Ile Asp Thr Leu Gly Glu Pro Glu Glu Met
225                 230                 235                 240

Lys Glu Asp Asn Thr Thr Tyr Thr Gly Pro Glu Val Ser Asp Pro Met
                245                 250                 255

Ser Ser Thr Tyr Ile Glu Glu Leu Gly Lys Arg Glu Ser Thr Leu Pro
            260                 265                 270

Pro Lys Tyr Lys Glu Leu Leu Asn Lys Glu Glu Gly Ile Ala Gly Pro
    275                 280                 285

Pro Pro Asp Ser Leu Lys Pro Leu Gly Pro Asn Asp Ala Ile Asp Ala
    290                 295                 300

Leu Ser Ser Asp Phe Thr Cys Ser Ser Pro Thr Ala Asp Ala Lys Lys
305                 310                 315                 320
```

```
Thr Glu Lys Glu Lys Ser Thr Glu Glu Ala Leu Lys Ala Gln Ser Ala
                325                 330                 335

Gly Val Ile Arg Ser Ala Ala Pro Pro Gln Glu Lys Lys Arg Lys Val
            340                 345                 350

Glu Lys Asp Ala Met Thr Glu His Ala Leu Glu Ala Leu Ser Ala Ser
        355                 360                 365

Leu Gly Thr Arg Lys Pro Glu Pro Glu Leu Asp Pro Ser Ser Ile Lys
    370                 375                 380

Glu Val Asp Glu Ala Lys Ala Lys Glu Lys Val Lys Lys Cys Gly
385                 390                 395                 400

Glu Asp Glu Glu Thr Val Pro Ser Glu Tyr Arg Leu Lys Pro Ala Thr
                405                 410                 415

Asp Lys Asp Gly Lys Pro Leu Leu Pro Glu Ala Glu Glu Lys Pro Lys
            420                 425                 430

Pro Leu Ser Glu Ser Glu Leu Ile Asp Glu Leu Ser Glu Asp Phe Asp
        435                 440                 445

Gln Ser Lys Cys Lys Glu Lys Gln Ser Lys Pro Thr Glu Lys Thr Glu
    450                 455                 460

Ala Ser Pro Ala Ala Ala Pro Val Pro Val Ala Glu Asp Val Pro Arg
465                 470                 475                 480

Thr Ser Met Cys Ser Val Gln Ser Ala Pro Pro Thr Ala Ala Pro Ala
                485                 490                 495

Lys Gly Met Val Pro Asp Asp Ala Val Glu Ala Leu Ala Gly Ser Leu
            500                 505                 510

Gly Lys Lys Glu Ala Asp Pro Glu Asp Gly Lys Pro Val Glu Asp Lys
        515                 520                 525

Val Lys Glu Lys Ala Lys Glu Asp Arg Glu Lys Leu Gly Glu Lys
    530                 535                 540

Glu Glu Thr Ile Pro Pro Asp Tyr Arg Leu Glu Glu Ala Lys Asp Lys
545                 550                 555                 560

Asp Gly Lys Pro Leu Leu Pro Lys Glu Val Lys Glu Pro Leu Pro Pro
                565                 570                 575

Leu Ser Glu Asp Val Leu Leu Asp Ala Leu Ser Lys Asp Phe Thr Val
            580                 585                 590

Pro Ser Asp Thr Ser Ser Pro Gln Phe Glu Asp Ala Lys Leu Ser Ala
        595                 600                 605

Val Val Ser Glu Val Val Ser Gln Thr Pro Ala Pro Thr Thr Gln Ala
    610                 615                 620

Ala Gly Pro Pro Pro Ser Thr Ala Gln Arg Asp Asn Lys Glu Leu Asp
625                 630                 635                 640

Asp Ala Leu Asp Gln Leu Ser Asp Ser Leu Gly Gln Arg Gln Pro Asp
                645                 650                 655

Pro Asp Glu Asn Lys Pro Val Glu Asp Lys Val Lys Glu Lys Ala Lys
            660                 665                 670

Ala Glu His Arg Asp Lys Leu Gly Glu Arg Asp Asp Thr Ile Pro Pro
        675                 680                 685

Lys Tyr Gln His Leu Leu Asp Asp Asn Lys Glu Gly Thr Pro Gly Lys
    690                 695                 700

Pro Lys Ala Ser Glu Lys Pro Lys Ala Ser Lys Pro Ala Gly Ala
705                 710                 715                 720

Gln Asp Pro Ile Asp Ala Leu Ser Gly Asp Phe Asp Ser Cys Pro Ser
                725                 730                 735
```

```
Thr Thr Glu Thr Ser Thr Asp Thr Pro Lys Asp Lys Asp Lys Lys Pro
            740                 745                 750

Ala Ser Ser Ala Glu Ala Pro Arg Asn Gly Gly Lys Ala Lys Asp Ser
        755                 760                 765

Thr Lys Ala Lys Glu Glu Thr Ser Lys Pro Lys Ala Asp Gly Lys Ser
    770                 775                 780

Thr Ser
785

<210> SEQ ID NO 10
<211> LENGTH: 27
<212> TYPE: DNA
<213> ORGANISM: Bos taurus

<400> SEQUENCE: 10
caggctggtg aaaaagcccc ggtcccc                                     27

<210> SEQ ID NO 11
<211> LENGTH: 27
<212> TYPE: DNA
<213> ORGANISM: Bos taurus

<400> SEQUENCE: 11
caggctgatg aaaaagccct ggtcccc                                     27

<210> SEQ ID NO 12
<211> LENGTH: 10
<212> TYPE: DNA
<213> ORGANISM: Bos taurus

<400> SEQUENCE: 12
ctgttggggg                                                        10

<210> SEQ ID NO 13
<211> LENGTH: 10
<212> TYPE: DNA
<213> ORGANISM: Bos taurus

<400> SEQUENCE: 13
ctgtgggggg                                                        10

<210> SEQ ID NO 14
<211> LENGTH: 21
<212> TYPE: DNA
<213> ORGANISM: Bos taurus

<400> SEQUENCE: 14
atgaaagaaa gaaagaaagt g                                           21

<210> SEQ ID NO 15
<211> LENGTH: 25
<212> TYPE: DNA
<213> ORGANISM: Bos taurus

<400> SEQUENCE: 15
atgaaagaaa gaaagaaaga aagtg                                       25

<210> SEQ ID NO 16
<211> LENGTH: 19
<212> TYPE: DNA
<213> ORGANISM: Bos taurus

<400> SEQUENCE: 16
```

-continued

```
gctgaaagaa agaaagaaa                                          19

<210> SEQ ID NO 17
<211> LENGTH: 23
<212> TYPE: DNA
<213> ORGANISM: Bos taurus

<400> SEQUENCE: 17
atggaaagaa agaaagaaag aaa                                     23

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaatttgcgg ttgaccacac tgtta                                   25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgttatgcct gttgctttgt acctc                                   25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gattcttgct gaatttggag ggaag                                   25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggggtctcaa agagttggat acgat                                   25
```

CALPASTATIN MARKERS FOR FERTILITY AND LONGEVITY

INCORPORATION BY REFERENCE

This application claims benefit of U.S. provisional patent application Ser. No. 60/756,383 filed Jan. 5, 2006. Reference is made to international patent application PCT/IB2005/002983 filed Jul. 18, 2005 and published as WO 2006/097787 on Sep. 21, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the identification of genetic markers (single nucleotide polymorphisms (SNPs) and a short tandem repeat (STR)) within the bovine genes encoding calpastatin ("CAST") and their associations with economically relevant traits in Dairy production. The invention further relates to methods and systems, including network-based processes, to manage the SNP/STR data and other data relating to specific animals and herds of animals, veterinarian care, diagnostic and quality control data and management of livestock which, based on genotyping, have predictable fertility and longevity traits, husbandry conditions, animal welfare, food safety information, audit of existing processes and data from field locations.

BACKGROUND OF THE INVENTION

Reproductive decline has been a challenge facing the dairy industry worldwide for several decades and has typically been blamed on selection for increased milk production [Sheldon I M, Dobson H. Reproductive challenges facing the cattle industry at the beginning of the 21st century. Reprod Suppl. 2003; 61:1-13]. In the United States alone, first service to conception rate has declined from approximately 65% in 1951 to 40% in 1996 [Butler W R. Review: effect of protein nutrition on ovarian and uterine physiology in dairy cattle. J Dairy Sci. 1998; 81:2533-2539], while the number of services per conception has increased from approximately 1.8 in 1970 to approximately 3 in 2000 [Lucy M C. Reproductive loss in high-producing dairy cattle: where will it end? J Dairy Sci. 2001; 84:1277-1293]. It was reported that during 1976 to 1978, the average number of days open (days between calving and the subsequent conception) was 122 days for Jerseys and 124 days for Holsteins [Washburn S P, Silvia W J, Brown C H, McDaniel B T, McAllister A J. Trends in reproductive performance in Southeastern Holstein and Jersey DHI herds. J Dairy Sci. 2002; 85:244-251]. However, days open increased to 152 days for Jerseys and 168 days for Holsteins by 1997 to 1999. In the United Kingdom, the conception rate to first service of dairy cows has declined from 65.4% (1975-82) to 44.3% (1995-98) at a rate of approximately 1% per year [Royal M D, Darwash A O, Flint A P, Webb R, Woolliams J A, Lamming G E. Declining fertility in dairy cattle: changes in traditional and endocrine parameters of fertility. Anim Sci 2000; 70:487-502]. Equivalent decreases in first—service conception rate have been also observed in dairy cattle in Ireland [Roche J F, Mackey D, Diskin M D. Reproductive management of postpartum cows. Anim Reprod Sci 2000; 61:703-712] and Australia [Macmillan K L, Lean I J, Westwood C T. The effects of lactation on the fertility of dairy cows. Aust Vet J 1996; 73:141-147]. Understanding the genetic causes of reduced fertility is essential to halt the currently observed fertility decline in lactating dairy cows.

To address the difficulties of achieving desired levels of reproductive performance in today's milking herds, a new fertility trait, the daughter pregnancy rate (DPR) was introduced as an indicator of sire fertility for genetic selection [VanRaden P M, Sanders A H, Tooker M E, Miller R H, Norman H D, Kuhn M T, Wiggans G R. Development of a national genetic evaluation for cow fertility. Dairy Sci 2004; 87:2285-2292]. Pregnancy rate is defined as the percentage of nonpregnant cows that become pregnant during each 21-day period. In fact, data for calculating DPR are taken from reported days open, which are calculated as date pregnant minus previous calving date. Date pregnant is determined from last reported breeding or from subsequent calving minus expected gestation length. For calculation of genetic evaluations, days open are converted to daughter pregnancy rate by the linear transformation of pregnancy rate=0.25 (233-days open). Evaluations are expressed as predicted transmitting ability (PTA) for DPR, and calculations are generated as a direct result of a bull's daughters performance [VanRaden P M, Sanders A H, Tooker M E, Miller R H, Norman H D, Kuhn M T, Wiggans G R. Development of a national genetic evaluation for cow fertility. Dairy Sci 2004; 87:2285-2292]. In addition, cow fertility is a major component of productive life (PL) or longevity. Improving both DPR and PL would lead to the increased productivity and profitability to the dairy industry.

Calpastatin (CAST) is an endogenous protease inhibitor that specifically acts on two $Ca^{2+}$-independent proteases, µ-calpain and m-calpain by binding and forming an inactive complex. CAST is widely expressed in mammalian cells and tissues, including those related to reproduction. For example, the CAST gene is expressed in the human pituitary gland [Kitahara A, Takano E, Ontsuki H, Kirihata Y, Yamagata Y, Knaagi R, Murachi T. Reversed distribution of calpains and calpastatin in human pituitary gland and selective localization of calpastatin in adrenocorticotropin-producing cells as demonstrated by immunohistochemistry. J Clin Endocrinol Metab 1986; 63:343-348], the human placenta [Thompson V F, Saldana S, Cong J, Luedke D M, Goll D E. The calpain system in human placenta. Life Sci 2002; 70:2493-508], the human oocyte [Ben-Aharon I, Ben-Yosef D, Amit A, Shalgi R. Expression and immunolocalization of the calpain-calpastatin system in the human oocyte. Fertil Steril 2005; 83:1807-1813], the bovine corpus luteum [Orwig K E, Bertrand J E, Ou B R, Forsberg N E, Stormshak F. Involvement of protein kinase-C, calpains, and calpastatin in prostaglandin F2 alpha-induced oxytocin secretion from the bovine corpus luteum. Endocrinology 1994; 134:78-83], as well as during spermatogenesis in the testes of humans [Liang Z G, O'Hem P A, Yavetz B, Yavetz H, Goldberg E. Human testis cDNAs identified by sera from infertile patients: a molecular biological approach to immunocontraceptive development. Reprod Fertil Dev 1994; 6:297-305; Li S, Liang Z G, Wang G Y, Yavetz B, Kim E D, Goldberg E. Molecular cloning and characterization of functional domains of a human testis-specific isoform of calpastatin. Biol Reprod 2000; 63:172-178 and Wei S G, Wang L F, Miao S Y, Zong S D, Koide S S. Expression of the calpastatin gene segment during spermiogenesis in human testis: an in situ hybridization study. Arch Androl 1995; 34:9-12.], mice [Li S, Goldberg E. A novel N-terminal domain directs membrane localization of mouse testis-specific calpastatin. Biol Reprod 2000; 63:1594-1600] and rabbits [Wang L F, Miao S Y, Yan Y C, Li Y H, Zong C, Koide S S. Expression of a sperm protein gene during spermatogenesis in mammalian testis: an in situ hybridization study. Mol Reprod Dev 1990; 26:1-5]. Interestingly, the CAST protein was identified as one of the target antigens for anti-sperm antibodies found in infertile women [Koide S S, Wang L, Kamada M. Antisperm antibodies associated with infertility: properties and encoding genes of target antigens. Proc Soc Exp Biol Med 2000; 224:123-132]. In vivo, CAST anti-BS-17 antibodies can block the fertilizing capacity of mouse sperm to fertilize ova by significantly reducing the numbers of developing embryos [Koide S S, Wang L, Kamada M. Antisperm antibodies associated with infertility: properties and encoding genes of target antigens. Proc Soc Exp Biol Med 2000; 224:123-132]. All these results indicate that the CAST gene plays an important role in reproductive biology.

The primary structure of the calpastatin amino-acid sequence includes four internally repetitive domains (Domains 1-4) and one non-homologous domain at the amino-terminal end (Domain L) [Murachi T. Calpain and calpastatin. Rinsho Byori 1990; 38:337-346]. However, a new N-terminal peptide domain, named domain XL, was identified in cattle [Cong M, Thompson V F, Goll D E, Antin P B. The bovine calpastatin gene promoter and a new N-terminal region of the protein are targets for cAMP-dependent protein kinase activity. J Biol Chem 1998; 273:660-666]. This "XL" region contains sixty-eight amino acids, but shares no homology with other regions of calpastatin or with any known proteins. In vivo experiments showed that the "XL" region is a substrate for phosphorylation by protein kinase [Cong M, Thompson V F, Goll D E, Antin P B. The bovine calpastatin gene promoter and a new N-terminal region of the protein are targets for cAMP-dependent protein kinase activity. J Biol Chem 1998; 273:660-666].

It remains advantageous to provide further SNPs/STRs that may more accurately predict the fertility and longevity phenotypes of an animal and also a business method that provides for increased production efficiencies in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

The present invention relates to the identification of genetic markers (single nucleotide polymorphisms (SNPs) and a short tandem repeat (STR)) within the bovine genes encoding calpastatin ("CAST") and their associations with economically relevant traits in dairy production.

The invention encompasses a method for sub-grouping animals according to genotype wherein the animals of each sub-group have a similar polymorphism in a CAST gene which may comprise determining the genotype of each animal to be sub-grouped by determining the presence of a SNP/STR in the CAST gene, and segregating individual animals into sub-groups wherein each animal in a sub-group has a similar polymorphism in the CAST gene.

The invention also encompasses a method for sub-grouping animals according to genotype wherein the animals of each sub-group have a similar genotype in the CAST gene which may comprise determining the genotype of each animal to be sub-grouped by determining the presence of a single nucleotide polymorphism(s) of interest in the CAST gene, and segregating individual animals into sub-groups depending on whether the animals have, or do not have, the single nucleotide polymorphism(s) of interest in the CAST gene.

The genetic polymorphism(s) of interest may be selected from the group consisting of missense mutations in the XL domain region, especially missense mutations in exon 3 that result in G48D and P52L substitutions (NM_174003.2: c.271G>A and 283C>T), a G/T substitution in intron 3 (AAFC020603 81.1:g.2110G>T) and a GAAA short tandem repeat in intron 8 (AAFC02060381.1:g.6700[(GAAA)4]+[(GAAA)5]. The invention further relates to a method for sub-grouping animals according to genotype wherein the animals of each sub-group have a similar genotype in the CAST gene which may comprise determining the genotype of each animal to be sub-grouped by determining the presence of any one of the above SNPs/STR, and segregating individual animals into sub-groups depending on whether the animals have, or do not have, any one of the above SNPs/STR in the CAST gene.

The invention also relates to method for identifying an animal having a desirable phenotype as compared to the general population of animals of that species, which may comprise determining the presence of a single nucleotide polymorphism in the CAST gene of the animal, wherein the presence of the SNP/STR is indicative of a desirable phenotype.

In an advantageous embodiment, the animal may be a bovine. In another advantageous embodiment, the CAST gene may be a bovine CAST gene.

The invention also encompasses computer-assisted methods and systems for improving the production efficiency for livestock having fertility and longevity and in particular the genotype of the animals as it relates to CAST SNPs/STRs. Methods of the invention encompass obtaining a genetic sample from each animal in a herd of livestock, determining the genotype of each animal with respect to specific quality traits as defined by a panel of at least two single polynucleotide polymorphisms (SNPs)/STRs, grouping animals with like genotypes, and optionally, further sub-grouping animals based on like phenotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP/STR within the CAST gene related to fertility and longevity traits of the breed of animal and associating those data with other data about the animal or its herd, and maintaining those data in ways that are accessible. Another aspect of the invention encompasses a computer-assisted method for predicting which livestock animals possess a biological difference in fertility and longevity, and which may include the steps of using a computer system, e.g., a programmed computer comprising a processor, a data storage system, an input device and an output device, the steps of: (a) inputting into the programmed computer through the input device data that includes a genotype of an animal as it relates to any one of the CAST SNPs/STRs described herein, (b) correlating fertility and longevity predicted by the CAST genotype using the processor and the data storage system and (c) outputting to the output device the fertility and longevity correlated to the CAST genotype, thereby predicting which livestock animals possess a particular fertility and longevity.

Yet another aspect of the invention relates to a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic intake, growth or carcass merit in beef cattle and the genotype is a CAST genotype.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIGS. 2A-2E provides a nucleotide sequence (SEQ ID NO: 1) of the promoter, 5'UTR (Bolded), exon 1 (Italics and Underlined) and partial intron 1 sequence of the bovine CAST gene (AAFC02060382). Each exon-intron boundary is Boxed.

FIGS. 3A-3D provides a nucleotide sequence (SEQ ID NO: 2) of the partial intron 1, exon 2 (Italics and Underlined) and partial intron 2 sequence of the bovine CAST gene (AAFC02161394). Each exon-intron boundary is Boxed.

FIGS. 4A-4C provides a nucleotide sequence (SEQ ID NO: 3) of the partial intron 2, exon 3 (Italics and Underlined) and partial intron 3 sequence of the bovine CAST gene (AAFC02179490). Each exon-intron boundary is Boxed. Three mutations: G/A, C/T and T/G (were Bolded), which were associated with both fertility and longevity in dairy cattle.

FIGS. 5A-5F provides a nucleotide sequence (SEQ ID NO: 4) of the partial intron 3, exon 4 (Italics and Underlined) and partial intron 4 sequence of the bovine CAST gene (AAFC02060385). Each exon-intron boundary is Boxed.

FIG. 6A-6E provides a nucleotide sequence (SEQ ID NO: 5) of the partial intron 5, exons 5-16 (Italics and Underlined), introns 5-15 and partial intron 16 sequence of the bovine CAST gene (AAFC02060381). Each exon-intron boundary is Boxed. A STR polymorphism (GAAA) was BOLDED and associated with fertility and longevity in dairy cattle.

FIG. 7 provides a nucleotide sequence (SEQ ID NO: 6) of the partial intron 16, exon 17 (Italics and Underlined) and partial intron 17 sequence of the bovine CAST gene (AAFC02197217). Each exon-intron boundary is Boxed.

FIGS. 8A-8H provides a nucleotide sequence (SEQ ID NO: 7) of the partial intron 17, exons 18-32 (Italics and Underlined), introns 18-31 and 3'UTR sequence of the bovine CAST gene (AAFC02067026). Each exon-intron boundary is Boxed.

FIGS. 9A-9B provides a nucleotide sequence (SEQ ID NO: 8) and amino acid sequence (SEQ ID NO: 9) of the coding sequence and in silico cSNP identification. The potential SNPs were Boxed.

DETAILED DESCRIPTION

Figure 1:
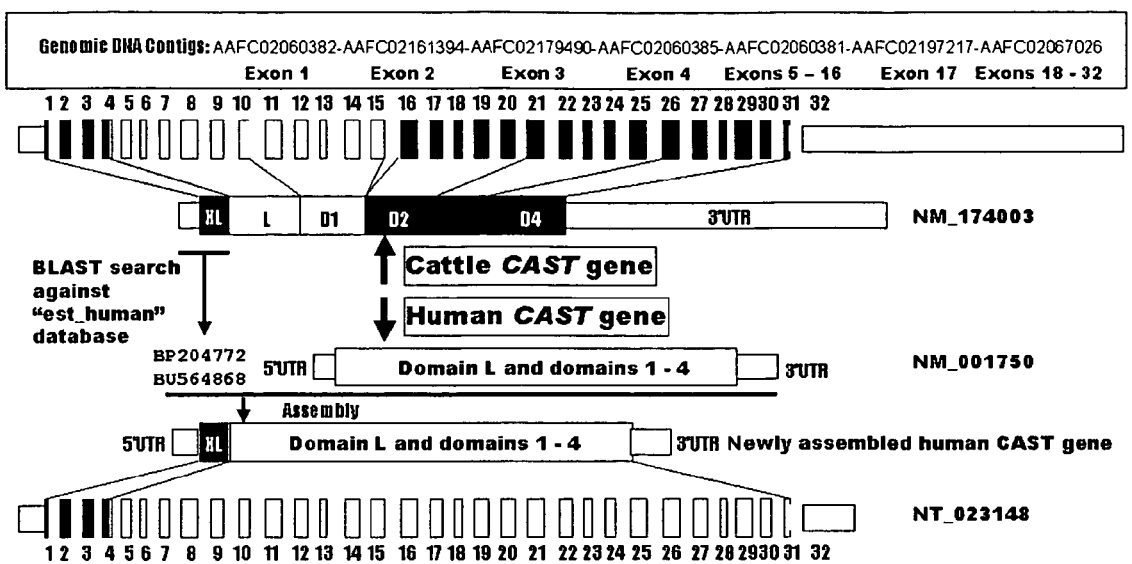
FIG. 1 provides a comparative annotation of both human and bovine CAST genes. The annotation recovered the XL domain in the human CAST protein, showing the same gene structure found in the bovine CAST gene. The sizes of each exon (human/cattle) are as follows: exon 1, 30/30 bp; exon 2, 63/63 bp; exon 3, 72/72 bp; exon 4, 60/60 bp; exon 5, 66 bp; exon 6, 42/42 bp; exon 7, 57/57 bp; exon 8, 114/114 bp; exon 9, 81/87 bp; exon 10, 69/69 bp; exon 11, 99/99 bp; exon 12, 81/81 bp; exon 13, 39/39 bp; exon 14, 93/93 bp; exon 15, 87/90 bp; exon 16, 102/102 bp; exon 17, 84/84 bp; exon 18, 48/48 bp; exon 19, 96/96 bp; exon 20, 96/93 bp; exon 21, 102/102 bp; exon 22, 84/84 bp; exon 23, 51/51 bp; exon 24, 72/72 bp; exon 25, 99/99 bp; exon 26, 105/108 bp; exon 27, 93/93 bp; exon 28, 45/48 bp; exon 29, 93/93 bp; exon 30, 72/72 bp; exon 31, 59/66 bp (including partial non-coding sequence) and exon 32, 198/2045 bp (3'UTR sequences in both species). The 5'UTR is 148 bp in human and 128 bp long in cattle. The gap distance between any two exons is not proportional to the intron size.

Calpastatin (CAST) gene is widely expressed in reproductive tissues/organs. However, how this gene is related to fertility remains largely undetermined. In the present study, the inventors discovered previously unreported significant associations of missense mutations in a newly identified XL domain of bovine CAST gene with fertility (daughter pregnancy rate, DPR) and longevity (productive life, PL) in dairy cattle using 652 sires derived from seven grandsires. Alignment of both cDNA and genomic DNA sequences revealed three provisional missense mutations, but two of them (G48D and P52L) in exon 3 (NM_174003.2:c.271 G>A and 283C>7), which corresponds to the XL domain region, were confirmed by sequencing analysis of two DNA pools and seven grandsires. These two confirmed missense mutations plus one mutation in intron 3 (AAFC020603 81.1:g.2110G>7) and a GAAA repeat in intron 8 (AAFC02060381.1:g.6700[(GAAA)4]+[(GAAA)5] formed only two haplotypes. A C/T transition was then genotyped with restriction enzyme MspI and used for an initial association screening and a final comprehensive analysis. Across family analyses indicated that individual genotype was a significant source of variation (P<0.0001) for DPR and PL, but not for the milk traits (P>0.05). The realized heritabilities were estimated to be 0.55 for DPR and 0.66 for PL, indicating that the bovine calpastatin gene, when utilized in marker-assisted selection should accelerate improvement of fertility in dairy cattle.

Particular aspects provide four novel polymorphisms including two missense mutations that form two haplotypes in a new N-terminal domain of the bovine calpastatin gene show significant associations with fertility and longevity in dairy cattle.

In specific aspects, two mutations in the "XL" region of the bovine CAST gene were identified, which lead to amino acid changes (G48D and P52L) at both positions. Genotyping of the markers on 652 animals from seven sire families revealed a strong association with DPR and PL in dairy cattle. Present results indicate that different forms of CAST gene might be involved in different pathways of various cells/tissues by expressing a pleiotrophic effect on different functions.

Particular aspects provide novel markers for fertility (e.g., daughter pregnancy rate, DPR) and longevity (e.g., productive life, PL) in, for example, dairy cattle.

Additional aspects provide for novel methods comprising marker-assisted selection to improve fertility and/or longevity in dairy cattle. In particular embodiments, a combination of genetic selection based on one or more of the novel CAST markers, and high PTA (predicted transmitting ability) potentials of milk production traits, provides for improved reproductive traits in association with continued high milk production traits.

Further aspects disclose a previously unrecognized XL domain in the human CAST gene, and thus provide for the use of human CAST XL domain mutants/variants as markers for human fertility and longevity.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol I and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 600 Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, daughter pregnancy rate (i.e., fertility), productive life (i.e., longevity) and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene of interest is bovine CAST, the bovine CAST nucleotide sequence can be selected from, but is not limited to, the sequence corresponding to GenBank Accession Nos. AAFC02060382 (SEQ ID NO: 1), AAFC02161394 (SEQ ID NO: 2), AAFC02179490 (SEQ ID NO: 3), AAFC02060385 (SEQ ID NO: 4), AAFC02060381 (SEQ ID NO: 5), AAFC02197217 (SEQ ID NO: 6), AAFC02067026 (SEQ ID NO: 7) or a fragment thereof or a region of the bovine genome that comprises this sequence.

The present invention, therefore, provides isolated nucleic acids that may specifically hybridize to the nucleotide sequence can be selected from, but is not limited to, the sequence corresponding to GenBank Accession Nos. AAFC02060382 (SEQ ID NO: 1), AAFC02161394 (SEQ ID NO: 2), AAFC02179490 (SEQ ID NO: 3), AAFC02060385 (SEQ ID NO: 4), AAFC02060381 (SEQ ID NO: 5), AAFC02197217 (SEQ ID NO: 6), AAFC02067026 (SEQ ID NO: 7), or the complement thereof, and which comprises the polymorphic site corresponding to.

The single nucleotide polymorphism(s) of interest may be selected from the group consisting of missense mutations in the XL domain region, especially missense mutations in exon 3 that result in G48D and P52L substitutions (NM_174003.2:c.271G>A and 283C>T), a G/T substitution in intron 3 (AAFC020603 81.1:g.2110G>T) and a GAAA repeat in intron 8 (AAFC02060381.1:g.6700[(GAAA)4]+[(GAAA)5].

The SNP/STR advantageous in the present invention is associated with certain economically valuable and heritable traits relating to fertility and longevity in bovines. Therefore, it is an object of the present invention to determine the genotype of a given animal of interest as defined by the CAST locus SNP/STR according to the present invention. It is also contemplated that the genotype of the animal(s) may be defined by additional SNPs/STRs within the CAST gene or within other genes identified with desirable traits or other characteristics, and in particular by a panel or panels of SNPs/STRs.

There are many methods known in the art for determining the sequence of DNA in a sample, and for identifying whether a given DNA sample contains a particular SNP/STR. Any such technique known in the art may be used in performance of the methods of the present invention.

The methods of the present invention allow animals with certain economically valuable heritable traits to be identified based on the presence of SNPs/STRs in their genomes and particularly with missense mutations in exon 3 of the CAST gene. The methods further allow, by computer-assisted methods of the invention, to correlate the SNP/STR-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 μl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP/STR of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP/STR of interest can be amplified using the polymerase chain reaction. The amplified region of DNA form can then be sequenced using any method known in the art, for example using an automatic nucleic acid sequencer. The detection of a given SNP/STR can then be performed using hybridization of probes and or using PCR-based amplification methods. Such methods are described in more detail below.

The methods of the present invention may use oligonucleotides useful as primers to amplify specific nucleic acid sequences of the CAST gene, advantageously of the region encompassing a CAST SNP/STR. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with a CAST gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in a CAST gene which are unique to a CAST gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3H$, $^{125}I$, $^{35}S$, $^{14}C$, $^{32}P$, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP/STR according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP/STR to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g. horseradish peroxidase, alkaline phosphatase etc.) colorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and MacBeath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A SNP/STR-specific probe can also be used in the detection of the SNP/STR in amplified specific nucleic acid sequences of the target gene, such as the amplified PCR products generated using the primers described above. In certain embodiments, these SNP/STR-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs/STRs associated with that trait. Several economically relevant traits may be characterized by the presence or absence of one or more SNPs/STRs and by a plurality of SNPs/STRs in different genes. One or more panels of SNPs/STRs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as fertility (daughter pregnancy rate) and longevity (productive life). Continuous selection and breeding of animals, such as livestock, that are at least heterozygous and advantageously homozygous for desirable alleles of the CAST gene polymorphic sites associated with economically relevant traits of growth, feed intake, efficiency and/or carcass merit, and reproduction and longevity would lead to a breed, line, or population having higher numbers of offspring with economically relevant traits of growth, feed intake, efficiency and carcass merit, and reproduction and longevity. Thus, the CAST SNPs/STRs of the present invention can be used as a selection tool.

Desirable phenotypes include, but are not limited to, feed intake, growth rate, body weight, carcass merit and composition, and reproduction and longevity, and milk yield. Specific carcass traits with desirable phenotypes include, but are not limited to, additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF %, %), marbling score (MBS, 10 to 99), marbling score divided by days on feed (MBS/DOF), quality grade, less than or equal to select versus greater than or equal to choice (QG, <Se vs, >Ch), ribeye area (REA, in$^2$), ribeye area per hundred weight HCW (REA/cwt HCW, in$^2$/100 lb hot carcass weight (HCW) and subcutaneous fat depth (SFD).

One aspect of the present invention provides for grouping animals and methods for managing livestock production comprising grouping livestock animals such as cattle according the genotype as defined by panels of SNPs/STRs, each panel comprising at least one SNP/STR, one or more of which are in the CAST gene of the present invention. Other SNPs that may be included in panels of SNPs include, but not limited to, SNPs found in the GHR gene, FABP4 gene, ghrelin gene, leptin gene, NPY gene, ob gene, TFAM gene, CRH gene, UASMS1 gene, UASMS2 gene, UASMS3 gene and/or the UCP3 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as fertility, longevity, breeding, feed intake, carcass/meat quality and milk production. The present invention provides methods of screening livestock to determine those more likely to develop a desired body condition by identifying the presence or absence of one or more gene polymorphisms correlated with fertility and longevity.

As described above, and in the Examples, there are various phenotypic traits with which the SNPs/STRs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by SNP/STR genotype. The cattle are tested to determine homozygosity or heterozygosity with respect to the SNP/STR alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of SNPs/STRs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, dairy production management, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP/STR-based genotype results for each animal or the data for each animal can be associated or linked to other databases containing data, for example, which may be helpful in selecting traits for grouping or sub-grouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin, MMI (Meta Morphix Inc.), bovine spongiform encephalopathy (BSE) diagnosis, brucellosis vaccination, FMD (foot and mouth disease) vaccination, BVD (bovine viral diarrhea) vaccination, Sure Health pre-conditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are CAST sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the CAST sequences described herein.

Another embodiment of the invention is an oligonucleotide that specifically hybridizes under high stringency conditions to any one of the polymorphic sites of the CAST gene, wherein the oligonucleotide is between about 18 nucleotides and about 50 nucleotides.

In another embodiment of the invention, the oligonucleotide comprises a central nucleotide specifically hybridizing with a CAST gene polymorphic site of the portion of the nucleic acid molecule.

Another aspect of the invention is a method of identifying a CAST polymorphism in a nucleic acid sample comprising isolating a nucleic acid molecule encoding CAST or a fragment thereof and determining the nucleotide at the polymorphic site.

Another aspect of the invention is a method of screening cattle to determine those bovines more likely to exhibit a biological difference in fertility and longevity comprising the steps of obtaining a sample of genetic material from a bovine; and assaying for the presence of a genotype in the bovine which is associated with fertility and longevity, the genotype characterized by a polymorphism in the bovine CAST gene.

In other embodiments of this aspect of the invention, the step of assaying is selected from the group consisting of: restriction fragment length polymorphism (RFLP) analysis, minisequencing, MALD-TOF, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the CAST gene or a portion thereof that contains the polymorphism. In other embodiments of the invention, the amplification may include the step of selecting a forward and a reverse sequence primer capable of amplifying a region of the CAST gene.

Another aspect of the invention is a computer-assisted method for predicting which livestock animals possess a biological difference in fertility and longevity comprising: using a computer system, e.g., a programmed computer comprising a processor, a data storage system, an input device and an output device, the steps of: (a) inputting into the programmed computer through the input device data comprising a CAST genotype of an animal, (b) correlating fertility and longevity predicted by the CAST genotype using the processor and the data storage system and (c) outputting to the output device the fertility and longevity correlated to the CAST genotype, thereby predicting which livestock animals possess a particular fertility and longevity.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

Materials and Methods

Animals and DNA preparation. Semen samples from 652 sires that had sired various numbers of daughters plus seven grandsires were donated by the Dairy bull DNA repository in Beltsville, Md. for analysis. The sires PTAs for six traits were obtained from the U.S. Department of Agriculture Animal Improvement Programs Laboratory sire list evaluations for all Holstein bulls (http://aipl.arsusda.gov/). Traits analyzed included daughter pregnancy rate (DPR), productive life (PL), protein yield (PY), milk yield (MY), fat yield (FY), somatic cell score (SCS) and net merit in dollars (NM). The average PTA, standard deviation and variation range for each of these traits in our sampled population plus overall estimated heritability for each trait are listed in Table 1. DNA from the sperm was extracted using a phenol chloroform extraction and purification protocol previously described [Ashwell M S, Heyen D W, Sonstegard T S, Van Tassell C P, Da Y, VanRaden P M, Ron M, Weller J I, Lewin H A. Detection of quantitative trait loci affecting milk production, health, and reproductive traits in Holstein cattle. J. Dairy Sci 2004; 87:468-475].

TABLE 1

Phenotypic and genetic parameters of quantitative traits in seven sire families

| Trait | N | Mean | Std Dev | Minimum | Maximum | h² |
|---|---|---|---|---|---|---|
| DPR | 652 | −0.53 | 1.06 | −3.6 | 2.5 | 0.04 |
| PL | 652 | −0.78 | 1.37 | −4.5 | 2.7 | 0.085 |
| PY | 652 | 6.29 | 16.28 | −43 | 64 | 0.25-0.35 |
| MY | 652 | 28.18 | 618.31 | −1915 | 2067 | 0.25-0.35 |
| FY | 652 | 3.81 | 22.05 | −57 | 82 | 0.25-0.35 |
| SCS | 652 | 3.03 | 0.18 | 2.56 | 3.56 | 0.12 |
| NM | 652 | −12.34 | 144.51 | −380 | 538 | N/A |

In silico mutation detection and primer design. A cDNA sequence of the bovine calpastatin gene (NM_174003) consisting of the new XL-domain was used as a reference to search the genomic DNA sequences of the same gene against the bovine genome sequencing database (http://www.hgsc.bcm.tmc.edu/projects/bovine/). A total of seven genomic contigs (FIGS. 1-8) were retrieved and the alignment of both cDNA and genomic DNA sequences revealed 11 potential single nucleotide polymorphisms (SNPs) in the coding region (FIG. 9). Among them, three provisional SNPs would result in amino acid changes in the protein sequence, including two located in putative exon 3 and one in putative exon 8 of the bovine gene. The new XL-domain DNA sequence spans exons 1-3 and partial exon 4. Two primer pairs were designed to cover both potential polymorphic exons based on the genomic DNA sequences. To ensure each exon region was completely amplified and sequenced, at least 100 bp of flanking sequences were included in the products. The primer sequences for amplifying the exon 3 product were: forward, 5'-AAA TTT GCG GTT GAC CAC ACT GTT A-3' (SEQ ID NO: 18) and reverse, 5'-TGT TAT GCC TGT TGC TTT GTA CCT C-3' (SEQ ID NO: 19) (GenBank accession number: AAFC02179490). The primer sequences for amplifying the entire tentative exon 8 were: forward, 5'-GAT TCT TGC TGA ATT TGG AGG GAA G-3' (SEQ ID NO: 20) and reverse, 5'-GGG GTC TCA AAG AGT TGG ATA CGA T-3' (SEQ ID NO: 21) (GenBank accession number: AAFC02060381).

Mutation validation and detection by pooled DNA sequencing. DNA from animals exhibiting extreme phenotypes was pooled to validate the putative mutations described above and detect new polymorphisms in both products that include exon 3 and exon 8 of the bovine CAST gene plus their flanking intron sequences. To target the fertility related phenotypes, animals were sorted by PTA for DPR. Two pooled DNA samples were formed, utilizing the top 60 animals with the highest PTA's for DPR and the 60 animals with the lowest PTA's for DPR. PCR reactions were performed using 25 ng of bovine genomic DNA as template in a final volume of 10 µL containing 12.5 ng of each primer, 200 µM dNTPs, 1.5-3 mM MgCl$_2$, 50 mM KCl, 20 mM Tris-HCl and 0.2U of Platinum Taq polymerase (Invitrogen, Carlsbad, Calif.). Touchdown PCR conditions were carried out as follows: 95° C. for 10 min; 8 cycles of 94° C. for 30 s, 71° C. for 30 s and 72° C. 30 s followed by 37 cycles of 94° C. for 30 s, 63° C. for 30 s and 72° C. for 30 s plus 1 cycle at 72° C. for 5 min and then an extended hold at 4° C. until use. PCR products were examined by electrophoresis through a 1.5% agrose gel with 1×TBE buffer in order to determine the quality and quantity for DNA sequencing. Sequencing was performed on an ABI 3730 sequencer in the Laboratory for Biotechnology and Bioanalysis (Washington State University) using a standard protocol. Nucleotide polymorphisms were identified by comparison of sequence patterns between these DNA pools.

Haplotype detection by grandsire individual sequencing and marker genotyping. The pooled DNA sequences of both products revealed genetic polymorphisms in the population of dairy sires derived from seven grandsires. To determine potential haplotypes among these mutations in the bovine CAST gene, the PCR products from the seven grandsires were amplified and submitted for sequencing individually. A total of four polymorphisms including three SNPs and a simple tandem repeat were observed, but they formed only two haplotypes among these seven grandsires. A C/T substitution was, therefore, chosen for genotyping as it could be revealed using a PCR-RFLP (restriction fragment length polymorphism) approach. The PCR amplicons that contained the exon 3 region and flanking intron sequence was digested at 37° C. for three hours with 2U of MspI (New England Biolabs, Beverly, Mass., USA). Visualization of enzyme digestion and genotype scoring of individuals were conducted by electrophoresis on a 2% agrose gel containing ethidium bromide.

Association analysis of CAST gene with fertility and longevity in dairy cattle. Three steps were employed to investigate the association of the bovine calpastatin gene with DPR and PL in our sampled population. The first step was to genotype the marker on 60 high and 60 low DPR samples. Fisher's exact test was used to examine differences in allele frequencies for initial association screening between these two groups of animals. In the second step, the same marker was genotyped on progeny from the sire family with the highest PTA for DPR and the sire family with the lowest PTA for DPR. Fisher's exact test was used to examine differences in allele frequencies to validate initial associations identified in the first step. The last step was to comprehensively analyze the data from all individuals for the fertility traits of DPR and PL, the production traits of milk yield, protein, milk fat, and overall net merit value for all combined traits. The association between the PTA's of the traits previously described and the son's genotype, CC, CT and TT was examined, using the mixed model function of SAS (Version 9.1 Carey N.C.). Effect of sire family was also included in the model as a fixed effect and son's genotype as a random effect:

$$y_{ijk} = \mu + s_i + g_j + e_{ijk}$$

Where $y_{ijk}$ is the PTA of traits examined; µ is the overall mean value of the trait; $s_i$ is sire family effect (i=1, 2, ..., 7) and $g_j$ is the son's genotypic effect (j=CC, CT, TT). $e_{ijk}$ is the residual effect corresponding to $y_{ijk}$ and was assumed to be normally distributed. The interaction effect between sire family and son's genotype was also included initially in the model, but was excluded in the final model because it was not significant. The model residual was weighted by 1/r in the analysis, where r is reliability for PTA. Significance level of the model was set at P<0.05. Following a significant F-test, individual means for the different genotypes were compared using pre-planned pairwise comparisons using the pdiff function of SAS (Version 9.1, Carey N.C.).

Comparative re-annotation of the human CAST gene. The current GenBank database revealed that the human CAST protein, even at its longest isoform only consisted of an N-terminal domain L and four repetitive calpain-inhibition domains (domains 1-4), thus lacking the XL domain that was detected in the bovine CAST protein. To further validate this observation, the human CAST gene was re-annotated using a three step process as follows: 1) BLAST searches against the "est_human" databases in GenBank using a full-length cDNA sequence of the bovine CAST gene as a reference to retrieve all human ESTs (expressed sequence tags) that are orthologous to the XL-domain-specific sequence of the bovine gene; 2) assembly of newly searched human ESTs with the current longest isoform cDNA sequence to form a full-length cDNA sequence of the human gene; and 3) alignment of newly-annotated cDNA sequences and genomic DNA sequences to determine the complete genomic organization of the human CAST gene.

Results

Genomic Organization and Functional Polymorphisms in the Bovine CAST Gene.

A BLAST search using the cDNA sequence of the bovine CAST gene (NM_174003) retrieved seven genomic contigs with a total sequence of 116,129 bp from a 6× bovine genome sequence assembly (http://www.hgsc.bcm.tmc.edu/projects/bovine/) (FIGS. 2-9). Alignment of both cDNA and genomic DNA sequence indicated that the bovine CAST gene contained at least 32 exons and 31 introns (FIG. 1). However, exons 1-31 are coding exons with coding sequence varying from 30 bp (exon 1) to 114 bp (exon 8) in length. Exon 31 also contained 12 bp of the 3' untranslated sequence and exon 32 possessed no coding sequence at all. Among the 31 introns, twenty-five had complete intronic sequences. Intron 23 was the smallest intron with a sequence of 173 bp, while intron 4 could be the largest intron in the gene with more than 22 kb of sequence (FIG. 1). The XL domain of the protein spanned exons 1-3 and part of exon 4; domain L corresponds to part of exon 4, exons 5-9 and part of exon 10; domain 1 flanked part of exon 10 and exons 11-15; domain 2 extended from exons 16-20 and part of exon 21; domain 3 was coded by part of exon 21, exons 22-25 and part of exon 26; and domain 4 included part of exon 26, exons 27-30 and part of exon 31, respectively (FIG. 1). A cDNA search against the bovine genomic DNA database indicated that only one copy of the calpastatin gene existed in the bovine genome.

Figure 10:
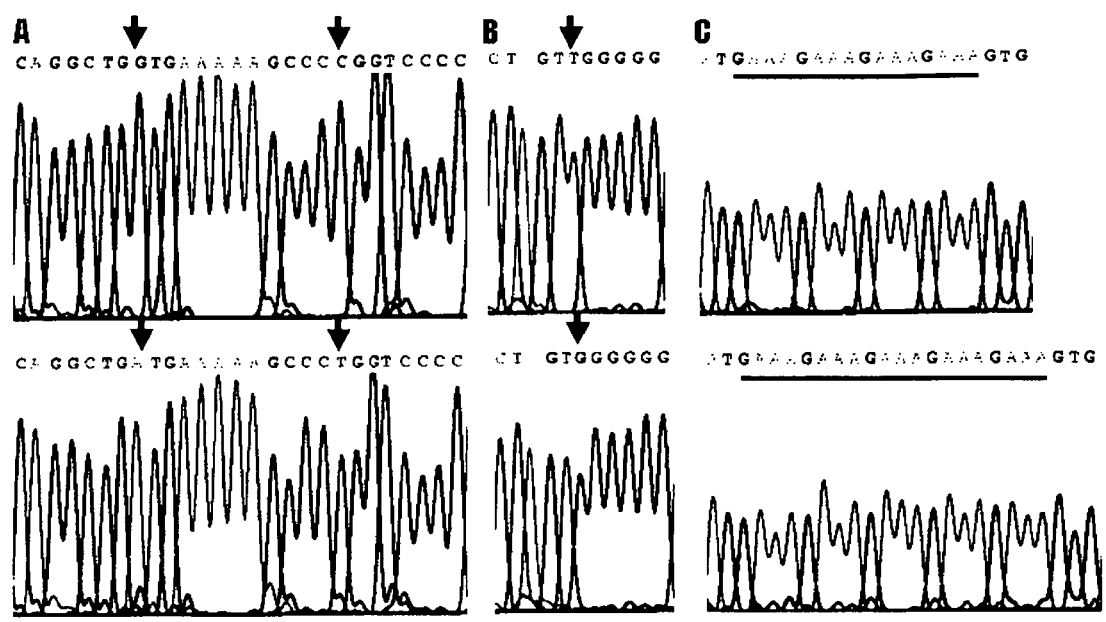
FIGS. 10A-10C provide a nucleotide sequence polymorphisms in the bovine CAST gene. A, two missence mutations A/G and C/T in exon 3 (SEQ ID NOS. 10 and 11); B, a T/G substitution in intron 3 (SEQ ID NOS. 12 and 13); and C, a GAAA repeat in intron 8 (SEQ ID NOS. 14 and 15). Two haplotypes exist in the population: G-C-T-GAAAGAAA-GAAAGAAA (SEQ ID NO: 16) (top row) and A-T-G-GAAAGAAAGAAAGAAAGAAA (SEQ ID NO: 17) (bottom row).

Aligning the cDNA sequence with the genomic DNA sequence of the bovine CAST gene also revealed 11 putative SNPs in the coding region; including four G/A transitions, three C/T transitions, two T/A transversions, one G/T and one CA substitution (FIG. 9). However, only three cSNPs were found to alter the amino acid sequence of the bovine CAST protein: G48D, P52L and I128K. The remaining SNP's were silent mutations. The G48D and P52L substitutions were located in exon 3, corresponding to the XL domain. The I128L was located on exon 8 coding for the domain L. All three missense coding SNPs altered the second base in the codon, leading the amino acid changes. The sequences of the high/low pooled DNA and seven individual grandsires confirmed the G48D and P52L SNP's in the XL domain (FIG. 10A), but not the I128K substitution in the L domain. As both PCR products contained partial intronic sequences, a G/T substitution was detected in intron 3 (FIG. 10B) and a GAAA tetra-nucleotide repeat in intron 8, close to the exon-intron junction region. The GAAA repeat appeared in bi-allelic forms: four repeats in one allele and 5 repeats in another (FIG. 10C). Among these four polymorphisms, only two haplotypes existed in the seven grandsires. Haplotype 1 was G-C-T-GAAAGAAAGAAAGAAA (SEQ ID NO: 16), and haplotype 2 was A-T-G-GAAAGAAAGAAAGAAAGAAA (SEQ ID NO: 17), respectively (FIG. 10).

High-Low Individual and Family Comparisons for Establishment of Initial Associations.

Figure 11:
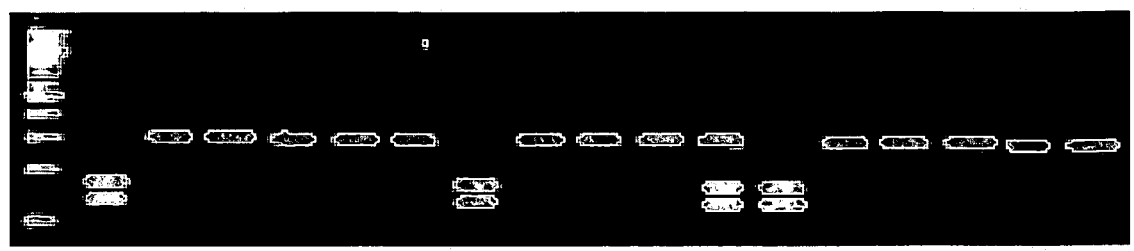
FIG. 11 illustrates PCR-RFLP genotyping of a C/T substitution in exon 3 of bovine CAST gene. TT=308 bp, CT=135+173+308 bp and CC=135+173 bp, respectively.

As indicated above, only two haplotypes existed among the seven grandsires examined, so genotyping one of the haplotypes was sufficient. Of three SNPs identified in the exon 3 products, the C/T transition, which altered the amino acid at position 52 from a proline to a leucine resulted in the gain/loss of a restriction enzyme cut site for MspI. A fragment of 308 bp was amplified for the region, which contained only one cut site for the restriction enzyme. Therefore, digestion with MspI yielded three bands of 135 bp, 173 bp and 308 bp, respectively (FIG. 11). Animals homozygous for the C allele have one MspI site, and after complete digestion exhibited two bands of 135 bp and 173 bp. Animals homozygous for the T allele lost this MspI site which resulted in one band of 308 bp after the digestion reaction. Heterozygous animals showed three bands after MspI digestion (FIG. 11).

The C/T transition was then genotyped in the top and bottom 60 individuals with the highest DPR values. Among the top 60 individuals, the number of TT, CT and CC genotypes were 24 (40%), 22 (36.7%) and 14 (23.3%), respectively. However, of the bottom 60 individuals, TT genotypes accounted for 65% (39/60), while only three individuals (5%) showed CC genotype and 18 animals (30%) were heterozygous (Table 2). Chi-square analysis revealed an association between DPR and genotype frequency between the top and bottom groups ($\chi^2=11.10$, P<0.01). This association between bovine CAST polymorphisms and DPR was further confirmed by genotyping this marker on all progeny of one high and one low DPR sire family. This analysis supported the initial analysis and revealed a highly significant association between DPR and genotype ($\chi^2=92.91$; P<0.0001; Table 2). Fisher's exact tests of differences in allele frequencies were also highly significant between the top and bottom groups (Fisher's p=0.000146) as well as between the progeny of high and low families (Fisher's p=0.000000) (Table 2).

TABLE 2

Initial association analysis of the bovine CAST polymorphism with DPR in dairy cattle

| Group | N | CC | CT | TT | Significance | C | T | Fisher's p value |
|---|---|---|---|---|---|---|---|---|
| Individual-level | | | | | | | | |
| Top | 60 | 14 | 22 | 24 | $\chi^2=11.10$ | 0.42 | 0.58 | p = 0.000146 |
| Bottom | 60 | 3 | 18 | 39 | P < 0.01 | 0.20 | 0.80 | |
| Family-level | | | | | | | | |
| Top | 69 | 27 | 42 | 0 | $\chi^2=92.69$ | 0.70 | 0.30 | p = 0.000000 |
| Bottom | 59 | 0 | 17 | 42 | P < 0.001 | 0.13 | 0.87 | |

Significant associations of CAST gene with fertility and longevity in dairy cattle. Initially, a total of 659 sons from seven sire families were genotyped for this C/T transition in the bovine CAST gene. After genotype verification based on the pedigree analysis, seven animals were removed from the data set due to irregular genotypes. The remaining 652 animals included 62 homozygous CC animals, 378 homozygous TT and 212 heterozygous CT animals. The frequencies of allele C and allele T in the population were 0.26 and 0.74, respectively. Across family analyses for three genotypes of CC, CT and TT indicated that individual genotype was a significant source of variation (P<0.0001) when examining DPR and PL, but was not a significant source of variation when examining the milk production traits (P>0.05) (Table 3).

In DPR values, cattle with the homozygous (CAST: c.283CC) genotype had an additional 0.82 and 0.57 PTA units (3.28 and 2.28 days open equivalent) compared to the CAST.c.283TT homozygous and CAST.c.283CT heterozygous animals (P<0.05) (Table 1). The longevity PTA was 1.22 units greater between CAST:c.283CC and TT animals and 0.89 different between CAST.c.283CC and CT animals (P<0.05). Improvement of both DPR and longevity in CAST: c.283CC animals led to an increase of the economic value by $67.86 and $51.14 per cow compared to the TT homozygotes and CT heterozygotes (P<0.05) (Table 3). The additive (a) and dominance (d) effects of C to T substitution and their units in standard deviation (SD) are also listed in Table 3.

TABLE 3

Associations of the bovine CAST gene (NM_174003.2:c.283 C > T) with reproductive and productive traits in dairy cattle[1]

| Trait | CC | CT | TT | F value | P | a[2] | a in SD[3] | d[4] | d in SD[3] |
|---|---|---|---|---|---|---|---|---|---|
| DPR | 0.13[a] | −0.44[b] | −0.69[b] | 17.83 | <0.0001 | 0.41 | 0.39 | −0.16 | −0.15 |
| PL | 0.22[a] | −0.67[b] | −1.00[b] | 23.41 | <0.0001 | 0.61 | 0.45 | −0.28 | −0.21 |
| PY | 8.08[a] | 6.68[a] | 5.79[a] | 0.62 | 0.5402 | 1.15 | 0.07 | −0.25 | −0.02 |
| MY | 115.18[a] | 68.25[a] | −8.56[a] | 1.73 | 0.1781 | 61.87 | 0.10 | 14.94 | 0.02 |
| FY | 5.39[a] | 3.72[a] | 3.52[a] | 0.18 | 0.8361 | 0.94 | 0.04 | 0.74 | 0.03 |
| SCS | 2.98[a] | 3.03[ab] | 3.03[b] | 2.03 | 0.1316 | −0.02 | −0.14 | 0.02 | 0.14 |
| NM | 43.63[a] | −7.51[b] | −24.23[b] | 6.14 | 0.0023 | 33.93 | 0.24 | −17.21 | −0.12 |

[1] Differing superscripts indicate a significant difference of P < .05 within each row.
[2] Additive effect.
[3] SD = Standard Deviation.
[4] Dominance effect.

Genotyping of seven grandsires indicated there were one CC sire, two CT sires and four TT sires. Grandsire genotype was shown to be a significant source of variation for both DPR and PL (P<0.0001). When examining DPR, the average PTA value for the progeny of the CC sire was 1.50 (0.61 vs-0.89) and 0.94 units (0.60 vs-0.34) higher than that for the progeny of TT and CT sires, respectively (P<0.05). The PL PTA values were 0.62, −0.51 and −1.24 in the progeny of CC, CT and TT sire families, and were significantly different between any two sire family groups (P<0.05). If we consider the differences between the progeny of CC and TT grandsires as selection differentials, and the differences between CC and TT individuals of the cross families as selection response, the realized heritabilities were estimated to be 0.55 (0.82/1.50) for DPR and 0.66 (1.22/1.86) for PL, respectively.

Existence of the XL domain in human CAST gene. The BLAST search against the "est_human" database at NCBI using the cDNA sequence of the bovine CAST gene (NM_174003) identified two human ESTs (BP2044772 and BU5644868) that showed high sequence similarity to the XL domain sequence of the bovine CAST gene. Assembly of these two EST sequences with the current longest form of the human CAST gene (NM_001750) generated a consensus sequence of 2,876 bp, including 151 bp 5'UTR, 2,331 bp coding sequence and 394 bp 3'UTR sequences (FIG. 1). Overall, the newly translated human CAST protein is 10 amino acids shorter than the bovine CAST protein sequence, but both have the same number of amino acids (68 amino acids) in the XL domain. The XL domain similarity between the human and bovine CAST gene was 85% in nucleotide sequence and 77% in amino acid sequence.

Alignment of the newly assembled human cDNA sequence with the genomic DNA sequence revealed that the longest human CAST gene contained 32 exons and 31 introns (FIG. 1). Like the bovine CAST gene, exons 1-31 are coding exons with coding sequence varying from 30 bp (exon 1) to 114 bp (exon 8) in length. Exon 31 also contained 23 bp of 3' untranslated sequence and exon 32 comprised the remaining 3'UTR sequence. Compared to the bovine CAST gene, the human gene had shorter coding sequences in exons 9, 15, 26, 28 and 31 by 6, 3, 3, 3 and 18 bp, respectively. However, exon 20 of human CAST gene had a 3 bp longer coding sequence than that observed in cattle. In the human CAST gene, intron 23 was also the smallest intron with a sequence of 89 bp, while intron 3 was the largest intron in the gene with about 27 kb of sequence (FIG. 1).

Discussion

It has been reported that the calpastatin gene is expressed in multiple reproductive tissues, including, but not limited to the testis, ovary, uterus, pituitary, mammary gland, germ cells and the prostate gland [Kitahara A, Takano E, Ontsuki H, Kirihata Y, Yamagata Y, Knaagi R, Murachi T. Reversed distribution of calpains and calpastatin in human pituitary gland and selective localization of calpastatin in adrenocorticotropin-producing cells as demonstrated by immunohistochemistry. J Clin Endocrinol Metab 1986; 63:343-348; Thompson V F, Saldana S, Cong J, Luedke D M, Goll D E. The calpain system in human placenta. Life Sci 2002; 70:2493-508; Ben-Aharon I, Ben-Yosef D, Amit A, Shalgi R. Expression and immunolocalization of the calpain-calpastatin system in the human oocyte. Fertil Steril 2005; 83:1807-1813; Orwig K E, Bertrand J E, Ou B R, Forsberg N E, Stormshak F. Involvement of protein kinase-C, calpains, and calpastatin in prostaglandin F2 alpha-induced oxytocin secretion from the bovine corpus luteum. Endocrinology 1994; 134:78-83; Liang Z G, O'Hern P A, Yavetz B, Yavetz H, Goldberg E. Human testis cDNAs identified by sera from infertile patients: a molecular biological approach to immunocontraceptive development. Reprod Fertil Dev 1994; 6:297-305; Li S, Liang Z G, Wang G Y, Yavetz B, Kim E D, Goldberg E. Molecular cloning and characterization of functional domains of a human testis-specific isoform of calpastatin. Biol Reprod 2000; 63:172-178; Li S, Liang Z G, Wang G Y, Yavetz B, Kim E D, Goldberg E. Molecular cloning and characterization of functional domains of a human testis-specific isoform of calpastatin. Biol Reprod 2000; 63:172-178; Li S, Goldberg E. A novel N-terminal domain directs membrane localization of mouse testis-specific calpastatin. Biol Reprod 2000; 63:1594-1600 and Wang L F, Miao S Y, Yan Y C, Li Y H, Zong C, Koide S S. Expression of a sperm protein gene during spermatogenesis in mammalian testis: an in situ hybridization study. Mol Reprod Dev 1990; 26:1-5]. A strong association was found between the calpastatin and fertility in the present study. It was also observed that animals with the desirable genotype for fertility did not exhibit a decreased level of milk production: animals with higher PTA values for DPR exhibited similar milk production traits as animals with the less fertile genotypes (Table 3). This is an optimal situation as it was initially thought that selection for fertility would result in a loss of milk production or visa versa. Therefore, involvement of the calpastatin gene in different physiological and/or biochemical pathways that lead to various functions should be further evaluated.

Pleiotropic effects of the CAST gene. As there is evidence that postmortem calpastatin activity is highly related to meat tenderness in different species [Koohmaraie M, Whipple G, Kretchmar D H, Crouse J D, Mersmann H J. Postmortem proteolysis in longissimus muscle from beef, lamb, and pork carcasses. J Anim Sci 1991; 69:617-624], several association studies have been performed to search for genetic polymorphisms in calpastatin as a source of genetic markers that may influence meat tenderness. For example, Schenkel and colleagues (unpublished data) identified a G/C substitution in intron 4 of the bovine CAST gene that was associated with shear force (P=0.024) in beef cattle. In pigs, Ciobanu and coworkers [Ciobanu D C, Bastiaansen J W, Lonergan S M, Thomsen H, Dekkers J C, Plastow G S, Rothschild M F. New alleles in calpastatin gene are associated with meat quality traits in pigs. J Anim Sci 2004; 82:2829-2839] reported that one CAST haplotype was significantly associated with lower Warner-Bratzler shear force, cooking loss and higher juiciness. In the present study, results clearly demonstrated that functional mutations of the bovine CAST XL domain region were associated with fertility and longevity in Holstein dairy cattle. The haplotype G-C-T-GAAAGAAAGAAAGAAA (SEQ ID NO: 16) is more desirable than the haplotype A-T-G-GAAAGAAAGAAAGAAAGAAA (SEQ ID NO: 17) by increasing PTA values of 0.82 units in DPR and 1.22 units in PL (Table 3). These data indicate that the CAST gene plays a pleiotropic role in different physiological pathways and involved in different functions. In addition, the present study reported two missense mutations in the bovine CAST gene, which are located in the newly identified XL domain region. The potential impact of this beneficial CAST haplotype for DPR and PL on meat quality warrants further investigation.

Benefits of the CAST gene for marker assisted selection. Reproductive decline in dairy cows has been largely blamed for the intensive selection for milk traits. For example, based on the linear regression of breeding values for days open on breeding values for 3.7% FCM (fat-corrected milk), Abdallah and McDaniel [Abdallah J M, McDaniel B T. Genetic parameters and trends of milk, fat, days open, and body weight after calving in North Carolina experimental herds. J Dairy Sci 2000; 83:1364-1370] estimated that for each 1000-kg increase in the breeding values for 3.7% FCM, breeding values for days open increased by 8 days. In Spain, milk yield per cow increased from 7800 kg in 1991 to 10,200 kg in 2000. However, each 1000 kg increase in average milk yield was accompanied by a decrease of 3.2% to 6% in pregnancy rate, 4.4% to 7.6% in cyclicity, and an increase of 4.6% and 8% in the incidence of inactive ovaries [Lopez-Gatius F. Is fertility declining in dairy cattle? A retrospective study in northeastern Spain. Theriogenology 2003; 60:89-99]. Negative genetic correlations were also reported between milk yield and other reproductive traits, such as calving interval and first service conception rates [Pryce J E, Veerkamp R F. The incorporation of fertility indices in genetic improvement programmes. In Fertility in the high producing dairy cows, British Society of Animal Science Occas 2003; 26:237-249]. Results from the present study suggest that selection for the beneficial allele/haplotype in the bovine CAST gene would not necessarily result in a decrease in milk production traits in dairy cows. Therefore, we anticipate that a combination of genetic selection based on the CAST marker and high PTA potentials of milk production traits will improve reproductive traits while allowing for the continued high milk production traits. In addition, if the CAST gene were applied in marker assisted selection programs, the heritability of DPR could be dramatically increased. Compared to estimated heritability of 0.04 for DPR and 0.085 for PL (Table 1), using the calpastatin gene in marker assisted selection would thus accelerate improvement of fertility in dairy cattle, which has declined for several decades. The low frequency of the desirable allele/haplotype (0.26) in the current dairy population studied was consistent with the low fertility in exhibited in this population, indicating that marker assisted selection is urgently needed.

CAST gene and human infertility. Infertility is one of the most important social and economical health issues in humans. For example, although the world's population has increased remarkably and is projected to reach nine billion by 2050, it is estimated that 50-80 million couples in the world will remain childless due to infertility [Montoya J M, Bernal A, Borrero C. Diagnostics in assisted human reproduction Reprod Biomed Online 2002; 5:198-210]. In the present study, re-annotation of human CAST gene revealed that the human gene also has the XL domain as the bovine gene does. As CAST protein was identified as one of the target antigens for anti-sperm antibodies found in infertile women [Koide S S, Wang L, Kamada M. Antisperm antibodies associated with infertility: properties and encoding genes of target antigens. Proc Soc Exp Biol Med 2000; 224:123-132], its involvement in the human reproduction needs to be further explored Example 2

Figure 12:
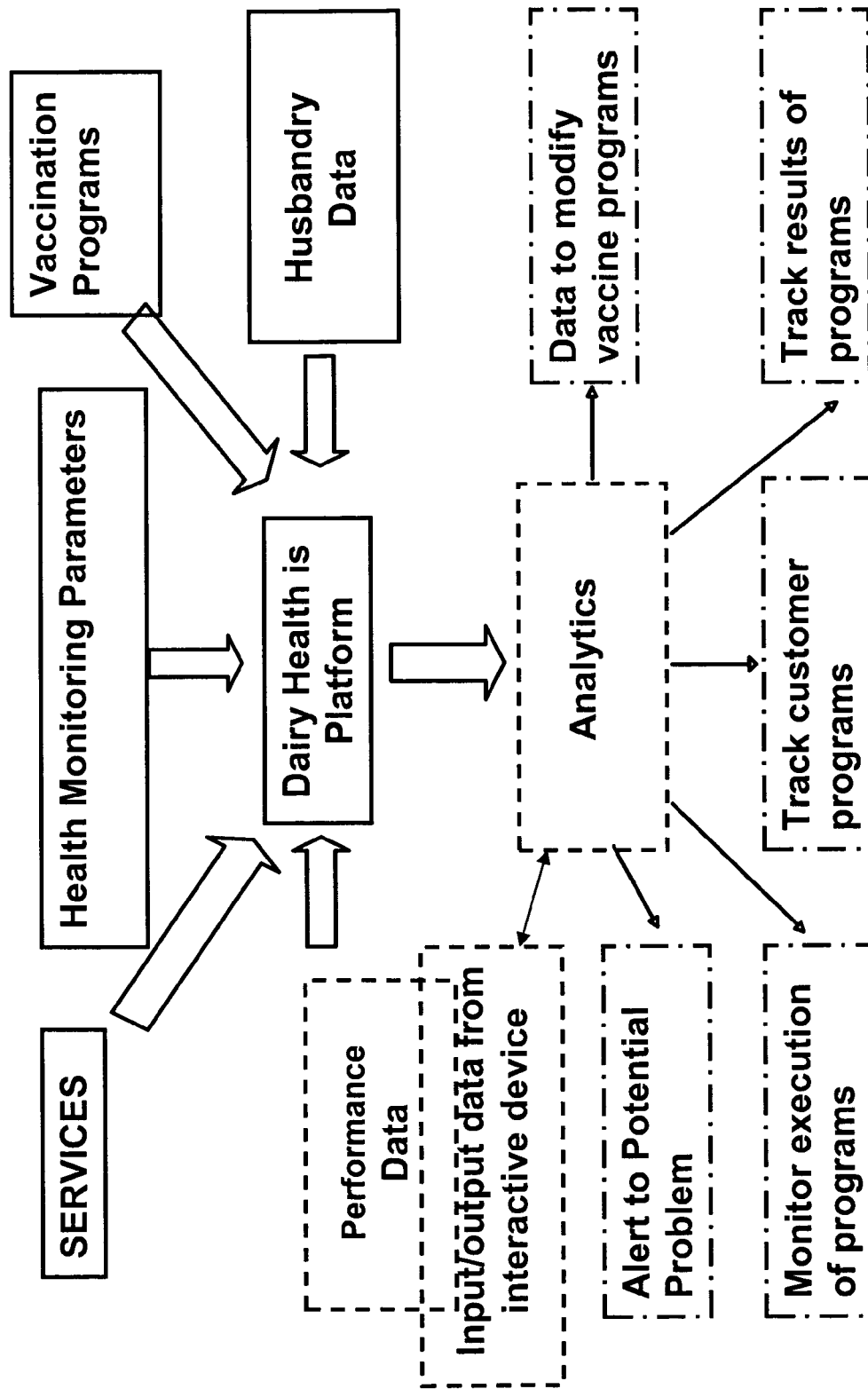
FIG. 12 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

FIG. 12 shows a flowchart of the input of data and the output of results from the analysis and correlation of the data pertaining to the breeding, veterinarian histories and performance requirements of a group of animals such as from bovines. The flowchart illustrated in FIG. 7 further indicates the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 13:
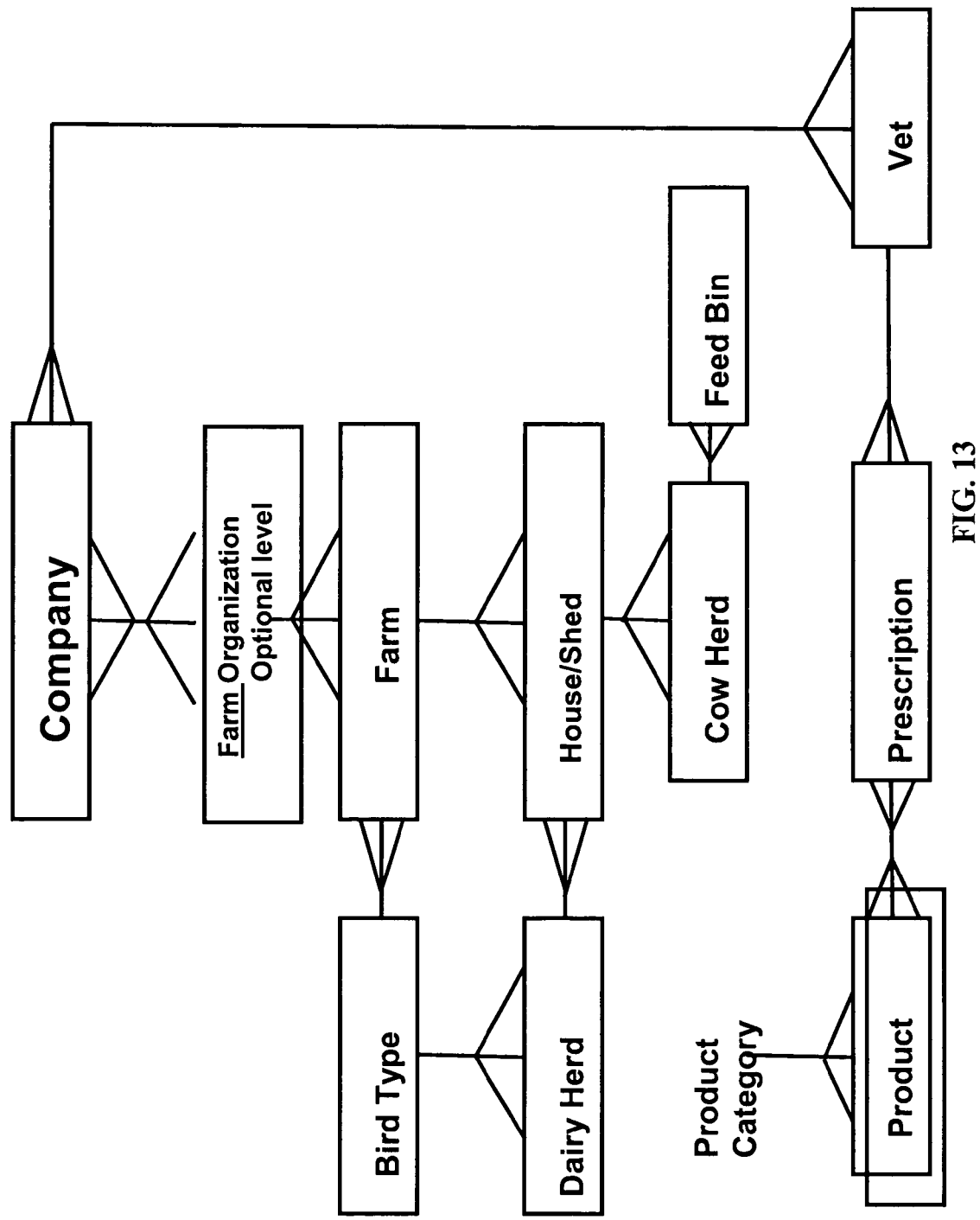
FIG. 13 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 13 illustrates potential relationships between the data elements to be entered into the system. Unidirectional arrows indicate, for example, that a barn is typically owned by only one farm, whereas a farm may own several barns. Similarly, a prescription may include veterinarian products.

Figure 14A:
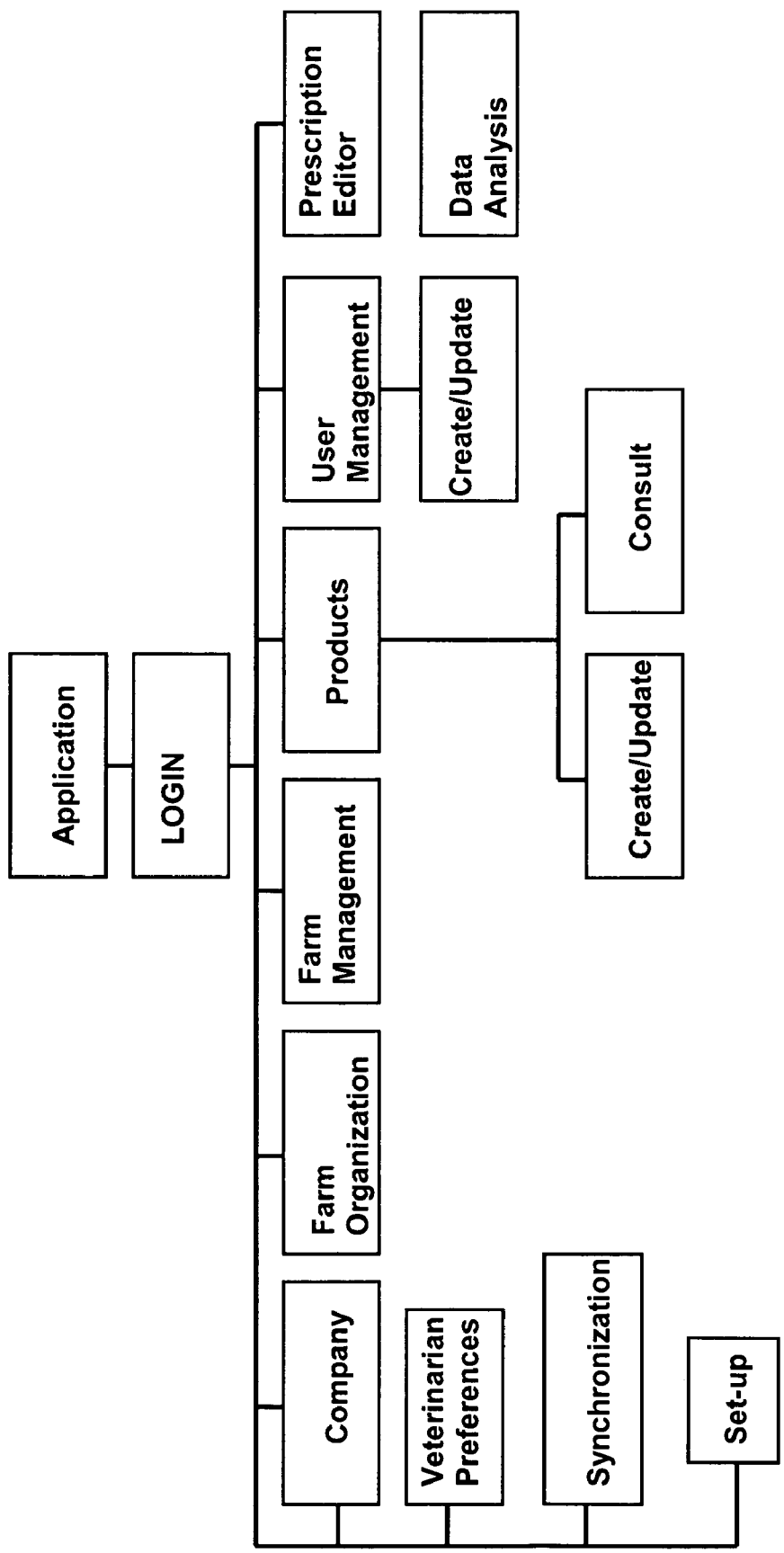
FIG. 14A illustrates the flow of events in the use of the portable computer-based system for data entry on the breeding and rearing of a herd of cows.
Figure 14B:
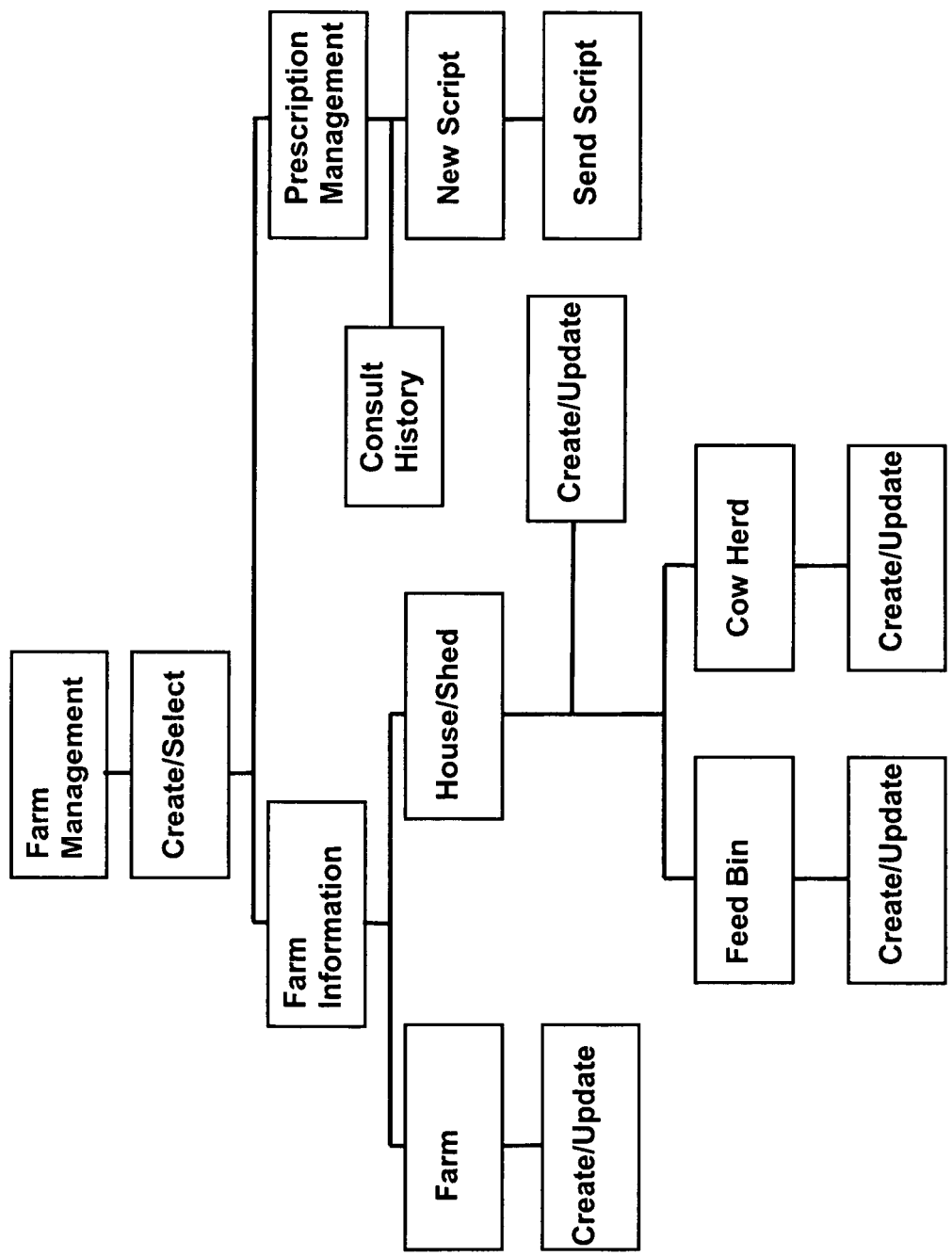
FIG. 14B illustrates the flow of events through the sub-routines related to data entry concerning farm management.
Figure 14C:
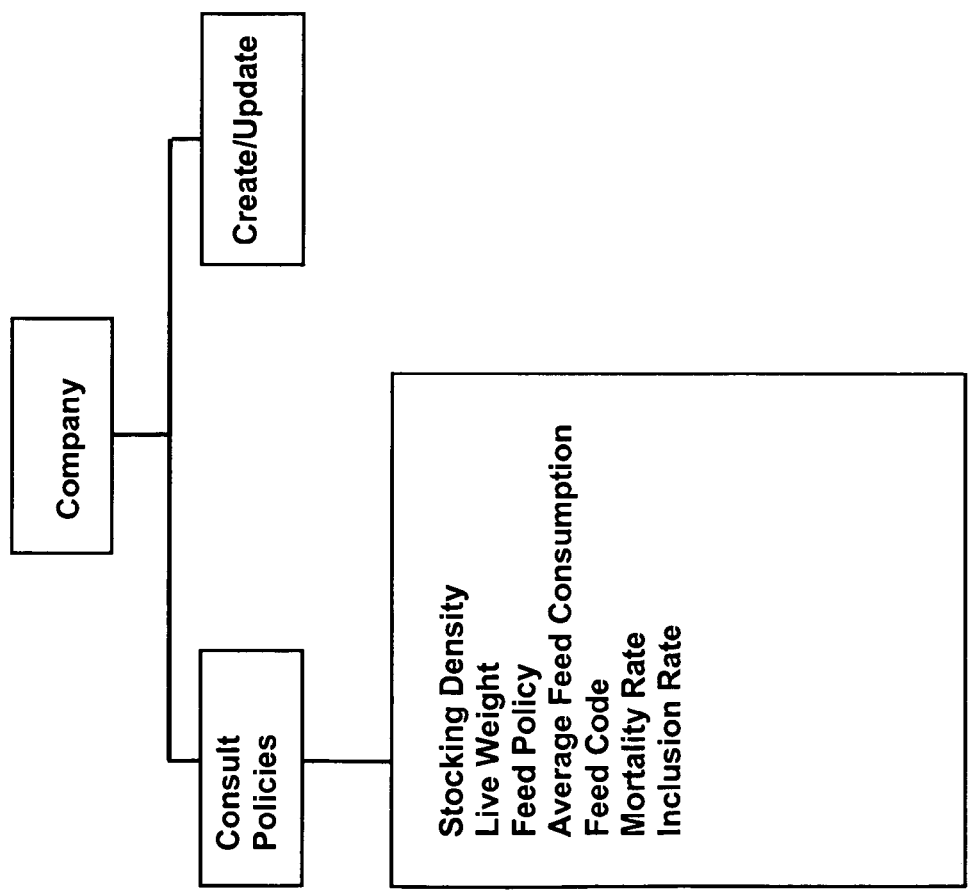
FIG. 14C illustrates the flow of events through the sub-routines related to data entry concerning data specific to a company.

FIG. 14A illustrates the flow of events in the use of the portable computer-based system for data entry on the breeding and rearing of a herd of cows. FIG. 14B illustrates the flow of events through the sub-routines related to data entry concerning farm management. FIG. 14C illustrates the flow of events through the sub-routines related to data entry concerning data specific to a company.

Figure 15:
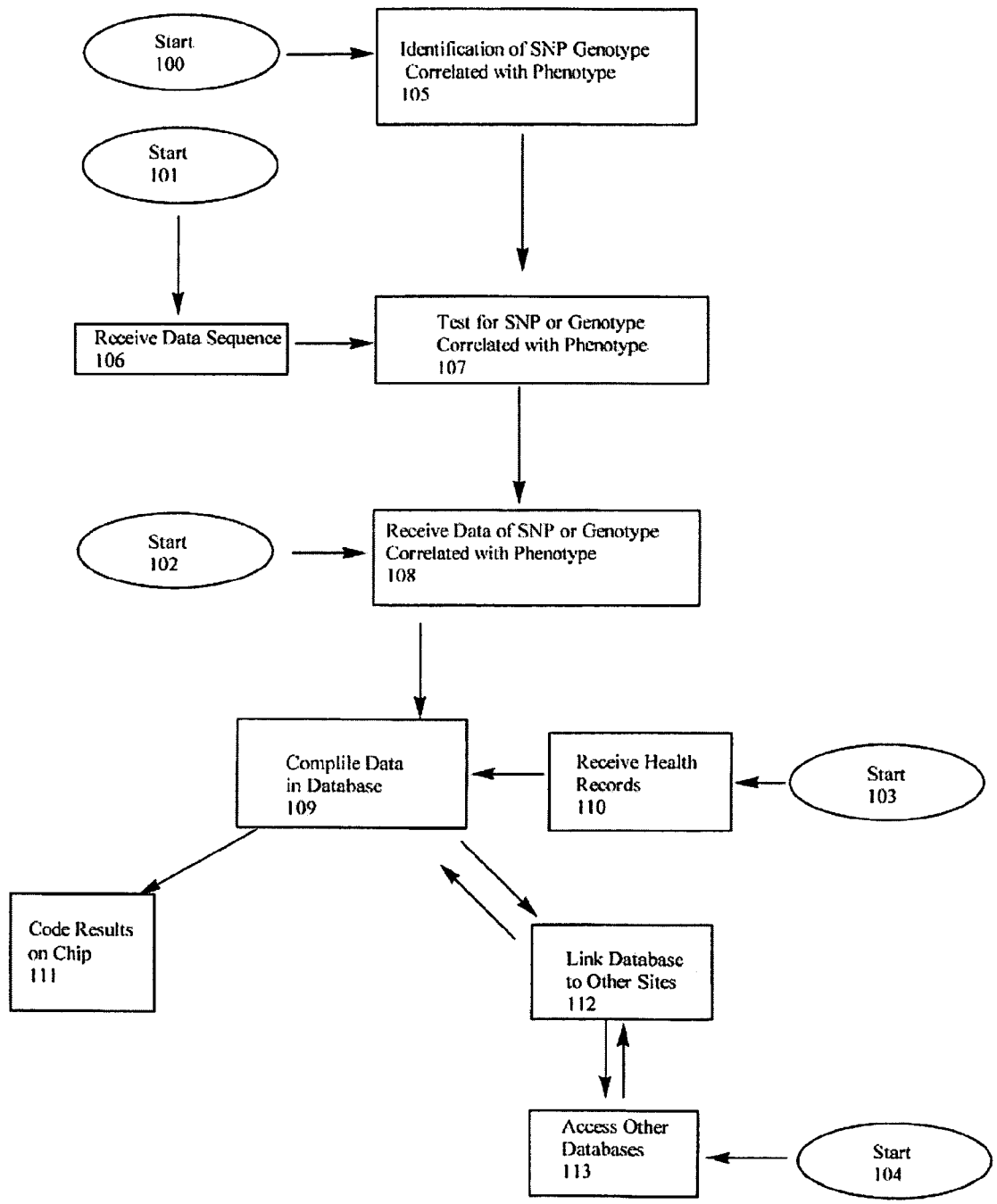
FIG. 15 illustrates a flow chart of the input of data and the output of results from the analysis and the correlation of the data pertaining to the breeding, veterinarian histories, and performance requirements of a group of animals.

FIG. 15 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub-grouping animals according to genotype wherein the animals of each sub-group have a similar polymorphism in a calpastatin ("CAST") gene comprising:

(a) determining the genotype of each animal to be sub-grouped by determining the presence of SNPs/STRs in the CAST gene, and (b) segregating individual animals into sub-groups wherein each animal in a sub-group has a similar polymorphism in the CAST gene.

2. A method for sub-grouping animals according to genotype wherein the animals of each sub-group have a similar genotype in the CAST gene comprising:

(a) determining the genotype of each animal to be sub-grouped by determining the presence of SNPs/STRs of interest in the CAST gene, (b) segregating individual animals into sub-groups depending on whether the animals have, or do not have, the single nucleotide polymorphism(s)/short tandem repeats of interest in the CAST gene.

3. The method of paragraphs 1 or 2, wherein the SNPs/STRs of interest is selected from the group consisting of missense mutations in exon 3 that result in G48D or P52L substitutions (NM_174003.2:c.271G>A and 283C>T), a G/T substitution in intron 3 (AAFC02060381.1:g.2110G>T) and a GAAA repeat in intron 8 (AAFC02060381.1:g 6700 [(GAAA)4]+[(GAAA)5].

4. A method for sub-grouping animals according to genotype wherein the animals of each sub-group have a similar genotype in the CAST gene comprising:

(a) determining the genotype of each animal to be sub-grouped by determining the presence of missense mutations in exon 3 that result in G48D or P52L substitutions (NM_174003.2:c.271G>A and 283C>T), a G/T substitution in intron 3 (AAFC02060381.1:g.2110G>T) and a GAAA repeat in intron 8 (AAFC020603 81.1:g.6700[(GAAA)4]+[(GAAA)5], and (b) segregating individual animals into sub-groups depending on whether the animals have, or do not have, missense mutations in exon 3 that result in G48D or P52L substitutions (NM_174003.2:c.271G>A and 283C>T), a G/T substitution in intron 3 (AAFC02060381.1:g.2110G>T) and a GAAA repeat in intron 8 (AAFC020603 81.1:g.6700[(GAAA)4]+[(GAAA)5] in the CAST gene.

5. A method for identifying an animal having a desirable phenotype as compared to the general population of animals of that species, comprising determining the presence of a SNP/STR in the CAST gene of the animal, wherein the polymorphism is selected from the group consisting of missense mutations in exon 3 that result in G48D or P52L substitutions (NM_174003.2:c.271G>A and 283C>T), a G/T substitution in intron 3 (AAFC02060381.1:g.2110G>T) and a GAAA repeat in intron 8 (AAFC020603 81.1:g.6700[(GAAA)4]+[(GAAA)5] in the CAST gene single nucleotide polymorphism/short tandem repeat is indicative of a desirable phenotype.

6. The method of paragraph 5, wherein the desirable phenotype is daughter pregnancy rate (DPR), productive life (PL), protein yield (PY), milk yield (MY), fat yield (FY), somatic cell score (SCS) and net merit in dollars (NM) or any combination thereof.

7. The method of paragraph 5 or 6, wherein the desirable phenotype is additional fertility, longevity and economic net merit or any combination thereof.

8. The method of any one of paragraphs 1 to 7 wherein the animal is a bovine.

9. The method of any one of paragraphs 1 to 8 wherein the CAST gene is a bovine CAST gene.

10. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

11. The method according to paragraph 10, wherein the computer system is an interactive system whereby modifications to the output of the computer-assisted method may be correlated according to the input from the interactive device.

12. The method according to paragraph 10 or 11, further comprising the steps of inputting into the programmed computer diagnostic data related to the health of the cow or herd of cows; and correlating the diagnostic data to the breeding and veterinary histories of the cow or herd of cows.

13. The method according to any one of paragraphs 10 to 12, wherein the veterinary data comprises a vaccination record for a cow or herd of cows.

14. The method according to any one of paragraphs 10 to 13 wherein the health data is selected from the group consisting of husbandry condition data, herd history, and food safety data.

15. The method according to any one of paragraphs 10 to 14, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

16. The method according to any one of paragraphs 10 to 15, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

17. The computer-assisted method according to any one of paragraphs 10 to 16 for optimizing efficiency of feedlots for livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

18. A method of transmitting data comprising transmission of information from such methods according to any one of paragraphs 10 to 16, selected from the group consisting of telecommunication, telephone, video conference, mass communication, a presentation, a computer presentation, a POWERPOINT™ presentation, internet, email, and documentary communication.

19. An interactive computer system according to any one of paragraphs 10 to 16 for tracking breeding and welfare histories of cows comprising breeding and veterinarian data corresponding to a bovine or herd of bovines, and wherein the computer system is configured to allow the operator thereof to exchange data with the device or a remote database.

20. The interactive computer system according to paragraph 19, wherein the input and output devices are a personal digital assistant or a pocket computer.

21. A method of doing business for tracking breeding and welfare histories of livestock comprising breeding and veterinarian data corresponding to one or more livestock animals comprising providing to a user the computer system of paragraph 19.

22. A method of doing business for tracking breeding and welfare histories of livestock comprising breeding and veterinarian data corresponding to one or more livestock animals comprising providing to a user the computer system of paragraph 20.

23. The method of doing business according to paragraph 21, further comprising providing the animal owner or customer with sample collection equipment, such as swabs and tags useful for collecting samples from which genetic data may be obtained, and wherein the tags are optionally packaged in a container which is encoded with identifying indicia.

24. The method of doing business according any one of paragraphs 10 to 16, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

25. The method of any one of paragraphs 8 to 24 wherein the data comprises presence or absence of one or more of a single nucleotide polymorphism(s)/STR of interest in the CAST gene.

26. The method of paragraph 25 wherein the single nucleotide polymorphism(s)/short tandem repeats of interest is selected from the group consisting of missense mutations in exon 3 that result in G48D or P52L substitutions (NM_174003.2:c.271G>A and 283C>T), a G/T substitution in intron 3 (AAFC020603 81.1:g.2110G>T) and a GAAA repeat in intron 8 (AAFC02060381.1:g.6700[(GAAA)4]+[(GAAA)5] of the CAST gene.

27. A method for the diagnosis or monitoring of fertility and/or longevity in a subject, comprising: obtaining a biological sample from a subject; and determining, using a suitable assay, a presence or absence in the sample of one or more XL domain CAST markers, as described herein.

28. The method of claim 27, wherein the subject is bovine.

29. A method for marker-assisted selection to improve fertility and/or longevity, comprising screening, as part of a selection scheme, based on one or more XL domain CAST markers, as described herein, to enhance selection for fertility and/or longevity.

30. The method of claim 29, wherein selecting is to enhance bovine fertility and/or longevity.

31. The method of claim 29, further comprising genetic selection based on high PTA potential of one or more milk production traits, to provide for improved fertility and/or longevity, in association with high milk production.

32. The method of claim 31, wherein selecting is to enhance bovine fertility and/or longevity, in association with high milk production.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal having a higher daughter pregnancy rate (DPR) or longer productive life (PL), said method comprising:

(a) obtaining a biological sample from said bovine animal, said biological sample comprising nucleic acids encoding the bovine calpastatin (CAST) gene from said bovine;

(b) detecting in said nucleic acids the presence of at least one of:
  (i) a G in both alleles of the CAST gene at position corresponding to position 7549 of SEQ ID NO: 3;
  (ii) a C in both alleles of the CAST gene at position corresponding to position 7561 of SEQ ID NO: 3;
  (iii) a T in both alleles of the CAST gene at position corresponding to position 7626 of SEQ ID NO: 3;
  (iv) only four GAAA repeats in both alleles of the CAST gene at a position corresponding to position 5433 of SEQ ID NO: 5;
(c) correlating the presence of the nucleic acid content of (b) with a higher daughter pregnancy rate (DPR) or longer productive life (PL) in said bovine animal.

\* \* \* \* \*